(12) United States Patent
Koseki et al.

(10) Patent No.: US 10,968,392 B2
(45) Date of Patent: Apr. 6, 2021

(54) LIQUID CRYSTAL ALIGNING AGENT FOR PHOTOALIGNMENT, LIQUID CRYSTAL ALIGNMENT FILM AND LIQUID CRYSTAL DISPLAY DEVICE USING IT, AND DIAMINE AND POLYMER

(71) Applicants: JNC CORPORATION, Tokyo (JP); JNC PETROCHEMICAL CORPORATION, Tokyo (JP)

(72) Inventors: Yohei Koseki, Chiba (JP); Takehiko Kanbara, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 122 days.

(21) Appl. No.: 16/174,450

(22) Filed: Oct. 30, 2018

(65) Prior Publication Data

US 2019/0127643 A1 May 2, 2019

(30) Foreign Application Priority Data

Oct. 31, 2017 (JP) .............................. JP2017-210174
May 22, 2018 (JP) .............................. JP2018-098334

(51) Int. Cl.
*C09K 19/56* (2006.01)
*G02F 1/1337* (2006.01)
(Continued)

(52) U.S. Cl.
CPC .......... *C09K 19/56* (2013.01); *C08G 73/1017* (2013.01); *C08G 73/1042* (2013.01); *G02F 1/133719* (2013.01); *G02F 1/133723* (2013.01); *G02F 1/133788* (2013.01); *B32B 2457/202* (2013.01); *C07C 211/49* (2013.01);
(Continued)

(58) Field of Classification Search
CPC ................ C09K 19/56; C09K 2323/02; C09K 2323/025; C09K 2323/027; G02F 1/133723; G02F 1/133788; G02F 1/133719; G02F 2001/133761; C08G 73/1017; C08G 73/1042; C08G 73/1085; C08G 73/1067; Y10T 428/1005; Y10T 428/1018;
(Continued)

(56) References Cited

U.S. PATENT DOCUMENTS

2010/0189930 A1* 7/2010 Kuwana .................... C08F 4/04
428/1.2
2015/0119522 A1* 4/2015 Ooki ...................... C09K 19/56
524/538

FOREIGN PATENT DOCUMENTS

JP        11-249142      9/1999
JP      2005-275364    10/2005
(Continued)

*Primary Examiner* — Eli D. Strah
(74) *Attorney, Agent, or Firm* — Wenderoth, Lind & Ponack, L.L.P.

(57) ABSTRACT

Provided are a liquid crystal alignment film capable of being given anisotropy through photoalignment and stable to light, and a liquid crystal display device capable of keeping a high voltage holding ratio without degradation of display quality even when exposed to strong light for a long period of time. To provide these, used is a liquid crystal aligning agent for photoalignment which contains a polymer having a structural unit containing a photoreactive structure and in which the structural unit containing a photoreactive structure undergoes chemical reaction by heating.

18 Claims, 2 Drawing Sheets

(51) Int. Cl.
    *C08G 73/10*     (2006.01)
    *G02B 1/12*      (2006.01)
    *C07C 245/08*    (2006.01)
    *C07C 211/49*    (2006.01)

(52) U.S. Cl.
    CPC ........ *C07C 245/08* (2013.01); *C09K 2323/02* (2020.08); *C09K 2323/025* (2020.08); *C09K 2323/027* (2020.08); *G02B 1/12* (2013.01); *G02F 2001/133761* (2013.01)

(58) Field of Classification Search
    CPC ........ Y10T 428/1023; B32B 2457/202; C07C 211/49; C07C 245/08; G02B 1/12; C09D 179/08
    See application file for complete search history.

(56) References Cited

FOREIGN PATENT DOCUMENTS

| | | |
|---|---|---|
| JP | 2007-248637 | 9/2007 |
| JP | 2009-069493 | 4/2009 |
| JP | 2010-197999 | 9/2010 |
| JP | 2015-135464 | 7/2015 |
| WO | 2013/157463 | 10/2013 |
| WO | 2013/161569 | 10/2013 |
| WO | 2015/016118 | 2/2015 |
| WO | 2017/119376 | 7/2017 |

* cited by examiner

LIQUID CRYSTAL ALIGNING AGENT FOR PHOTOALIGNMENT, LIQUID CRYSTAL ALIGNMENT FILM AND LIQUID CRYSTAL DISPLAY DEVICE USING IT, AND DIAMINE AND POLYMER

BACKGROUND

Technical Field

The present invention relates to a liquid crystal aligning agent, a liquid crystal alignment film and a liquid crystal display device using the film. Precisely, the present invention relates to a liquid crystal aligning agent for forming a photoalignment-type liquid crystal alignment film (hereinafter this may be abbreviated as a photoalignment film), a photoalignment-type liquid crystal alignment film formed using the liquid crystal aligning agent, and a liquid crystal display device having the liquid crystal alignment film. In addition, the present invention also relates to a polymer such as a polyamic acid or polyimide for use for the liquid crystal aligning agent, and a diamine compound to be a raw material for the polymer.

Description of Related Art

Liquid crystal display devices of various drive modes are known, including those of a TN (twisted nematic) mode, an STN (super-twisted nematic) mode, an IPS (in-plane switching) mode, an FFS (fringe field switching) mode, and a multi-domain VA (vertical alignment) mode. These liquid crystal display devices are applied to televisions, mobile phones and image display devices of various electronic appliances, and development thereof is under way for further improvement of display quality. Specifically, performance improvement of liquid crystal display devices is attained not only by improving the driving system and the device structure but also by the structural members for use in the devices. Among the structural members for use in liquid crystal display devices, in particular, a liquid crystal alignment film is one important material that participates in display quality, and for satisfying the requirement of improving the quality of liquid crystal display devices, various studies relating to liquid crystal alignment films are also being made actively.

Here, a liquid crystal alignment film is provided on a pair of substrates arranged on both sides of a liquid crystal layer of a liquid crystal display device, adjacent to the liquid crystal layer, and has a function of aligning the liquid crystal molecules constituting the liquid crystal layer under predetermined regularity relative to the substrate. Using a liquid crystal alignment film having high liquid crystal alignment performance realizes a liquid crystal display device having a high contrast and improved in image sticking reduction (for example, see patent documents 1 and 2).

For forming such a liquid crystal alignment film, at present, a solution (varnish) prepared by dissolving a polyamic acid, or a soluble polyimide or polyamic acid ester in an organic solvent is mainly used. In forming a liquid crystal alignment film using such a varnish, the varnish is applied to a substrate, then the coating film is solidified by heating to form a polyimide-type liquid crystal alignment film, and optionally this is treated for alignment suitable for the above-mentioned display mode. As the alignment treatment method, there are known a rubbing method of rubbing the surface of the alignment film with a cloth or the like to thereby regulate the direction of the polymer molecules in the film, and a photoalignment method of irradiating the alignment film with linearly-polarized ultraviolet rays to cause photochemical change such as photoisomerization or dimerization in the polymer molecules to thereby impart anisotropy to the film; and among these, the photoalignment method is advantageous in that the alignment uniformity is high as compared with that in the rubbing method, and that the film is not damaged since the method is a non-contact alignment treatment method, and another advantage thereof is that the risks such as dusting or static electricity to cause display failures of liquid crystal display devices can be reduced.

Regarding the liquid crystal alignment film using such a photoalignment method, for example, patent documents 1 to 6 disclose production of a photoalignment film having large anchoring energy and good liquid crystal alignment performance by applying the technique of photoisomerization.

CITATION LIST

Patent Documents

Patent Document 1: JP 2010-197999 A
Patent Document 2: WO2013/157463
Patent Document 3: JP 2005-275364 A
Patent Document 4: JP 2007-248637 A
Patent Document 5: JP 2009-069493 A
Patent Document 6: WO2015/016118
Patent Document 7: JP Hei-11-249142 A
Patent Document 8: WO2013/161569
Patent Document 9: JP 2015-135464 A
Patent Document 10: WO2017/119376

SUMMARY

As described above, a liquid crystal alignment film produced by alignment treatment of a polyimide-type liquid crystal alignment film according to a photoalignment method is known. However, the polyimide-type liquid crystal alignment film produced according to a photoalignment method is generally poor in electric properties as compared with a polyimide-type liquid crystal alignment film produced through rubbing treatment, and therefore tends to worsen the display quality of liquid crystal display devices using the film. This is considered to be because the specific sites (photoreactive groups) introduced for photochemical reaction, especially the azo group may readily generate radicals after absorption of light and therefore the voltage holding ratio (hereinafter abbreviated as VHR) of the liquid crystal display device may be thereby lowered.

Regarding this, investigations for suppressing the voltage holding ratio by devising and modifying layer configurations while using already-existing polyimide-type liquid crystal alignment films have heretofore been made (for example, see patent documents 7 to 10).

Recently, however, liquid crystal display devices are required to have a higher display quality, while, on the other hand, in consideration of outdoor use of the display devices, the brightness of the backlight to be a light source for them is required to be higher than before. In consideration of the situation to which such a high-brightness backlight is exposed, degradation of the electric characteristics of the devices owing to the polyimide-type liquid crystal alignment film therein could not be evaded even when the configurations described in patent documents 7 to 10 are employed, and in such a case, in fact, it would be actually difficult to realize a sufficient display quality capable of satisfying the requirements in recent years.

Accordingly, for the purpose of solving the technical problems in the art as above, the present inventors have made assiduous studies in an attempt to provide a liquid crystal alignment film capable of being given anisotropy through photoalignment treatment and capable of being stable to light, and to provide a liquid crystal aligning agent capable of forming such a liquid crystal alignment film. In addition, the present inventors have further made assiduous studies in an attempt to provide a liquid crystal display device that can keep a high voltage holding ratio without degradation of display quality even when exposed to strong light for a long period of time.

As a result of assiduous studies made for solving the above-mentioned problems, the present inventors have reached a finding that, when a polymer having a structural unit containing a photoreactive structure in which the structural unit containing a photoreactive structure undergoes chemical reaction by heating is used as a liquid crystal aligning agent, then the structural unit can be converted into a structure not containing a photoreactive group in a heating and baking step after the photoalignment treatment of the coating film of the liquid crystal aligning agent, and accordingly, a liquid crystal alignment film stable to light can be thereby realized. The present invention has been attained on the basis of this finding, and specifically includes the following constitutions.

[1] A liquid crystal aligning agent for photoalignment, which contains a polymer having a structural unit containing a photoreactive structure and in which the structural unit containing a photoreactive structure undergoes chemical reaction by heating.

[2] The liquid crystal aligning agent for photoalignment according to [1], wherein the chemical reaction is cyclization reaction.

[3] The liquid crystal aligning agent for photoalignment according to [1] or [2], wherein the structural unit containing a photoreactive structure contains a structure represented by the following formula (a-1) or the following formula (a-2):

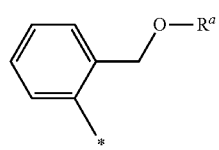

(a-1)

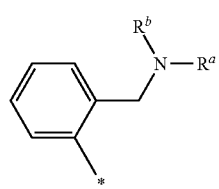

(a-2)

wherein $R^a$ represents a hydrogen atom, a substituted or unsubstituted alkyl group, a substituted or unsubstituted alkanoyl group, or a substituted or unsubstituted arylcarbonyl group;

$R^b$ and $R^c$ each independently represent a hydrogen atom, a substituted or unsubstituted alkyl group, a substituted or unsubstituted alkanoyl group, or a substituted or unsubstituted arylcarbonyl group;

* represents a bonding position to a photoreactive group.

[4] The liquid crystal aligning agent for photoalignment according to any one of [1] to [3], wherein the photoreactive structure is a photoisomerization structure or a photo-Fries rearrangement structure.

[5] The liquid crystal aligning agent for photoalignment according to any one of [1] to [4], wherein the photoreactive structure has a structure represented by the following formula (1):

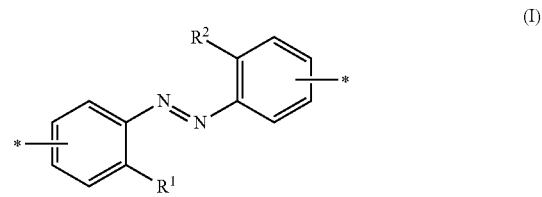

(I)

wherein $R^1$ and $R^2$ each independently represent a hydrogen atom, or a group represented by the following formula (1-1) or formula (1-2), at least one of $R^1$ and $R^2$ is a group represented by the formula (1-1) or the formula (1-2);

* represents a bonding position at the benzene ring, and is a position substitutable with a hydrogen atom in one benzene ring, or a position substitutable with a hydrogen atom in the other benzene ring;

a hydrogen atom in the benzene ring may be substituted with a substituent,

(1-1)

(1-2)

wherein $R^4$ and $R^5$ each independently represent a hydrogen atom, a substituted or unsubstituted alkyl group, a substituted or unsubstituted alkanoyl group, or a substituted or unsubstituted arylcarbonyl group;

* represents a bonding position to the benzene ring in the formula (1).

[6] The liquid crystal aligning agent for photoalignment according to any one of [1] to [5], which contains a polymer of a reaction product from a raw material containing a tetracarboxylic acid dianhydride and a diamine, and wherein:

the polymer contains at least one selected from the group consisting of a polyamic acid, a polyimide, a partial polyimide, a polyamic acid ester, a polyamic acid-polyamide copolymer, and a polyamideimide, the raw material contains at least one diamine represented by the following formula (2):

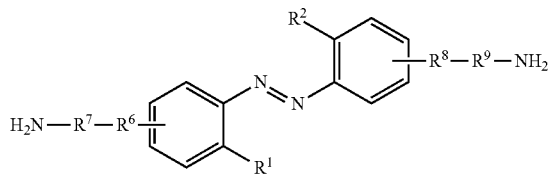
(2)

wherein $R^1$ and $R^2$ each independently represent a hydrogen atom, or a group represented by the following formula (1-1) or (1-2), at least one of $R^1$ and $R^2$ is a group represented by the formula (1-1) or (1-2);

$R^6$ and $R^8$ each independently represent a linear alkylene group having 1 to 20 carbon atoms, —COO—, —OCO—, —NHCO—, —CONH—, —N(CH$_3$)CO—, —CON(CH$_3$)—, or a single bond, and in $R^6$ and $R^8$, one or two (—CH$_2$—)'s not adjacent to each other in the linear alkylene group may be substituted with —O—;

$R^7$ and $R^9$ each independently represent a monocyclic hydrocarbon, a condensed polycyclic hydrocarbon, a hetero ring or a single bond;

the bonding position of H$_2$N—R$^7$—R$^6$— is a position substitutable with a hydrogen atom in one benzene ring, and the bonding position of H$_2$N—R$^9$—R$^8$— is a position substitutable with a hydrogen atom in the other benzene ring;

a hydrogen atom in the benzene ring may be substituted with a substituent,

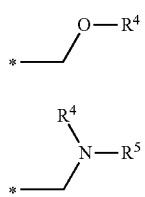
(1-1)

(1-2)

wherein $R^4$ and $R^5$ each independently represent a hydrogen atom, a substituted or unsubstituted alkyl group, a substituted or unsubstituted alkanoyl group, or a substituted or unsubstituted arylcarbonyl group;

* represents a bonding position to the benzene ring in the formula (2).

[7] The liquid crystal aligning agent for photoalignment according to [6], wherein the diamine represented by the formula (2) is a diamine represented by any of the following formulae (3) to (8):

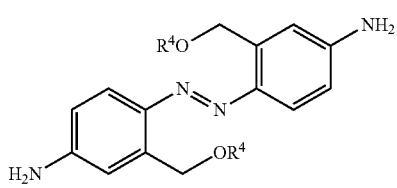
(3)

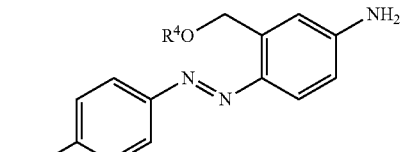
(4)

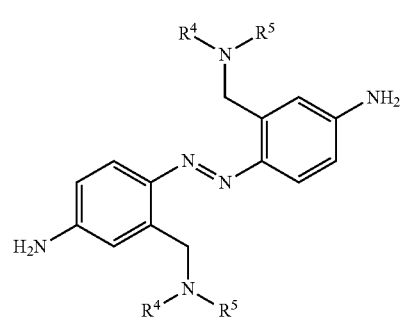
(5)

(6)

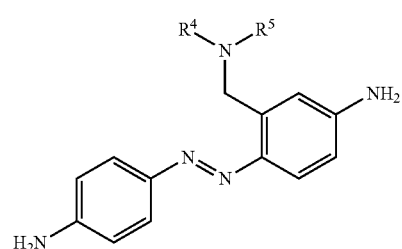
(7)

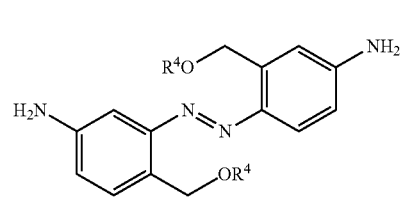
(8)

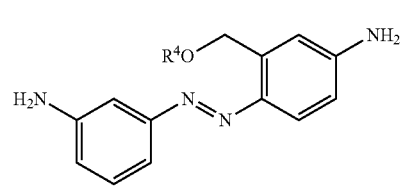

wherein $R^4$ independently represents a hydrogen atom, a substituted or unsubstituted alkyl group, a substituted or unsubstituted alkanoyl group, or a substituted or unsubstituted arylcarbonyl group;

a hydrogen atom in the benzene ring may be substituted with a substituent;

$R^5$ independently represents a hydrogen atom, a substituted or unsubstituted alkyl group, a substituted or unsubstituted alkanoyl group, or a substituted or unsubstituted arylcarbonyl group.

[8] The liquid crystal aligning agent for photoalignment according to [6] or [7], wherein the diamine is a diamine represented by any of the following formulae (3-1) to (3-8), formulae (4-1) to (4-8), formula (5-1), formula (5-2), formula (6-1), formula (6-2), formulae (7-1) to (7-3), and formulae (8-1) to (8-3):

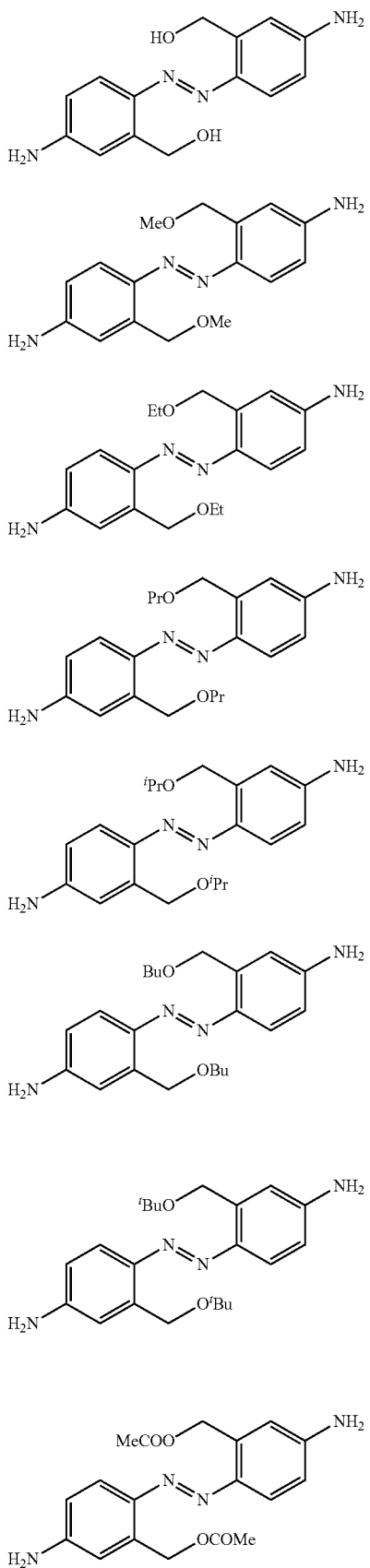

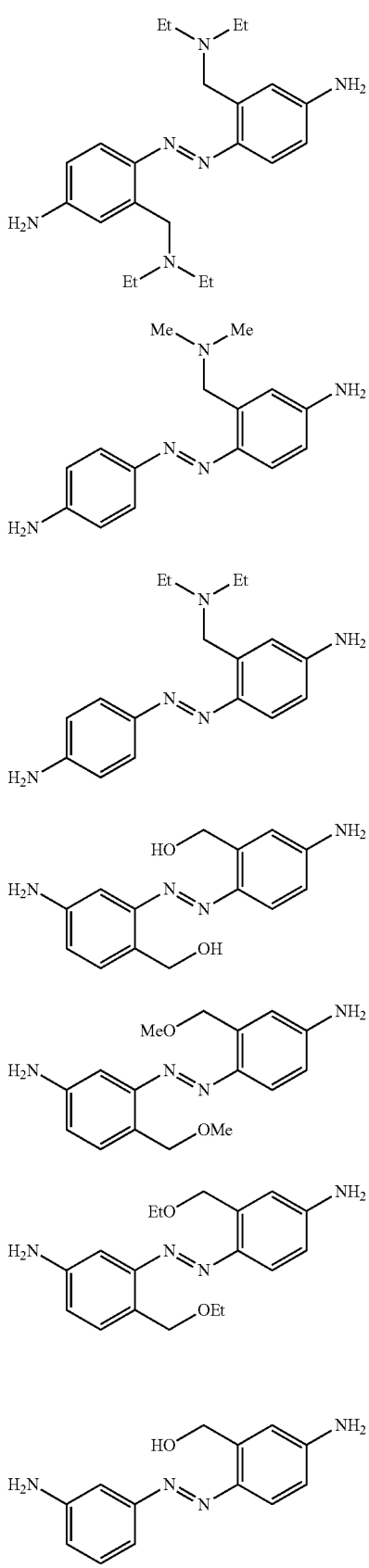

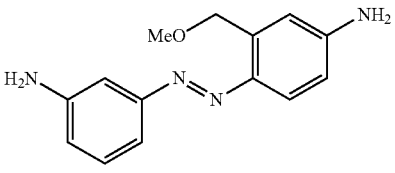

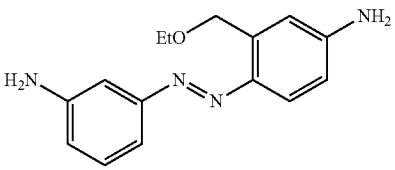

wherein Me represents a methyl group, Et represents an ethyl group, Pr represents a propyl group, $^i$Pr represents an isopropyl group, Bu represents a butyl group, $^t$Bu represents a t-butyl group.

[9] The liquid crystal aligning agent for photoalignment according to any one of [1] to [8], wherein, when a film formed of the liquid crystal aligning agent for photoalignment is heated and baked at 230° C. for 30 minutes, the transmittance at 365 nm of the film increases by 25% or more from the transmittance at 365 nm of the film before heating and baking.

[10] The liquid crystal aligning agent for photoalignment according to any one of [1] to [9], which is used for production of horizontal field type liquid crystal display devices.

[11] A liquid crystal alignment film formed of the liquid crystal aligning agent for photoalignment of any one of [1] to [10].

[12] A liquid crystal display device having the liquid crystal alignment film of [11].

[13] A horizontal field type liquid crystal display device having the liquid crystal alignment film of [11].

[14] A method for forming a liquid crystal alignment film using a liquid crystal aligning agent for photoalignment containing a polymer having a photoreactive structure, wherein:

the liquid crystal aligning agent for photoalignment of any one of [1] to [10] is applied to a substrate, and then given anisotropy through irradiation with a polarized light, and the photoreactive structure is cyclized in heating and baking to be a non-photoreactive structure.

[15] The method for forming a liquid crystal alignment film according to [14], wherein heating and baking carried out in two or more stages at different heating temperatures.

[16] A method for producing a liquid crystal display device, including forming a liquid crystal alignment film according to the liquid crystal alignment film formation method of [14] or [15].

[17] A method for producing a horizontal field type liquid crystal display device, including forming a liquid crystal alignment film according to the liquid crystal alignment film formation method of [14] or [15].

[18] An azobenzene derivative represented by the following formula (4P):

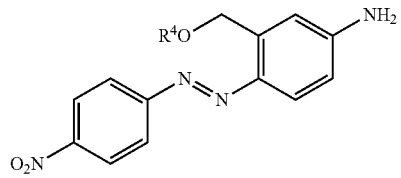
(4P)

wherein $R^4$ represents a hydrogen atom, an alkyl group having 1 to 10 carbon atoms, or an alkanoyl group having 1 to 10 carbon atoms.

[19] A diamine represented by the following formula (2):

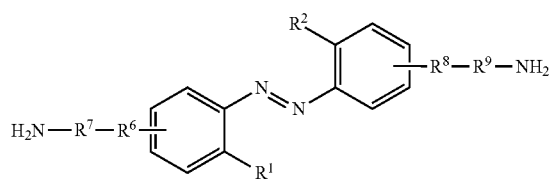
(2)

wherein $R^1$ and $R^2$ each independently represent a hydrogen atom, or a group represented by the following formula (1-1) or (1-2), at least one of $R^1$ and $R^2$ is a group represented by the formula (1-1) or (1-2);

$R^6$ and $R^8$ each independently represent a linear alkylene group having 1 to 20 carbon atoms, —COO—, —OCO—, —NHCO—, —CONH—, —N(CH$_3$)CO—, —CON(CH$_3$)—, or a single bond, and in $R^6$ and $R^8$, one or two (—CH$_2$—)'s not adjacent to each other in the linear alkylene group may be substituted with —O—;

$R^7$ and $R^9$ each independently represent a monocyclic hydrocarbon, a condensed polycyclic hydrocarbon, a hetero ring or a single bond;

the bonding position of H$_2$N—$R^7$—$R^6$— is a position substitutable with a hydrogen atom in one benzene ring, and the bonding position of H$_2$N—$R^9$—$R^8$— is a position substitutable with a hydrogen atom in the other benzene ring;

a hydrogen atom in the benzene ring may be substituted with a substituent,

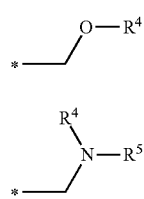
(1-1)

(1-2)

wherein $R^4$ and $R^5$ each independently represent a hydrogen atom, a substituted or unsubstituted alkyl group, a substituted or unsubstituted alkanoyl group, or a substituted or unsubstituted arylcarbonyl group;

* represents a bonding position to the benzene ring in the formula (2).

[20] The diamine according to [19], which is represented by any of the following formulae (3-1) to (3-8), formulae (4-1) to (4-8), formula (5-1), formula (5-2), formula (6-1), formula (6-2), formulae (7-1) to (7-3), and formulae (8-1) to (8-3):

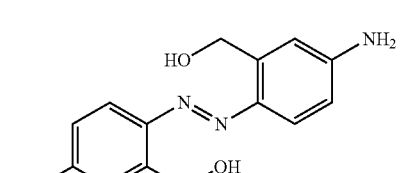
(3-1)

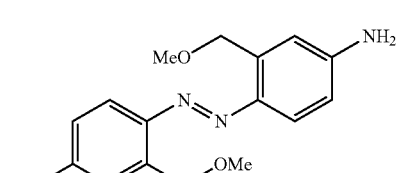
(3-2)

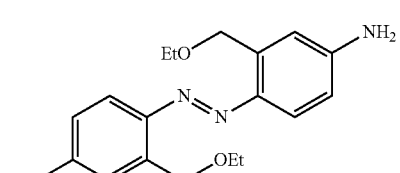
(3-3)

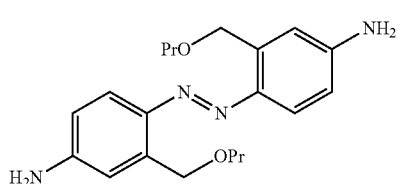
(3-4)

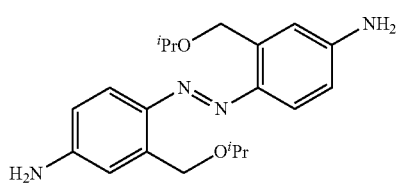
(3-5)

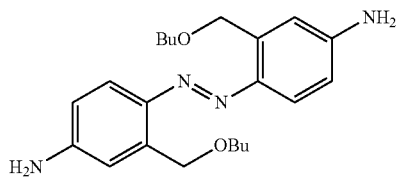
(3-6)

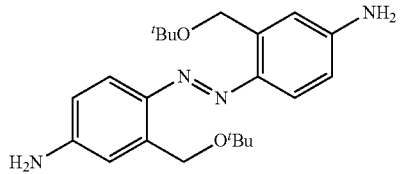
(3-7)

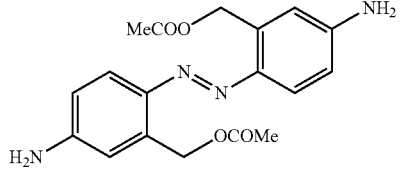
(3-8)

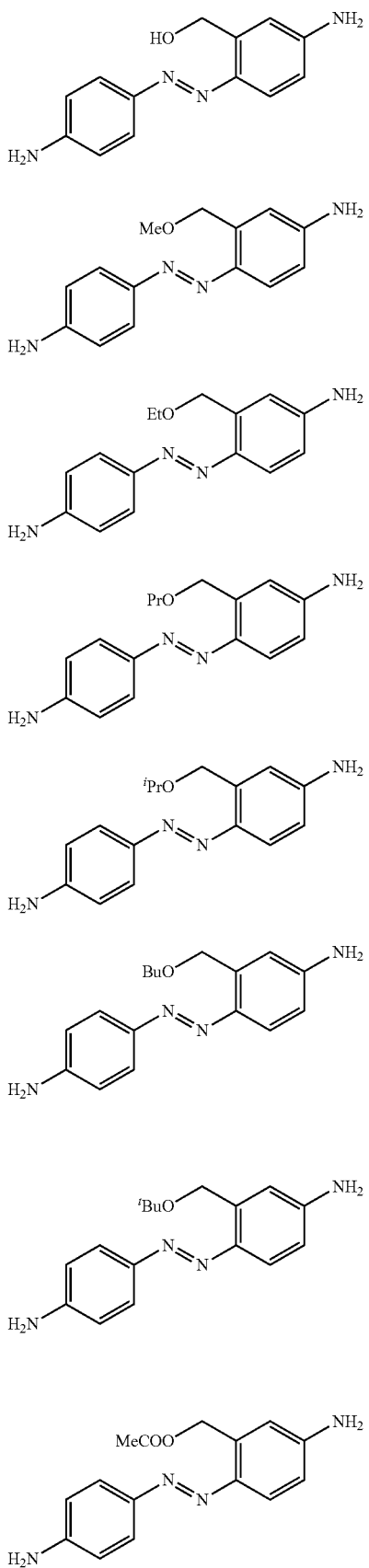
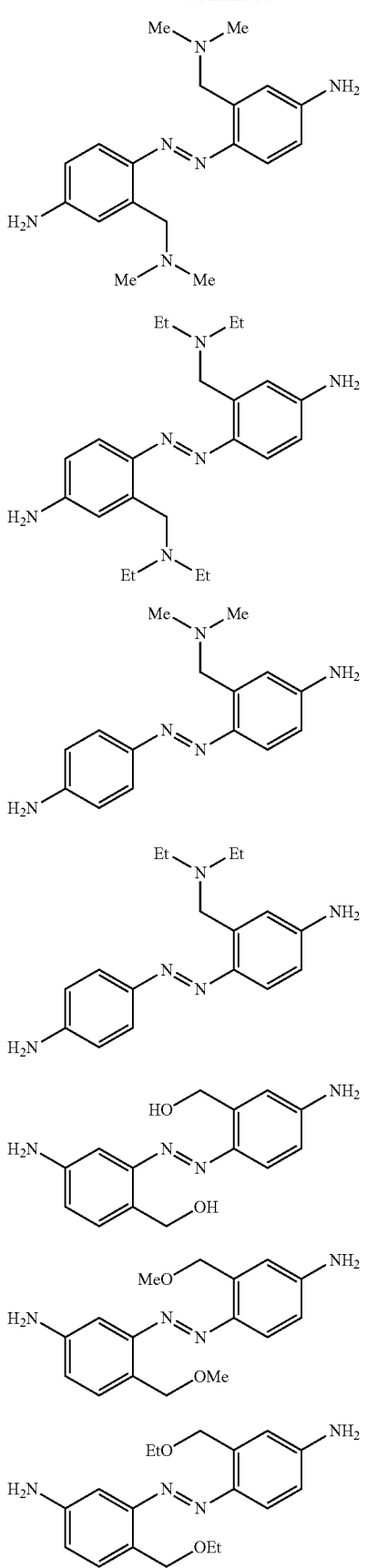

(8-1)

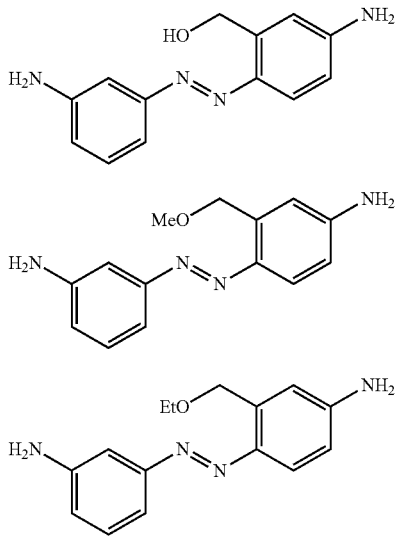

(8-2)

(8-3)

wherein Me represents a methyl group, Et represents an ethyl group, Pr represents a propyl group, $^i$Pr represents an isopropyl group, Bu represents a butyl group, $^t$Bu represents a t-butyl group.

[21] A diamine represented by the following formula (10):

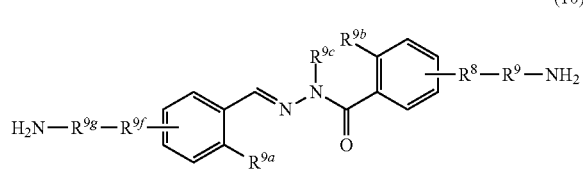

(10)

wherein $R^{9a}$ represents a group represented by the following formula (9-1) or (9-2);
$R^{9b}$ represents a hydrogen atom or a group represented by the formula (9-1) or (9-2);
$R^{9c}$ represents a hydrogen atom, a substituted or unsubstituted alkyl group, a substituted or unsubstituted alkanoyl group, or a substituted or unsubstituted arylcarbonyl group;
$R^{9f}$ and $R^{9h}$ each independently represent a linear alkylene group having 1 to 20 carbon atoms, —COO—, —OCO—, —NHCO—, —CONH—, —N(CH$_3$)CO—, —CON(CH$_3$)—, or a single bond, and in $R^{9f}$ and $R^{9h}$, one or two (—CH$_2$—)'s not adjacent to each other in the linear alkylene group may be substituted with —O—;
$R^{9g}$ and $R^{9i}$ each independently represent a monocyclic hydrocarbon, a condensed polycyclic hydrocarbon, a hetero ring or a single bond;
the bonding position of —$R^{9f}$—$R^{9g}$—NH$_2$ is a position substitutable with a hydrogen atom in one benzene ring, and the bonding position of —$R^{9h}$—$R^{9i}$—NH$_2$ is a position substitutable with a hydrogen atom in the other benzene ring;
a hydrogen atom in the benzene ring may be substituted with a substituent,

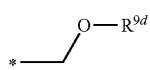

(9-1)

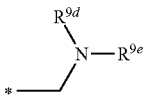

(9-2)

wherein $R^{9d}$ and $R^{9e}$ each independently represent a hydrogen atom, a substituted or unsubstituted alkyl group, a substituted or unsubstituted alkanoyl group, or a substituted or unsubstituted arylcarbonyl group;
* represents a bonding position to the benzene ring in the formula (10).

[22] A polymer having a structural unit containing a photoreactive structure in the main chain thereof, in which the structural unit containing a photoreactive structure undergoes chemical reaction by heating.

[23] The polymer according to [22], which is a reaction product from a raw material containing a tetracarboxylic acid dianhydride and a diamine, and wherein:
the raw material contains at least one diamine represented by the following formula (2):

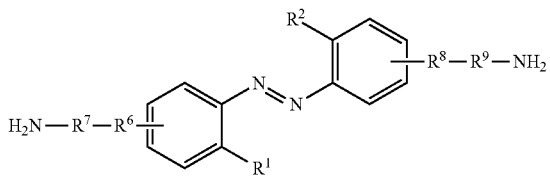

(2)

wherein $R^1$ and $R^2$ each independently represent a hydrogen atom, or a group represented by the following formula (1-1) or (1-2), at least one of $R^1$ and $R^2$ is a group represented by the formula (1-1) or (1-2);
$R^6$ and $R^8$ each independently represent a linear alkylene group having 1 to 20 carbon atoms, —COO—, —OCO—, —NHCO—, —CONH—, —N(CH$_3$)CO—, —CON(CH$_3$)—, or a single bond, and in $R^6$ and $R^8$, one or two (—CH$_2$—)'s not adjacent to each other in the linear alkylene group may be substituted with —O—;
$R^7$ and $R^9$ each independently represent a monocyclic hydrocarbon, a condensed polycyclic hydrocarbon, a hetero ring or a single bond;
the bonding position of H$_2$N—$R^7$—$R^6$— is a position substitutable with a hydrogen atom in one benzene ring, and the bonding position of H$_2$N—$R^9$—$R^8$— is a position substitutable with a hydrogen atom in the other benzene ring;
a hydrogen atom in the benzene ring may be substituted with a substituent,

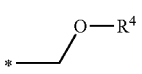

(1-1)

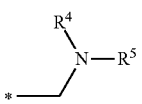

(1-2)

wherein R⁴ and R⁵ each independently represent a hydrogen atom, a substituted or unsubstituted alkyl group, a substituted or unsubstituted alkanoyl group, or a substituted or unsubstituted arylcarbonyl group;

* represents a bonding position to the benzene ring in the formula (2).

[24] The polymer according to [22] or [23], which is a polyamic acid, a polyimide, a partial polyimide, a polyamic acid ester, a polyamic acid-polyamide copolymer, or a polyamideimide.

Using the liquid crystal aligning agent for photoalignment of the present invention, anisotropy may be given to a liquid crystal alignment film according to a photoalignment method, and a liquid crystal alignment film stable to light can be formed. In addition, using the liquid crystal alignment film formed with the liquid crystal aligning agent for photoalignment of the present invention, a liquid crystal display device can be realized, whose advantages are that the liquid crystal layer therein is highly aligned, the display device is excellent in image sticking reduction, and, even when a high-brightness backlight is mounted therein, a high voltage holding ratio can be maintained and the display quality does not worsen.

DETAILED DESCRIPTION OF THE INVENTION

Figure 1:
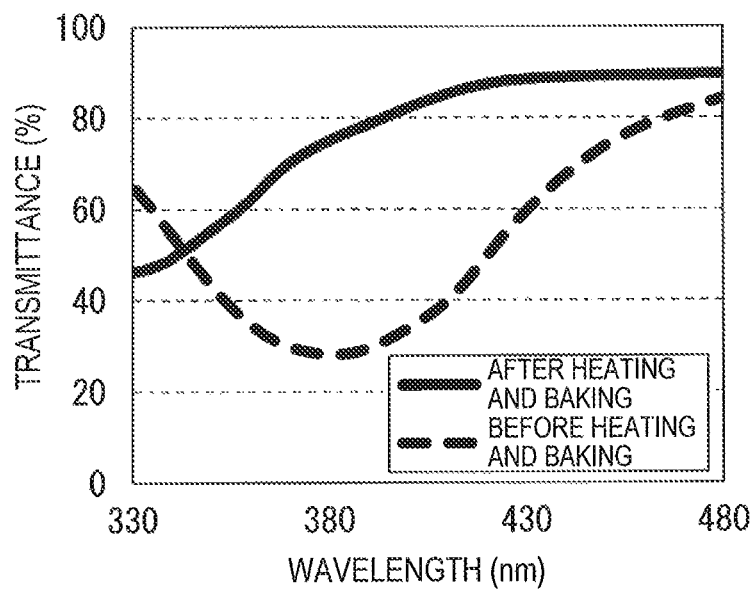
FIG. 1 shows UV-visible light transmittance spectra of a substrate with a liquid crystal alignment film formed thereon using the aligning agent 1.

In the following, the present invention is described in detail. The description of the constitutive elements of the invention given hereinunder is for some typical embodiments or specific examples of the invention, to which, however, the invention should not be limited. In this description, the numerical range expressed by the wording "a number to another number" means the range that falls between the former number indicating the lower limit of the range and the latter number indicating the upper limit thereof. The "liquid crystal aligning agent for photoalignment" in the present invention means a liquid crystal aligning agent which, when applied to a substrate to form a film thereon, can impart anisotropy to the film through irradiation with a polarized light, and in this description, this may be simply referred to as "liquid crystal aligning agent".

Liquid Crystal Aligning Agent for Photoalignment of the Invention

The liquid crystal aligning agent for photoalignment of the present invention contains a polymer having a structural unit containing a photoreactive structure, in which the structural unit containing a photoreactive structure undergoes chemical reaction by heating.

The "photoreactive structure" in the present invention means an atomic group whose structure changes through irradiation with light. Such a photoreactive structure generally has a specific site (photoreactive group) that undergoes chemical change through absorption of light, and owing to the chemical change of the photoreactive group, the structure of the polymer changes. In the following description, the chemical reaction at the photoreactive structure that occurs through such light absorption is referred to as "photochemical reaction", and the structure change to be caused by the photochemical reaction is referred to as photochemical change. Photochemical reaction is a chemical reaction to be caused by excitation of electrons through light absorption, and is differentiated from chemical reaction to occur by heating. Specific examples of photochemical change include photoisomerization and photo-Fries rearrangement. The wavelength of light to cause change in a photoreactive structure is not specifically limited, but is preferably 150 to 800 nm, more preferably 200 to 400 nm, even more preferably 300 to 400 nm. The photoirradiation intensity necessary for change in a photoreactive structure is preferably 0.05 to 20 J/cm².

The "structural unit containing a photoreactive structure" in the present invention is a structural unit to constitute a polymer, and this contains the above-mentioned photoreactive structure and undergoes chemical reaction by heating. The chemical reaction is not specifically limited, but is preferably a reaction that converts the photoreactive group in the photoreactive structure into a non-photoreactive structure, and is more preferably a cyclization reaction between the photoreactive group and any other group. Through the reaction, the polymer may have an increased linearity and may form a liquid crystal alignment film having a higher alignment level. The heating temperature to cause the chemical reaction is preferably 40 to 300° C., more preferably 100 to 300° C., even more preferably 150 to 280° C. The heating time is preferably 1 minute to 3 hours, more preferably 5 minutes to 1 hour, even more preferably 15 minutes to 45 minutes. Regarding the heating temperature and the heating time to cause the chemical reaction, the heating time at a heating temperature of 40 to 180° C. is preferably 10 minutes to 3 hours, and the heating time at a heating temperature of 180 to 300° C. is preferably 1 minute to 1 hour. Above all, from the viewpoint of increasing the reaction efficiency, more preferably, the heating temperature is 150 to 280° C. and the heating time is 10 minutes to 1 hour, and even more preferably, the heating temperature is 180 to 250° C. and the heating time is 15 minutes to 45 minutes.

The liquid crystal aligning agent for photoalignment (liquid crystal aligning agent) of the present invention is used for forming a liquid crystal alignment film. For forming a liquid crystal alignment film using the liquid crystal aligning agent of the present invention, for example, the liquid crystal aligning agent is applied to a substrate to form a film thereon, and then irradiated with a polarized light for photoalignment. Accordingly, the photoreactive structure of the polymer main chain that is nearly parallel to the polarization direction selectively undergoes photochemical reaction to change the structure, and the component facing in a specific direction among the polymer main chain (the component that has come to face in a specific direction as a result of structure change) becomes a dominant one. Specifically, the polymer main chain constituting the film comes to be in a state facing in a specific direction (in a state given anisotropy). Subsequently, the photoaligned film is heated and baked to be a solid liquid crystal alignment film. At this time, in the polymer used in the present invention, the structural unit having a photoreactive structure undergoes chemical reaction by heating to lose the photoreactive group therein and, as a result, the number of the photoreactive groups in the entire film may decrease or a photoreactive group could no more exist in the film. Consequently, the formed liquid crystal alignment film could hardly generate a radical even when exposed to strong light and shows high stability to light. In addition, at this time, the polymer used in the present invention may enjoy alignment amplification by heating and can therefore exhibit high alignment performance. Here, "alignment amplification" means such a phenomenon that a polymer whose molecular motion has been activated by heating can align along the component of the polymer main chain facing in a specific direction trough photoalignment treatment to thereby amplify the anisotropy of the resultant polymer.

Regarding the detailed conditions for forming a liquid crystal alignment film, the description in the section of liquid crystal alignment film may be referred to.

In the following, the polymer having a structural unit containing a photoreactive structure, which the liquid crystal aligning agent of the present invention contains, is described. In the following description, the "polymer having a structural unit containing a photoreactive structure" may be referred to as "a polymer containing a photoreactive structure".

[Polymer Having a Structural Unit Containing a Photoreactive Structure]

The polymer that the liquid crystal aligning agent of the present invention contains has a structural unit containing a photoreactive structure.

All the structural units constituting the polymer may be structural units containing a photoreactive structure, or a part thereof may be structural units containing a photoreactive structure and the remaining part thereof may be structural units not containing a photoreactive structure. The number of the structural units containing a photoreactive structure in the polymer is not specifically limited, but is preferably 3 to 100 units per one molecule of the polymer, more preferably 5 to 50 units, even more preferably 5 to 30 units. When the polymer has 2 or more structural units having a photoreactive structure, the plural structural units may be the same as or different from each other.

(Structural Unit Containing a Photoreactive Structure)

The structural unit containing a photoreactive structure contains a photoreactive structure that changes through irradiation with light, and undergoes chemical reaction by heating.

The structural unit containing a photoreactive structure may be formed of a photoreactive structure, or may contain any other structure. The number of the photoreactive structures that the structural unit contains may be one or may also be two or more. When the structural unit contains 2 or more photoreactive structures, the photoreactive structures may be the same as or different from each other.

Preferably, the structural unit containing a photoreactive structure contains at least one of the structure represented by the following formula (a-1) and the structure represented by the following formula (a-2). In the structural unit having such a structure, when the coating film of the liquid crystal aligning agent is heated, the substituent group in the benzene ring of each formula and a photoreactive group react for cyclization to lose the photoreactive group, and consequently, the number of the photoreactive groups in the entire film may decrease or a photoreactive group could no more exist in the film. As a result, a liquid crystal alignment film stable to light can be formed.

Here, the structural unit may contain a structure represented by the formula (a-1) alone, or may contain a structure represented by the formula (a-2) alone, or may contain both a structure represented by the formula (a-1) and a structure represented by the formula (a-2). The number of the structures represented by the formula (a-1) and the number of the structures represented by the formula (a-2), which the structural unit contains, each may be one or may be 2 or more. When the structural unit contains 2 or more structures represented by the formula (a-1), the structures may be the same as or different from each other, and when the structural unit contains 2 or more structures represented by the formula (a-2), the structures may be the same as or different from each other.

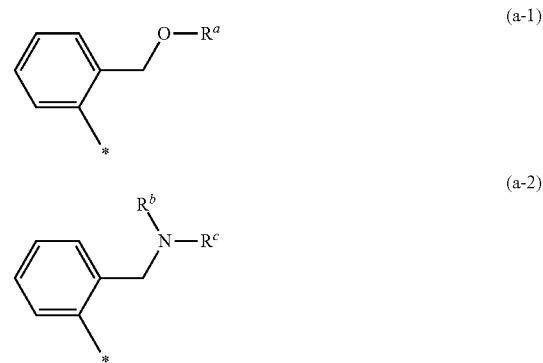

In the formula (a-1), $R^a$ represents a hydrogen atom, a substituted or unsubstituted alkyl group, a substituted or unsubstituted alkanoyl group, or a substituted or unsubstituted arylcarbonyl group. In the formula (a-2), $R^b$ and $R^c$ each independently represent a hydrogen atom, a substituted or unsubstituted alkyl group, a substituted or unsubstituted alkanoyl group, or a substituted or unsubstituted arylcarbonyl group. $R^b$ and $R^c$ may be the same as or different from each other. In the formulae (a-1) and (a-2), * represents a bonding position to a photoreactive group. * may directly bond to a photoreactive group, or may bond to a photoreactive group via a divalent group.

In the formula (a-1), the alkyl group of $R^a$ may be linear, branched or cyclic. The carbon number of the alkyl group is preferably 1 to 10, more preferably 1 to 6, even more preferably 1 t 4, and further more preferably 1 to 3. Specific examples of the alkyl group include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 1-ethylpropyl group, a hexyl group, an isohexyl group, a 1-methylpentyl group, and a 1-ethylbutyl group.

The alkanoyl group of $R^a$ may be linear, branched or cyclic. The carbon number of the alkanoyl group is preferably 1 to 10, more preferably 1 to 6, even more preferably 1 to 2, and further more preferably 1. Specific examples of the alkanoyl group include a methanoyl group, an ethanoyl group, a propanoyl group, an isopropanoyl group, a butanoyl group, an isobutanoyl group, a sec-butanoyl group, a tert-butanoyl group, a pentanoyl group, an isopentanoyl group, a neopentanoyl group, a tert-pentanoyl group, a 1-methylbutanoyl group, a 1-ethylpropanoyl group, a hexanoyl group, an isohexanoyl group, a 1-methylpentanoyl group, and a 1-ethylbutanoyl group.

The aryl group of the arylcarbonyl group of $R^a$ may be a single ring or a condensed ring. The carbon number of the aryl group is preferably 6 to 22, more preferably 6 to 14, even more preferably 6 to 10. Specific examples of the aryl group include a phenyl group, a 1-naphthyl group, and a 2-naphthyl group. Specific examples of the arylcarbonyl group include a phenylcarbonyl group, and a 1-naphthylcarbonyl group.

The alkyl group, the alkanoyl group and the arylcarbonyl group of $R^a$ each may be substituted with a substituent. The substituent includes a hydroxyl group, an amino group and a halogeno group.

Among these, from the viewpoint of bettering the performance of the liquid crystal alignment film to be produced finally, $R^a$ is preferably a methyl group, an ethyl group, a propyl group, a hydrogen atom, a methanoyl group or a phenyl group.

Regarding the description, the preferred range and specific examples of the alkyl group, the alkanoyl group and the arylcarbonyl group of $R^b$ and $R^c$ and the substituent for these groups in the formula (a-2), reference may be made to the description, the preferred range and specific examples of the alkyl group, the alkanoyl group and the arylcarbonyl group of $R^a$ and the substituent for these groups in the formula (a-1).

In the formulae (a-1) and (a-2), the photoreactive group bonding to * includes, though not specifically limited thereto, an azo group, a 1,2-ethenediyl group, a 1,2-ethynediyl group, an imino group, a carbonyl group, and an oxycarbonyl group.

A hydrogen atom in each benzene ring in the formulae (a-1) and (a-2) may be substituted with a substituent. Regarding the preferred range and specific examples of the substituent, reference may be made to the preferred range and specific examples of the substituent for the benzene ring in the formula (1) mentioned below.

Examples of the photoreactive structure that the structural unit contains include a photoisomerization structure such as an azobenzene structure, a stilbene structure, and an acylhydrazone structure; and a photo-Fries rearrangement structure such as a phenyl ester structure. The photoreactive structure that the structural unit of the polymer for use in the present invention contains is preferably a photoisomerization structure such as an azobenzene structure, a stilbene structure, or an acylhydrazone structure, and is, above all, especially preferably an azobenzene structure or an acylhydrazone structure.

Preferred examples of the photoreactive structure having an azobenzene structure include structures represented by the following formula (1). When the structure represented by the following formula (1) is irradiated with UV rays, the azo group therein undergoes trans-cis isomerization to change the direction of the polymer main chain. Accordingly, a liquid crystal alignment film in which the polymer main chain has aligned in a specific direction may be thereby obtained.

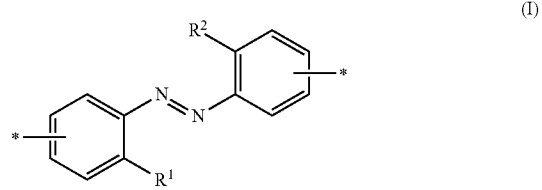

In the formula (1), $R^1$ and $R^2$ each independently represent a hydrogen atom, or a group represented by the following formula (1-1) or formula (1-2), and at least one of $R^1$ and $R^2$ is a group represented by the formula (1-1) or the formula (1-2). Both or one of $R^1$ and $R^2$ may be a group represented by the formula (1-1) or (1-2). When both $R^1$ and $R^2$ are groups represented by the formula (1-1) or (1-2), the groups may be the same as or different from each other.

* represents a bonding position to the structure on both sides of the structure represented by the formula (1), and is a position substitutable with a hydrogen atom in one benzene ring, or a position substitutable with a hydrogen atom in the other benzene ring.

In the formula (1-1), $R^4$ represents a hydrogen atom, a substituted or unsubstituted alkyl group, a substituted or unsubstituted alkanoyl group, or a substituted or unsubstituted arylcarbonyl group. In the formula (1-2), $R^4$ and $R^5$ each independently represent a hydrogen atom, a substituted or unsubstituted alkyl group, a substituted or unsubstituted alkanoyl group, or a substituted or unsubstituted arylcarbonyl group. $R^4$ and $R^5$ may be the same as or different from each other. In the formulae (1-1) and (1-2), * represents a bonding position to the benzene ring in the formula (1). Regarding the description, the preferred range and specific examples of the alkyl group, the alkanoyl group and the arylcarbonyl group of $R^4$ and $R^5$ and the substituent for these groups, reference may be made to the description, the preferred range and specific examples of the alkyl group, the alkanoyl group and the arylcarbonyl group of $R^a$ and the substituent for these groups in the formula (a-1).

A hydrogen atom in the benzene ring in the formula (1) may be substituted with a substituent. Preferred examples of the substituent include an alkyl group, an alkoxy group, a halogenoalkyl group, a halogeno group, and a carboxyalkyl group. The alkyl group may be linear, branched or cyclic. The carbon number of the alkyl group is preferably 1 to 4, more preferably 1 to 2. Specific examples of the alkyl group include a methyl group, an ethyl group, a propyl group, an isopropyl group, a butyl group, an isobutyl group, a sec-butyl group, and a tert-butyl group. The carbon number of the alkoxy group is preferably 1 to 4, more preferably 1 to 2. Specific examples of the alkoxy group include a methoxy group, an ethoxy group, a propoxy group, an isopropoxy group, a butoxy group, an isobutoxy group, a sec-butoxy group, and a tert-butoxy group. Specific examples of the halogenoalkyl group include a trifluoromethyl group. Specific examples of the halogeno group include a fluoro group, a chloro group, a bromo group, and an iodo group. Specific examples of the carboxyalkyl group include a carboxymethyl group, and a carboxyethyl group.

Preferred examples of the photoreactive structure having an acylhydrazone structure include structures represented by the following formula (9). When irradiated with UV rays, the structure represented by the formula (9) undergoes trans-cis isomerization to change the direction of the polymer main chain having the structure. Accordingly, a liquid crystal alignment film in which the polymer main chain has aligned in a specific direction may be obtained.

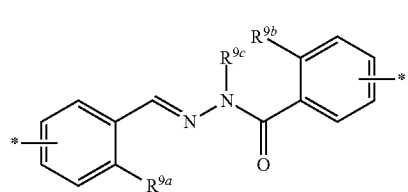

(9)

In the formula (9), $R^{9a}$ represents a group represented by the following formula (9-1) or (9-2), and represents a hydrogen atom, or a group represented by the formula (9-1) or (9-2). Both $R^{9a}$ and $R^{9b}$ are groups represented by the formula (9-1) or (9-2), these groups may be the same as or different from each other. In the formula (9), $R^{9c}$ independently represents a hydrogen atom, a substituted or unsubstituted alkyl group, a substituted or unsubstituted alkanoyl group, or a substituted or unsubstituted arylcarbonyl group. Regarding the description, the preferred range and specific examples of the alkyl group, the alkanoyl group and the arylcarbonyl group of $R^{9c}$ and the substituent for these groups, reference may be made to the description, the preferred range and specific examples of the alkyl group, the alkanoyl group and the arylcarbonyl group of $R^{a}$ and the substituent for these groups in the formula (a-1).

* represents a bonding position to the structure on both sides of the structure represented by the formula (9), and is a position substitutable with a hydrogen atom in one benzene ring, or a position substitutable with a hydrogen atom in the other benzene ring.

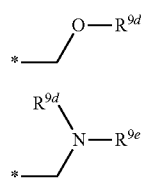

(9-1)

(9-2)

In the formula (9-1), $R^{9d}$ represents a hydrogen atom, a substituted or unsubstituted alkyl group, a substituted or unsubstituted alkanoyl group, or a substituted or unsubstituted arylcarbonyl group. In the formula (9-2), $R^{9d}$ and $R^{9e}$ each independently represent a hydrogen atom, a substituted or unsubstituted alkyl group, a substituted or unsubstituted alkanoyl group, or a substituted or unsubstituted arylcarbonyl group. $R^{9d}$ and $R^{9e}$ may be the same as or different from each other. Regarding the description, the preferred range and specific examples of the alkyl group, the alkanoyl group and the arylcarbonyl group of $R^{9d}$ and $R^{9e}$ and the substituent for these groups, reference may be made to the description, the preferred range and specific examples of the alkyl group, the alkanoyl group and the arylcarbonyl group of $R^{a}$ and the substituent for these groups in the formula (a-1). * represents a bonding position to the benzene ring in the formula (9).

A hydrogen atom in the benzene ring in the formula (9) may be substituted with a substituent. Regarding the description, the preferred range and specific examples of the substituent, reference may be made to the description, the preferred range and specific examples of the substituent in the formula (1).

(Chemical Reaction in the Structural Unit Having a Photoreactive Structure by Heating)

The polymer having a photoreactive structure for use in the liquid crystal aligning agent of the present invention is characterized in that the structural unit having a photoreactive structure therein undergoes chemical reaction by heating. With that, the polymer is, after given anisotropy through photoalignment (after the photoreactive structure is subjected to structure change through photoirradiation), heated to lose the photoreactivity of the photoreactive structure, and the structure can be therefore converted into a structure stable to light.

In the following, described is a mechanism of losing the photoreactive group through chemical reaction by heating in a structural unit where the photoreactive structure is an azobenzene structure, an acylhydrazone structure, a phenyl ester structure or an N-benzylidene-aniline structure.

(A) Cyclization Reaction of Azobenzene Structure: Formation of 5-Membered Ring

In a structural unit having an azobenzene structure having a substituent $R^{14}$ at the ortho-position relative to the azo group of one benzene ring, namely, an azobenzene structure represented by the following formula (A-1), the azo group reacts with the substituent $R^{14}$ of the benzene ring by heating to form an indazole ring and the azo group therefore disappears, as shown in the following reaction formula. Regarding the details of the reaction, reference may be made to New J. chem., 1999, 23, 1223-1230.

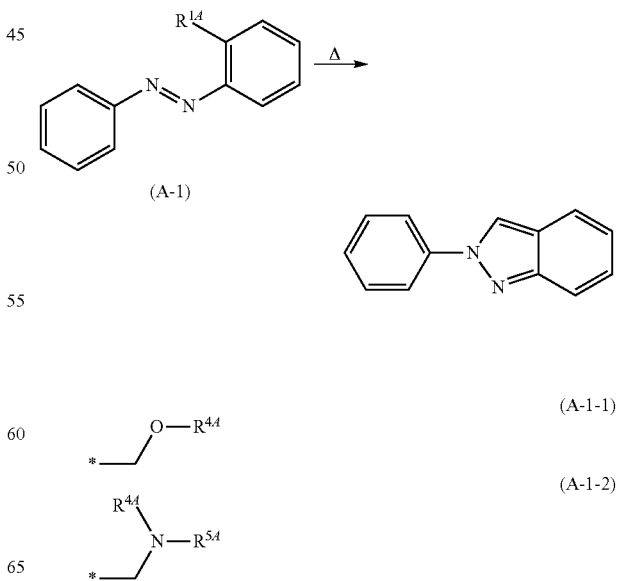

In the formula (A-1), $R^{1A}$ represents a group represented by the formula (A-1-1) or (A-1-2). In the formulae (A-1-1) and (A-1-2), $R^{4A}$ and $R^{5A}$ each independently represent a hydrogen atom, a substituted or unsubstituted alkyl group, a substituted or unsubstituted alkanoyl group, or a substituted or unsubstituted arylcarbonyl group. Regarding the description, the preferred range and specific examples $R^{4A}$ and $R^{5A}$, reference may be made to the description, the preferred range and specific examples of the alkyl group, the alkanoyl group and the arylcarbonyl group of $R^a$ and the substituent for these groups in the formula (a-1).

(B) Cyclization Reaction of Azobenzene Structure: Formation of 6-Membered Ring

In a structural unit having an azobenzene structure having a substituent (—$CH_2COOR^{1B}$) at the ortho-position relative to the azo group of one benzene ring, namely, an azobenzene structure represented by the following formula (B-1), the azo group reacts with the substituent (—$CH_2COOR^{1B}$) of the benzene ring by heating to form a cyclic structure and the azo group therefore disappears, as shown in the following reaction formula.

Scheme 2

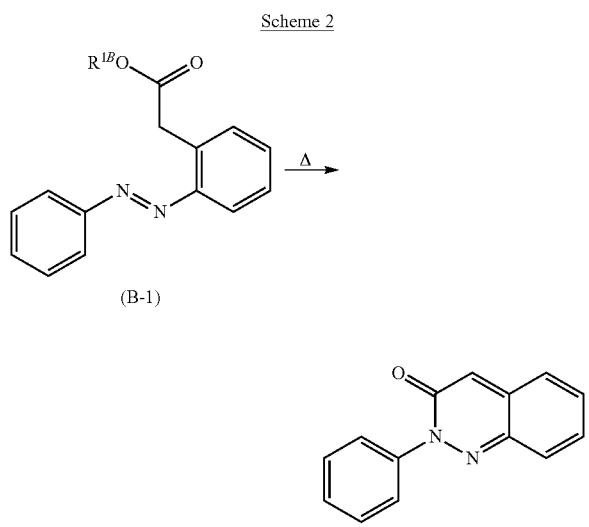

(B-1)

In the formula (B-1), $R^{1B}$ represents a hydrogen atom, or a substituted or unsubstituted alkyl group. Regarding the description, the preferred range and specific examples of the alkyl group and the substituent that may be substituted for the alkyl group, reference may be made to the description, the preferred range and specific examples of the alkyl group and the substituent for it in $R^a$ in the formula (a-1).

(C) Cyclization Reaction of Acylhydrazone Structure: Formation of 5-Membered Ring In a structural unit having an acylhydrazone structure having a substituent $R^{1C}$ at the ortho-position relative to the imino group of a benzene ring, namely, an acylhydrazone structure represented by the following formula (C-1), the imino group (=NR) reacts with the substituent $R^{1C}$ of the benzene ring by heating to form a cyclic structure and the imino group therefore disappears, as shown in the following reaction formula.

Scheme 3

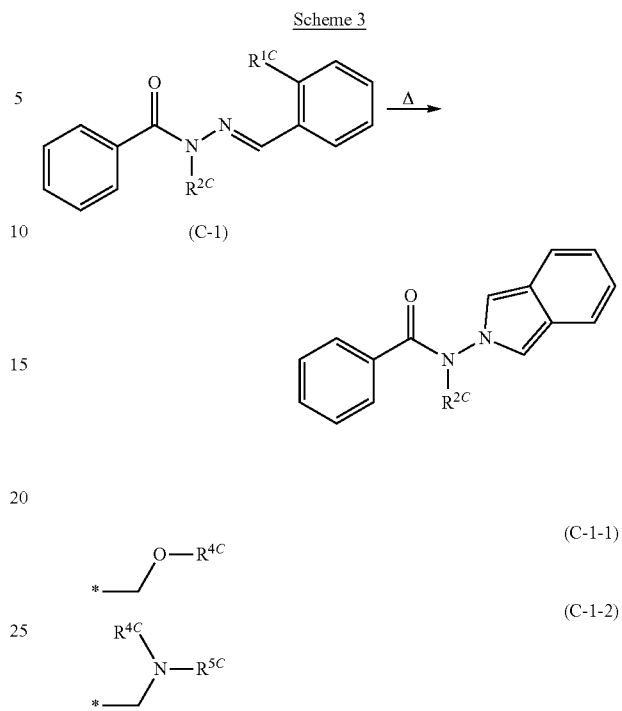

In the formula (C-1), $R^{1C}$ represents a group represented by the formula (C-1-1) or (C-1-2). In the formulae (C-1), (C-1-1) and (C-1-2), $R^{2C}$, $R^{4C}$ and $R^{5C}$ each independently represent a hydrogen atom, a substituted or unsubstituted alkyl group, a substituted or unsubstituted alkanoyl group, or a substituted or unsubstituted arylcarbonyl group. Regarding the description, the preferred range and specific examples of the alkyl group, the alkanoyl group and the arylcarbonyl group of $R^{2C}$, $R^{4C}$, and $R^{5C}$ and the substituent for these groups, reference may be made to the description, the preferred range and specific examples of the alkyl group, the alkanoyl group and the arylcarbonyl group of $R^a$ and the substituent for these groups in the formula (a-1).

(D) Cyclization Reaction after Fries Rearrangement of Phenyl Ester Structure: Formation of 5-Membered Ring In a phenyl ester structure having a substituent (—$CH_2NHR^{1D}$) at the ortho-position relative to the ester bonding position of the benzene ring, namely, a phenyl ester structure represented by the following formula (D-1), the carbonyl group reacts with the substituent (—$CH_2NHR^{1D}$) of the benzene ring after Fries rearrangement to form a cyclic structure, and the carbonyl group therefore disappears, as shown in the following reaction formula.

Scheme 4

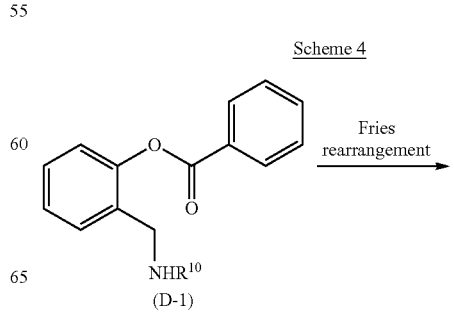

(D-1)

-continued

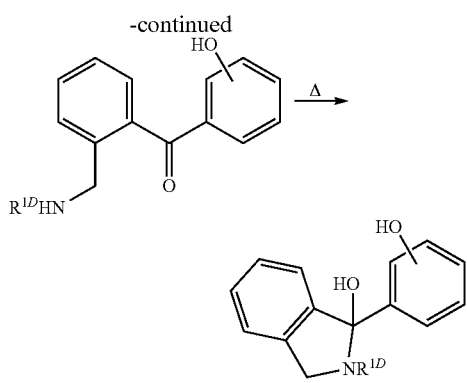

In the formula (D-1), $R^{1D}$ represents a substituted or unsubstituted alkyl group. Regarding the description, the preferred range and specific examples of the alkyl group and the substituent that may be substituted for the alkyl group, reference may be made to the description, the preferred range and specific examples of the alkyl group and the substituent for it in $R^a$ in the formula (a-1).

(E) Cyclization Reaction of N-Benzylidene-Aniline Structure: Formation of 5-Membered Ring In an N-benzylidene-aniline structure having a substituent $R^{1E}$ at the ortho-position relative to the imino group in the benzene ring, namely, an N-benzylidene-aniline structure represented by the following formula (E-1), the imino group (=NR) reacts with the substituent $R^{1E}$ of the benzene ring to form a cyclic structure, and the imino group therefore disappears, as shown in the following reaction formula.

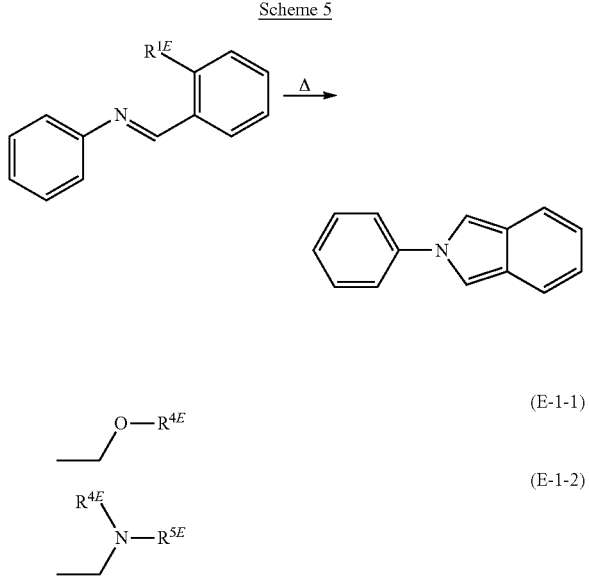

In the formula (E-1), $R^{1E}$ represents a group represented by the formula (E-1-1) or (E-1-2). In the formulae (E-1-1) and (E-1-2), $R^{4E}$ and $R^{5E}$ each independently represent a hydrogen atom, a substituted or unsubstituted alkyl group, a substituted or unsubstituted alkanoyl group, or a substituted or unsubstituted arylcarbonyl group. Regarding the description, the preferred range and specific examples of the alkyl group, the alkanoyl group and the arylcarbonyl group of $R^{4E}$ and $R^{5E}$ and the substituent for these groups, reference may be made to the description, the preferred range and specific examples of the alkyl group, the alkanoyl group and the arylcarbonyl group of $R^a$ and the substituent for these groups in the formula (a-1).

Whether or not the structural unit containing a photoreactive structure has undergone chemical reaction may be confirmed through UV-visible light absorption spectrometry (transmittance), nuclear magnetic resonance (NMR) spectrometry or infrared (IR) absorption spectrometry. For example, in the case where the photoreactive structure is an azobenzene structure, occurrence of the above-mentioned cyclization reaction may be confirmed by increase in the transmittance at 365 nm that is an absorption wavelength of azobenzene. Here, regarding the liquid crystal aligning agent that contains an azobenzene structure in the structural unit of a polymer, preferably, the transmittance at 365 nm of the agent increases by 25% or more after chemical reaction by heating. Specifically, when a film of the liquid crystal aligning agent for photoalignment is heated and baked at 230° C. for 30 minutes, the transmittance at 365 nm of the film preferably increases by 25% or more from the transmittance at 365 nm of the film before heating and baking. In such a liquid crystal aligning agent for photoalignment, the photoreactivity of the azobenzene structure can be surely reduced by heating and, as a result, a liquid crystal alignment film having high light stability and showing good liquid crystal alignment performance can be formed.

(Type of Polymer)

The polymer having a photoreactive structure for use in the liquid crystal aligning agent of the present invention may be any one having a structural unit containing a photoreactive structure as described above, and the type of the polymer is not specifically limited. Regarding the type of the polymer having a photoreactive structure for use in the liquid crystal aligning agent, one type alone or two or more types of such polymers may be used. Namely, the liquid crystal aligning agent of the present invention may contain a polymer having two or more types of photoreactive structures.

For example, the polymer in which a structure represented by the formula (1) or (9) can be readily introduced into the main chain includes a polyamic acid, a polyamic acid derivative, a polyester, a polyamide, a polysiloxane, a cellulose derivative, a polyacetal, a polystyrene derivative, a poly(styrene-phenylmaleimide) derivative, and a poly(meth) acrylate. Above all, the polymer containing a photoreactive structure for use in the present invention is preferably a polyamic acid, or a polyamic acid derivative. Polymers of the present invention to be mentioned below are also preferably used as the polymer containing a photoreactive structure.

Here, a polyamic acid is a polymer synthesized through polymerization reaction of a diamine represented by the following formula (D1) and a tetracarboxylic acid dianhydride represented by the following formula (AN), and has a structural unit represented by the following formula (PAA). Imidation of the polyamic acid gives a polyimide liquid crystal alignment film having a structural unit represented by the following formula (PI). Using a compound having a structure with an amino group bonding to the bonding position * in the structure represented by the formula (1), as a diamine, the structure represented by the formula (1) can be readily introduced into the main chain of the polymer. In the diamine, the amino group may directly bond to the bonding position * in the structure represented by the formula (1), or may bond thereto via a divalent linking group. Using a compound having a structure with an amino group bonding to the bonding position * in the structure represented by the formula (9), as a diamine, the structure represented by the formula (9) can be readily introduced into the main chain of the polymer. In the diamine, the amino group may directly bond to the bonding position * in the structure represented by the formula (9), or may bond thereto via a divalent linking group.

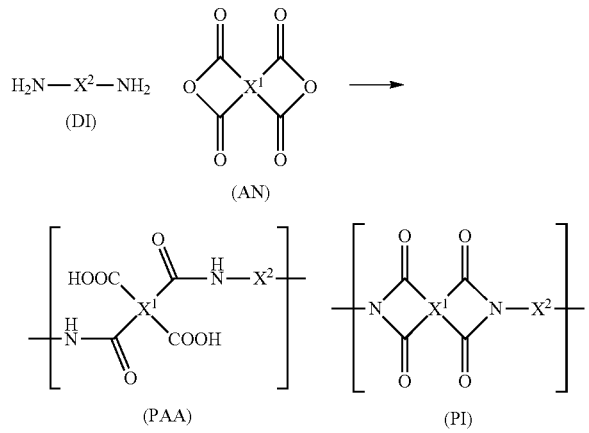

In the formulae (AN), (PAA) and (PI), $X^1$ represents a tetravalent organic group. In the formulae (DI), (PAA) and (PI), $X^2$ represents a divalent organic group. Regarding the preferred range and specific examples of the tetravalent organic group of $X^1$, reference may be made to the structure corresponding to the tetracarboxylic acid dianhydride described in the section of tetracarboxylic acid dianhydride given hereinunder. Regarding the preferred range and specific examples of the divalent organic group or $X^2$, reference may be made to the description relating to the corresponding structures of diamines or dihydrazines described in the section of diamines and dihydrazines of the formula (1) or the formula (9) as well as known diamines and dihydrazines given hereinunder.

A polyamic acid derivative is a compound modified from a polyamic acid by substituting a part of a polyamic acid with any other atom or atomic group to give a compound having modified characteristics, and is preferably so modified as to have a higher solubility in a solvent for use for a liquid crystal aligning agent. Examples of such a polyamic acid derivative include soluble polyimides, polyamic acid esters and polyamic acid amides. More specifically, they include 1) a polyimide produced by dehydrating cyclization at all amino groups and carboxyl groups in a polyamic acid, 2) a partial polyimide produced by partial dehydrating cyclization, 3) a polyamic acid ester produced by converting the carboxyl group of a polyamic acid into an ester, 4) a polyamic acid-polyamide copolymer produced by substituting a part of the acid dianhydride contained in a tetracarboxylic acid dianhydride with an organic dicarboxylic acid and reacting it, and 5) a polyamideimide produced by partly or wholly dehydrating cyclization of the polyamic acid-polyamide copolymer. Among these derivatives, for example, the polyimide includes those containing a structural unit represented by the formula (PI), and the polyamic acid ester includes those having a structural unit represented by the following formula (PAE).

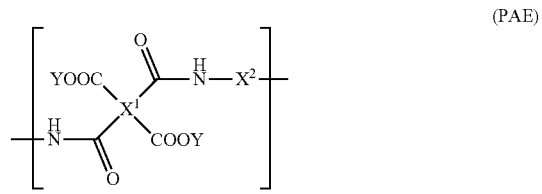

In the formula (PAE), $X^1$ represents a tetravalent organic group, $X^2$ represents a divalent organic group, Y represents an alkyl group. Regarding the preferred range and specific examples of $X^1$ and $X^2$, reference may be made to the description relating to $X^1$ and $X^2$ in the formula (PAA). Regarding the preferred range and specific examples of Y, reference may be made to the preferred range and specific examples of the alkyl group of $R^a$ in the formula (a-1) given hereinabove.

As preferred examples of the polymer containing a photoreactive structure for use in the liquid crystal aligning agent of the present invention, a polyamic acid and derivatives thereof are described in detail hereinunder.

(Polyamic Acid and Derivatives Thereof)

In the present invention, the polyamic acid and derivatives thereof to be used as a polymer containing a photoreactive structure include, for example, those having a structural unit containing a structure represented by the formula (1) in the main chain thereof. The polyamic acid and derivatives thereof to be used as a polymer containing a photoreactive structure also include those having a structure represented by the formula (9) in the main chain thereof, and those having both a structure represented by the formula (1) and a structure represented by the formula (9) in the main chain thereof. For example, a polyamic acid may be obtained as a reaction product of a diamine having a structure with an amino group bonding to the bonding position * of the structure represented by the formula (1) or the formula (9), and a tetracarboxylic acid dianhydride. In the following description, a diamine having a structure with an amino group bonding to the bonding position * of the structure represented by the formula (1) is referred to as "diamine having a structure represented by the formula (1)", a diamine having a structure with an amino group bonding to the bonding position * of the structure represented by the formula (9) is referred to as "diamine having a structure represented by the formula (9)", and the "structure represented by the formula (1)" and the "structure represented by the formula (9)" are collectively referred to as "structure represented by the formula (1) or the formula (9)". The amino group in the diamine may directly bond to the bonding position * of the structure represented by the formula (1) or the formula (9), or may bond thereto via a divalent linking group.

As the diamine having a structure represented by the formula (1) or the formula (9), the diamine of the present invention to be mentioned hereinunder is preferably used. Regarding the description, the preferred range and specific examples of the diamine, reference may be made to the description in the section of diamine to be given hereinunder. Regarding the description, the preferred range and specific examples of the tetracarboxylic acid dianhydride, reference may be made to the description in the section of tetracarboxylic acid dianhydride to be given hereinunder. One type alone or two or more types of the diamine having a structure represented by the formula (1) or the formula (9) and the tetracarboxylic acid dianhydride may be used in polyamic acid production. A diamine having a structure represented by the formula (1) and a diamine having a structure represented by the formula (9) may be used as combined for the polymerization reaction. In addition to the diamine having a structure represented by the formula (1) or the formula (9) and a tetracarboxylic acid dianhydride, any other monomer may be additionally used to thereby introduce the structural unit derived from the additional monomer into the resultant polyamic acid. The other monomer includes other diamines than the two diamines, the diamine having a structure represented by the formula (1) and the diamine having a structure represented by the formula (9), and dihydrazides. Regarding the description, the preferred range and specific examples of the other monomers, reference may be made to the section of other diamines than the two diamines, the diamine represented by the formula (2) and the diamine represented by the formula (10), and other monomers.

The polyamic acid having a structure represented by the formula (1) or the formula (9) in the main chain thereof and derivatives thereof may be produced in the same manner as that for known polyamic acids or derivatives thereof that are used for forming polyimide films.

For example, the total charge-in amount of tetracarboxylic acid dianhydride is preferably 0.9 to 1.1 moles relative to 1 mol of the total amount of diamine.

In the case where a polyamic acid having a structure represented by the formula (1) or the formula (9) in the main chain thereof is modified into a polyamic acid derivative, a polyamide having a structure represented by the formula (1) or the formula (9) in the main chain thereof, the resultant polyamic acid solution is imidated along with a dehydrating agent, an acid anhydride such as acetic anhydride, propionic anhydride or trifluoroacetic anhydride, and a dehydrating ring-closure catalyst, a tertiary amine such as triethylamine, pyridine or collidine, at a temperature of 20 to 150° C. to give a polyimide. Alternatively, the polyamic acid is precipitated from the resultant polyamic acid solution using a large amount of a poor solvent (alcohol solvent such as methanol, ethanol or isopropanol, or glycol solvent), and the precipitated polyamic acid is then imidated in a solvent such as toluene or xylene, along with the above-mentioned dehydrating agent and the dehydrating ring-closure catalyst, at a temperature of 20 to 150° C. to give a polyimide.

In the imidation reaction, the ratio of the dehydrating agent and the dehydrating ring-closure catalyst is preferably 0.1 to 10 (molar ratio). The total amount of the dehydrating agent and the dehydrating ring-closure catalyst is preferably 1.5 to 10 times by mol relative to the total molar amount of the tetracarboxylic acid dianhydride used in producing the polyamic acid. The imidation degree may be controlled by appropriately selecting and controlling the dehydrating agent to be used in the imidation reaction, the catalyst amount, the reaction temperature and the reaction time, and accordingly, a partial polyimide where only a part of polyamic acid has been imidated can be obtained. The resultant polyimide may be isolated from the solvent used in the reaction and redissolved in any other solvent, and may be thus used as a liquid crystal aligning agent, or not isolated from the solvent, the polyimide may be used as a liquid crystal aligning agent directly as it is.

A polyamic acid ester having a structure represented by the formula (1) or the formula (9) in the main chain thereof may be produced according to a method where the polyamic acid having a structure represented by the formula (1) or the formula (9) in the main chain thereof is reacted with a hydroxyl group-containing compound, a halide or an epoxy group-containing compound, or a method where a tetracarboxylic acid diester or a tetracarboxylic acid diester dichloride derived from a tetracarboxylic acid anhydride is reacted with a diamine having a structure represented by the formula (1) or the formula (9). The tetracarboxylic acid diester derived from a tetracarboxylic acid dianhydride may be produced, for example, by reacting a tetracarboxylic acid dianhydride and 2 equivalents of an alcohol for ring opening; and the tetracarboxylic acid diester dichloride may be produced, for example, by reacting a tetracarboxylic acid diester and 2 equivalents of a chlorinating agent (e.g., thionyl chloride). The polyamic acid ester may have an amic acid ester structure alone or may be a partial ester having both an amic acid structure and an amic acid ester structure.

The liquid crystal aligning agent for photoalignment of the present invention may contain one alone or two more of these polyamic acids, polyamic acid esters and polyimides obtained through imidation thereof.

The molecular weight of the polyamic acid having a structure represented by the formula (1) or the formula (9) in the main chain thereof or a derivative thereof is, in terms of the polystyrene-equivalent weight-average molecular weight (Mw) thereof, preferably 7,000 to 500,000, more preferably 10,000 to 200,000. The molecular weight of the polyamic acid or a derivative thereof may be measured through gel permeation chromatography (GPC).

The presence of the polyamic acid having a structure represented by the formula (1) or the formula (9) in the main chain thereof or a derivative thereof may be confirmed through analysis of the solid component obtained by precipitation with a large amount of a poor solvent, in IR (infrared spectrometry) or NMR (nuclear magnetic resonance). Alternatively, an extract with an organic solvent of a decomposed product of the polyamic acid or a derivative thereof, as decomposed with an aqueous solution of a strong alkali such as KOH or NaOH, may be analyzed through GC (gas chromatography), HPLC (high-performance liquid chromatography) or GC-MS (gas chromatography mass spectrometry) to identify the monomers used in the polymer.

[Other Components]

The liquid crystal aligning agent for photoalignment of the present invention may be composed of a polymer having a photoreactive structure alone or may contain any other component. The other component includes a polymer not having a photoreactive structure, and a solvent to dissolve polymers.

[Cyclization Onset Temperature and Alignment Amplification Onset Temperature]

As described above, the polymer that the liquid crystal aligning agent of the present invention contains has a structural unit containing a photoreactive structure, in which the structural unit containing a photoreactive structure undergoes chemical reaction by heating. In the case where the polymer that the liquid crystal aligning agent of the present invention contains is such that the structural unit containing a photoreactive structure therein undergoes cyclization by heating, the cyclization onset temperature of the polymer may be lower than or higher than the alignment amplification onset temperature thereof. For example, when the cyclization onset temperature is lower than the alignment amplification onset temperature, the film of the liquid crystal aligning agent is first kept at a temperature falling within a range of not lower than the cyclization onset temperature and lower than the alignment amplification onset temperature in heating and baking after photoalignment treatment thereof, whereby the cyclization may be promoted in some degree prior to the alignment amplification. Afterwards, the film is heated and kept at a temperature not lower than the alignment amplification onset temperature to cause alignment amplification. Contrary to this, when the cyclization onset temperature is higher than the alignment amplification onset temperature, the film of the liquid crystal aligning agent is first kept at a temperature falling within a range not lower than the alignment amplification onset temperature and lower than the cyclization onset temperature in heating and baking after photoalignment treatment thereof, whereby the alignment amplification may be promoted in some degree prior to the cyclization. Afterwards, the film is heated and kept at a temperature not lower than the cyclization onset temperature to cause cyclization. In that manner, the onset time for cyclization may be made to differ from that for alignment amplification to thereby better the alignment performance of the resultant liquid crystal alignment film.

Here, "keeping at a temperature falling within a range" in keeping the film within a specific temperature range includes not only a case where the film is kept at a specific temperature but also a case where the film is heated or cooled, or heated and/or cooled without overstepping the defined temperature range. The time for which the film is kept within the defined temperature range may be generally 1 minute to 1 hour, preferably 1 minute to 30 minutes.

For measuring the polymer cyclization onset temperature, for example, the film containing the polymer is heat-treated at a different temperature and then the transmittance thereof is measured, and a correlation diagram is drawn where the heating temperature is on the horizontal axis and the transmittance is on the vertical axis. On the correlation diagram, the temperature at the boundary at which the transmittance curve changes from flat to slope to the right is referred to as "cyclization onset temperature". Here, the transmittance is an index of cyclization reaction, and the transmittance of light which falls within an absorption wavelength range of the polymer and whose absorbance decreases in occurrence of polymer cyclization (that is, the transmittance of the light increases) is used here. For example, for the polymer having an azobenzene structure, the transmittance thereof at 365 nm may be an index of cyclization of the polymer, and from the correlation diagram between the transmittance and the heating temperature, the cyclization onset temperature of the polymer may be determined. The film that contains polymer to be analyzed for measurement of the transmittance thereof may be one treated for photoalignment.

For measuring the alignment amplification onset temperature of the polymer for use herein, for example, a film containing the polymer is, after photoalignment treatment, heat-treated at a different temperature, and the retardation value thereof is measured. With that, a correlation diagram is drawn where the heating temperature is on the horizontal axis and the retardation value is on the vertical axis. On the correlation diagram, the temperature at the boundary at which the retardation value curve changes from flat to slope to the right is referred to as "alignment amplification onset temperature". Here, the retardation value is an index of alignment of the polymer main chain, and a larger retardation value means a higher alignment of the polymer chain. For measurement of the retardation value, light at 400 to 700 nm may be used.

Regarding the concrete conditions for measurement of the transmittance and the retardation value, reference may be made to the description in the section of Examples to be given hereinunder.

When a film of a liquid crystal aligning agent is kept in a specific temperature range, the film may be heated up to the intended temperature falling within the range at a time, but preferably, after preheating (prebaking) the film at a temperature lower than the intended temperature (for example, at 90 to 180° C.), the film is heated and kept at the intended temperature (for example 185° C. or higher). In that manner, cyclization and alignment amplification may be carried out stably. Regarding the concrete conditions for heating and baking, reference may be made to the description relating to the heating and baking step in the section of liquid crystal alignment film to be given hereinunder.

The cyclization onset temperature for the polymer for use in the liquid crystal aligning agent is preferably within a range of 100 to 200° C., and for example, a polymer having a cyclization onset temperature in a range of 110 to 160° C. may be used here. The polymer cyclization onset temperature may be controlled by changing the type of the diamine having a structure represented by the formula (1) or (9) for use in polymer production.

The alignment amplification onset temperature of the polymer for use in the liquid crystal aligning agent is preferably within a range of 100 to 200° C., and for example, a polymer having an alignment amplification onset temperature falling within a range of 110 to 180° C. may be used here. The alignment amplification onset temperature of the polymer may be controlled by changing the type and the composition ratio of the acid dianhydride and the other diamine than the diamine having a structure represented by the formula (1) or (9) for use in polymer production.

Diamine

Next, the diamine of the present invention is described.

The diamine of the present invention has a structure represented by the formula (2) or (10) mentioned below.

[Diamine Represented by Formula (2)]

The diamine represented by the formula (2) has an azobenzene structure common to the structure represented by the formula (1), and for example, using this as a monomer, a polymer such as a polyamic acid, a polyimide, a polyamide, a partial polyimide, a polyamic acid ester, a polyamic acid-polyamide copolymer or a polyamideimide may be produced to give a polymer having a structural unit containing the structure represented by the formula (1) in the main chain thereof. Accordingly, the diamine of the present invention is highly useful as a raw material for the polymer for use in the liquid crystal aligning agent of the present invention. In addition, a polymer produced using the diamine of the present invention as a monomer is also usable for optical anisotropic materials, retardation films, optical compensation films, antireflection films, other various films and optical members, in addition to liquid crystal alignment films.

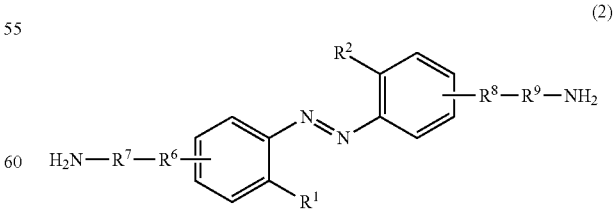

(2)

In the formula (2), $R^1$ and $R^2$ each independently represent a hydrogen atom, or a group represented by the following formula (1-1) or (1-2), at least one of $R^1$ and $R^2$ is a group represented by the formula (1-1) or (1-2). Regarding the description of $R^1$ and $R^2$ in the formula (2), reference may be made to the description of $R^1$ and $R^2$ in the formula (1).

$R^6$ and $R^8$ each independently represent a linear alkylene group having 1 to 20 carbon atoms, —COO—, —NHCO—, —CONH—, —N(CH$_3$)CO—, —CON(CH$_3$)—, or a single bond. In $R^6$ and $R^8$, one or two (—CH$_2$—)'s not adjacent to each other in the linear alkylene group may be substituted with —O—. $R^6$ and $R^8$ may be the same as or different from each other. $R^7$ and $R^9$ each independently represent a monocyclic hydrocarbon, a condensed polycyclic hydrocarbon, a hetero ring or a single bond. $R^7$ and $R^9$ may be the same as or different from each other.

The monocyclic hydrocarbon of $R^7$ and $R^9$ may be an alicyclic ring or an aromatic ring. The carbon number of the monocyclic hydrocarbon is preferably 6 to 12, more preferably 6 to 10, even more preferably 6 to 8. Specific examples of the monocyclic hydrocarbon include a benzene ring, a cyclohexane ring, and a cyclohexene ring.

The carbon number of the condensed polycyclic hydrocarbon of $R^7$ and $R^9$ is preferably 10 to 26, more preferably 10 to 18, even more preferably 10 to 14. Specific examples of the condensed polycyclic hydrocarbon include a naphthalene ring, an anthracene ring, and a phenanthrene ring.

The hetero ring of $R^7$ and $R^9$ may be an alicyclic ring or an aromatic ring. The carbon number of the hetero ring is preferably 1 to 26, more preferably 3 to 14, even more preferably 3 to 8. The hetero atom that the hetero ring contains as the ring atom thereof includes a nitrogen atom, an oxygen atom and a sulfur atom. Specific examples of the hetero ring include a pyridine ring, a pyrazine ring, a pyrimidine ring, a pyridazine ring, an indole ring, and an oxazole ring.

In the formula (2), —$R^6$—$R^7$—NH$_2$ bonds to one benzene ring in the formula (2), and the bonding position thereof is a position substitutable with a hydrogen atom of the benzene ring. —$R^8$—$R^9$—NH$_2$ bonds to the other benzene ring in the formula (2), and the bonding position thereof is a position substitutable with a hydrogen atom of the benzene ring. The remaining substitutable positions of the benzene ring may be unsubstituted or substituted with a substituent. Regarding the preferred range and specific examples of the substituent, reference may be made to the preferred range and specific examples of the substituent substitutable on the benzene ring in the formula (1) mentioned above.

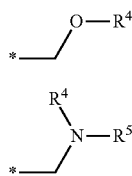

In the formula (1-1), $R^4$ represents a hydrogen atom, a substituted or unsubstituted alkyl group, a substituted or unsubstituted alkanoyl group, or a substituted or unsubstituted arylcarbonyl group. In the formula (1-2), $R^4$ and $R^5$ each independently represent a hydrogen atom, a substituted or unsubstituted alkyl group, a substituted or unsubstituted alkanoyl group, or a substituted or unsubstituted arylcarbonyl group. In the formulae (1-1) and (1-2), * represents a bonding position to the benzene ring in the formula (2). Regarding the description of $R^4$, $R^5$, and * in the formulae (1-1) and (1-2), reference may be made to the description of $R^4$, $R^5$, and * in the formulae (1-1) and (1-2) in the formula (1) mentioned hereinabove.

The diamine represented by the formula (2) is, from the viewpoint of easiness in production and easy availability of raw materials, and from the viewpoint of high liquid crystal alignment performance in the case where the diamine is used as a raw material for liquid crystal aligning agents, preferably a diamine represented by any of the following formulae (3) to (8).

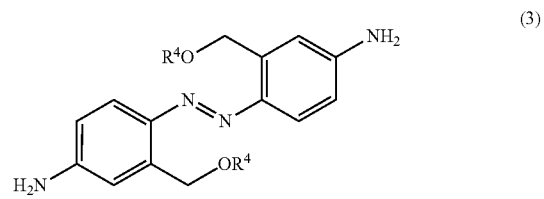

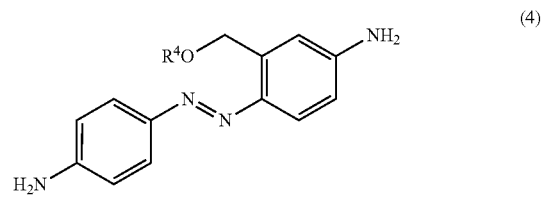

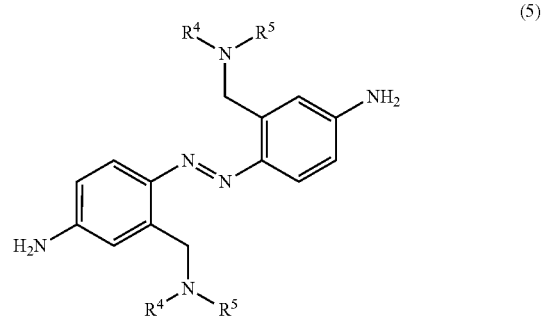

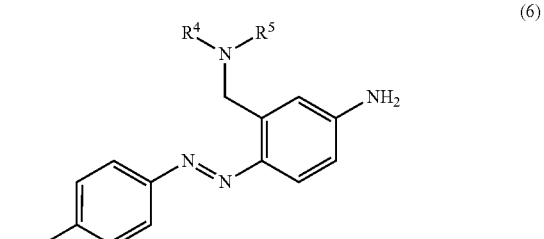

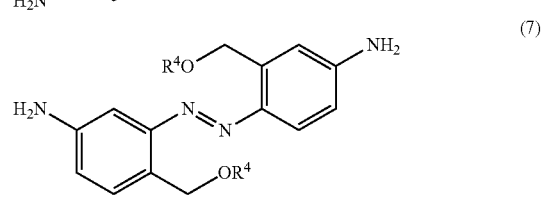

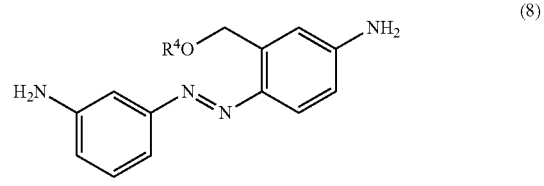

In the formulae (3) to (8), $R^4$ and $R^5$ have the same meanings as those of $R^4$ and $R^5$ in the formulae (1-1) and (1-2) of the formula (2). Preferably, $R^4$ and $R^5$ each independently represent a hydrogen atom, an alkyl group having 1 to 10 carbon atoms, or an alkanoyl group having 1 to 10 carbon atoms. R⁴'s in the formulae (3) and (7), R⁴'s, R⁵'s and R⁴ and R⁵ in the formula (5), and R⁴ and R⁵ in the formula (6) each may be the same as or different from each other, but are preferably the same.

Preferred examples of the diamine represented by any of the formulae (3) to (8) include diamines represented by any of the following formulae (3-1) to (3-8), (4-1) to (4-8), (5-1), (5-2), (6-1), (6-2), (7-1) to (7-3), and (8-1) to (8-3). Polymers produced using any of these diamines as a monomer tend to exhibit high liquid crystal alignment performance. In each formula, Me represents a methyl group, Et represents an ethyl group, Pr represents a propyl group, $^i$Pr represents an isopropyl group, Bu represents a butyl group, and $^t$Bu represents a t-butyl group.

(3-1)

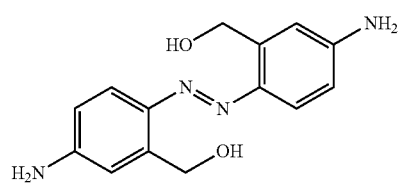

(3-2)

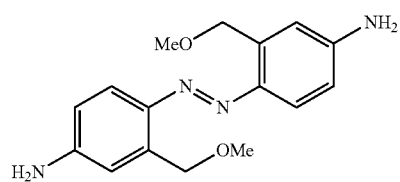

(3-3)

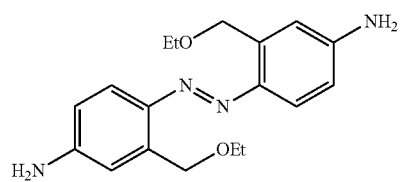

(3-4)

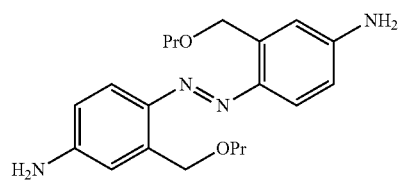

(3-5)

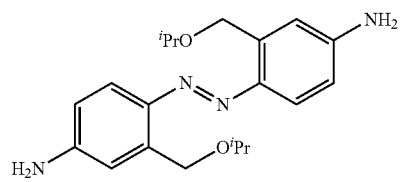

(3-6)

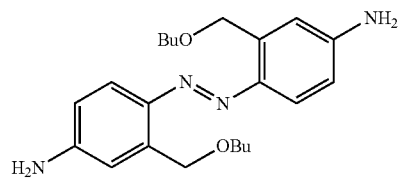

-continued (3-7)

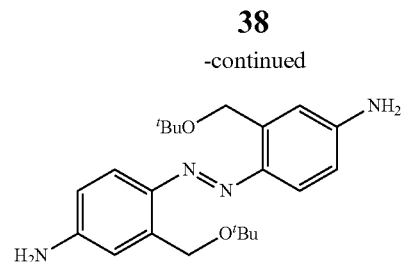

(3-8)

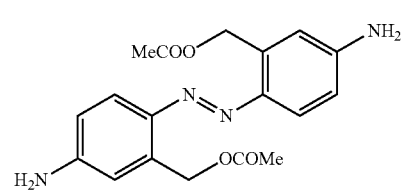

(4-1)

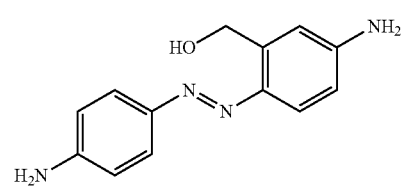

(4-2)

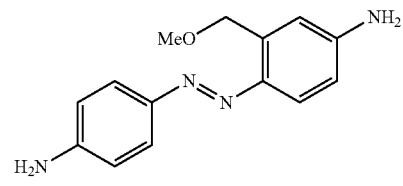

(4-3)

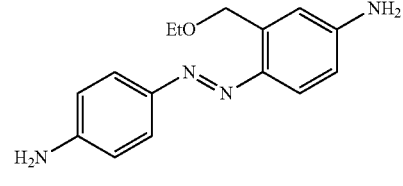

(4-4)

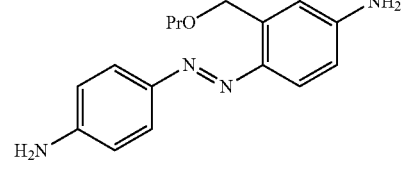

(4-5)

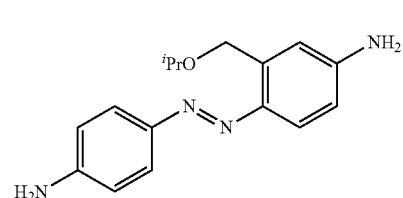

(4-6)

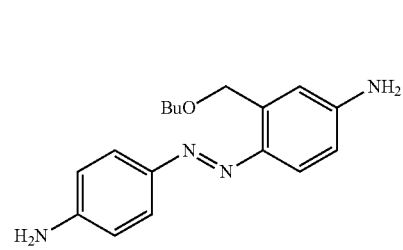

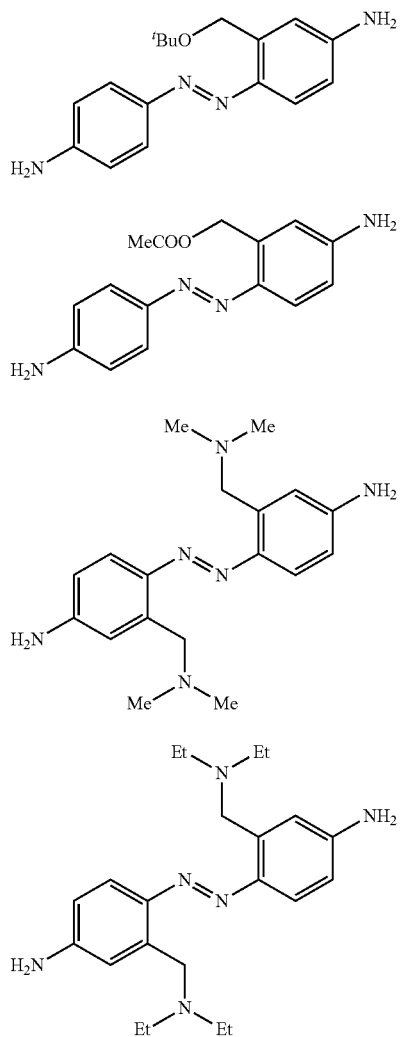
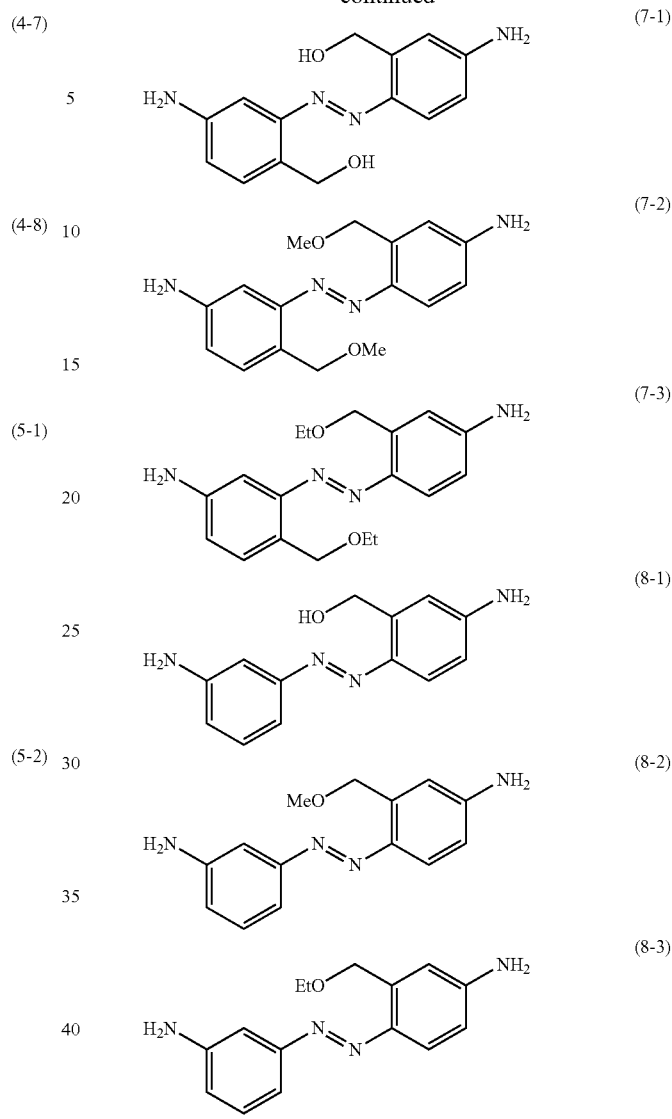
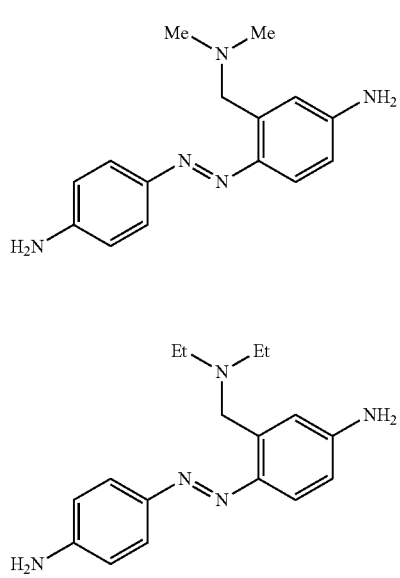

(Synthesis of Diamine)

The diamines represented by the above-mentioned formulae (3) to (8) may be produced as follows.

For producing the diamine represented by the formula (3), a commercial product, 5-nitroanthranilic acid is reduced to give 2-amino-5-nitrophenylmethanol, and then the resultant aromatic amine is oxidized to give an azobenzene having a hydroxymethyl group at the ortho-position of the benzene ring and having a nitro group at the para-position thereof. Subsequently, the hydroxyl group is converted to a trifluoromethanesulfonate and then to an alkoxy group through nucleophilic substitution reaction. Finally, the nitro group is reduced to give the intended diamine.

For producing the diamine represented by the formula (4), a commercial product, 1-bromomethyl-3-nitrobenzene is converted into a 1-alkoxymethyl-3-nitrobenzene through nucleophilic substitution reaction, and then the nitro group is reduced to give a 3-alkoxymethylaniline. Subsequently, this is reacted with 4-nitroaniline in a mode of diazocoupling to give an azobenzene, and the nitro group is reduced to give the intended diamine. Preferred examples of the azobenzene of a diamine precursor include compounds represented by the following formula (4P).

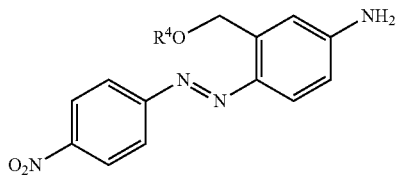

(4P)

In the formula (4P), $R^4$ represents a hydrogen atom, an alkyl group having 1 to 10 carbon atoms, or an alkanoyl group having 1 to 10 carbon atoms.

For producing the diamine represented by the formula (5), a commercial product, 5-nitroanthranilic acid is reduced to give 2-amino-5-nitrophenylmethanol, and then the resultant aromatic amine is oxidized to give an azobenzene having a hydroxymethyl group at the ortho-position of the benzene ring and having a nitro group at the para-position thereof. Subsequently, the hydroxyl group is converted to a trifluoromethanesulfonate and then to an N,N'-dialkylamino group through nucleophilic substitution reaction. Finally, the nitro group is reduced to give the intended diamine.

For producing the diamine represented by the formula (6), a commercial product, 1-bromomethyl-3-nitrobenzene is converted into an N,N'-dialkyl-1-(3-nitrophenyl)methanamine through nucleophilic substitution reaction, and then the nitro group is reduced to give a dialkylaminomethyl-3-nitrobenzene. Subsequently, this is reacted with 4-nitroaniline in a mode of diazocoupling to give an azobenzene, and the nitro group is reduced to give the intended diamine.

For producing the diamine represented by the formula (7), a commercial product, 4-nitroanthranilic acid is reduced to give 2-amino-4-nitrophenylmethanol, which is then reacted with a commercial product, 3-aminobenzyl alcohol in a mode of diazocoupling to give an azobenzene. Subsequently, the hydroxyl group is converted to a trifluoromethanesulfonate and then to an alkoxy group through nucleophilic substitution reaction. Finally, the nitro group is reduced to give the intended diamine.

For producing the diamine represented by the formula (8), a commercial product, 1-bromomethyl-3-nitrobenzene is converted into a 1-alkoxymethyl-3-nitrobenzene through nucleophilic substitution reaction, and then the nitro group is reduced to give a 3-alkoxymethylaniline. Subsequently, this is reacted with 3-nitroaniline in a mode of diazocoupling to give an azobenzene, and the nitro group is reduced to give the intended diamine.

These diamines may be purified according to recrystallization or column chromatography before use herein.

For providing a liquid crystal aligning agent capable of forming a liquid crystal alignment film having better liquid crystal alignment performance, at least one diamine of the formulae (4-1), (4-2), (4-3), (4-4), (4-5) and (6-1) among these compounds is preferably used as the raw material for polymers.

[Diamine Represented by Formula (10)]

The diamine represented by the formula (10) has an acylhydrazone structure common to the structure represented by the formula (9), and for example, using this as a monomer, a polymer such as a polyamic acid, a polyimide, a polyamide, a partial polyimide, a polyamic acid ester, a polyamic acid-polyamide copolymer or a polyamideimide may be produced to give a polymer having a structural unit containing the structure represented by the formula (9) in the main chain thereof. Accordingly, the diamine of the present invention is highly useful as a raw material for the polymer for use in the liquid crystal aligning agent of the present invention. In addition, a polymer produced using the diamine of the present invention as a monomer is also usable for optical anisotropic materials, retardation films, optical compensation films, antireflection films, other various films and optical members, in addition to liquid crystal alignment films.

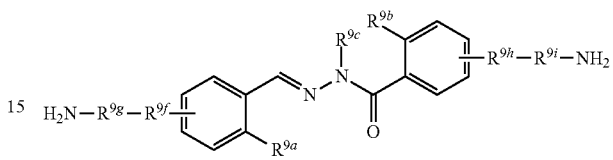

(10)

In the formula (10), $R^{9a}$ represents a group represented by the following formula (9-1) or (9-2); $R^{9b}$ represents a hydrogen atom or a group represented by the formula (9-1) or (9-2); when both $R^{9a}$ and $R^{9b}$ are groups represented by the formula (9-1) or (9-2), the groups may be the same as or different from each other. In the formula (10), $R^{9c}$ independently represents a hydrogen atom, a substituted or unsubstituted alkyl group, a substituted or unsubstituted alkanoyl group, or a substituted or unsubstituted arylcarbonyl group. Regarding the description, the preferred range and specific examples of the alkyl group, the alkanoyl group and the arylcarbonyl group of $R^{9c}$ and the substituent for these groups, reference may be made to the description, the preferred range and specific examples of the alkyl group, the alkanoyl group and the arylcarbonyl group of $R^a$ and the substituent for these groups in the formula (a-1). Regarding the description of $R^{9a}$ and $R^{9b}$ in the formula (10), reference may be made to the description of $R^{9a}$ and $R^{9b}$ in the formula (9).

$R^{9f}$ and $R^{9h}$ each independently represent a linear alkylene group having 1 to 20 carbon atoms, —COO—, —OCO—, —NHCO—, —CONH—, —N(CH$_3$)CO—, —CON(CH$_3$)—, or a single bond, In $R^{9f}$ and $R^{9h}$, one or two (—CH$_2$—)'s not adjacent to each other in the linear alkylene group may be substituted with —O—. $R^{9f}$ and $R^{9h}$ may be the same as or different from each other. $R^{9g}$ and $R^{9i}$ each independently represent a monocyclic hydrocarbon, a condensed polycyclic hydrocarbon, a hetero ring or a single bond. $R^{9g}$ and $R^{9i}$ may be the same as or different from each other.

The monocyclic hydrocarbon of $R^{9g}$ and $R^{9i}$ may be an alicyclic ring or an aromatic ring. The carbon number of the monocyclic hydrocarbon is preferably 6 to 12, more preferably 6 to 10, even more preferably 6 to 8. Specific examples of the monocyclic hydrocarbon include a benzene ring, a cyclohexane ring, and a cyclohexene ring.

The carbon number of the condensed polycyclic hydrocarbon of $R^{9g}$ and $R^{9i}$ is preferably 10 to 26, more preferably 10 to 18, even more preferably 10 to 14. Specific examples of the condensed polycyclic hydrocarbon include a naphthalene ring, an anthracene ring, and a phenanthrene ring.

The hetero ring of $R^{9g}$ and $R^{9i}$ may be an alicyclic ring or an aromatic ring. The carbon number of the hetero ring is preferably 1 to 26, more preferably 3 to 14, even more preferably 3 to 8. The hetero atom that the hetero ring contains as the ring atom thereof includes a nitrogen atom, an oxygen atom and a sulfur atom. Specific examples of the hetero ring include a pyridine ring, a pyrazine ring, a pyrimidine ring, a pyridazine ring, an indole ring, and an oxazole ring.

In the formula (10), —$R^{9f}$—$R^{9g}$—$NH_2$ bonds to one benzene ring in the formula (10), and the bonding position thereof is a position substitutable with a hydrogen atom in the benzene ring. —$R^{9h}$—$R^{9i}$—$NH_2$ bonds to the other benzene ring in the formula (10), and the bonding position thereof is a position substitutable with a hydrogen atom in the benzene ring. The remaining substitutable positions of the benzene ring may be unsubstituted or substituted with a substituent. Regarding the preferred range and specific examples of the substituent, reference may be made to the preferred range and specific examples of the substituent substitutable on the benzene ring in the formula (9) mentioned above.

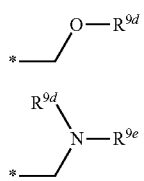

(9-1)

(9-2)

In the formula (9-1), $R^{9d}$ represents a hydrogen atom, a substituted or unsubstituted alkyl group, a substituted or unsubstituted alkanoyl group, or a substituted or unsubstituted arylcarbonyl group. In the formula (9-2), $R^{9d}$ and $R^{9e}$ each independently represent a hydrogen atom, a substituted or unsubstituted alkyl group, a substituted or unsubstituted alkanoyl group, or a substituted or unsubstituted arylcarbonyl group. In the formulae (9-1) and (9-2), * represents a bonding position to the benzene ring in the formula (10). Regarding the description of $R^{9d}$, $R^{9e}$, and * in the formulae (9-1) and (9-2), reference may be made to the description of $R^{9d}$, $R^{9e}$, and * in the formulae (9-1) and (9-2) in the formula (9) mentioned hereinabove.

The diamine represented by the formula (10) is, from the viewpoint of easiness in production and easy availability of raw materials, and from the viewpoint of high liquid crystal alignment performance in the case where the diamine is used as a raw material for liquid crystal aligning agents, preferably a diamine represented by any of the following formulae (11) to (16).

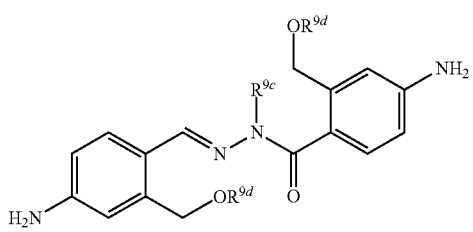

(11)

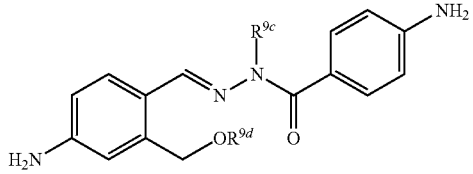

(12)

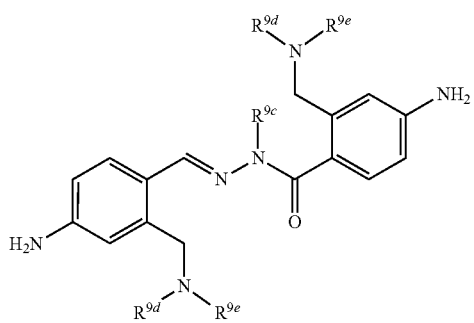

(13)

(14)

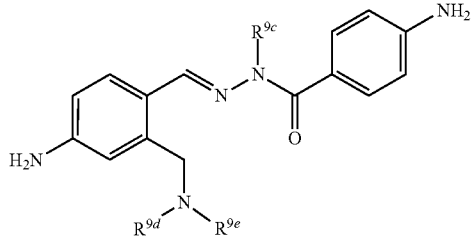

(15)

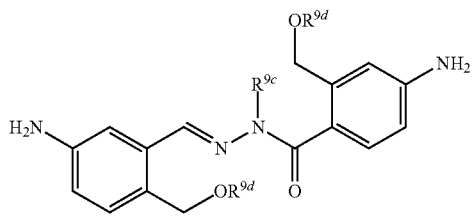

(16)

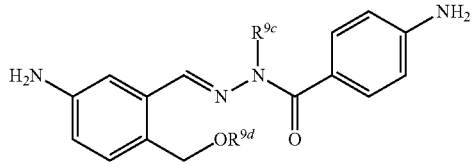

In the formulae (11) to (16), $R^{9d}$ and $R^{9e}$ have the same meanings as those of $R^{9d}$ and $R^{9e}$ in the formulae (9-1) and (9-2) of the formula (10), and $R^{9c}$ has the same meaning as $R^{9c}$ in the formula (10). Preferably, $R^{9d}$ and $R^{9e}$ each independently represent a hydrogen atom, an alkyl group having 1 to 10 carbon atoms, or an alkanoyl group having 1 to 10 carbon atoms. $R^{9d}$'s in the formulae (11) and (15), $R^{9d}$'s, $R^{9e}$'s and $R^{9d}$ and $R^{9e}$ in the formula (13), and $R^{9d}$ and $R^{9e}$ in the formula (14) each may be the same as or different from each other, but are preferably the same.

Preferred examples of the diamine represented by any of the formulae (11) to (16) include diamines represented by any of the following formulae (11-1) to (11-8), (12-1) to (12-8), (13-1), (13-2), (14-1), (14-2), (15-1) to (15-3), and (16-1) to (16-3). Polymers produced using any of these diamines as a monomer tend to exhibit high liquid crystal alignment performance. In each formula, Me represents a methyl group, Et represents an ethyl group, Pr represents a propyl group, $^i$Pr represents an isopropyl group, Bu represents a butyl group, and $^t$Bu represents a t-butyl group.

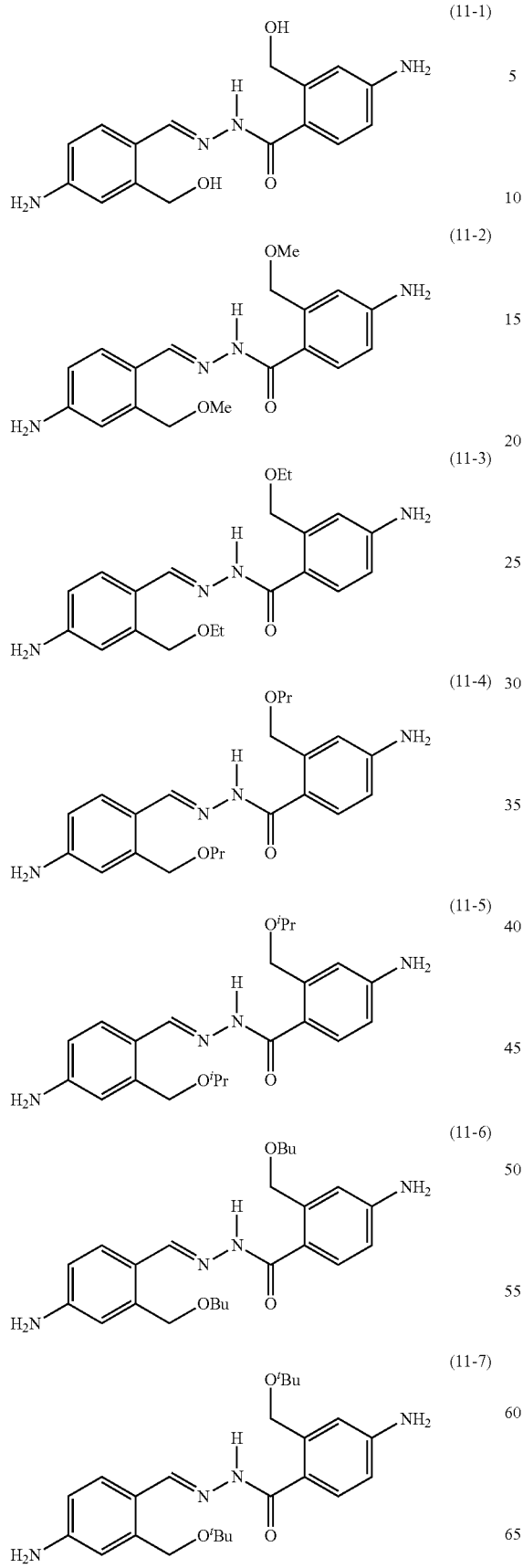
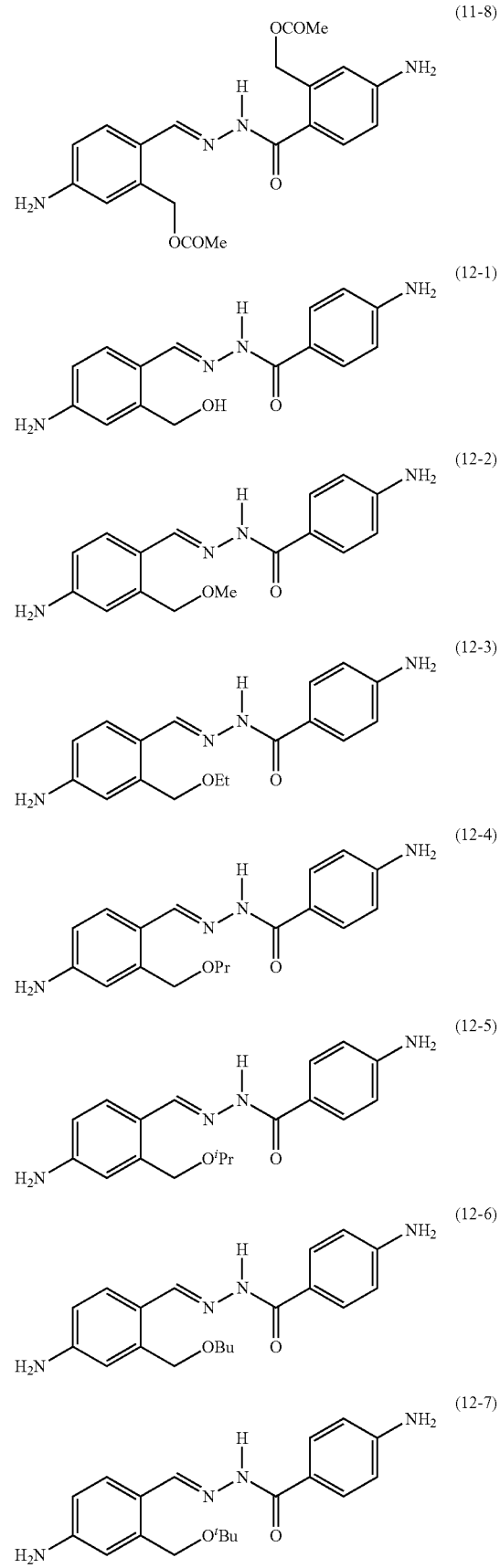

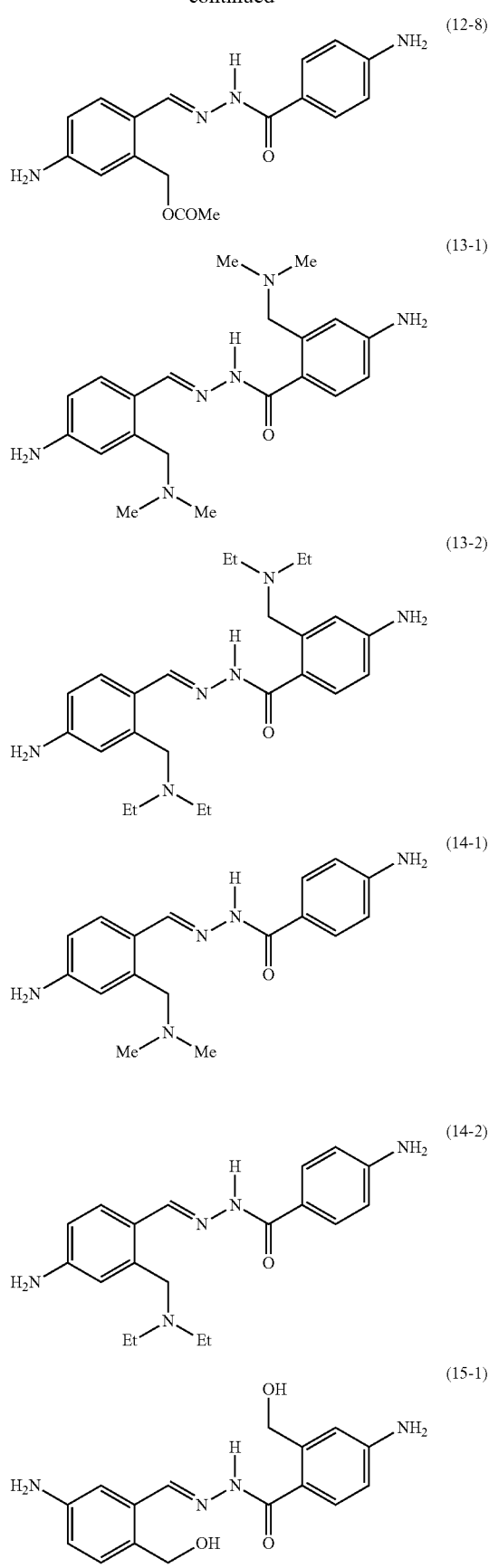
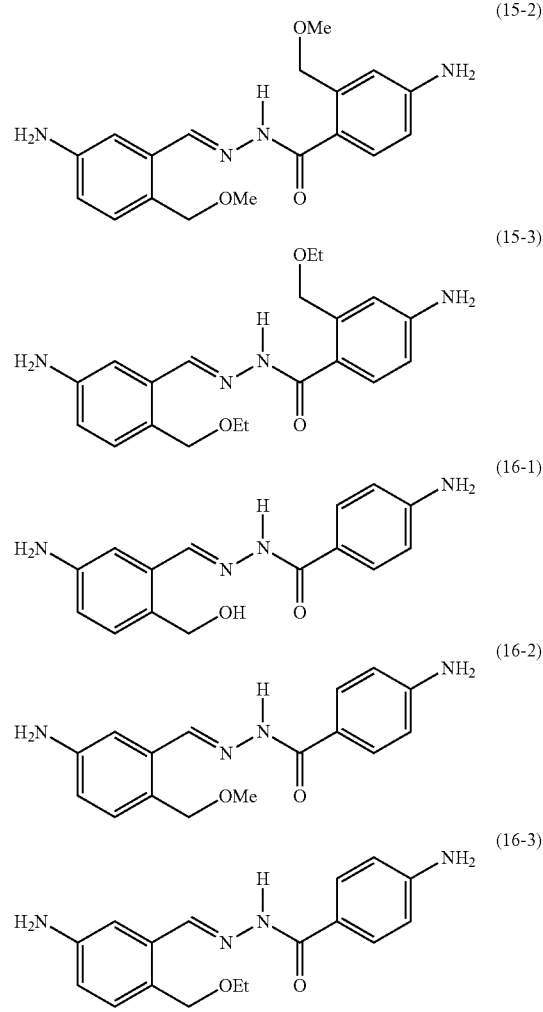

(Synthesis of Diamine)

The diamine represented by any of the above-mentioned formulae (11) to (16) may be produced as follows.

For producing the diamine represented by the formula (11), a commercial product, 2-bromo-5-nitrobenzoic acid is reduced to give 2-bromo-5-nitrophenylmethanol, and then the hydroxyl group is etherified. Subsequently, the resultant product is formylated to give a 2-alkoxymethyl-4-nitrobenzaldehyde. The aldehyde is oxidized to be a carboxylic acid, and then esterified to give a methyl 2-alkoxymethyl-4-nitrobenzoate. Next, this is hydrazidated to give a 2-alkoxymethyl-4-nitrobenzohydrazide. The 2-alkoxymethyl-4-nitrobenzaldehyde and the 2-alkoxymethyl-4-nitrobenzohydrazide are subjected to dehydration to give a dinitro compound. Subsequently, the nitro group is reduced to give the intended diamine.

For producing the diamine represented by the formula (12), a commercial product, methyl 4-nitrobenzoate is hydrazidated, and then subjected to dehydration along with the above-mentioned 2-alkoxymethyl-4-nitrobenzaldehyde to give a dinitro compound. Subsequently, the nitro group is reduced to give the intended diamine.

For producing the diamine represented by the formula (13), a commercial product, 2-bromo-5-nitrobenzoic acid is reduced to give 2-bromo-5-nitrophenylmethanol, and the hydroxyl group is halogenated and then dialkylaminated.

Subsequently, the resultant product is formylated to give a 2-dialkylaminomethyl-4-nitrobenzaldehyde. The aldehyde is oxidized to be a carboxylic acid, and then esterified to give a methyl 2-dialkylaminomethyl-4-nitrobenzoate. Next, this is hydrazidated to give a 2-dialkylaminomethyl-4-nitrobenzohydrazide. The 2-dialkylaminomethyl-4-nitrobenzaldehyde and the 2-dialkylaminomethyl-4-nitrobenzohydrazide are subjected to dehydration to give a dinitro compound. Subsequently, the nitro group is reduced to give the intended diamine.

For producing the diamine represented by the formula (14), a commercial product, methyl 4-nitrobenzoate is hydrazidated, and then subjected to dehydration along with the above-mentioned 2-dialkylaminomethyl-4-nitrobenzaldehyde to give a dinitro compound. Subsequently, the nitro group is reduced to give the intended diamine.

For producing the diamine represented by the formula (15), 6-nitrophthalide is decyclized to give 2-chloromethyl-5-nitrobenzoyl chloride, and then processed for esterification, etherification and ester reduction to give a 2-alkoxymethyl-5-nitrobenzaldehyde. This is subjected to dehydration along with the above-mentioned 2-alkoxymethyl-4-nitrobenzohydrazide to give a dinitro compound. Subsequently, the nitro group is reduced to give the intended diamine.

For producing the diamine represented by the formula (16), a commercial product, methyl 4-nitrobenzoate is hydrazidated, and then subjected to dehydration along with the above-mentioned 2-alkoxymethyl-5-nitrobenzaldehyde to give a dinitro compound. Subsequently, the nitro group is reduced to give the intended diamine.

These diamines may be purified according to recrystallization or column chromatography before use herein.

For providing a liquid crystal aligning agent capable of forming a liquid crystal alignment film having better liquid crystal alignment performance, at least one diamine of the formulae (12-1), (12-2), (12-3), (14-1), (14-2) and (16-3) among these compounds is preferably used as the raw material for polymers.

<Polymer>

Next, the polymer of the present invention is described.

The polymer of the present invention has a structural unit having a photoreactive structure in the main chain thereof, in which the structural unit containing a photoreactive structure undergoes chemical reaction by heating. The type of the polymer is not specifically defined, and examples thereof include a polyamic acid, a polyamic acid derivative, a polyester, a polyamide, a polysiloxane, a cellulose derivative, a polyacetal, a polystyrene derivative, a poly(styrenephenylmaleimide) derivative, and a poly(meth)acrylate. The polyamic acid derivative is a component that dissolves in a solvent when formed into a liquid crystal aligning agent containing a solvent to be mentioned below, and is a component which, when the liquid crystal aligning agent is formed into a liquid crystal alignment film, can form a liquid crystal alignment film having a polyimide as the main ingredient thereof. Examples of such a polyamic acid derivative include soluble polyimides, polyamic acid esters and polyamic acid amides. More specifically, they include 1) a polyimide produced by dehydrating cyclization at all amino groups and carboxyl groups in a polyamic acid, 2) a partial polyimide produced by partial dehydrating cyclization, 3) a polyamic acid ester produced by converting the carboxyl group of a polyamic acid into an ester, 4) a polyamic acid-polyamide copolymer produced by substituting a part of the acid dianhydride contained in a tetracarboxylic acid dianhydride compound with an organic dicarboxylic acid and reacting it, and 5) a polyamideimide produced by partly or wholly dehydrating cyclization of the polyamic acid-polyamide copolymer. One alone or two or more types of such polymers may be used in the liquid crystal aligning agent of the present invention.

For the polymer of the present invention, preferably, the raw material contains a diamine represented by the formula (2) or a diamine represented by the formula (10). One alone or two or more types of such diamines may be contained in the raw material.

As combined, a diamine represented by the formula (2) and a diamine represented by the formula (10) may be contained in the raw material. In the following description, "diamine represented by the formula (2)" and "diamine represented by the formula (10)" are collectively referred to as "diamine represented by the formula (2) or (10)".

Regarding the description of the diamine represented by the formula (2) or (10), reference may be made to the description in the section of diamine given hereinabove. Regarding the description of polyamic acid, polyimide, partial polyimide, polyamic acid ester, polyamic acid-polyamide copolymer and polyamideimide, reference may be made to the corresponding description in the sections of (Type of polymer) and (Polyamic acid and derivatives thereof) given hereinabove.

For the polymer of the present invention, the raw material contains a diamine represented by the formula (2) or (10), and therefore a structural unit containing a structure represented by the formula (1) or (9) can be introduced into the main chain of the polymer. In the structural unit containing a structure represented by the formula (1), the structure represented by the formula (1) is a photoreactive structure, and in addition, when heated, the azo group having a structure of the formula (1) disappears in at least a part of the structural unit to lose photoreactivity, and therefore, the polymer has high stability to light. On the other hand, in the structural unit containing a structure represented by the formula (9), the structure represented by the formula (9) is a photoreactive structure, and in addition, when heated, the imino group having a structure of the formula (9) disappears in at least a part of the structural unit to lose photoreactivity, and therefore, the polymer has high stability to light. Consequently, when the polymer is used as a liquid crystal aligning agent, the resultant film may be given anisotropy through photoalignment, and therefore a liquid crystal alignment film having high stability to heat can be realized.

In the following, a tetracarboxylic acid dianhydride, other diamines than both diamines of the diamine represented by the formula (2) and the diamine represented by the formula (10) and other monomers for use as raw materials for the polymer of the present invention are described.

Tetracarboxylic Acid Dianhydride

The tetracarboxylic acid dianhydride for use as a starting material for the polymer of the present invention may be selected with no specific limitation from known tetracarboxylic acid dianhydrides. Such tetracarboxylic acid dianhydrides may belong to any group of aromatic compounds where a dicarboxylic acid anhydride directly bonds to an aromatic ring (including heterocyclic aromatic compounds) and aliphatic compounds where a dicarboxylic acid anhydride does not directly bond to an aromatic ring (including heterocyclic aliphatic compounds).

Preferred examples of such a tetracarboxylic acid dianhydride are, from the viewpoint of easy availability of raw materials, easiness in polymer production and electric properties of films, tetracarboxylic acid dianhydrides represented by the following formulae (AN-1) to (AN-V).

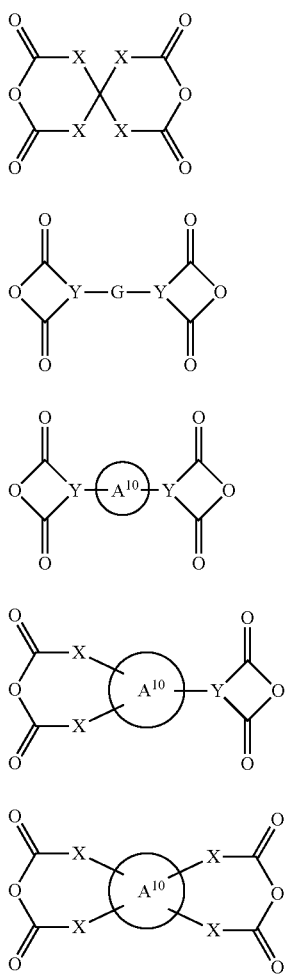

(AN-I)

(AN-II)

(AN-III)

(AN-IV)

(AN-V)

In the formulae (AN-I), (AN-IV) and (AN-V), X each independently represents a single bond or —CH$_2$—. In the formula (AN-II), G represents a single bond, an alkylene group having 1 to 20 carbon atoms, —CO—, —O—, —S—, —C(CH$_3$)$_2$—, —C(CF$_3$)$_2$—, or a divalent group represented by the following formula (G13-1), and —CH$_2$— may be substituted with —O—, —CO—, or —NH—.

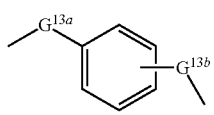

(G13-1)

In the formula (G13-1), G$^{13a}$ and G$^{13b}$ each independently represent a single bond, or a divalent group selected from —O—, —CONH— or —NHCO—. The phenylene group is preferably a 1,4-phenylene group or a 1,3-phenylene group.

In the formulae (AN-II) to (AN-IV), Y independently represents a group selected from the following trivalent groups. Each bond of the trivalent group arbitrarily bonds to the carbon atom, and at least one hydrogen atom may be substituted with a methyl group, an ethyl group or a phenyl group.

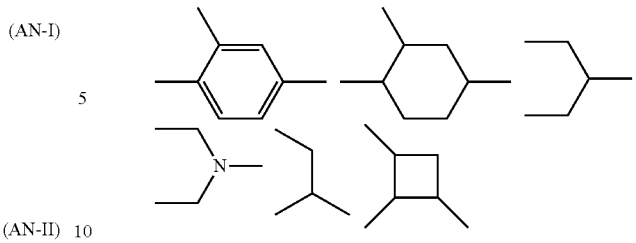

In the formulae (AN-III) to (AN-V), the ring A$^{10}$ is a cyclic group derived from a monocyclic hydrocarbon having 3 to 10 carbon atoms by removing therefrom hydrogen atoms of the same number as the number of the bonds, or a cyclic group derived from a condensed polycyclic hydrocarbon having 6 to 30 carbon atoms by removing therefrom hydrogen atoms of the same number as the number of the bonds. At least one hydrogen atom in each cyclic group may be substituted with a methyl group, an ethyl group or a phenyl group. The bond to each ring bonds to any arbitrary carbon atom constituting the ring, and two bonds may bond to one and the same carbon atom.

Further, the tetracarboxylic acid dianhydride for use in the invention includes the following formulae (AN-1) to (AN-16-15).

[Tetracarboxylic Acid Dianhydride Represented by Formula (AN-1)]

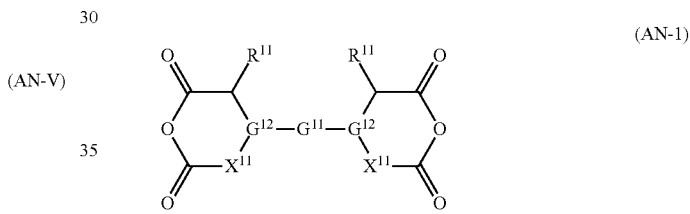

(AN-1)

In the formula (AN-1), G$^{11}$ represents a single bond, an alkylene group having 1 to 12 carbon atoms, a 1,4-phenylene group or a 1,4-cyclohexylene group. X$^{11}$ independently represents a single bond or —CH$_2$—. G$^{12}$ independently represents any of the following trivalent groups.

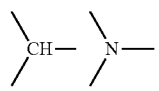

When G$^{12}$ is >CH—, the hydrogen atom of >CH— may be substituted with a methyl group. When G$^{12}$ is >N—, G$^{11}$ is neither a single bond nor —CH$_2$—, and X$^{11}$ is not a single bond. R$^{11}$ represents a hydrogen atom or a methyl group.

Examples of the tetracarboxylic acid dianhydride represented by the formula (AN-1) include compounds of the following formulae.

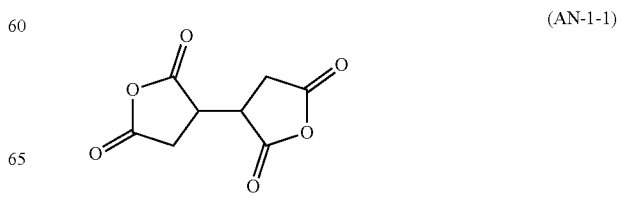

(AN-1-1)

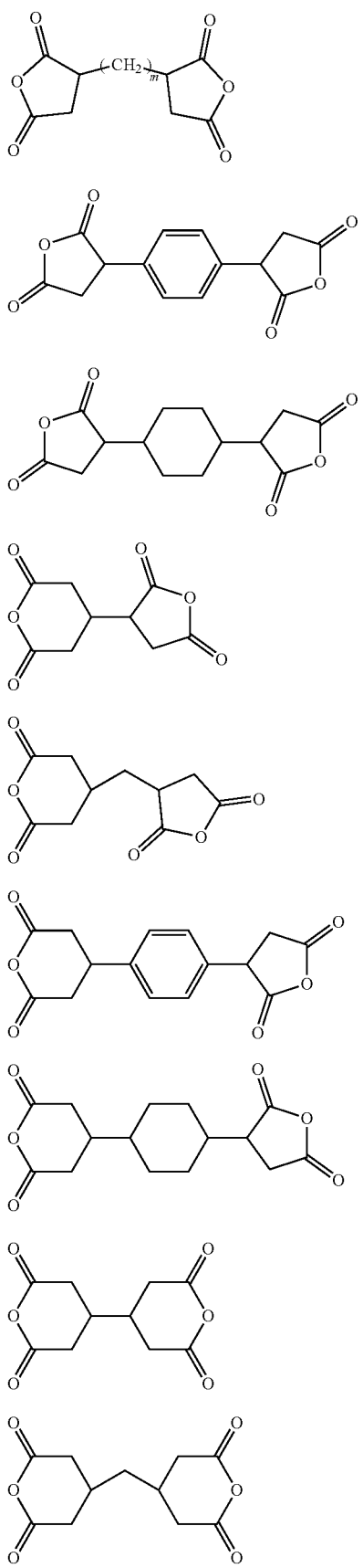

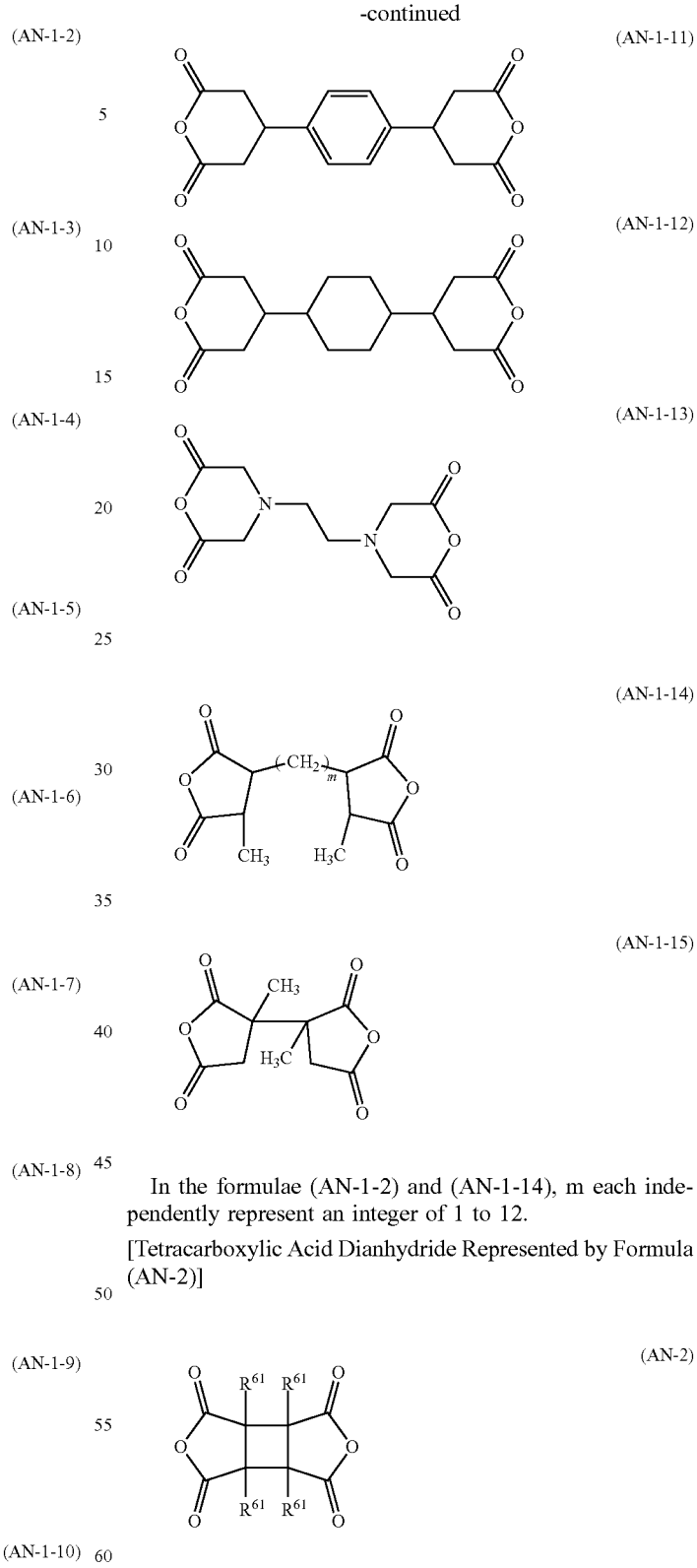

In the formulae (AN-1-2) and (AN-1-14), m each independently represent an integer of 1 to 12.

[Tetracarboxylic Acid Dianhydride Represented by Formula (AN-2)]

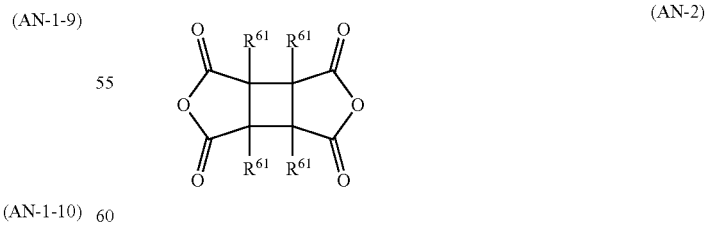

In the formula (AN-2), $R^{61}$ independently represents a hydrogen atom, an alkyl group having 1 to 5 carbon atoms, or a phenyl group.

Examples of the tetracarboxylic acid dianhydride represented by the formula (AN-2) include compounds of the following formulae.

(AN-2-1)

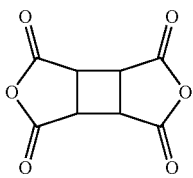

(AN-2-2)

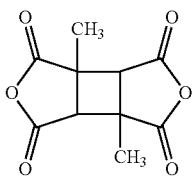

(AN-2-3)

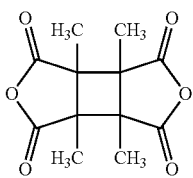

[Tetracarboxylic Acid Dianhydride Represented by Formula (AN-3)]

(AN-3)

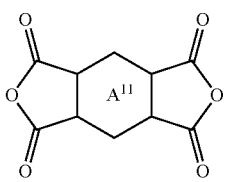

In the formula (AN-3), the ring A" represents a cyclohexane ring or a benzene ring.

Examples of the tetracarboxylic acid dianhydride represented by the formula (AN-3) include compounds of the following formulae.

(AN-3-1)

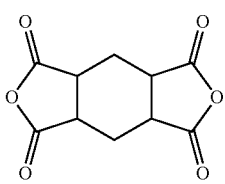

(AN-3-2)

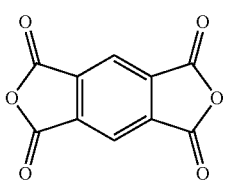

[Tetracarboxylic Acid Dianhydride Represented by Formula (AN-4)]

(AN-4)

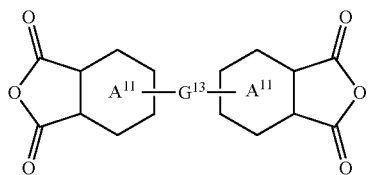

In the formula (AN-4), $G^{13}$ represents a single bond, —(CH$_2$)$_{ma}$—, —O—, —S—, —C(CH$_3$)$_2$—, —SO$_2$—, —CO—, —C(CF$_3$)$_2$—, or a divalent group represented by the following formula (G13-1), and m represents an integer of 1 to 12. The ring $A^{11}$ each independently represents a cyclohexane ring or a benzene ring. $G^{13}$ may bond to any position of the ring $A^{11}$.

(G13-1)

In the formula (G13-1), $G^{13a}$ and $G^{13b}$ each independently represent a single bond, or a divalent group represented by —O—, —CONH—, or —NHCO—. The phenylene group is preferably a 1,4-phenylene group or a 1,3-phenylene group.

Examples of the tetracarboxylic acid dianhydride represented by the formula (AN-4) include compounds represented by the following formulae.

(AN-4-1)

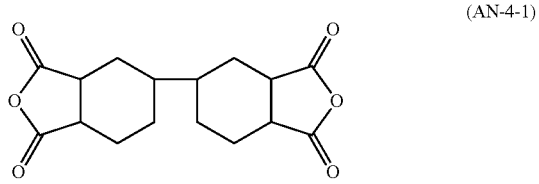

(AN-4-2)

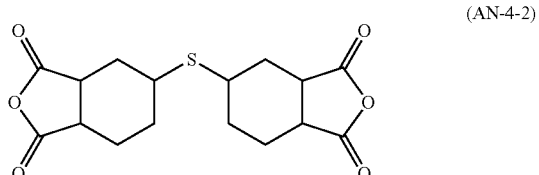

(AN-4-3)

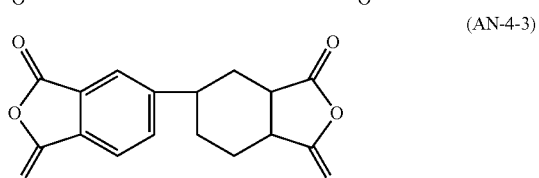

(AN-4-4)

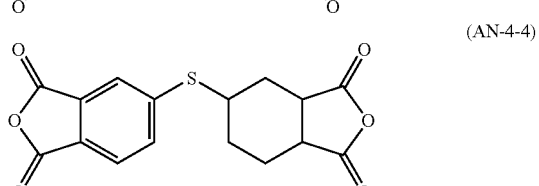

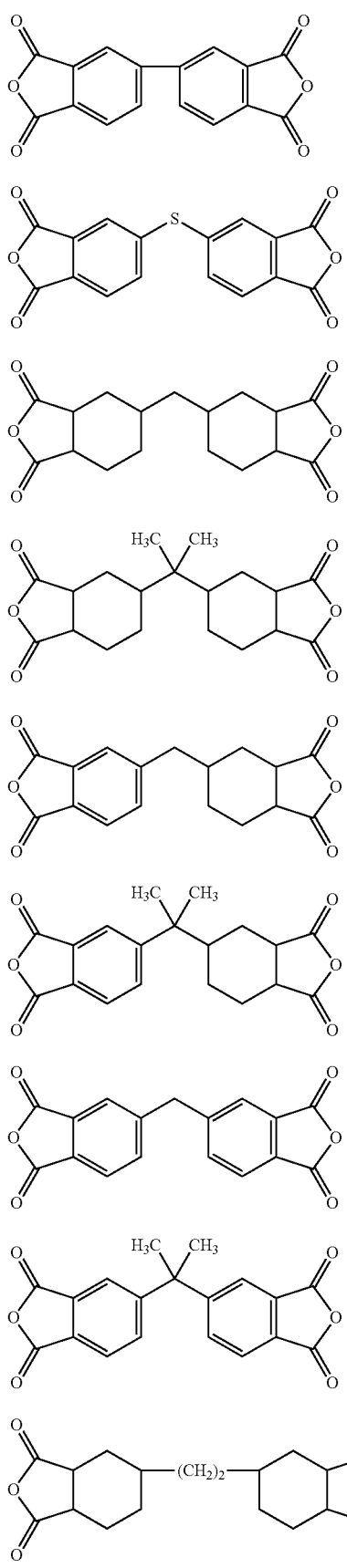
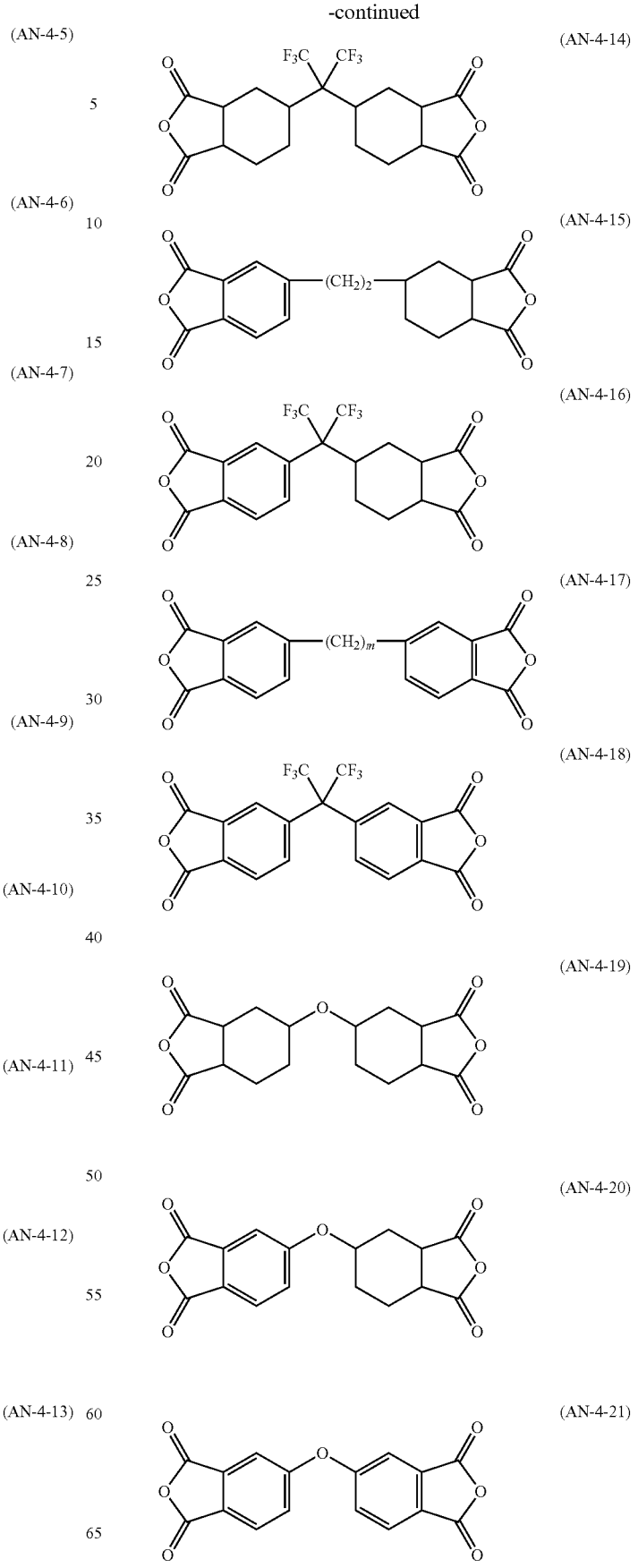

(AN-4-22)
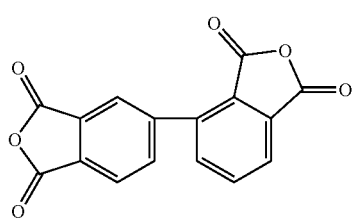

(AN-4-23)
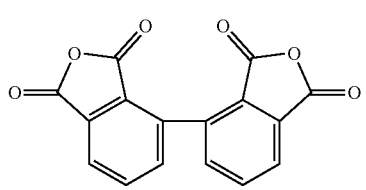

In the formula (AN-4-17), m represents an integer of 1 to 12.

(AN-4-24)
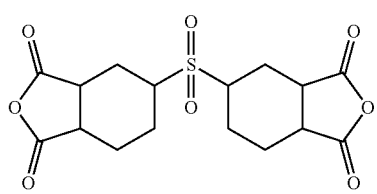

(AN-4-25)
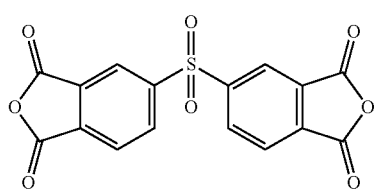

(AN-4-26)
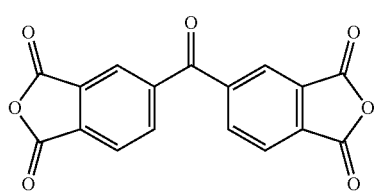

(AN-4-27)
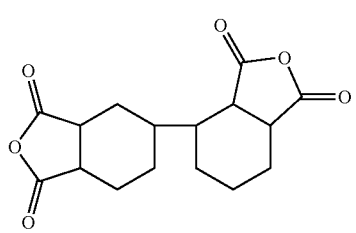

(AN-4-28)
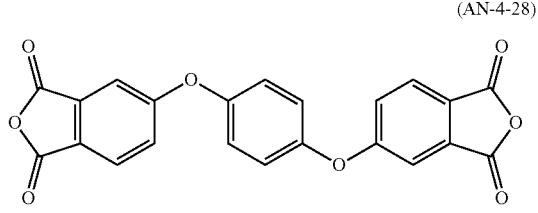

(AN-4-29)
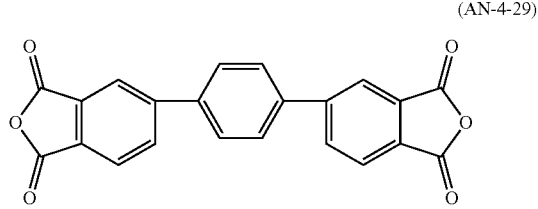

(AN-4-30)

(AN-4-31)

[Tetracarboxylic Acid Dianhydride Represented by Formula (AN-5)]

(AN-5)
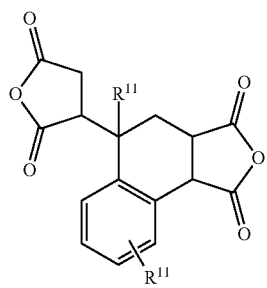

In the formula (AN-5), $R^{11}$ independently represents a hydrogen atom or a methyl group. Of the two $R^{11}$'s, $R^{11}$ at the benzene ring bonds to a substitutable position of the benzene ring.

Examples of the tetracarboxylic acid dianhydride represented by the formula (AN-5) include compounds of the following formulae.

(AN-5-1)
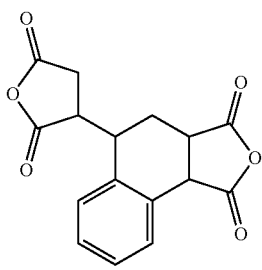

(AN-5-2)
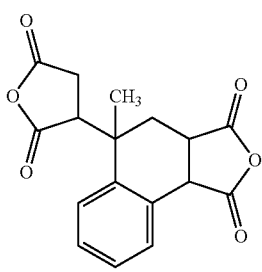

(AN-5-3)
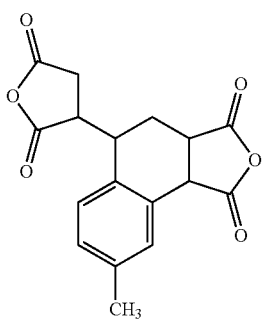

[Tetracarboxylic Acid Dianhydride Represented by Formula (AN-6)]

(AN-6)
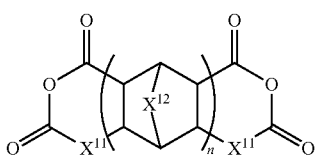

In the formula (AN-6), $X^{11}$ independently represents a single bond or —CH$_2$—. $x^{12}$ represents —CH$_2$—, —CH$_2$CH$_2$— or —CH=CH—. n represents 1 or 2. When n is 2, two $X^{12}$'s may be the same as or different from each other.

Examples of the tetracarboxylic acid dianhydride represented by the formula (AN-6) include compounds of the following formulae.

(AN-6-1)
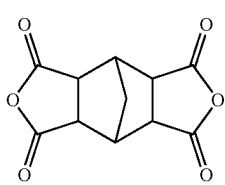

(AN-6-2)
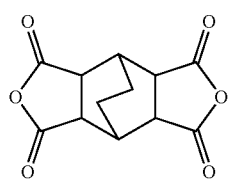

(AN-6-3)
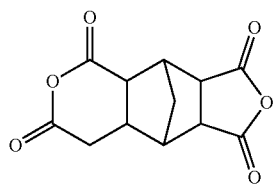

(AN-6-4)
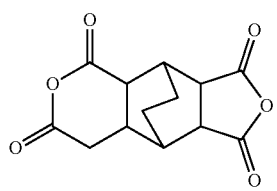

(AN-6-5)
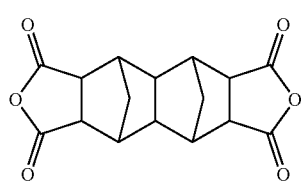

(AN-6-6)
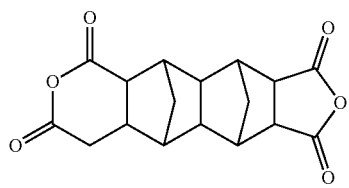

(AN-6-7)
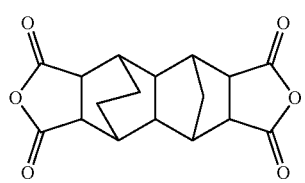

(AN-6-8)
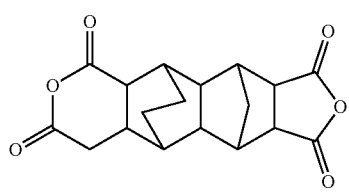

(AN-6-9)
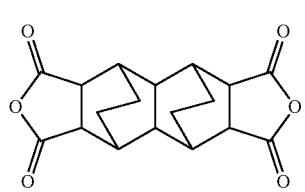

-continued (AN-6-10)
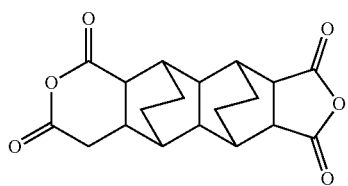

(AN-6-11)
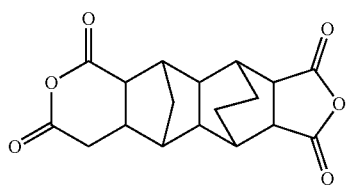

(AN-6-12)
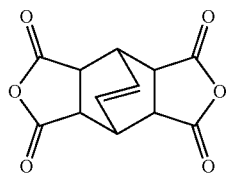

[Tetracarboxylic Acid Dianhydride Represented by Formula (AN-7)]

(AN-7)
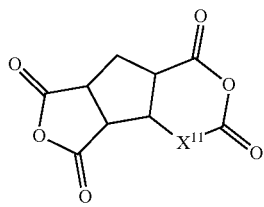

In the formula (AN-7), represents a single bond or —CH$_2$—.

Examples of the tetracarboxylic acid dianhydride represented by the formula (AN-7) include compounds of the following formulae.

(AN-7-1)
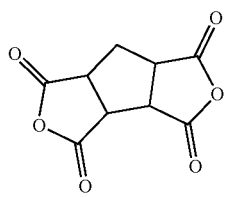

(AN-7-2)
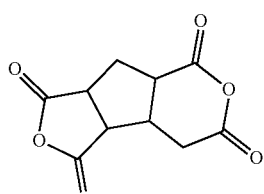

[Tetracarboxylic Acid Dianhydride Represented by Formula (AN-8)]

(AN-8)
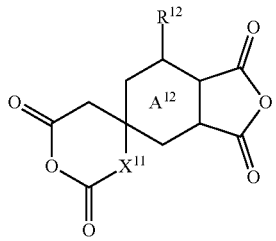

In the formula (AN-8), $X^{11}$ represents a single bond or —CH$_2$—. $R^{12}$ represents a hydrogen atom, a methyl group, an ethyl group or a phenyl group. The ring $A^{11}$ represents a cyclohexane ring or a cyclohexene ring.

Examples of the tetracarboxylic acid dianhydride represented by the formula (AN-8) include compounds of the following formulae.

(AN-8-1)
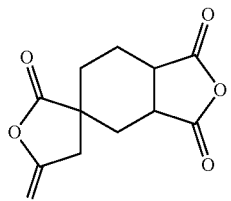

(AN-8-2)
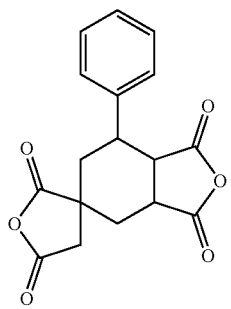

[Tetracarboxylic Acid Dianhydride Represented by Formula (AN-9)]

(AN-9)
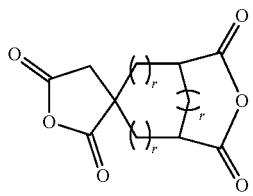

In the formula (AN-9), r each independently represents 0 or 1.

Examples of the tetracarboxylic acid dianhydride represented by the formula (AN-9) include compounds of the following formulae.

(AN-9-1)
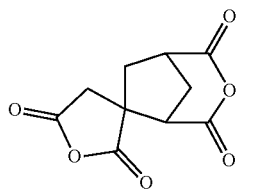

(AN-9-2)
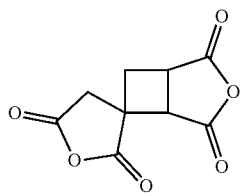

(AN-9-3)
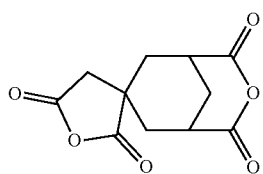

[Tetracarboxylic Acid Dianhydrides Represented by Formulae (AN-10-1) and (AN-10-2)]

(AN-10-1)
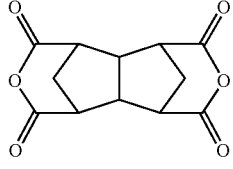

(AN-10-2)
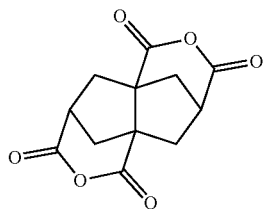

[Tetracarboxylic Acid Dianhydride Represented by Formula (AN-11)]

(AN-11)
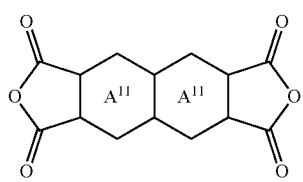

In the formula (AN-11), the ring $A^{11}$ independently represents a cyclohexane ring or a benzene ring.

Examples of the tetracarboxylic acid dianhydride represented by the formula (AN-11) include compounds of the following formulae.

(AN-11-1)
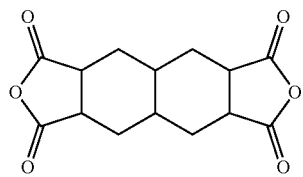

(AN-11-2)
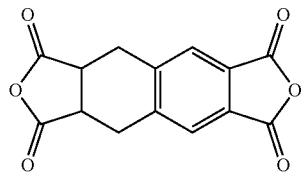

(AN-11-3)
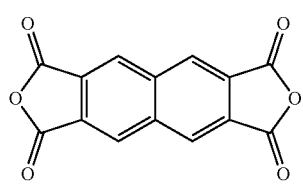

[Tetracarboxylic Acid Dianhydride Represented by Formula (AN-12)]

(AN-12)
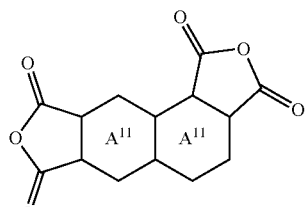

In the formula (AN-12), the ring $A^{11}$ independently represents a cyclohexane ring or a benzene ring.

Examples of the tetracarboxylic acid dianhydride represented by the formula (AN-12) include compounds of the following formulae.

(AN-12-1)
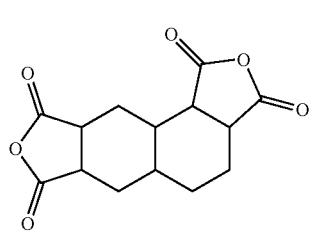

(AN-12-2)
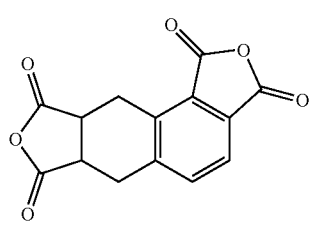

-continued (AN-12-3)

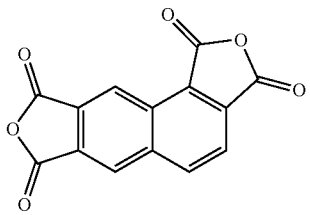

[Tetracarboxylic Acid Dianhydride Represented by Formula (AN-15)]

(AN-15)

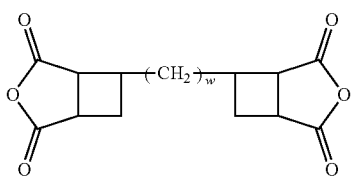

In the formula (AN-15), w represents an integer of 1 to 10.

Examples of the tetracarboxylic acid dianhydride represented by the formula (AN-15) include compounds of the following formulae.

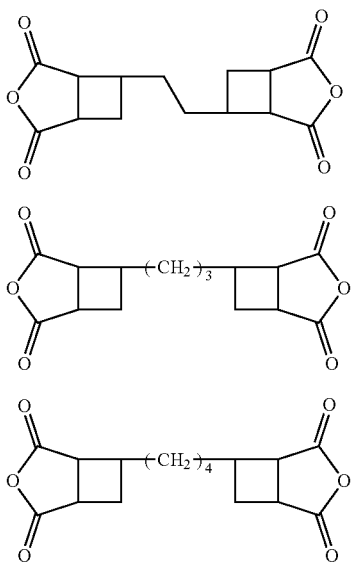

(AN-15-1)

(AN-15-2)

(AN-15-3)

As other tetracarboxylic acid dianhydrides than those mentioned above, the following compounds are mentioned.

(AN-16-1)

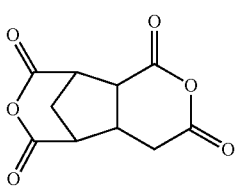

-continued (AN-16-2)

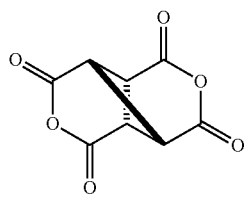

(AN-16-3)

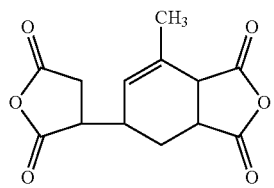

(AN-16-4)

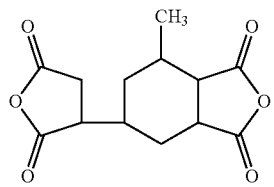

(AN-16-5)

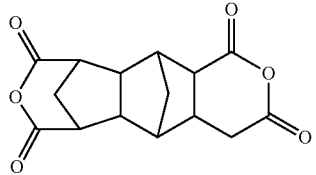

(AN-16-6)

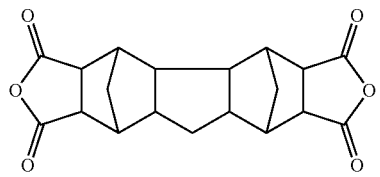

(AN-16-7)

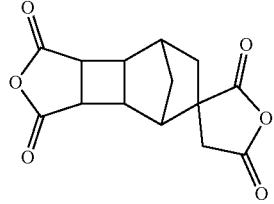

(AN-16-8)

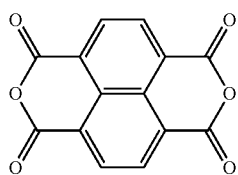

(AN-16-9)

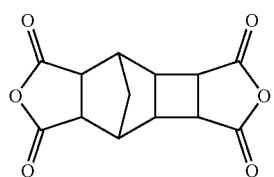

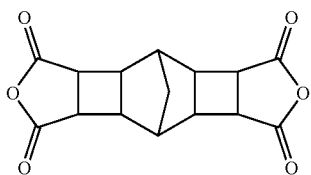
(AN-16-10)

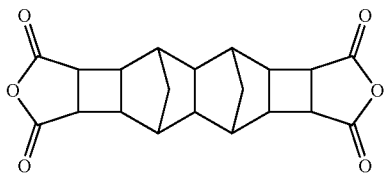
(AN-16-11)

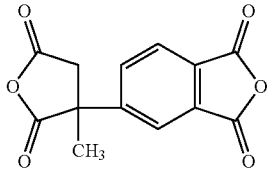
(AN-16-12)

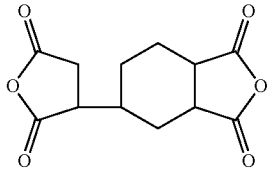
(AN-16-13)

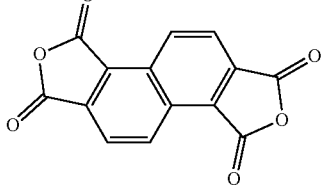
(AN-16-14)

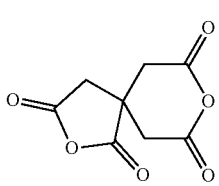
(AN-16-15)

Among the above-mentioned tetracarboxylic acid dianhydrides, those favorable for improving characteristics of liquid crystal alignment films to be formed to be mentioned below are described. In the case where liquid crystal alignment performance is considered to be important, compounds represented by the formulae (AN-1), (AN-3), and (AN-4) are preferred, and compounds represented by the formulae (AN-1-2), (AN-1-13), (AN-3-2), (AN-4-17), and (AN-4-29) are more preferred. In the formula (AN-1-2), preferably m=4 or 8, and in the formula (AN-4-17), preferably m=4 or 8, more preferably m=8.

In the case where improving transmittance of liquid crystal display devices is considered to be important, compounds represented by the formulae (AN-1-1), (AN-1-2), (AN-3-1), (AN-4-17), (AN-4-30), (AN-5-1), (AN-7-2), (AN-10-1), (AN-16-3), (AN-16-4), and (AN-2-1) are preferred, and above all, in the formula (AN-1-1), preferably, m=4 or 8, and in the formula (AN-4-17), preferably m=4 or 8, more preferably m=8.

In the case where improving VHR of liquid crystal display devices is considered to be important, compounds represented by the formulae (AN-1-1), (AN-1-2), (AN-3-1), (AN-4-17), (AN-4-30), (AN-7-2), (AN-10-1), (AN-16-3), (AN-16-4), and (AN-2-1) are preferred, in the formula (AN-1-2), preferably m=4 or 8, and in the formula (AN-4-17), preferably, m=4 or 8, more preferably m=8.

By lowering the volume resistivity of a liquid crystal alignment film, the relaxation rate of the residual charge (residual DC) in the liquid crystal alignment film may be improved, which is effective for a method of preventing seizure. In the case where the object is considered to be important, compounds represented by the formulae (AN-1-13), (AN-3-2), (AN-4-21), (AN-4-29), and (AN-11-3) are preferred.

Other Diamines than the Diamines Represented by Formulae (2) and (10), and Other Monomers The raw material for the polymer of the present invention may contain any other diamine than the two diamines, the diamine presented by the formula (2) and the diamine represented by the formula (10), and any other monomer. Examples of the other monomer include dihydrazides. With that, a structural unit derived from such monomers may be introduced into the polymer to control the properties of the polymer.

The other diamines than the two diamines, the diamine represented by the formula (2) and the diamine represented by the formula (10), and the dihydrazides may be selected from known diamines and dihydrazides with no specific limitation.

Diamines may be grouped into two types depending on the structure thereof. Specifically, when a skeleton bonding two amino groups is taken as a main chain, diamines may be grouped into two, one is a diamine having a group branching from the main chain, namely, having a side chain group, and the other is a diamine not having such a side chain group. In the following description, a diamine having such a side chain group may be referred to as a side chain-type diamine. A diamine not having such a side chain group may be referred to a non-side chain-type diamine. The side chain group is a group having an effect of enlarging a pretilt angle.

Suitably differentiating and using the non-side chain-type diamine and the side chain-type diamine, a polymer capable of satisfying a necessary pretilt angle can be produced.

Preferably, a side chain-type diamine is used in such a degree that the diamine would not detract from the advantageous effects of the present invention. Preferably, the side chain-type diamine and the non-side chain-type are suitably selected and used for the purpose of improving vertical alignment performance, VHR, seizure resistance and alignment performance for liquid crystals.

Known diamines and dihydrazides are shown below.

(DI-1)

(DI-2)

(DI-3)

(DI-4)

[Structure: H2N-(phenyl)-(CH2)s-(phenyl with CH2)s-NH2]

(DI-5)

[Structure: H2N-(phenyl)-G33-(phenyl)-NH2]

(DI-6)

[Structure: H2N-(phenyl)-G21-(phenyl)-G22-(phenyl)-NH2]

(DI-7)

[Structure: H2N-(phenyl)-G22-(phenyl)-G21-(phenyl)-G22-(phenyl)-NH2]

In the above formula (DI-1), $G^{20}$ represents —$CH_2$— or a group represented by the following formula (DI-1-a). When $G^{20}$ is —$CH_2$—, at least one of m (—$CH_2$—)'s may be substituted with —NH— or —O—, and at least one hydrogen atom in m (—$CH_2$—)'s may be substituted with a hydroxyl group or a methyl group. m represents an integer of 1 to 12. In DI-1 where m is 2 or more, plural $G^{20}$'s may be the same as or different from each other. However, when $G^{20}$ is a group represented by the formula (DI-1-a), m is 1.

(DI-1-a)

[Structure: piperazine with (CH2)v groups]

In the formula (DI-1-a), v each independently represents an integer of 1 to 6.

In the formulae (DI-3), (DI-6) and (DI-7), $G^{21}$ independently represents a single bond, —NH—, —$NCH_3$—, —O—, —S—, —S—S—, —$SO_2$—, —CO—, —COO—, —$CONCH_3$—, —CONH—, —$C(CH_3)_2$—, —$C(CF_3)_2$—, —$(CH_2)_m$—, —O—$(CH_2)_m$—O—, —$N(CH_3)$—$(CH_2)_k$—$N(CH_3)$—, —$(O—C_2H_4)_m$—O—, —O—$CH_2$—$C(CF_3)_2$—$CH_2$—O—, —O—$(CH_2)_m$—O—CO—$(CH_2)_m$—CO—O—, —CO—O—$(CH_2)_m$—O—CO—, —$(CH_2)_m$—NH—$(CH_2)_m$—, —CO—$(CH_2)_k$—NH—$(CH_2)_k$—, —(NH—$(CH_2)_m)_k$—NH—, —CO—$C_3H_6$—(NH—$C_3H_6)_n$—CO—, or —S—$(CH_2)_m$—S—; m independently represents an integer of 1 to 12, k represents an integer of 1 to 5, n represents 1 or 2. In the formula (DI-4), s independently represents an integer of 0 to 2.

In the formula (DI-5), $G^{33}$ represents a single bond, —NH—, —$NCH_3$—, —O—, —S—, —S—S—, —$SO_2$—, —CO—, —COO—, —$CONCH_3$—, —CONH—, —$C(CH_3)_2$—, —$C(CF_3)_2$—, —$(CH_2)_m$—, —O—$(CH_2)_m$—O—, —$N(CH_3)$—$(CH_2)_k$—$N(CH_3)$—, —$(O—C_2H_4)_m$—O—, —O—$CH_2$—$C(CF_3)_2$—$CH_2$—O—, —O—CO—$(CH_2)_m$—CO—O—, —CO—O—$(CH_2)_m$—O—CO—, —$(CH_2)_m$—NH—$(CH_2)_m$—, —CO—$(CH_2)_k$—NH—$(CH_2)_k$—, —(NH—$(CH_2)_m)_k$—NH—, —CO—$C_3H_6$—(NH—$C_3H_6)_n$—CO—, or —S—$(CH_2)_m$—S—, —N(Boc)-$(CH_2)_e$—N(Boc)-, —NH—$(CH_2)_e$—N(Boc)-, —N(Boc)-$(CH_2)_e$—, —$(CH_2)_m$—N(Boc)-CONH—$(CH_2)_m$—, —$(CH_2)_m$—N(Boc)-$(CH_2)_m$—, or a group represented by the following (DI-5-a) or (DI-5-b), m independently represents an integer of 1 to 12, k represents an integer of 1 to 5, e represents an integer of 2 to 10, and n represents 1 or 2. Boc represents a t-butoxycarbonyl group.

In the formulae (DI-6) and (DI-7), $G^{22}$ independently represents a single bond, —O—, —S—, —CO—, —$C(CH_3)_2$—, —$C(CF_3)_2$—, or an alkylene group having 1 to 10 carbon atoms.

At least one hydrogen atom of the cyclohexane ring and the benzene ring in the formulae (DI-2) to (DI-7) may be substituted with —F, —Cl, an alkylene group having 1 to 3 carbon atoms, —$OCH_3$, —OH, —$CF_3$, —$CO_2H$, —$CONH_2$, —$NHC_6H_5$, a phenyl group or a benzyl group, and in addition, in the formula (DI-4), at least one hydrogen atom of the cyclohexane ring and the benzene ring may be substituted with one selected from the groups of the following formulae (DI-4-a) to (DI-4-i). In the formula (DI-5) where $G^{33}$ is a single bond, at least one hydrogen atom of the cyclohexane ring and the benzene ring may be substituted with NHBoc or N(Boc)$_2$.

Regarding the group whose bonding position to the ring carbon atom is not fixed, the bonding position of the group to the ring is any arbitrary one. The bonding position of —$NH_2$ to the cyclohexane ring or the benzene ring is any other position than the bonding position of $G^{21}$, $G^{22}$ or $G^{33}$ to the ring.

(DI-4-a)

[Structure with OH, OH, and acetyl-N-R20]

(DI-4-b)

[Structure with HO, OH, OH and acetyl-N-R20]

(DI-4-c)

[Structure: HO-CH2CH2-N(-CH2CH2-OH)-C(=O)-CH=]

(DI-4-d)

[Structure: diallyl amine with N-methyl]

(DI-4-e)

[Structure: H3C-CH2-N(-CH2-CH3)-N-methyl]

(DI-4-f)

[Structure: Boc-NH-(CH2)m-]

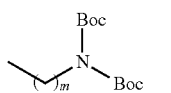 (DI-4-g)

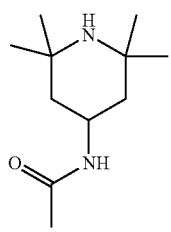 (DI-4-h)

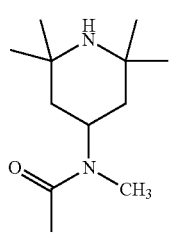 (DI-4-i)

In the formulae (DI-4-a) and (DI-4-b), $R^{20}$ independently represents a hydrogen atom or —$CH_3$. In the formulae (DI-4-f) and (DI-4-g), m each independently represents an integer of 0 to 12. Boc represents a t-butoxycarbonyl group.

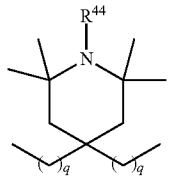 (DI-5-a)

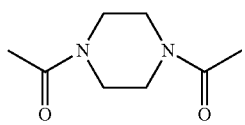 (DI-5-b)

In the formula (DI-5-a), q each independently represents an integer of 0 to 6. $R^{44}$ represents a hydrogen atom, —OH, an alkyl group having 1 to 6 carbon atoms, or an alkoxy group having 1 to 6 carbon atoms.

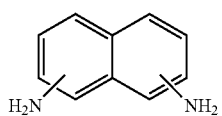 (DI-8)

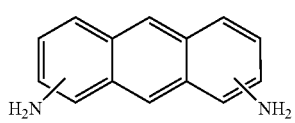 (DI-9)

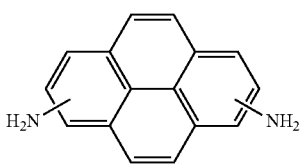 (DI-10)

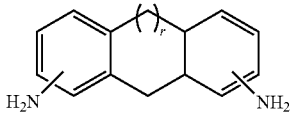 (DI-11)

In the formula (DI-11), r represents 0 or 1. In the formulae (DI-8) to (DI-11), the bonding position of —$NH_2$ bonding to the ring is any arbitrary position.

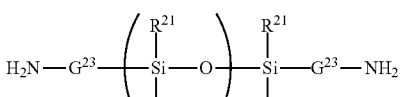 (DI-12)

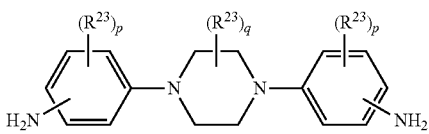 (DI-13)

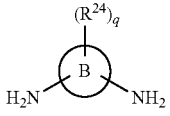 (DI-14)

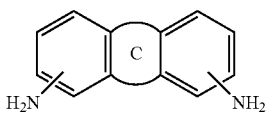 (DI-15)

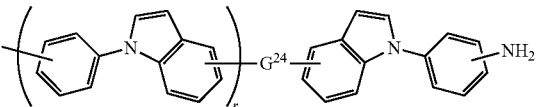 (DI-16)

In the formula (DI-12), $R^{21}$ and $R^{22}$ each independently represent an alkyl group having 1 to 3 carbon atoms, or a phenyl group, $G^{23}$ independently represent an alkylene group having 1 to 6 carbon atoms, a phenylene group, or a phenylene group substituted with an alkyl group, and w represents an integer of 1 to 10.

In the formula (DI-13), $R^{23}$ independently represents an alkyl group having 1 to 5 carbon atoms, an alkoxy group having 1 to 5 carbon atoms, or —CL, p independently represents an integer of 0 to 3, and q represents an integer of 0 to 4.

In the formula (DI-14), the ring B represents a monocyclic heterocyclic aromatic group, $R^{24}$ represents a hydrogen atom, —F, —Cl, or an alkyl, alkoxy, alkenyl or alkynyl group having 1 to 6 carbon atoms, and q independently represents an integer of 0 to 4. When q is 2 or more, plural $R^{24}$'s may be the same as or different from each other. In the formula (DI-15), the ring C represents a heterocyclic aromatic group or a heterocyclic aliphatic group. In the formula (DI-16), $G^{24}$ represents a single bond, an alkylene group having 2 to 6 carbon atoms, or a 1,4-phenylene group, and r represents 0 or 1. The group whose bonding position to the ring carbon atom is not fixed means that the bonding position thereof to the ring is any arbitrary one. In the formulae (DI-3) to (DI-16), the bonding position of —NH$_2$ to the ring is an arbitrary position.

Specific examples of the diamine not having a side chain of the above-mentioned formulae (DI-1) to (DI-16) include the following formulae (DI-1-1) to (DI-16-1).

Examples of the diamine of the formula (DI-1) are shown below.

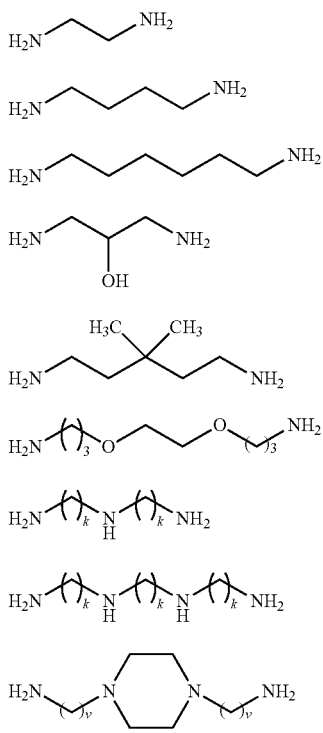

In the formulae (DI-1-7) and (DI-1-8), k each independently represents an integer of 1 to 3. In the formula (DI-1-9), v each independently represents an integer of 1 to 6.

Examples of the diamines of the formulae (DI-2) to (DI-3) are shown below.

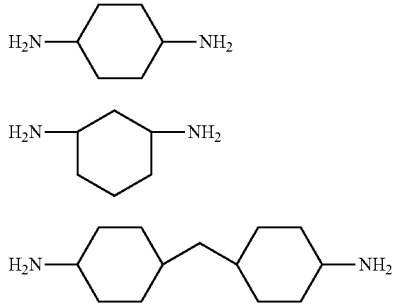

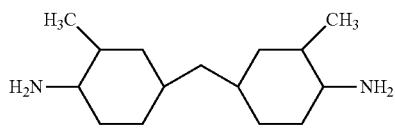

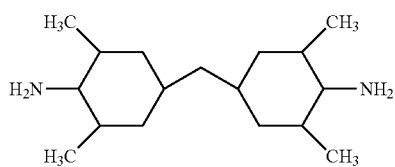

Examples of the diamine of the formula (DI-4) are shown below.

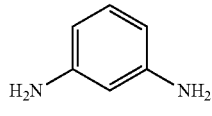

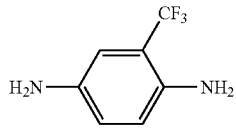

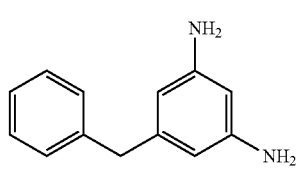

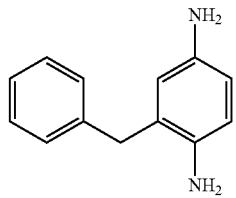

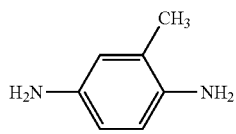

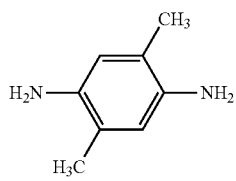

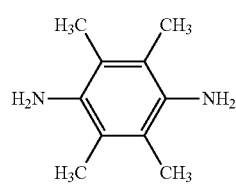 (DI-4-8)
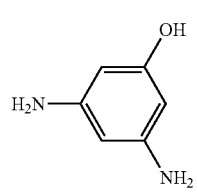 (DI-4-9)
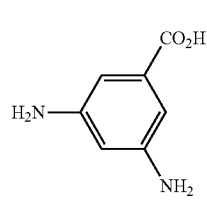 (DI-4-10)
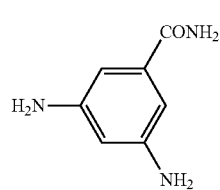 (DI-4-11)
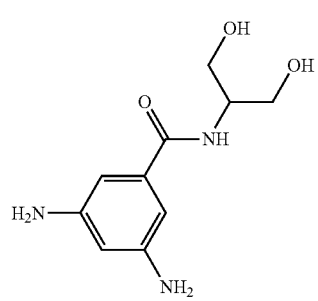 (DI-4-12)
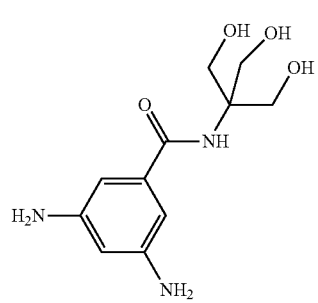 (DI-4-13)
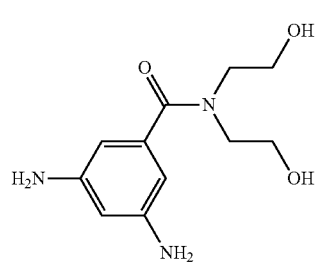 (DI-4-14)
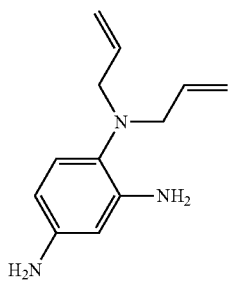 (DI-4-15)
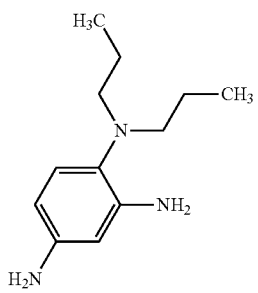 (DI-4-16)
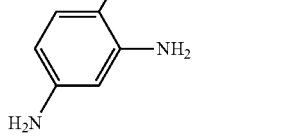 (DI-4-17)
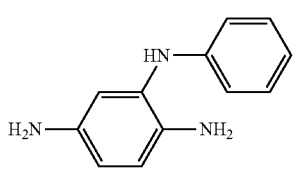 (DI-4-18)
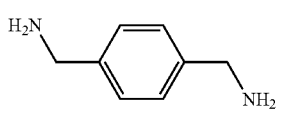 (DI-4-19)
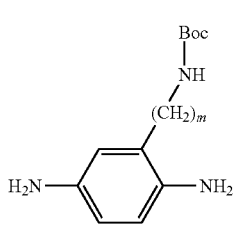 (DI-4-20)
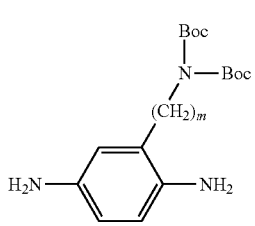 (DI-4-21)
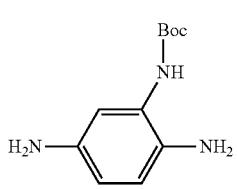 (DI-4-26)

(DI-4-27)
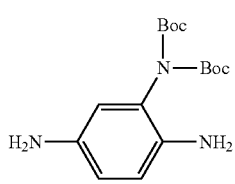
In the formulae (DI-4-20) and (DI-4-21), m each independently represents an integer of 1 to 12.
(DI-4-22)
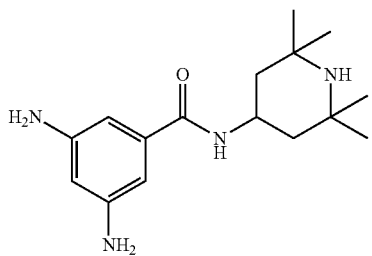
(DI-4-23)
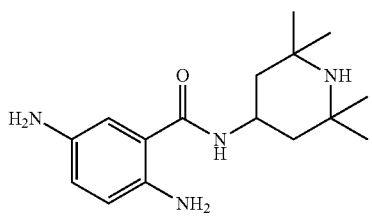
(DI-4-24)
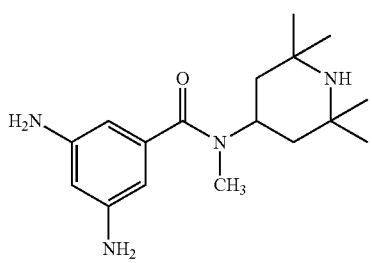
(DI-4-25)
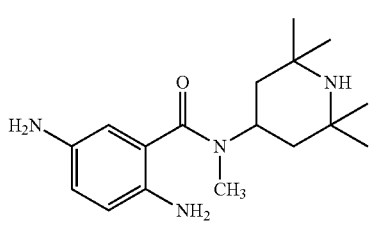
Examples of the diamine of the formula (DI-5) are shown below.
(DI-5-1)
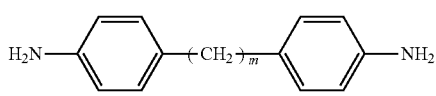
(DI-5-2)
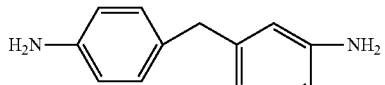
(DI-5-3)
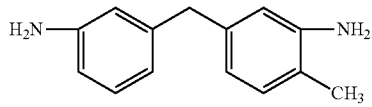
(DI-5-4)
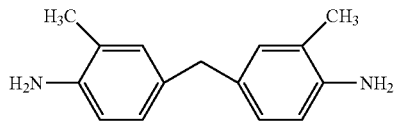
(DI-5-5)
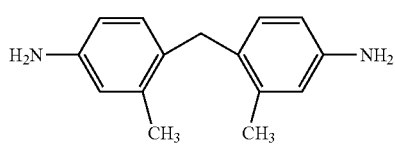
(DI-5-6)
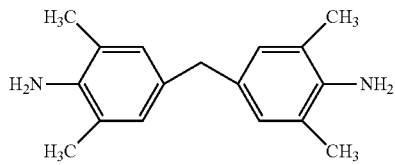
(DI-5-7)
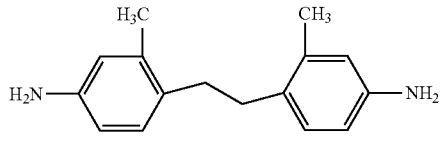
(DI-5-8)
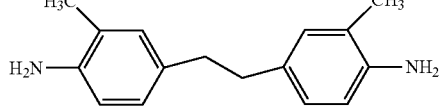
In the formula (DI-5-1), m represents an integer of 1 to 12.
(DI-5-9)
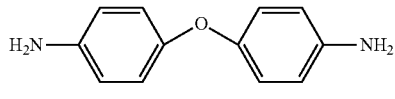
(DI-5-10)
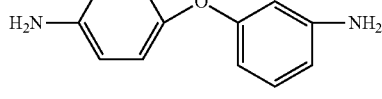
(DI-5-11)
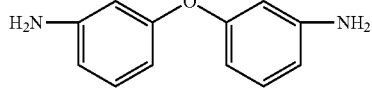
(DI-5-12)
(DI-5-13)
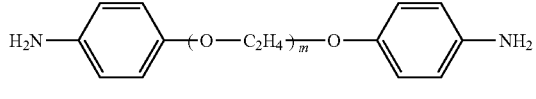
In the formulae (DI-5-12) and (DI-5-13), m each independently represents an integer of 1 to 12.

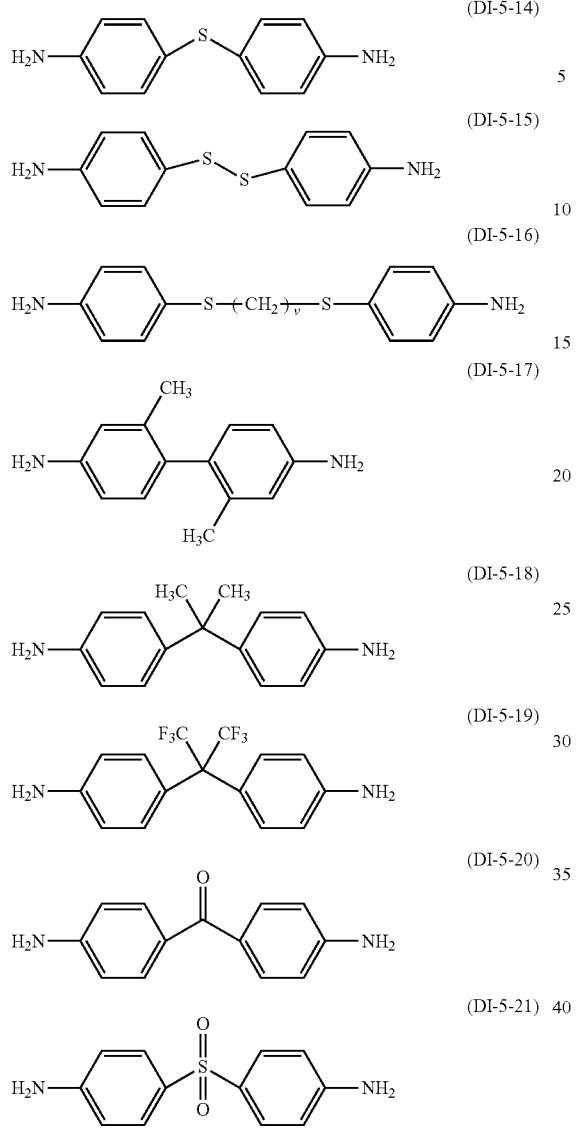
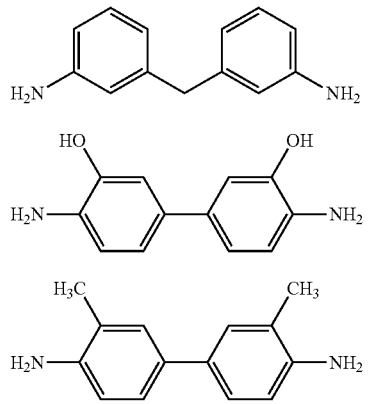
In the formula (DI-5-16), v represents an integer of 1 to 6.
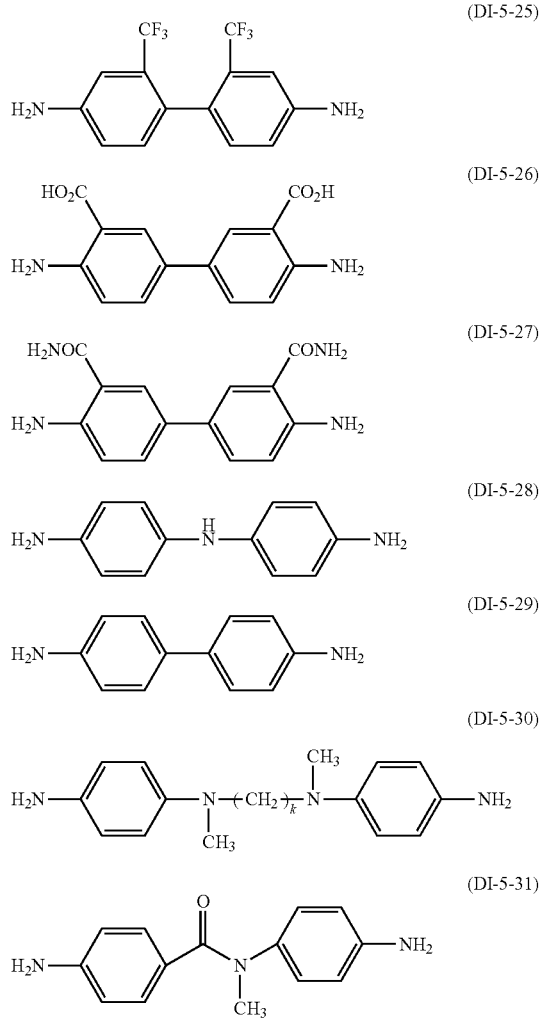
In the formula (DI-5-30), k represents an integer of 1 to 5.
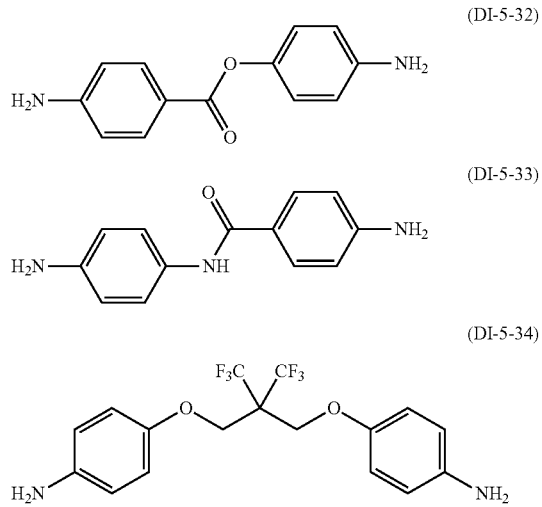

(DI-5-35)
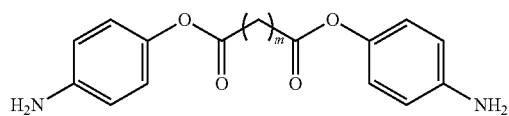

(DI-5-36)
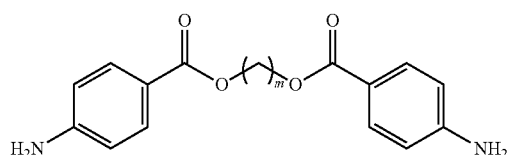

(DI-5-37)
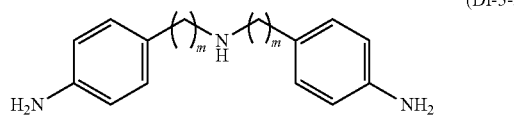

(DI-5-38)
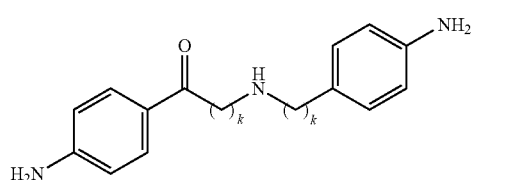

(DI-5-39)
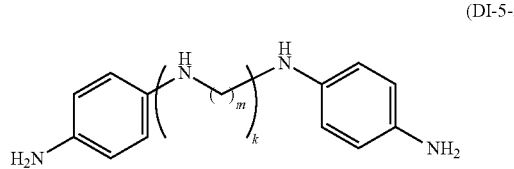

(DI-5-40)
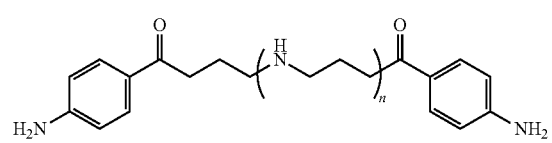

(DI-5-41)
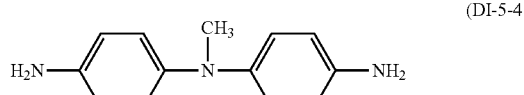

In the formulae (DI-5-35) to (DI-5-37), and (DI-5-39), m each independently represents an integer of 1 to 12, in the formulae (DI-5-38) and (DI-5-39), k each independently represents an integer of 1 to 5, and in the formula (DI-5-40), n represents an integer of 1 or 2.

(DI-5-42)
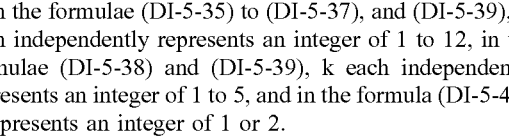

(DI-5-43)
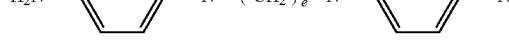

(DI-5-44)
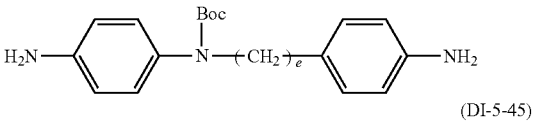

(DI-5-45)
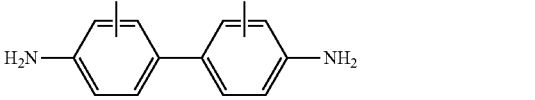

In the formulae (DI-5-42) to (DI-5-44), e each independently represents an integer of 2 to 10, and in the formula (DI-5-45), $R^{43}$ represents a hydrogen atom, —NHBoc, or —N(Boc)$_2$. In the formulae (DI-5-42) to (DI-5-44), Boc represents a t-butoxycarbonyl group.

(DI-5-46)
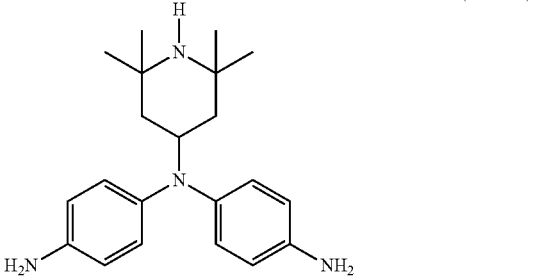

(DI-5-47)
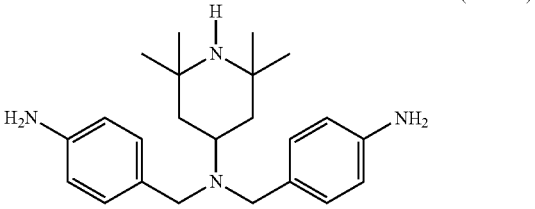

(DI-5-48)
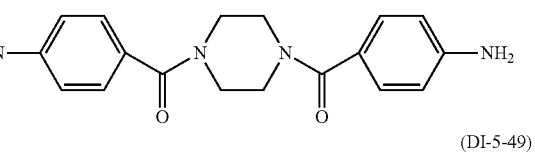

(DI-5-49)
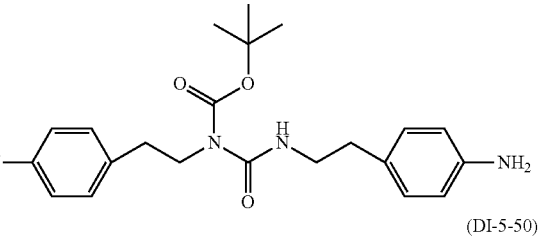

(DI-5-50)
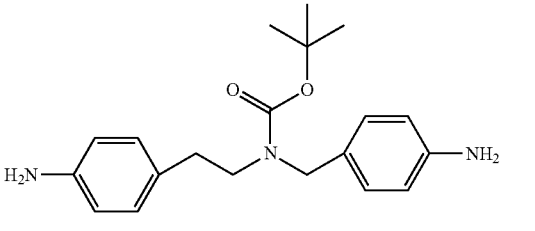

Examples of the diamine of the formula (DI-6) are shown below.
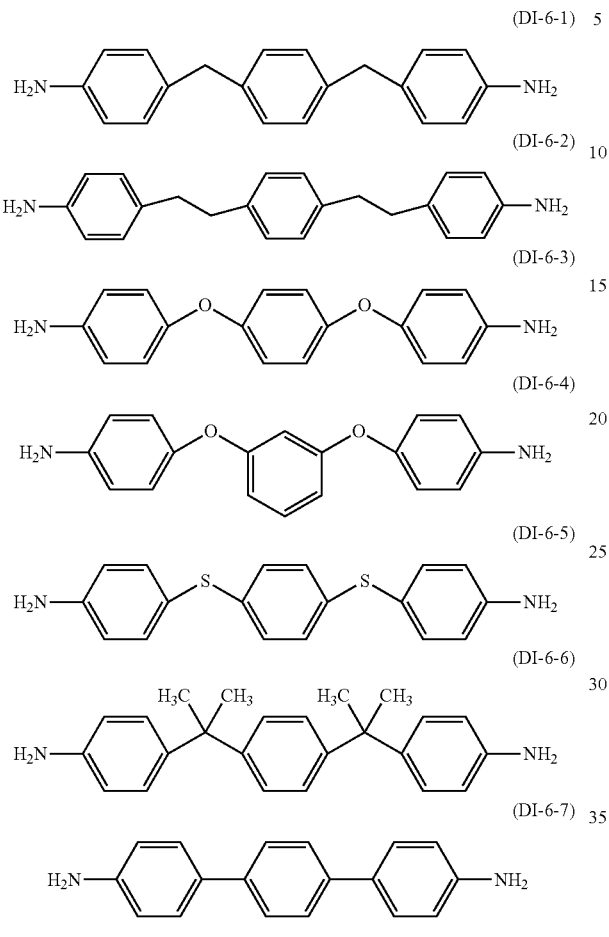
Examples of the diamine of the formula (DI-7) are shown below.
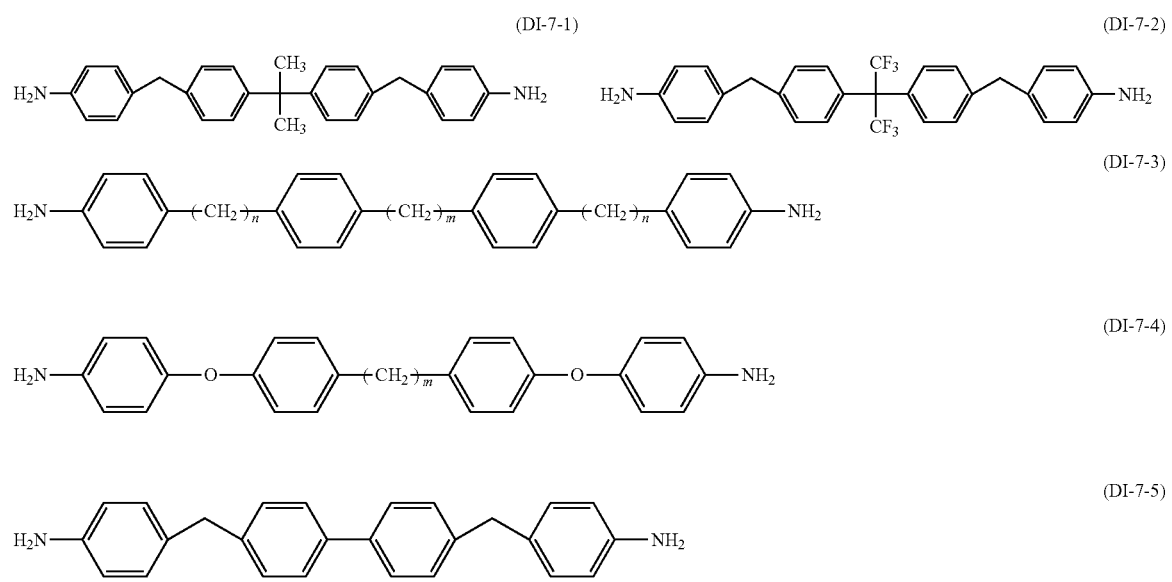

In the formulae (DI-7-3) and (DI-7-4), m each independently represents an integer of 1 to 12, and n independently represents 1 or 2.

(DI-7-6)
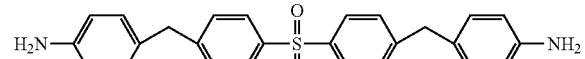

(DI-7-7)
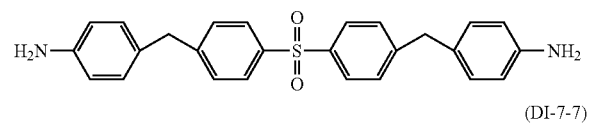

(DI-7-8)
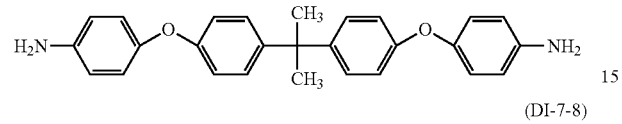

(DI-7-9)
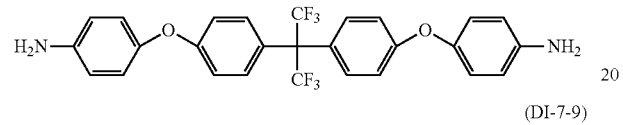

(DI-7-10)
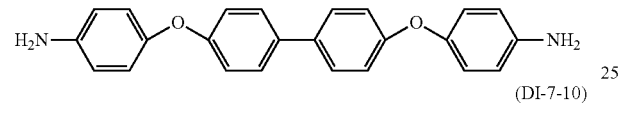

(DI-7-11)
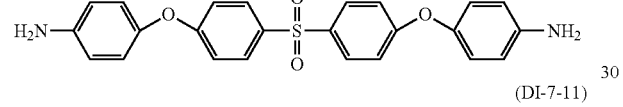

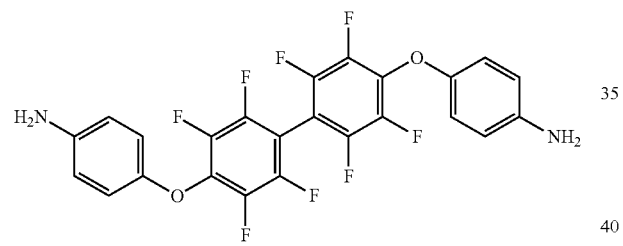

Examples of the diamine of the formula (DI-8) are shown below.

(DI-8-1)

(DI-8-2)
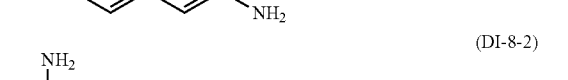

(DI-8-3)

(DI-8-4)
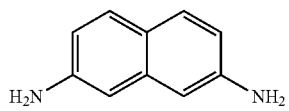

Examples of the diamine of the formula (DI-9) are shown below.

(DI-9-1)
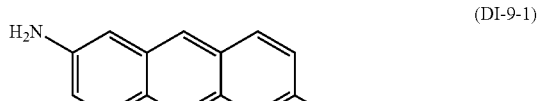

(DI-9-2)

(DI-9-3)
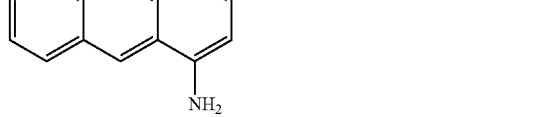

Examples of the diamine of the formula (DI-10) are shown below.

(DI-10-1)
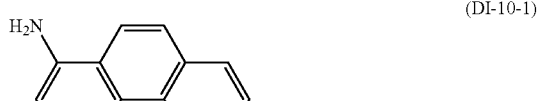

(DI-10-2)
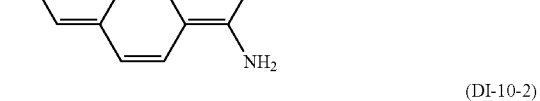

Examples of the diamine of the formula (DI-11) are shown below.

(DI-11-1)

(DI-11-2)
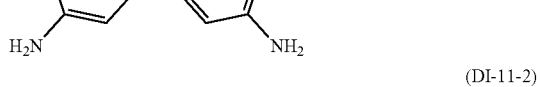

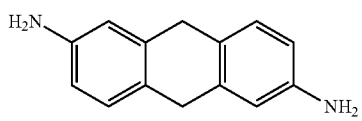
(DI-11-3)
An example of the diamine of the formula (DI-12) is shown below.
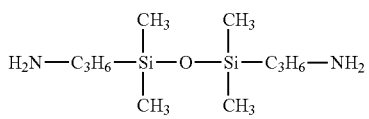
(DI-12-1)
Examples of the diamine of the formula (DI-13) are shown below.
(DI-13-1)
(DI-13-2)
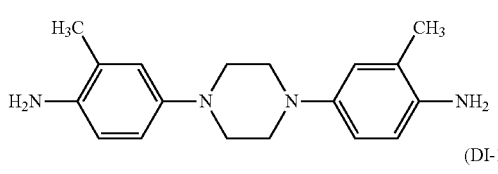
(DI-13-3)
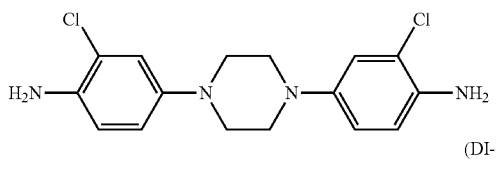
(DI-13-4)
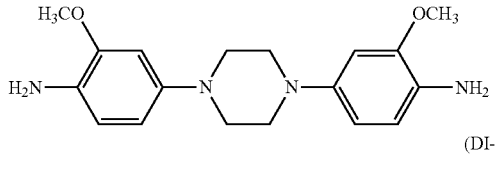
(DI-13-5)
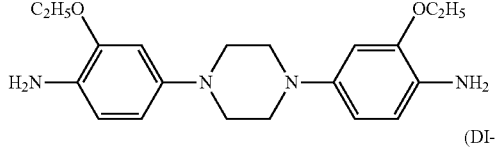
(DI-13-6)
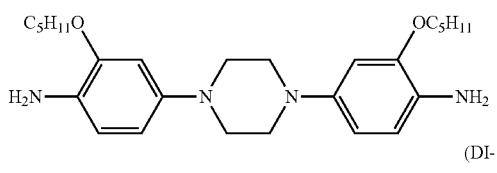
(DI-13-7)
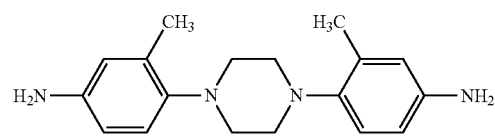
(DI-13-8)
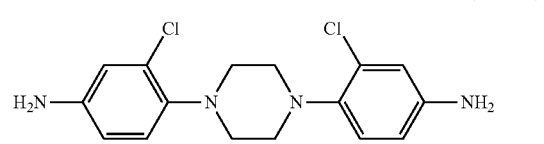
(DI-13-9)
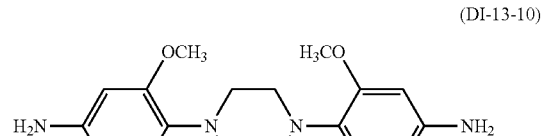
(DI-13-10)
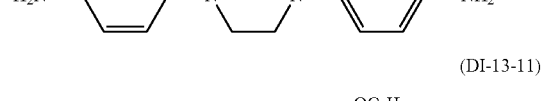
(DI-13-11)
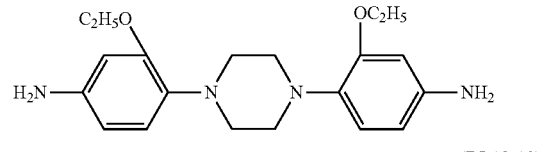
(DI-13-12)
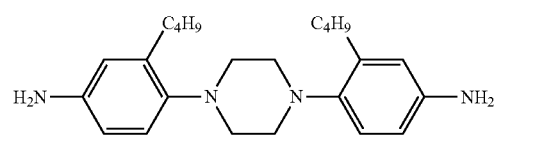
(DI-13-13)
Examples of the diamine of the formula (DI-14) are shown below.
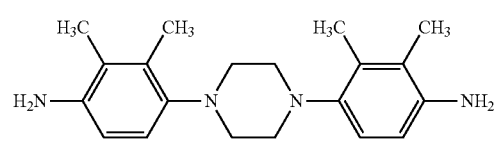
(DI-14-1)
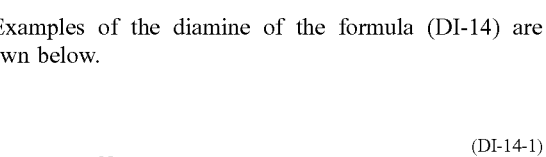
(DI-14-2)
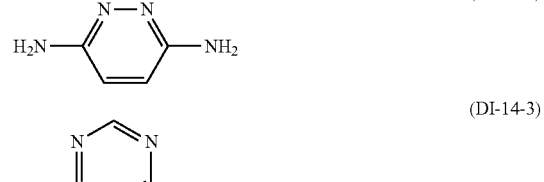
(DI-14-3)
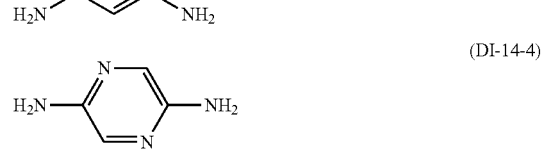
(DI-14-4)

Examples of the diamine of the formula (DI-15) are shown below.

An example of the diamine of the formula (DI-16) is shown below.

Next, dihydrazides to be used as a raw material for the polymer of the present invention are described. As known dihydrazides not having a side chain, compounds represented by the following formulae (DIH-1) to (DIH-3) are mentioned.

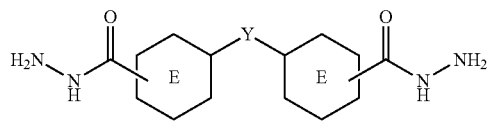
(DIH-3)

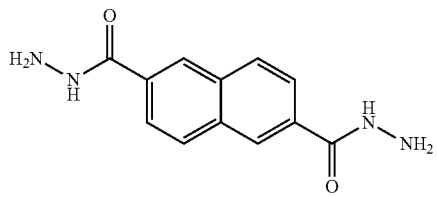
(DIH-2-3)

In the formula (DIH-1), $G^{25}$ represents a single bond, an alkylene group having 1 to 20 carbon atoms, —CO—, —O—, —S—, —SO$_2$—, —C(CH$_3$)$_2$—, or —C(CF$_3$)$_2$—.

In the formula (DIH-2), the ring D represents a cyclohexane ring, a benzene ring or a naphthalene ring, and at least one hydrogen atom of the ring may be substituted with a methyl group, an ethyl group or a phenyl group. In the formula (DIH-3), the ring each independently represents a cyclohexane ring or a benzene ring, and at least one hydrogen atom of the ring may be substituted with a methyl group, an ethyl group or a phenyl group. Plural E's may be the same as or different from each other. Y represents a single bond, an alkylene group having 1 to 20 carbon atoms, —CO—, —O—, —S—, —SO$_2$—, —C(CH$_3$)$_2$—, or —C(CF$_3$)$_2$—. In the formulae (DIH-2) and (DIH-3), the bonding position of —CONHNH$_2$ bonding to the ring may be any arbitrary position.

Examples of the compounds represented by the formulae (DIH-1) to (DIH-3) are mentioned below.

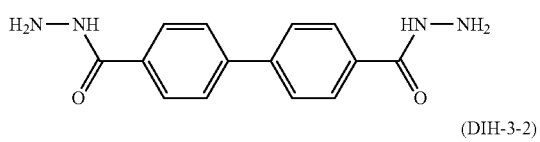
(DIH-3-1)

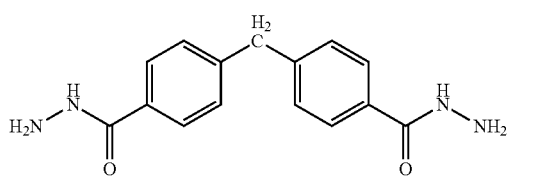
(DIH-3-2)

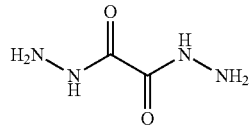
(DIH-1-1)

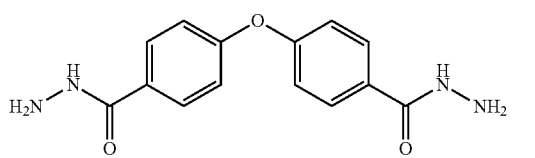
(DIH-3-3)

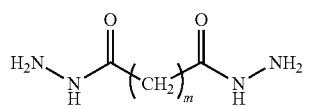
(DIH-1-2)

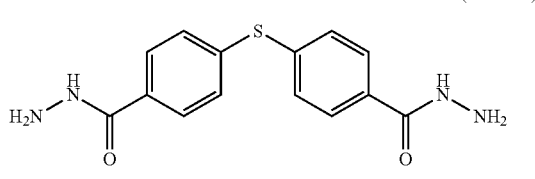
(DIH-3-4)

In the formula (DIH-1-2), m represents an integer of 1 to 12.

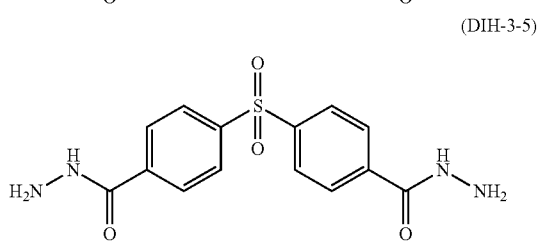
(DIH-3-5)

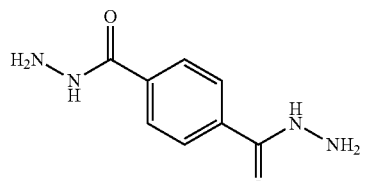
(DIH-2-1)

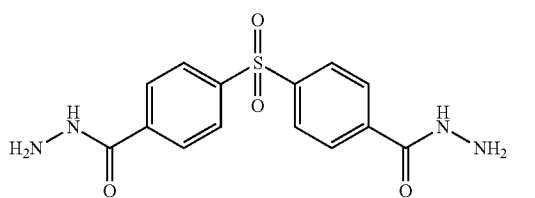
(DIH-3-6)

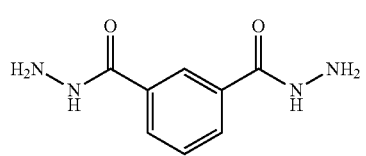
(DIH-2-2)

The above-mentioned diamines and dihydrazides have an effect of improving electric properties of, for example, lowering the ionic density of liquid crystal display devices.

Diamines suitable for enlarging a pretilt angle are described. As diamines having a side chain group suitable for the purpose of enlarging a pretilt angle, there are mentioned diamines represented by the following formulae (DI-31) to (DI-35) and formulae (DI-36-1) to (DI-36-8).

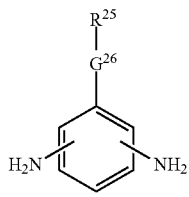

(DI-31)

In the formula (DI-31), $G^{26}$ represents a single bond, —O—, —COO—, —OCO—, —CO—, —CONH—, —CH$_2$O—, —OCH$_2$—, —OCF$_2$—, or —(CH$_2$)$_{ma}$—, and ma represents an integer of 1 to 12. Preferred examples of $G^{26}$ include a single bond, —O—, —OCO—, —CH$_2$O—, and an alkylene group having 1 to 3 carbon atoms, and especially preferred examples thereof include a single bond, —O—, —OCO—, —OCO—, —CH$_2$O—, —CH$_2$— and —CH$_2$CH$_2$—. $R^{25}$ represents an alkyl group having 3 to 30 carbon atoms, a phenyl group, a group having a steroid skeleton, or a group represented by the following formula (DI-31-1). In the alkyl group, at least one hydrogen atom may be substituted with —F, and at least one —CH$_2$— may be substituted with —O—, —CH=CH— or The hydrogen atom of the phenyl group may be substituted with —F, —CH$_3$, —OCH$_3$, —OCH$_2$F, —OCHF$_2$, —OCF$_3$, an alkyl group having 3 to 30 carbon atoms, or an alkoxy group having 3 to 30 carbon atoms. The bonding position of —NH$_2$ bonding to the benzene ring may be any arbitrary position in the ring, but the bonding position is preferably a meta-position or a para-position. Specifically, when the bonding position of the group $R^{25}$-$G^{26}$- is a 1-position, the two bonding positions are preferably 3- and 5-positions, or 2- and 5-positions.

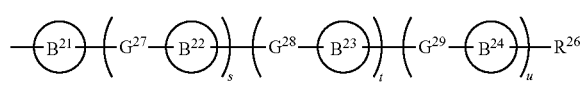

(DI-31-a)

In the formula (DI-31-a), $G^{27}$, $G^{28}$ and $G^{29}$ each represent a bonding group, and these are each independently a single bond, or an alkylene group having 1 to 12 carbon atoms, and one or more (—CH$_2$—)'s of the alkylene group may be substituted with —O—, —OCO—, —CONH—, or —CH=CH—. The ring $B^{21}$, the ring $B^{22}$, the ring $B^{23}$ and the ring $B^{24}$ each independently represent a 1,4-phenylene group, a 1,4-cyclohexylene group, a 1,3-dioxane-2,5-diyl group, a pyrimidine-2,5-diyl group, a pyridine-2,5-diyl group, a naphthalene-1,5-diyl group, a naphthalene-2,7-diyl group or an anthracene-9,10-diyl group, in the ring $B^{21}$, the ring $B^{22}$, the ring $B^{23}$ and the ring $B^{24}$, at least one hydrogen atom may be substituted with —F or —CH$_3$, s, t and u each independently represent an integer of 0 o 2, and the total of these is 1 to 5, when s, t or u is 2, two parenthesized bonding groups may be the same as or different from each other, and the two rings may be the same as or different from each other. $R^{26}$ represents a hydrogen atom, —F, —OH, an alkyl group having 1 to 30 carbon atom, a fluorine-substituted alkyl group having 1 to 30 carbon atoms, an alkoxy group having 1 to 30 carbon atoms, —CN, —OCH$_2$F, —OCHF$_2$, or —OCF$_3$, and at least one —CH$_2$— of the alkyl group having 1 to 30 carbon atoms may be substituted with a divalent group represented by the following formula (DI-31-b).

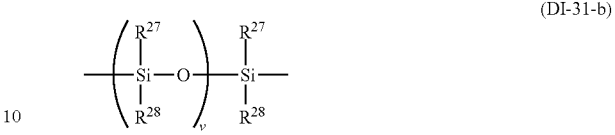

(DI-31-b)

In the formula (DI-31-b), $R^{27}$ and $R^{28}$ each independently represent an alkyl group having 1 to 3 carbon atoms, v represents an integer of 1 to 6. Preferred examples of $R^{26}$ are an alkyl group having 1 to 30 carbon atoms and an alkoxy group having 1 to 30 carbon atoms.

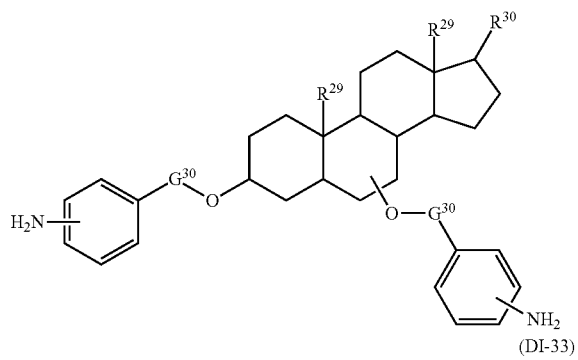

(DI-32)

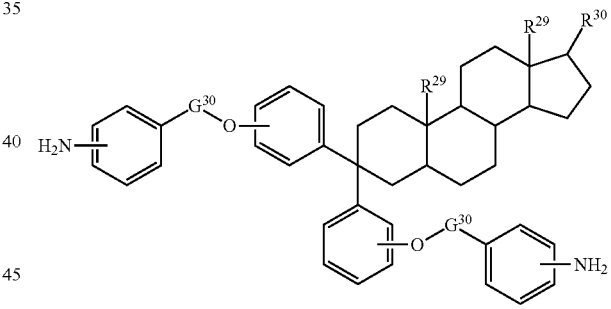

(DI-33)

In the formulae (DI-32) and (DI-33), $G^{30}$ independently represents a single bond, —CO— or —CH$_2$—, $R^{30}$ independently represents a hydrogen atom, an alkyl group having 1 to 20 carbon atoms, or an alkenyl group having 2 to 20 carbon atoms. At least one hydrogen atom of the benzene ring in the formula (DI-33) may be substituted with an alkyl group having 1 to 20 carbon atoms, or a phenyl group. The bonding position of the group not fixed to any hydrogen atom constituting the ring means that the bonding position thereof may be any arbitrary one. Preferably, one of the two (-phenylene-$G^{30}$-O—)'s in the formula (DI-32) bonds to the 3-position of the steroid nucleus and the other bonds to the 6-position of the steroid nucleus. Preferably, the bonding positions of the two (-phenylene-$G^{30}$-O—)'s in the formula (DI-33) are a meta-position and a para-position to the steroid nucleus. In the formula (DI-32) and the formula (DI-33), the bonding position of —NH$_2$ bonding to the benzene ring is an arbitrary position of the ring.

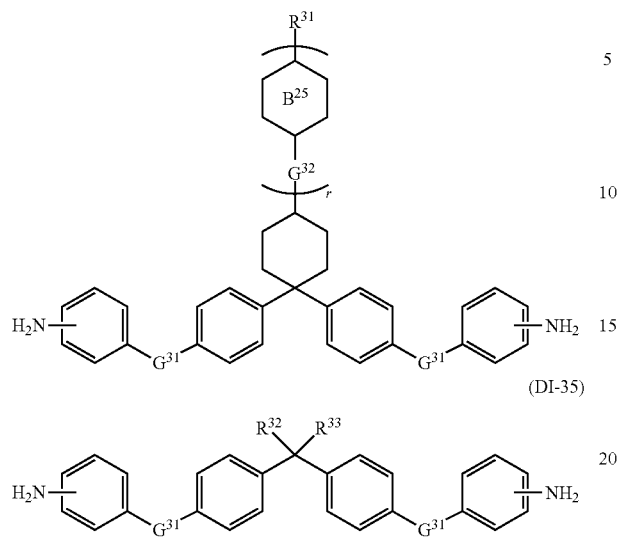

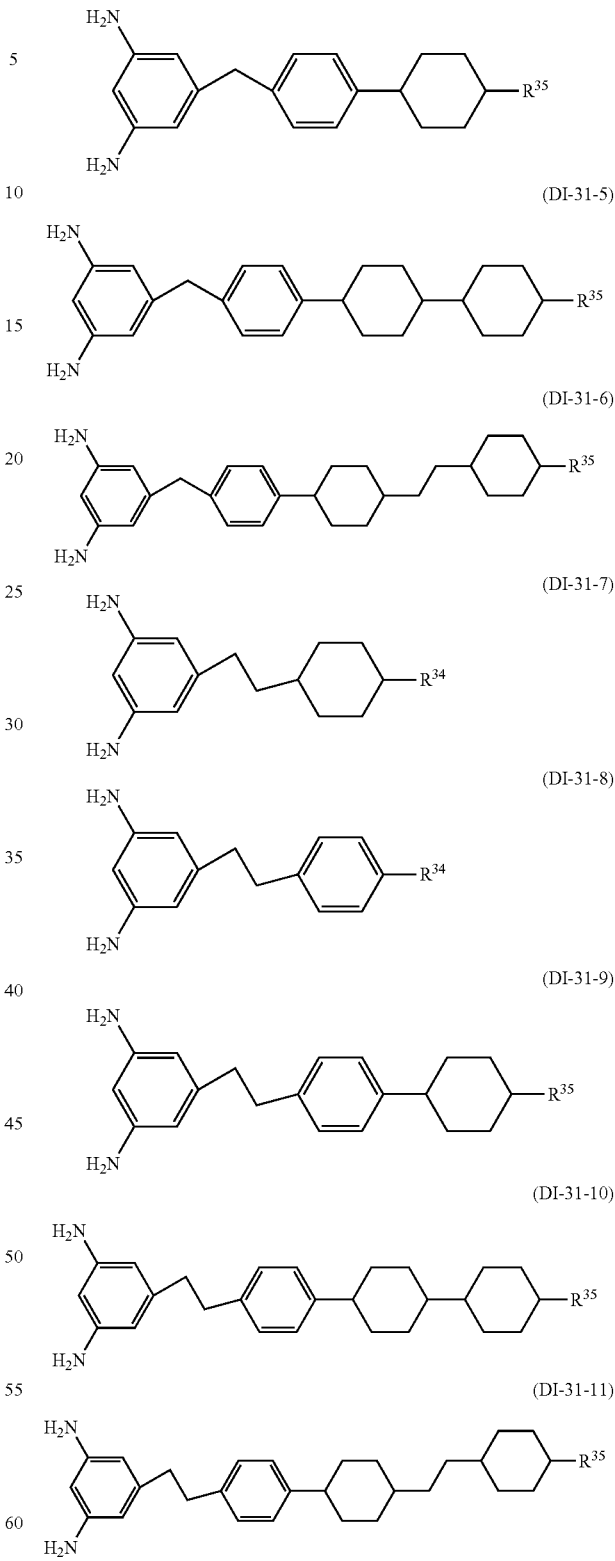

In the formulae (DI-34) and (DI-35), $G^{31}$ independently represents —O— or an alkylene group having 1 to 6 carbon atoms, $G^{32}$ represents a single bond or an alkylene group having 1 to 3 carbon atoms. $R^{31}$ represents a hydrogen atom, or an alkyl group having 1 to 20 carbon atoms, and at least one —CH$_2$— of the alkyl group may be substituted with —O—, —CH=CH— or $R^{32}$ represents an alkyl group having 6 to 22 carbon atoms, $R^{33}$ represents a hydrogen atom or an alkyl group having 1 to 22 carbon atoms. The ring $B^{25}$ represents a 1,4-phenylene group or a 1,4-cyclohexylene group, and r represents 0 or 1. The bonding position of —NH$_2$ bonding to the benzene ring is an arbitrary position, but is preferably independently a meta-position or a para-position relative to the bonding position of $G^{31}$.

Examples of the compound of the formula (DI-31) are shown below.

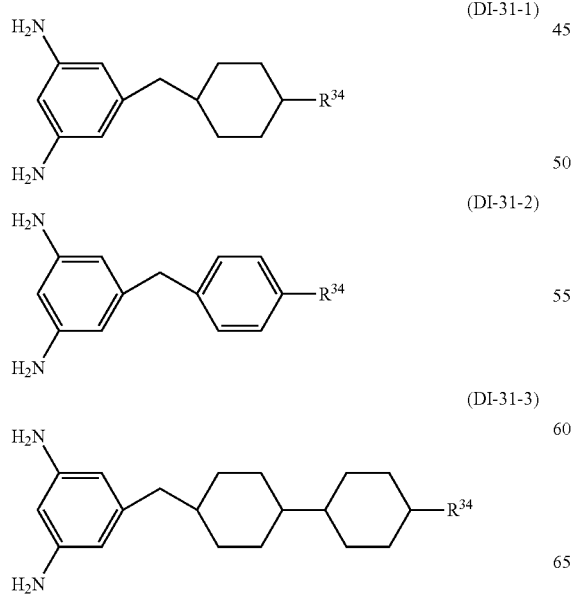

In the formulae (DI-31-1) to (DI-31-11), $R^{34}$ each independently represent an alkyl group having 1 to 30 carbon atoms or an alkoxy group having 1 to 30 carbon atoms, preferably an alkyl group having 5 to 25 carbon atoms or an alkoxy group having 5 to 25 carbon atoms. $R^{35}$ each independently represents an alkyl group having 1 to 30 carbon atoms or an alkoxy group having 1 to 30 carbon atoms, preferably an alkyl group having 3 to 25 carbon atoms or an alkoxy group having 3 to 25 carbon atoms.

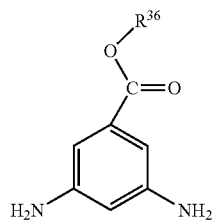
(DI-31-12)

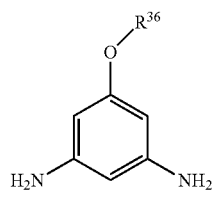
(DI-31-13)

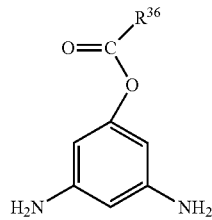
(DI-31-14)

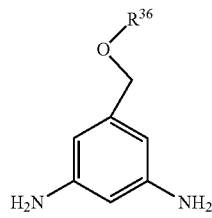
(DI-31-15)

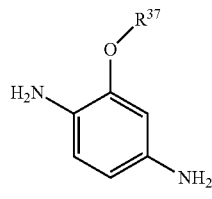
(DI-31-16)

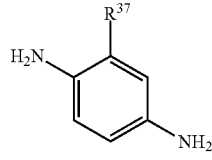
(DI-31-17)

In the formulae (DI-31-12) to (DI-31-17), $R^{36}$ each independently represents an alkyl group having 4 to 30 carbon atoms, preferably an alkyl group having 6 to 25 carbon atoms. $R^{37}$ each independently represents an alkyl group having 6 to 30 carbon atoms, preferably an alkyl group having 8 to 25 carbon atoms.

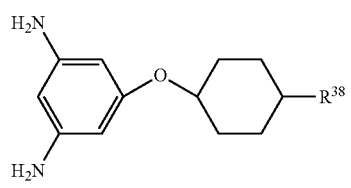
(DI-31-18)

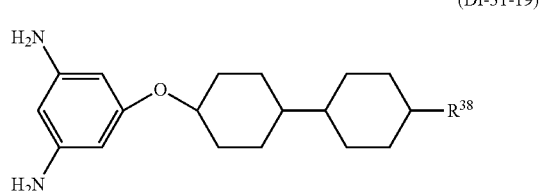
(DI-31-19)

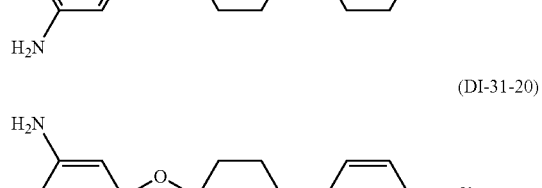
(DI-31-20)

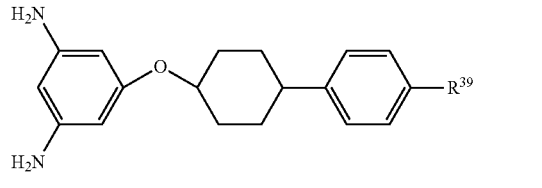
(DI-31-21)

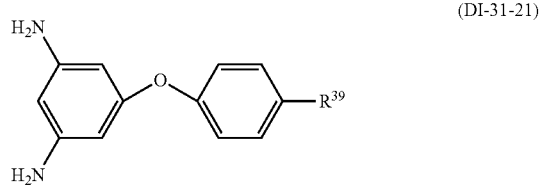
(DI-31-22)

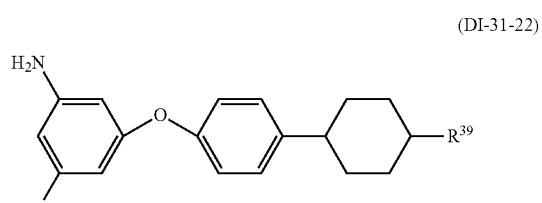
(DI-31-23)

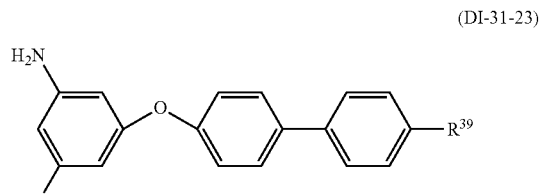
(DI-31-24)

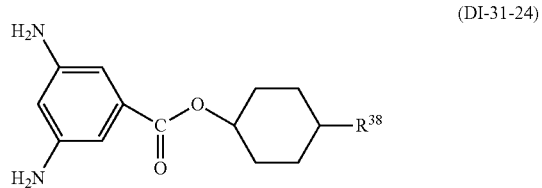
(DI-31-25)

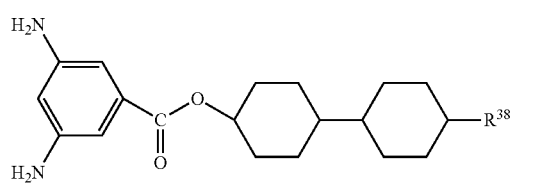

-continued
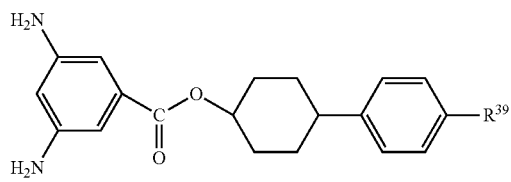
(DI-31-26)
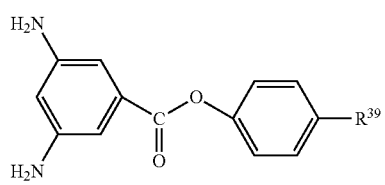
(DI-31-27)
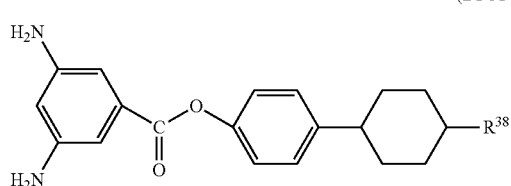
(DI-31-28)
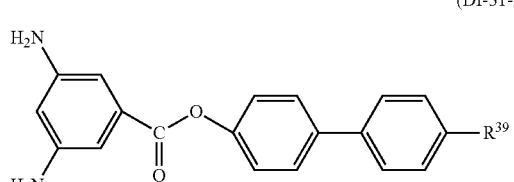
(DI-31-29)
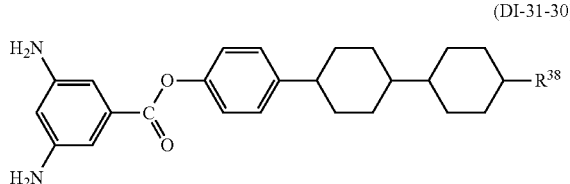
(DI-31-30)
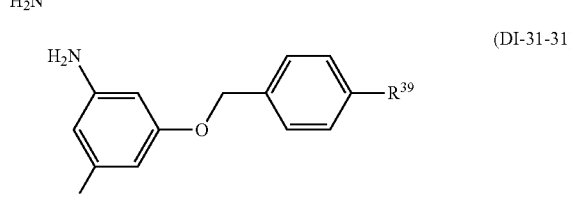
(DI-31-31)
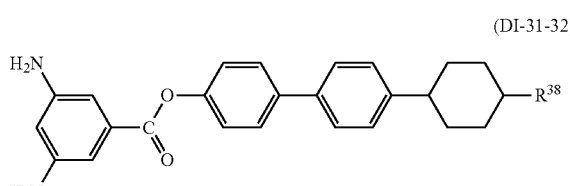
(DI-31-32)
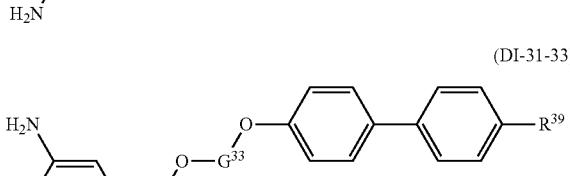
(DI-31-33)
-continued
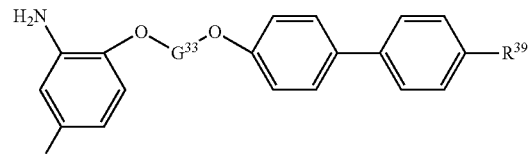
(DI-31-34)
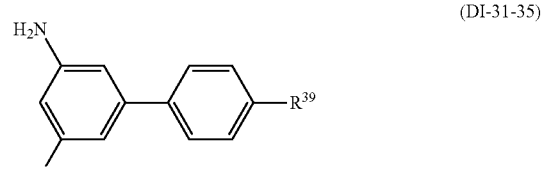
(DI-31-35)
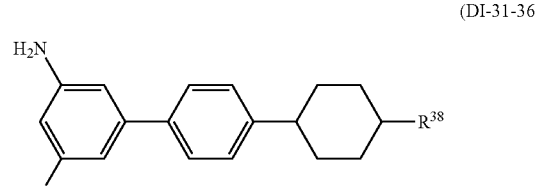
(DI-31-36)
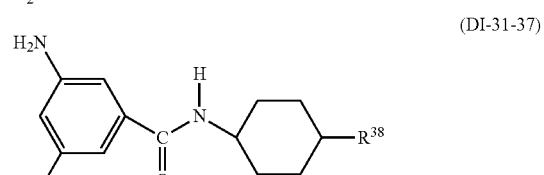
(DI-31-37)
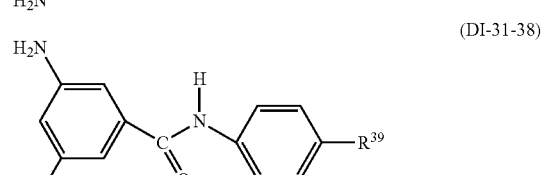
(DI-31-38)
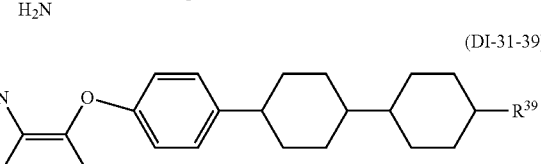
(DI-31-39)
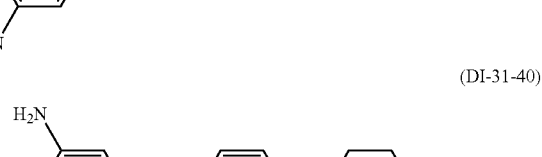
(DI-31-40)
(DI-31-41)

(DI-31-42)

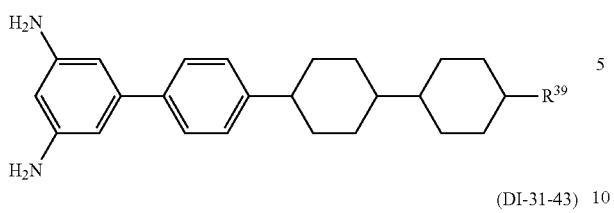

(DI-31-43)

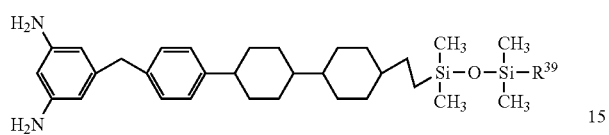

(DI-31-46)

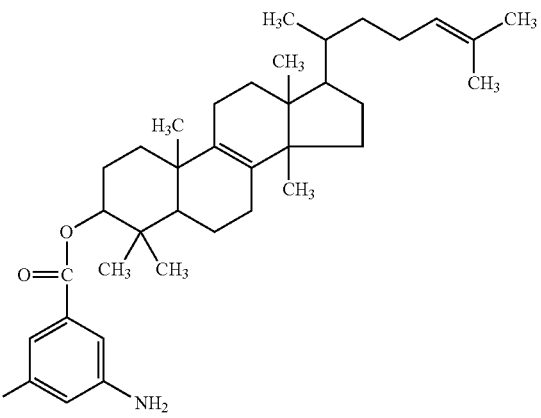

In the formulae (DI-31-18) to (DI-31-43), $R^{38}$ each independently represents an alkyl group having 1 to 20 carbon atoms or an alkoxy group having 1 to 20 carbon atoms, preferably an alkyl group having 3 to 20 carbon atoms or an alkoxy group having 3 to 20 carbon atoms. $R^{39}$ each independently represents a hydrogen atom, —F, an alkyl group having 1 to 30 carbon atoms, an alkoxy group having 1 to 30 carbon atoms, —CN, —OCH$_2$F, —OCHF$_2$ or —OCF$_3$, preferably an alkyl group having 3 to 25 carbon atoms or an alkoxy group having 3 to 25 carbon atoms. $G^{33}$ represents an alkylene group having 1 to 20 carbon atoms.

(DI-31-44)

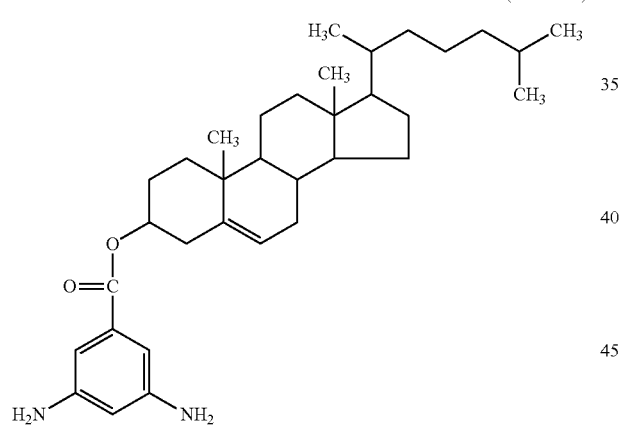

(DI-31-47)

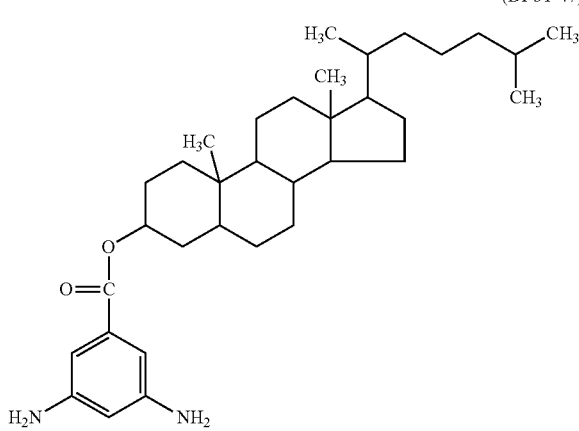

(DI-31-45)

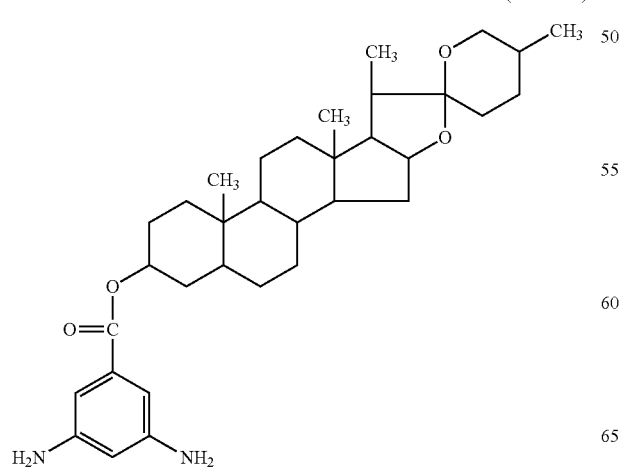

(DI-31-48)

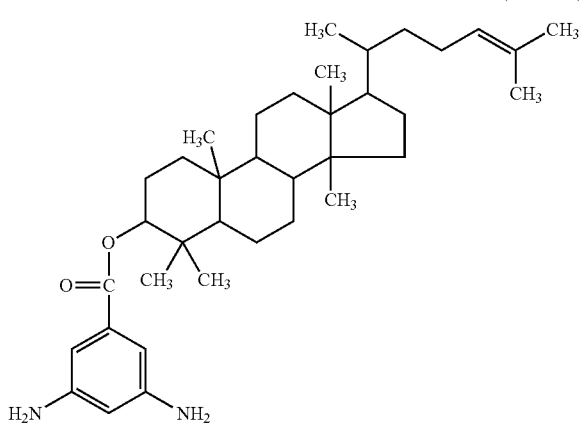

(DI-31-49)
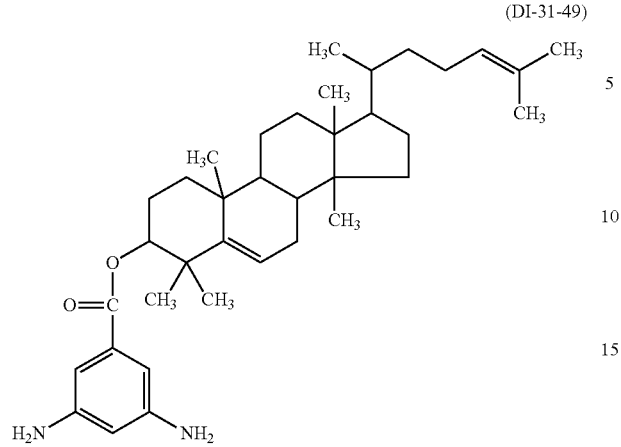
(DI-31-53)
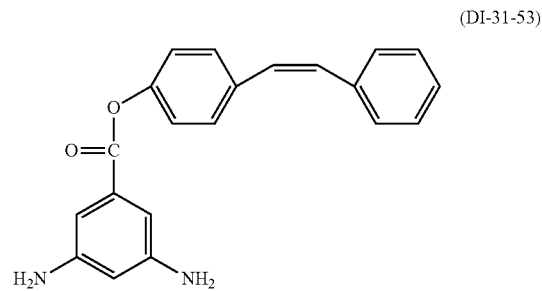
(DI-31-50)
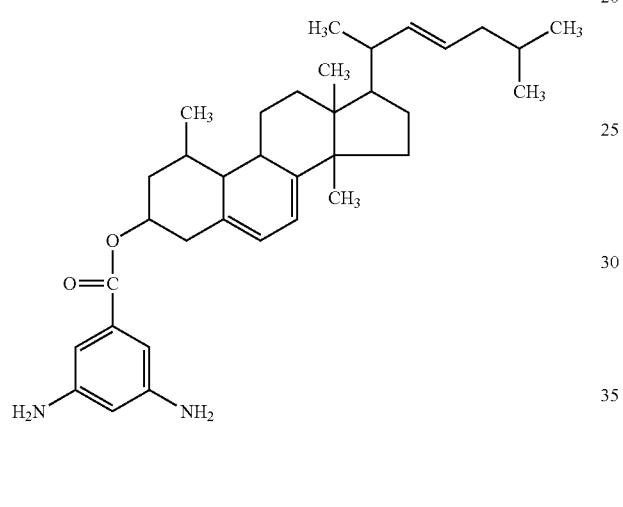
(DI-31-54)
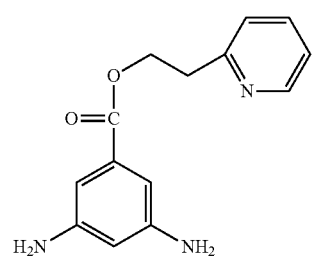
(DI-31-51)
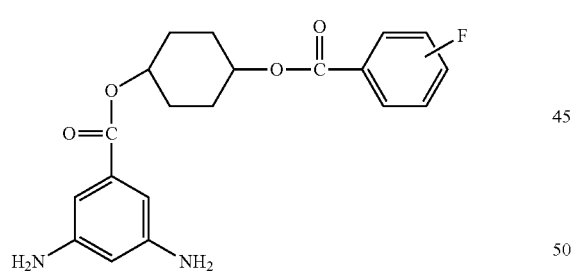
(DI-31-55)
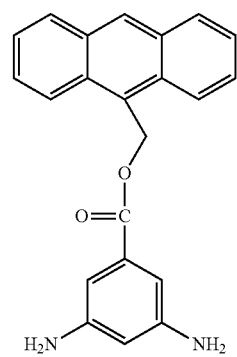
(DI-31-52)
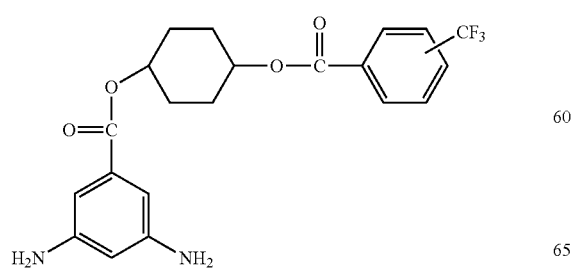

Examples of the compound represented by the formula (DI-32) are shown below.
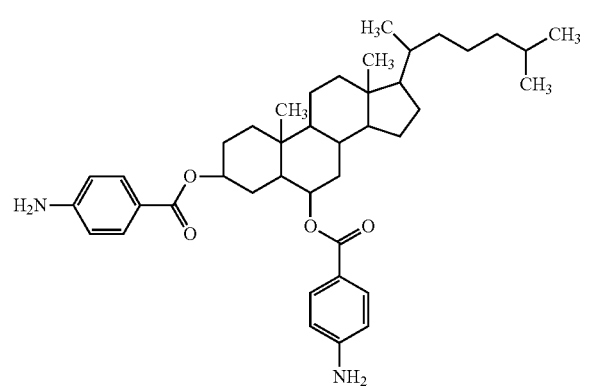
(DI-32-1)
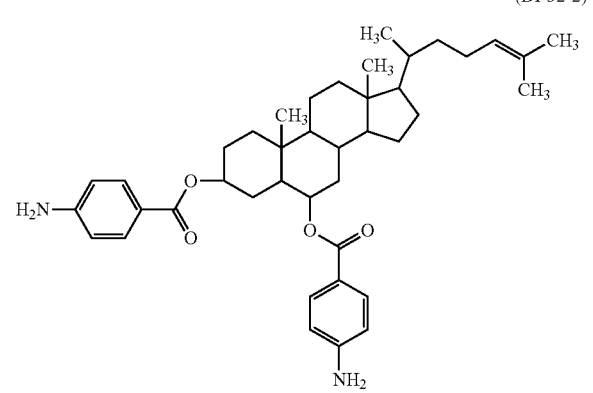
(DI-32-2)
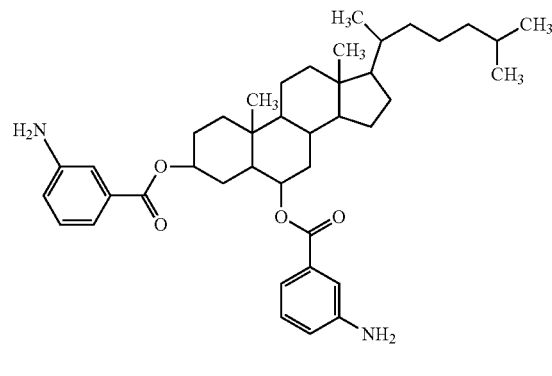
(DI-32-3)
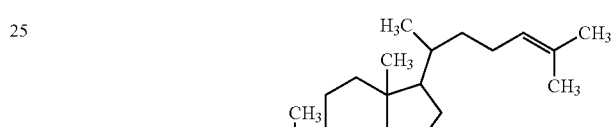
(DI-32-4)
Examples of the compound represented by the formula (DI-33) are shown below.
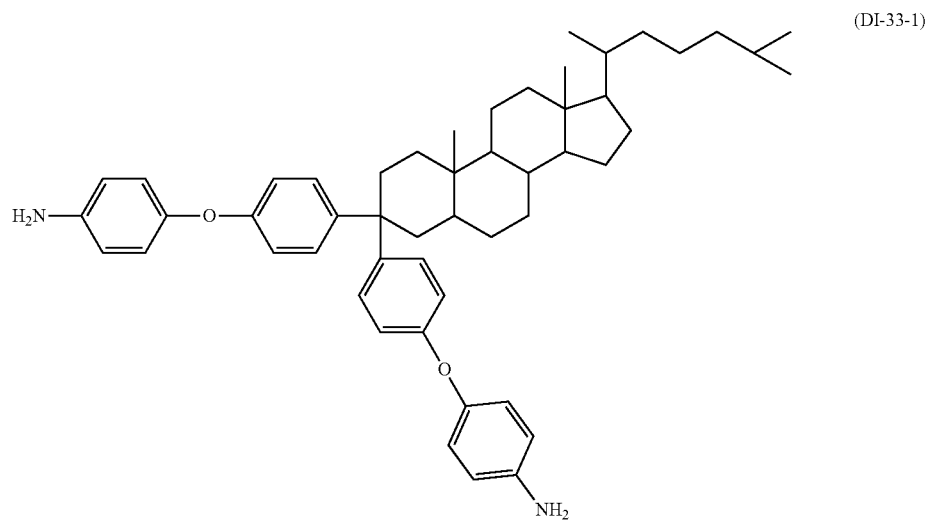
(DI-33-1)

-continued
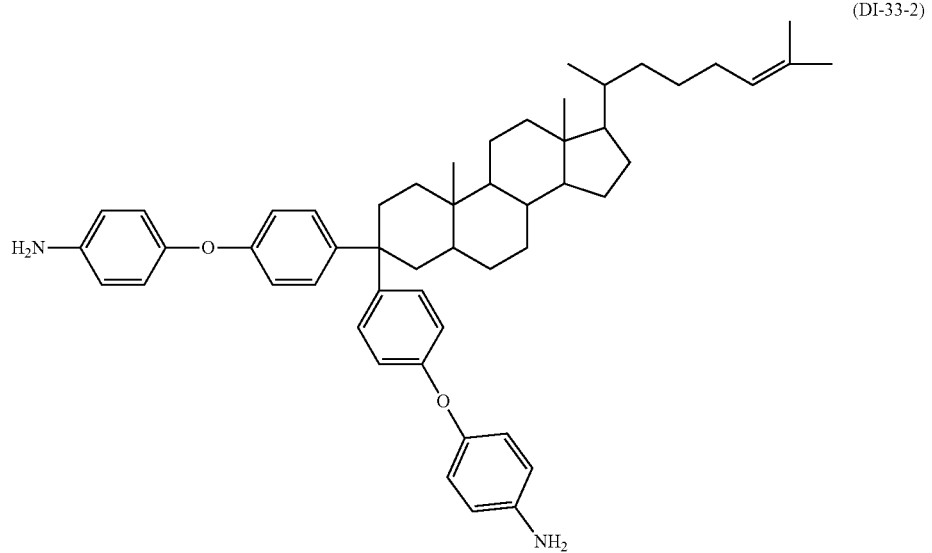
(DI-33-2)
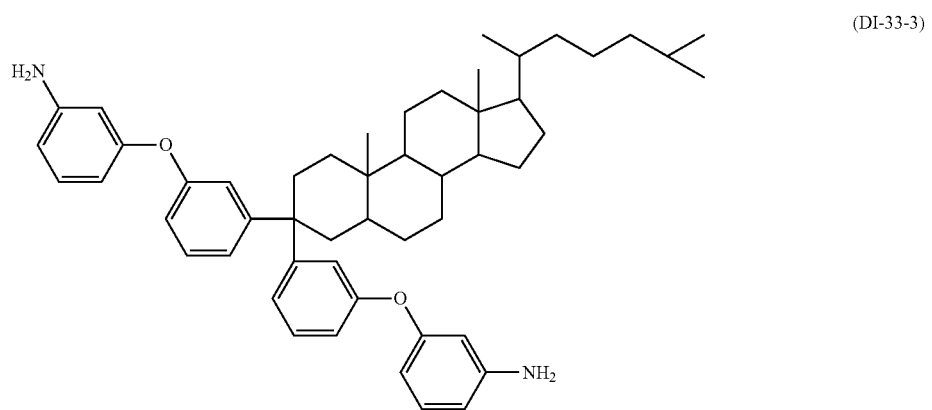
(DI-33-3)
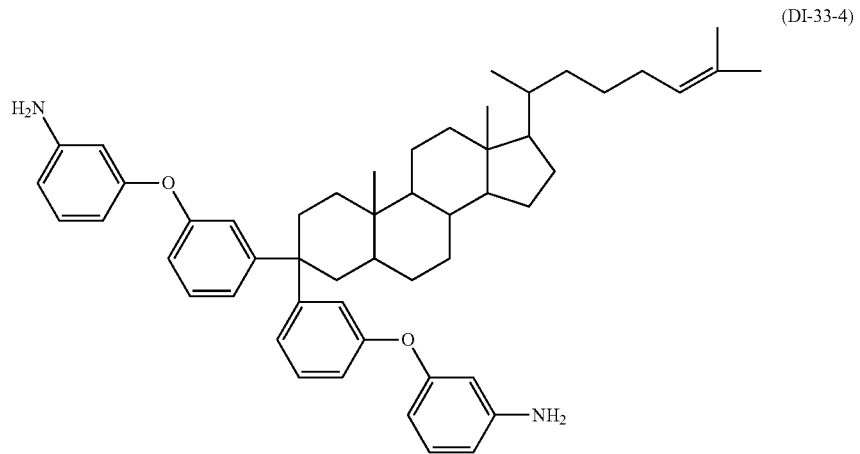
(DI-33-4)

-continued
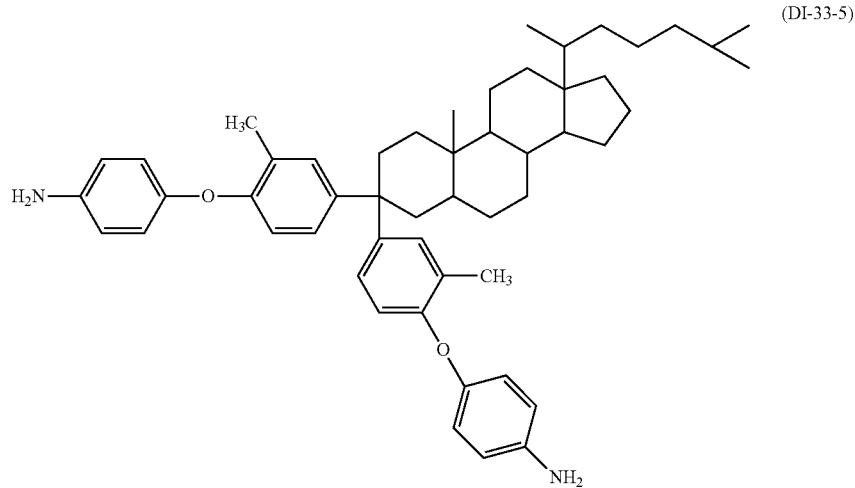
(DI-33-5)
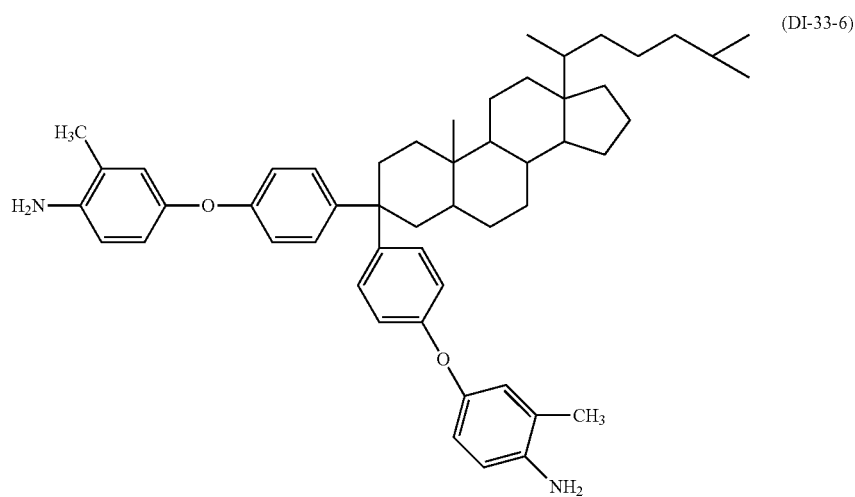
(DI-33-6)
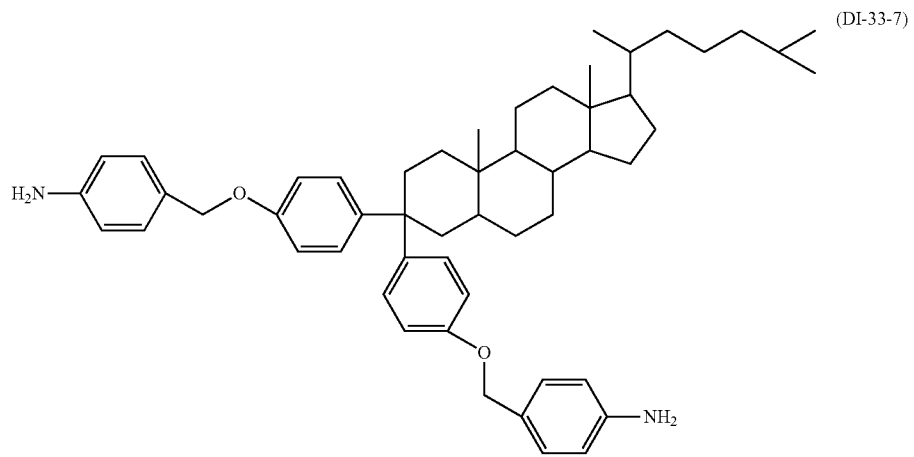
(DI-33-7)

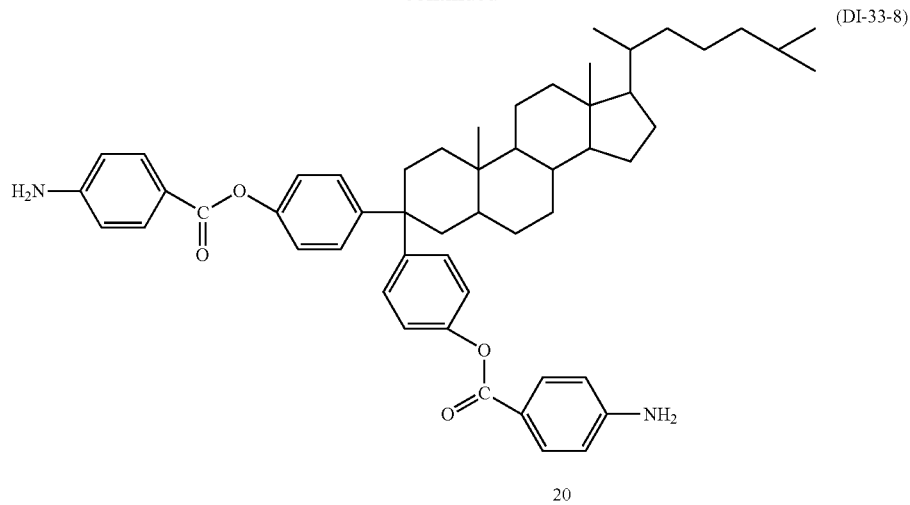
Examples of the compound represented by the formula (DI-34) are shown below.
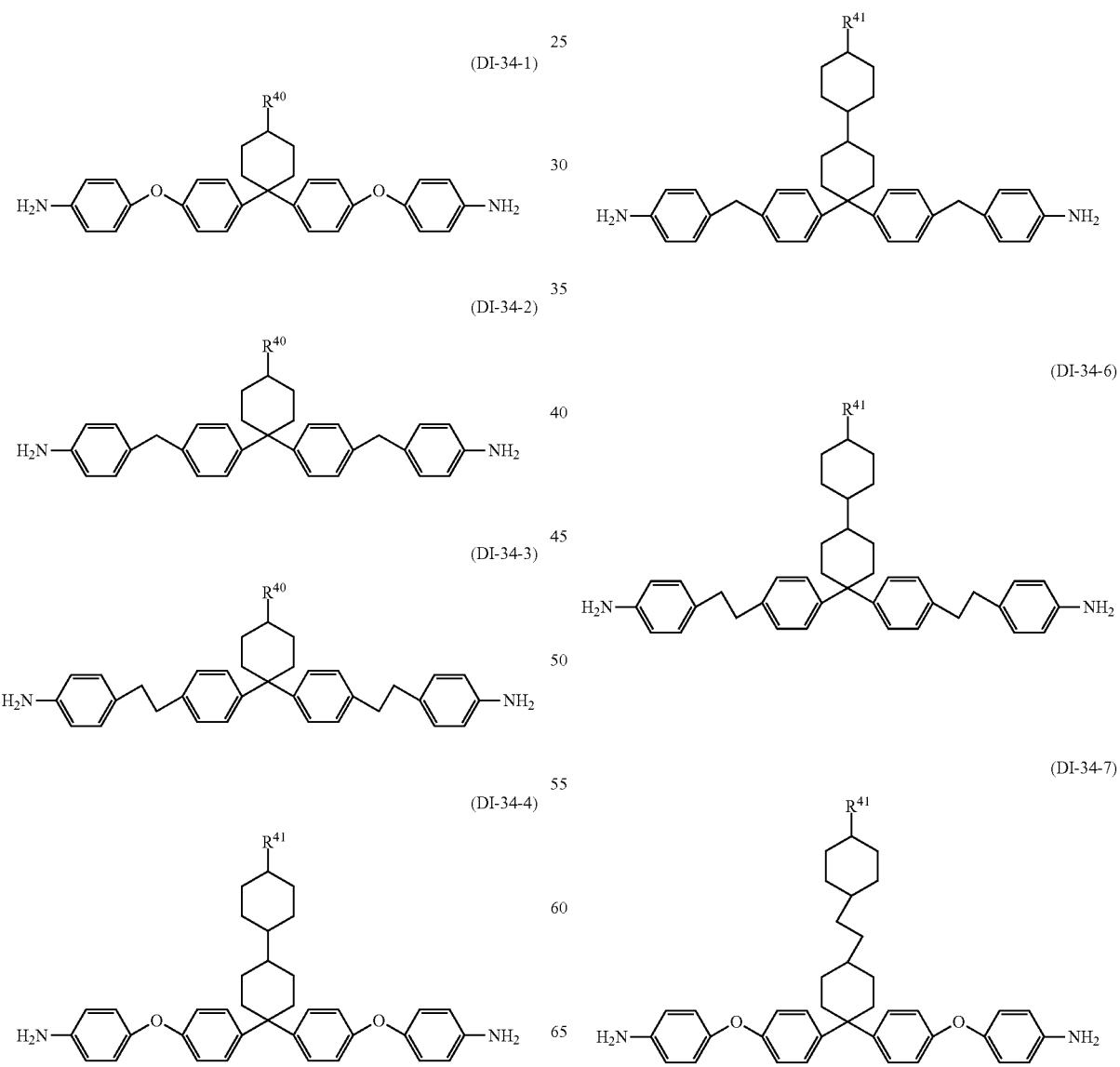

(DI-34-8)
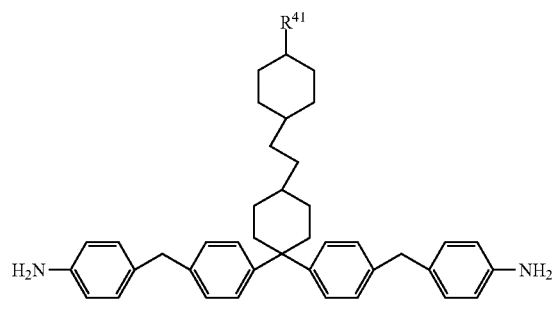
(DI-34-11)
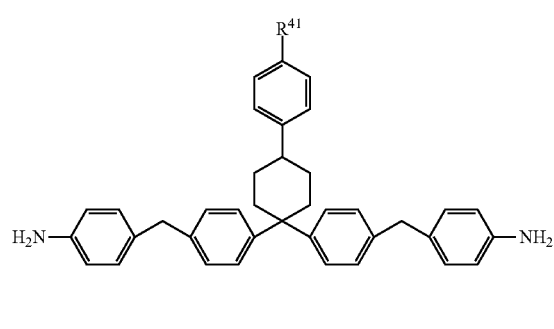
(DI-34-9)
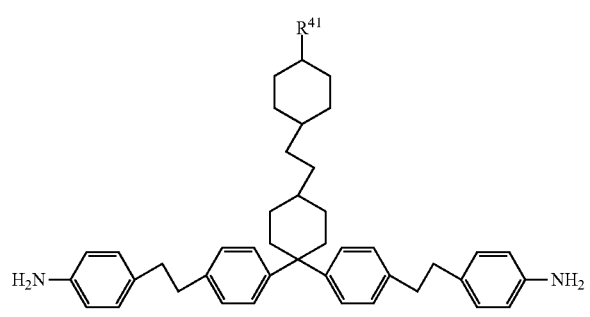
(DI-34-12)
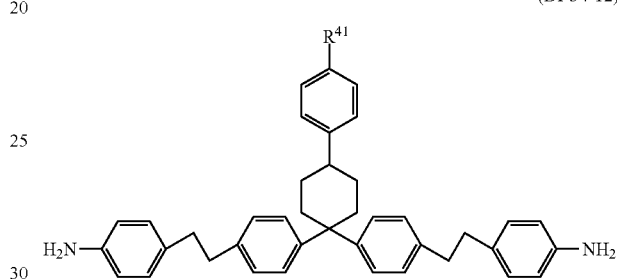
(DI-34-10)
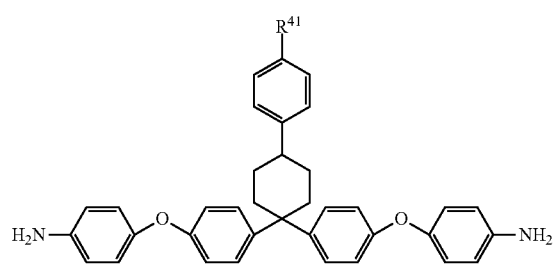
In the formulae (DI-34-1) to (DI-34-12), $R^{40}$ each independently represents a hydrogen atom or an alkyl group having 1 to 20 carbon atoms, preferably a hydrogen atom or an alkyl group having 1 to 10 carbon atoms, and $R^{41}$ each independently represents a hydrogen atom or an alkyl group having 1 to 12 carbon atoms.
Examples of the compound of the formula (DI-35) are shown below.
(DI-35-1)
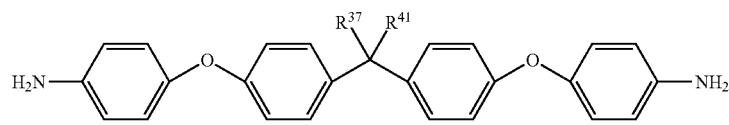
(DI-35-2)
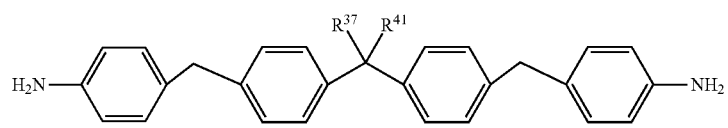
(DI-35-3)
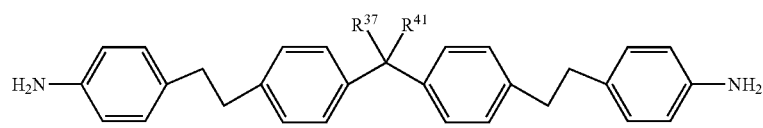

In the formulae (DI-35-1) to (DI-35-3), $R^{37}$ each independently represents an alkyl group having 6 to 30 carbon atoms, and $R^{41}$ each independently represents a hydrogen atom or an alkyl group having 1 to 12 carbon atoms.

Compounds of formulae (DI-36-1) to (DI-36-8) are shown below.

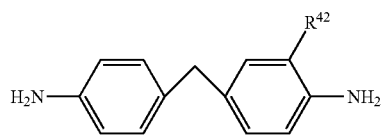
(DI-36-1)

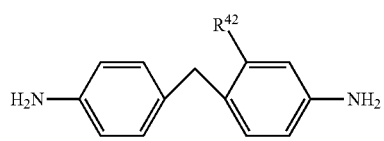
(DI-36-2)

(DI-36-3)

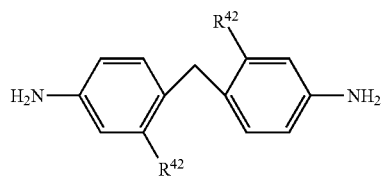
(DI-36-4)

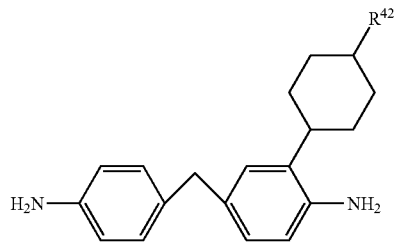
(DI-36-5)

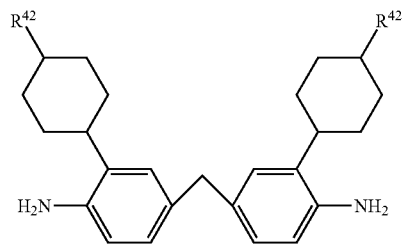
(DI-36-6)

(DI-36-7)

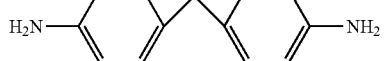
(DI-36-8)

In the formulae (DI-36-1) to (DI-36-8), $R^{42}$ each independently represents an alkyl group having 3 to 30 carbon atoms.

Among the above-mentioned diamines and dihydrazides, those favorable for improving characteristics of liquid crystal alignment films to be formed to be mentioned below are described. In the case where liquid crystal alignment performance is considered to be important, compounds represented by the formulae (DI-1-3), (DI-5-1), (DI-5-5), (DI-5-9), (DI-5-12), (DI-5-13), (DI-5-29), (DI-6-7), (DI-7-3), and (DI-11-2) are preferred. In the formula (DI-5-1), preferably m=2, 4 or 6, more preferably m=4. In the formula (DI-5-12), preferably m=2 to 6, more preferably m=5. In the formula (DI-5-13), preferably m=1 or 2, more preferably m=1.

In the case where improving transmittance of liquid crystal display devices is considered to be important, compounds represented by the formulae (DI-1-3), (DI-2-1), (DI-5-1), (DI-5-5), (DI-5-24), and (DI-7-3) are preferred, and compounds represented by the formula (DI-2-1) are more preferred. In the formula (DI-5-1), preferably m=2, 4 or 6, more preferably m=4. In the formula (DI-7-3), preferably m=2 or 3 and n=1 or 2, more preferably m=3 and n=1.

In the case where improving VHR of liquid crystal display devices is considered to be important, compounds represented by the formulae (DI-2-1), (DI-4-1), (DI-4-2), (DI-4-10), (DI-4-15), (DI-4-22), (DI-5-28), (DI-5-30), and (DI-13-1) are preferred, and diamines represented by the formulae (DI-2-1), (DI-5-1), and (DI-13-1) are more preferred. In the formula (DI-5-1), preferably m=1. In the formula (DI-5-30), preferably k=2.

By lowering the volume resistivity of a liquid crystal alignment film, the relaxation rate of the residual charge (residual DC) in the liquid crystal alignment film may be improved, which is effective for a method of preventing seizure. In the case where the object is considered to be important, compounds represented by the formulae (DI-4-1), (DI-4-2), (DI-4-10), (DI-4-15), (DI-5-1), (DI-5-12), (DI-5-13), (DI-5-28), (DI-4-20), (DI-4-21), (DI-7-12), and (DI-16-1) are preferred, and compounds represented by the formulae (DI-4-1), (DI-5-1), and (DI-5-13) are more preferred. In the formula (DI-5-1), preferably m=2, 4 or 6, more preferably m=4. In the formula (DI-5-12), preferably m=2 to 6, more preferably m=5. In the formula (DI-5-13), preferably m=1 or 2, more preferably m=1. In the formula (DI-7-12), preferably m=3 or 4, more preferably m=4.

Each diamine may be partly substituted with a monoamine in such a manner that the proportion of the monoamine to the diamine falls within a range of 40 mol % or less. Such substitution may cause termination of polymerization in forming a polyamic acid, therefore preventing further progression of any more polymerization. Accordingly, through such substitution, the molecular weight of the resultant polymer (polyamic acid or derivatives thereof) can be readily controlled, and for example, the coating performance of the liquid crystal aligning agent of the present invention can be improved without detracting from the advantageous effects of the present invention. One or more types of diamines may be substituted with a monoamine not detracting from the advantageous effects of the present invention. Examples of the monoamine include aniline, 4-hydroxyaniline, cyclohexylamine, n-butylamine, n-pentylamine, n-hexylamine, n-heptylamine, n-octylamine, n-nonylamine, n-decylamine, n-undecylamine, n-dodecylamine, n-tridecylamine, n-tetradecylamine, n-pentadecylamine, n-hexadecylamine, n-hetadecylamine, n-octadecylamine, and n-eicosylamine.

In the case where the polymer of the present invention is a polyamic acid or a derivative thereof, the raw material for the polymer may further contain a monoisocyanate compound as a monomer. When the raw material contains a monoisocyanate compound as a monomer, the terminal of the resultant polyamic acid or a derivative thereof may be modified and the molecular weight thereof can be therefore controlled. Using such a terminal-modified polyamic acid or a derivative thereof, for example, the coating performance of the liquid crystal aligning agent can be improved without detracting from the advantageous effects of the present invention. The content of the monoisocyanate compound in the monomer is, from the above-mentioned viewpoint, preferably 1 to 10 mol % of the total amount of the diamine and the tetracarboxylic acid dianhydride in the monomer. Examples of the monoisocyanate compound include phenyl isocyanate and naphthyl isocyanate.

[Amount of Diamine of Formula (2) in Raw Material]

In the case where the polymer of the present invention is a polyamic acid or a derivative thereof, preferably, the amount of the diamine represented by the formula (2) is 20 to 100 mol % of the total amount of the diamine to be used as the raw material, more preferably 50 to 100 mol %.

Use Mode of Polymer

The polymer of the present invention may be used as a material for liquid crystal alignment films, optical anisotropic materials, retardation films, optical compensation films, antireflection films, other various films or optical members. Here, in the case where the polymer of the present invention is used for liquid crystal alignment films, optical anisotropic materials, retardation films, optical compensation films, antireflection films, other various films or optical members, these may be formed of one polymer of the present invention, or may be formed of two or more polymers of the invention as combined. Among these uses, for use for which alignment performance is considered to be more important, for example, for retardation films, preferably, such films are formed of one polymer of the present invention.

(Liquid Crystal Aligning Agent of Polymer of the Invention)

The polymer of the present invention is favorable as a material for a liquid crystal aligning agent. Using a liquid crystal aligning agent formed of the polymer of the present invention, aligning performance may be given through photoalignment treatment, and in addition, photoreactivity can be reduced by heating, and accordingly, a liquid crystal alignment film having high light stability can be formed.

In the following, the liquid crystal alignment agent formed of the polymer of the present invention is described in detail. Here, the liquid crystal aligning agent formed of the polymer of the present invention is included in the category of the liquid crystal aligning agent for photoalignment of the present invention.

The liquid crystal aligning agent may be formed of one polymer of the present invention, or may be formed of two or more polymers of the present invention as combined. In the case where the liquid crystal alignment performance of the liquid crystal alignment film formed using the liquid crystal aligning agent of the present invention is considered to be important, preferably, a liquid crystal aligning agent prepared by mixing a polyamic acid or derivatives thereof among the polymers of the present invention is used. In this description, the liquid crystal aligning agent formed of one polymer may be referred to as a monolayer liquid crystal aligning agent. The liquid crystal aligning agent formed of two or more polymers as combined may be referred to as a blended liquid crystal aligning agent. In the following description, among the polyamic acid and derivatives thereof included in the scope of the polymer of the present invention, the polyamic acid and derivatives thereof containing the diamine represented by the formula (2) or (10) as the raw material may be referred to as a polyamic acid or derivatives thereof using the diamine of the formula (2) or (10).

In the case where the storage stability of the liquid crystal aligning agent, the printability of the liquid crystal aligning agent on a display device substrate, and the balance of properties of the liquid crystal alignment film to be formed are considered to be important, a blended liquid crystal aligning agent is preferred. Specifically, preferred is a liquid crystal aligning agent prepared by mixing polyamic acids or derivatives thereof using the diamine of the formula (2) or (10), or a liquid crystal aligning agent prepared by mixing a polyamic acid or a derivative thereof using the diamine of the formula (2) or (10) and a polyamic acid or a derivative thereof not using the diamine of the formula (2) or (10) as the raw material.

For producing the polyamic acid or a derivative thereof not using the diamine of the formula (2) or (10) as the raw material, preferably used are the tetracarboxylic acid dianhydride, the diamine and the dihydrazide mentioned hereinabove.

In the case where such a two-component polymer is used, for example, there may be employed an embodiment where a polymer having excellent liquid crystal alignment performance is selected for one component and a polymer excellent in improving electric properties of liquid crystal display devices is selected for the other component. In this embodiment, the structure and the molecular weight of each polymer may be controlled, and a liquid crystal alignment agent prepared by dissolving these polymers may be applied onto a substrate in the manner to be mentioned below, and in the process of pre-drying the thus-applied alignment agent to form a thin film on the substrate, the polymer having excellent liquid crystal alignment performance can be segregated as an upper layer of the thin film while the polymer excellent in improving electric properties of liquid crystal display devices can be segregated as a lower layer of the thin film. To this, a phenomenon that, in a polymer mixture, a polymer having a smaller surface energy can separate as an upper layer and a polymer having a larger surface energy can separate as a lower layer may be applied. For confirming such layer separation, the formed liquid crystal alignment film may be analyzed to confirm that the surface energy of the formed alignment film is the same as or near to the surface energy of the film formed of a liquid crystal aligning agent containing the polymer alone that is intended to be segregated as an upper layer.

As a method for expressing the layer separation, the molecular weight of the polymer that is intended to be segregated as an upper layer may be reduced.

In using a liquid crystal aligning agent produced by mixing polyamic acids, a polyimide is selected as the polymer that is intended to be segregated as an upper layer for layer separation.

The diamine represented by the formula (2) or (10) may be used as a raw material monomer for the polymer to be segregated as the upper layer of the thin film to be formed on a substrate, or may be used as a raw material monomer for the polymer to be segregated as the lower layer of the thin film.

The tetracarboxylic acid dianhydride to be used for producing the polyamic acid or a derivative thereof to be segregated as the upper layer of the thin film may be selected with no specific limitation from the known tetracarboxylic acid dianhydrides exemplified hereinabove.

The tetracarboxylic acid dianhydride to be used for producing the polyamic acid or a derivative thereof to be segregated as the upper layer of the thin film is preferably selected from the compounds of the formulae (AN-1-1), (AN-2-1), (AN-3-1), (AN-4-5), and (AN-4-17), more preferably the compound of the formula (AN-4-17). In the formula (AN-4-17), preferably m=4 or 8, more preferably m=8.

The diamine and the dihydrazide for use for producing the polyamic acid or a derivative thereof to be segregated as the upper layer of the thin film may be selected with no specific limitation from the above-exemplified known diamines.

The other diamine and dihydrazide than the two diamines, the diamine represented by the formula (2) and the diamine represented by the formula (10) for use for producing the polyamic acid or a derivative thereof to be segregated as the upper layer of the thin film are preferably the compounds represented by the formulae (DI-4-1), (DI-4-13), (DI-4-15), (DI-5-1), (DI-7-3), and (DI-13-1). Above all, the compounds represented by the formulae (DI-4-13), (DI-4-15), (DI-5-1), and (DI-13-1) are more preferred. In the formula (DI-5-1), preferably, m=1, 2 or 4, more preferably m=4. In the formula (DI-7-3), preferably m=3 and n=1.

Preferably, the non-photosensitive diamine to be used for producing the polyamic acid or a derivative thereof to be segregated as the upper layer of the thin film contains an aromatic diamine in an amount of 30 mol % or more of the total amount of the non-photosensitive diamine, more preferably 50 mol % or more.

The acid dianhydride and the diamine having an optical anisotropic structure mentioned above is preferably used for producing the polyamic acid or a derivative thereof to be segregated as the upper layer of the thin film.

The tetracarboxylic acid dianhydride to be used for producing the polyamic acid or a derivative thereof to be segregated as the lower layer of the thin film may be selected with no specific limitation from the known tetracarboxylic acid dianhydrides exemplified hereinabove.

The tetracarboxylic acid dianhydride to be used for producing the polyamic acid or a derivative thereof to be segregated as the lower layer of the thin film is preferably the compound selected from the formulae (AN-1-1), (AN-1-13), (AN-2-1), (AN-3-2), and (AN-4-21). The compounds of the formulae (AN-1-1), (AN-2-1), and (AN-3-2) are more preferred.

Preferably, the tetracarboxylic acid dianhydride to be used for producing the polyamic acid or a derivative thereof to be segregated as the lower layer of the thin film contains an aromatic tetracarboxylic acid dianhydride in an amount of 10 mol % or more of the total amount of the tetracarboxylic acid dianhydride, more preferably 30 mol % or more.

The diamine and the dihydrazide to be used for producing the polyamic acid or a derivative thereof to be segregated as the lower layer of the thin film may be selected with no specific limitation from the known diamines exemplified hereinabove.

The diamine and the dihydrazide to be used for producing the polyamic acid or a derivative thereof to be segregated as the lower layer of the thin film are preferably the compounds represented by the formulae (DI-4-1), (DI-4-2), (DI-4-10), (DI-4-18), (DI-4-19), (DI-5-9), (DI-5-28), (DI-5-30), (DI-13-1), and (DIH-2-1). Above all, the compounds represented by the formulae (DI-4-1), (DI-4-18), (DI-4-19), (DI-5-9), and (DI-13-1) are more preferred. The diamine of the formula (DI-5-30) where k=2 is preferred.

The diamine for use for producing the polyamic acid or a derivative thereof to be segregated as the lower layer of the thin film preferably contains an aromatic diamine in an amount of 30 mol % or more of the total diamine, more preferably 50 mol % or more.

Both the polyamic acid or a derivative thereof to segregate as the upper layer of the thin film, and the polyamic acid or a derivative thereto to segregate as the lower layer of the thin film may be produced according to the production method, as mentioned below, for the polyamic acid or a derivative thereof that is the indispensable component of the liquid crystal aligning agent of the present invention.

The proportion of the polyamic acid or a derivative thereof to segregate as the upper layer of the thin film to the total amount of the polyamic acid or a derivative thereof to segregate as the upper layer of the thin film and the polyamic acid or a derivative thereto to segregate as the lower layer of the thin film is preferably 5% by weight to 50% by weight, more preferably 10% by weight to 40% by weight.

Solvent

For example, from the viewpoint of improving the coatability with the liquid crystal aligning agent and controlling the concentration of the polyamic acid or a derivative thereof, the liquid crystal aligning agent of the present invention may further contain a solvent. Any solvent having an ability to dissolve polymer components is usable with no specific limitation. The solvent widely includes ordinary solvents generally used in a production process for polymer components such as polyamic acids and soluble polyimides or used in various applications, and may be appropriately selected and used herein depending on the use thereof. A single solvent of one alone or a mixed solvents of two or more types of solvents may be used.

The solvent includes good solvents for polyamic acids and derivatives thereof, and any other solvents for improving coatability.

An aprotic polar organic solvent that is a good solvent for polyamic acids and derivatives thereof includes N-methyl-2-pyrrolidone, N-ethyl-2-pyrrolidone, dimethylimidazolidinone, N-methylcaprolactam, N-methylpropionamide, N,N-dimethylacetamide, dimethyl sulfoxide, N,N-dimethylformamide, N,N-diethylformamide, dimethylacetamide, N,N-dimethylisobutylamide, and lactones such as γ-butyrolactone, γ-valerolactone.

Examples of the other solvent for improving coatability include diisobutyl ketone, alkyl lactate, diacetone alcohol, 3-methyl-3-methoxybutanol, 4-methyl-2-pentanol, diisobutyl carbinol, tetralin, isophorone, ethylene glycol monoalkyl ethers such as ethylene glycol monobutyl ether, diethylene glycol monoalkyl ethers such as diethylene glycol monoethyl ether, diethylene glycol dialkyl ethers such as diethylene glycol ethylmethyl ether, diethylene glycol diethyl ether and diethylene glycol butylmethyl ether, ethylene glycol monoalkyl or phenyl acetate, triethylene glycol monoalkyl ether, propylene glycol monoalkyl ethers such as propylene glycol monomethyl ether and 1-butoxy-2-propanol, dialkyl malonates such as diethyl malonate, dipropylene glycol monoalkyl ethers such as dipropylene glycol monomethyl ether, and ester compounds of those acetates.

Among these, more preferred as the solvent are N-methyl-2-pyrrolidone, dimethylimidazolidinone, γ-butyrolactone, γ-valerolactone, isobutyl ketone, 4-methyl-2-pentanol, diisobutyl carbinol, ethylene glycol monobutyl ether, diethylene glycol monoethyl ether, diethylene glycol ethylmethyl ether, diethylene glycol diethyl ether, diethylene glycol butylmethyl ether, 1-butoxy-2-propanol, propylene glycol monomethyl ether, dipropylene glycol monomethyl ether, and butyl cellosolve acetate.

Preferably, the concentration of the polyamic acid in the liquid crystal aligning agent of the present invention is 0.1 to 40% by weight. When the liquid crystal aligning agent is applied to a substrate, an operation of previously diluting the polyamic acid contained in the agent with a solvent for film thickness control may be needed.

The solid concentration in the liquid crystal aligning agent of the present invention is not specifically limited, for which an optimum value may be selected in accordance with various coating methods to be mentioned below. In general, for preventing unevenness and pin holes in coating, the solid concentration is preferably 0.1 to 30% by weight relative to the varnish weight, more preferably 1 to 10% by weight.

A preferred range of the viscosity of the liquid crystal aligning agent of the present invention varies, depending on the coating method, the concentration of the polyamic acid or a derivative thereof, the type of the polyamic acid or a derivative thereof to be used, and the type and the proportion of the solvent. For example, in coating with a printer, the viscosity is preferably 5 to 100 mPa·s (more preferably 10 to 80 mPa·s). When the viscosity is 5 mPa·s or more, a sufficient film thickness may be readily realized, and when 100 mPa·s or less, printing unevenness may be readily suppressed. In the case of spin coating, the viscosity is preferably 5 to 200 mPa·s (more preferably 10 to 100 mPa·s). In the case of coating with an inkjet coating apparatus, the viscosity is preferably 5 to 50 mPa·s (more preferably 5 to 20 mPa·s). The viscosity of the liquid crystal aligning agent may be measured with a rotary viscosity measuring apparatus, for example, with a rotary viscometer (TVE-20L Model by Toki Sangyo Co., Ltd.) at a measurement temperature of 25° C.

The liquid crystal aligning agent of the present invention may further contain additives. For example, the additives include alkenyl-substituted nadimide compounds, oxazine compounds, radical-polymerizable unsaturated double bond-having compounds, epoxy compounds, oxazole compounds and silane compounds described in JP 2007-286597 A, JP 2008-096979 A, JP 2009-109987 A, JP 2009-175715 A, JP 2010-054872 A, JP 2015-212807 A, and JP 2016-170409.

Liquid Crystal Alignment Film

Next, the liquid crystal alignment film of the present invention is described. The liquid crystal alignment film of the present invention is formed of the liquid-crystal aligning film for photoalignment of the present invention. The liquid crystal aligning agent for photoalignment of the present invention is such that, in a heating and baking step, the structural unit having a photoreactive structure in the agent undergoes chemical reaction and alignment amplification to form a liquid crystal alignment film. In the case where the polymer in the present invention is a polyamic acid or a derivative thereof, the polymer may further undergo imidation to form a liquid crystal alignment film. In the following description, explanation of imidation is omitted when the polymer is any other polymer than polyamic acids or derivatives thereof.

The following describes a method for forming a liquid crystal alignment film from the liquid crystal aligning agent for photoalignment of the present invention.

The liquid crystal alignment film of the present invention may be produced according to an ordinary method of forming a liquid crystal alignment film from a liquid crystal aligning agent for photoalignment. The liquid crystal alignment film of the present invention may be formed, for example, via a step of forming a coating film of a liquid crystal aligning agent for photoalignment of the present invention, a step of heating and drying the coating film to form a film of the liquid crystal aligning agent, a step of irradiating the film of the liquid crystal aligning agent with light to give anisotropy to the film, and a step of heating and baking the anisotropy-given film of the liquid crystal aligning agent. When heated and baked, the structural unit having a photoreactive structure in the liquid crystal aligning agent for photoalignment of the present invention undergoes chemical reaction and the photoreactive group reduces or disappears. Consequently, the liquid crystal alignment film of the present invention is produced preferably via the heating and baking step after given anisotropy through irradiation with light after the coating step and the heating and drying step. In this description, disappearance of the photoreactive group of a photoreactive structure may be referred to as conversion of a photoreactive group into a non-photoreactive group.

In the case where improvement of alignment performance is considered to be important, the heating and baking step for the liquid crystal alignment film of the present invention is preferably such that at least two steps of chemical reaction, alignment amplification and imidation are started at different times in the polymer that the liquid crystal aligning agent contains. The starting order of chemical reaction, alignment amplification and imidation is not specifically limited, and for example, chemical reaction, alignment amplification and imidation may be started in that order, or alignment amplification, chemical reaction and imidation may be started in that order. Anyhow, the starting times for chemical reaction, alignment amplification and imidation may differ from each other, and chemical reaction, alignment amplification and imidation may be temporally overlapped. Namely, so far as these treatments differ in the starting time, at least two of chemical reaction, alignment amplification and imidation may run on simultaneously. By shifting the starting times for chemical reaction, alignment amplification and imidation in that manner, a liquid crystal alignment film having increased anisotropy and stability to light and, in addition thereto, also having excellent alignment performance can be obtained. The starting times for chemical reaction, alignment amplification and imidation may be controlled by the heating and baking conditions for the liquid crystal aligning agent. For example, in the case where the chemical reaction onset temperature of the polymer that the liquid crystal aligning agent contains is lower than the alignment amplification onset temperature, the film of the liquid crystal aligning agent may be kept at a temperature falling within a range of the chemical reaction onset temperature or higher and lower than the alignment amplification onset temperature whereby chemical reaction may be started prior to alignment amplification, and after that, by increasing the temperature to be higher than the alignment amplification onset temperature and keeping the temperature as such, alignment amplification may be started after chemical reaction. Here, regarding the description of a cyclization onset temperature as one example of the chemical reaction onset temperature, and the alignment amplification onset temperature, reference may be made to the section of [Cyclization onset temperature and alignment amplification onset temperature] given hereinabove. Regarding the concrete conditions for heating and baking, reference may be made to the description relating to the heating and baking step given herein.

Like in formation of ordinary liquid crystal alignment films, the coating film may be formed by applying the liquid crystal aligning agent of the present invention to a substrate of a liquid crystal display device. The substrate includes glass substrates, silicon nitride substrates, acrylic substrates, polycarbonate substrates and polyimide substrates optionally provided with electrodes such as ITO (indium tin oxide), IZO ($In_2O_3$—ZnO) or IGZO (In—Ga—$ZnO_4$) electrodes or color filters.

As a method of applying the liquid crystal aligning agent to a substrate, generally known are a spinner method, a printing method, a dipping method, an instillation method, and an inkjet method. These methods are employable in the present invention.

As the heating and drying step, generally known are a heat-treating method in an oven or an IR furnace, and a heat-treating method on a hot plate. Preferably, the heating and drying step is carried out at a temperature falling within a range that enables solvent vaporization, more preferably at a relatively low temperature relative to the temperature in the heating and baking step. Specifically, the heating and drying temperature may fall within a range of 30° C. to 150° C., more preferably within a range of 50° C. to 120° C.

The heating and baking step may be carried out under the condition necessary for imidation of a polyamic acid or a derivative thereof. For baking the coating film, generally known are a heat-treating method in an oven or an IR furnace, and a heat-treating method on a hot plate. These methods are employable in the present invention. Preferably, the coating film is baked at a temperature of 100 to 300° C. or so for 1 minute to 3 hours, more preferably at 120 to 280° C., even more preferably at 150 to 250° C. The coating film may be baked plural times at different temperatures. Plural heating devices each set at a different temperature may be used, or one heating device may be used in which the heating temperature may be varied sequentially. In the case where the coating film is baked two times at different temperatures, preferably, the film is baked at 90 to 180° C. in the first time, and then at 185° C. or higher in the second time. The coating film may be baked at a temperature varying from a low temperature to a high temperature. In the case where the film is baked at varying temperatures, the initial temperature is preferably 90 to 180° C. The final temperature is preferably 185 to 300° C., more preferably 190 to 230° C. In the case where alignment performance is considered to be important, preferably, temperature increase in the heating step is moderate. For example, the coating film may be heated and baked while the heating temperature is varied from a low temperature to a high temperature, or may be heated and baked plural times at different temperatures that are stepwise elevated. In the case where the coating film is baked at varying temperatures, preferably, the time to be taken until arrival to the final temperature is 5 minutes or more, and the final temperature is preferably 185° C. to 300° C., more preferably 190 to 230° C. In the case where the coating film is heated and baked plural times, the first baking temperature is preferably 90 to 180° C., and the final temperature is preferably 185° C. to 300° C. For example, preferably, after heated and baked at 110° C., the coating film is then heated and baked at 220° C., or after heated and baked at 110° C., the coating film is then heated and baked at 230° C., or after heated and baked at 130° C., the coating film is then heated and baked at 220° C., or after heated and baked at 150° C., the coating film is then heated at 200° C., or after heated and baked at 150° C., the coating film is then heated and baked at 220° C., or after heated and baked at 150° C., the coating film is heated and baked at 230° C., or after heated and baked at 170° C., the coating film is then heated and baked at 200° C. Also preferably, the heating stages may be increased more and the coating film may be gently heated and baked in those stages. In the case where the coating film is heated and baked in two or more stages at different heating temperatures, the heating time in each heating stage is preferably 5 minutes to 30 minutes.

In the method for forming the liquid crystal alignment film of the present invention, a known photoalignment treatment may be favorably employed as a method of imparting anisotropy to the thin film in order to align liquid crystals in one direction relative to a horizontal direction and/or a vertical direction.

The method for forming the liquid crystal alignment film of the present invention according to a photoalignment treatment is described in detail. The liquid crystal alignment film of the present invention may be formed through photoalignment as follows. The thin film prepared after heating and drying the coating film is irradiated with a linearly-polarized radiation or an unpolarized radiation so as to be given anisotropy, and the resultant film is heated and baked to give a liquid crystal alignment film. Alternatively, the coating film is heated and dried, and then further heated and baked, and thereafter the film may be irradiated with a linearly-polarized radiation or an unpolarized radiation to give a liquid crystal alignment film. From the viewpoint of alignment performance, preferably, the radiation irradiation step is carried out before the heating and baking step.

For further enhancing the liquid crystal alignment performance of the liquid crystal alignment film, the coating film may be irradiated with a linearly-polarized radiation or an unpolarized radiation, while heated. Irradiation with a radiation may be carried out in the step of heating and drying the coating film, or in the step of heating and baking the coating film, or may be carried out between the heating and drying step and the heating and baking step. The heating and drying temperature in the step is preferably within a range of 30° C. to 150° C., more preferably within a range of 50° C. to 120° C. Also preferably, the heating and baking temperature in the step is within a range of 30° C. to 300° C., more preferably within a range of 50° C. to 250° C.

As the radiation, for example, UV ray or visible ray including a light having a wavelength of 150 to 800 nm may be used, but UV ray including a light of 300 to 400 nm is preferred. A linearly-polarized light or an unpolarized light may be used. The light is not specifically limited so far as it can impart liquid crystal alignment performance to the thin film, but in the case where the thin film is desired to express a strong alignment controlling force to liquid crystals, a linearly-polarized light is preferred.

The liquid crystal alignment film of the present invention can exhibit high-level liquid crystal alignment performance even in low-energy photoirradiation. The irradiation dose of linearly-polarized light in the radiation irradiation step is preferably 0.05 to 20 $J/cm^2$, more preferably 0.5 to 10 $J/cm^2$. The wavelength of the linearly-polarized light is preferably 200 to 400 nm, more preferably 300 to 400 nm. The irradiation angle with the linear-polarized light to the film surface is not specifically limited, but in the case where a strong alignment controlling force is desired to be expressed to liquid crystals, preferably, the irradiation light is as vertical as possible to the film surface from the viewpoint of shortening the alignment treatment time. When irradiated with a linearly-polarized light, the liquid crystal alignment film of the present invention can align liquid crystals in the direction vertical to the polarization direction of the linearly-polarized light.

The light source for use in the step of irradiation with a linearly-polarized radiation or an unpolarized radiation includes an ultra-high-pressure mercury lamp, a high-pressure mercury lamp, a low-pressure mercury lamp, a deep UV lamp, a halogen lamp, a metal halide lamp, a high-power metal halide lamp, a xenon lamp, a mercury-xenon lamp, an excimer lamp, a KrF excimer laser, a fluorescent lamp, an LED lamp, a sodium lamp, and a microwave-excited electrodeless lamp, and these may be used with no specific limitation.

The liquid crystal alignment film of the present invention can be favorably obtained according to a process additionally including any other step than the above-mentioned steps. For example, the liquid crystal alignment film of the present invention does not indispensably require a step of washing the film after baking or after radiation irradiation with a washing liquid, but may take a washing step depending on the other steps for the film.

A washing step with a washing liquid includes brushing, jet spraying, vapor washing or ultrasonic washing, and these methods may be carried out singly or in combination. The washing liquid usable herein includes, though not limited thereto, pure water, various alcohols such as methyl alcohol, ethyl alcohol and isopropyl alcohol, aromatic hydrocarbons such as benzene, toluene and xylene, halogen solvents such as methylene chloride, and ketones such as acetone and methyl ethyl ketone. Needless-to-say, the washing liquid for use herein is well purified to contain few impurities. Such a washing method is also applicable to the washing step in forming the liquid crystal alignment film of the present invention.

For increasing the liquid crystal alignment performance of the liquid crystal alignment film of the present invention, before and after the heating and baking step, or before and after irradiation with a polarized or unpolarized radiation, the film may be annealed by heat or light. In the annealing treatment, the annealing temperature is preferably 30 to 180° C., more preferably 50 to 150° C., and the time is preferably 1 minute to 2 hours. The annealing light for the annealing treatment includes a UV lamp, a fluorescent lamp, and an LED lamp. The light irradiation dose is preferably 0.3 to 10 $J/cm^2$.

The thickness of the liquid crystal alignment film of the present invention is not specifically limited, but is preferably 10 to 300 nm, more preferably 30 to 150 nm. The thickness of the liquid crystal alignment film of the present invention may be measured using a known film thickness measuring device such as a step gauge or an ellipsometer.

The liquid crystal alignment film of the present invention is characterized by having a high-level alignment anisotropy. The level of anisotropy may be evaluated according to the method of using polarized IR described in JP 2005-275364 A. It may also be evaluated according to a method of ellipsometry. Precisely, the retardation value of the liquid crystal alignment film may be measured with a spectral ellipsometer. The retardation value of the film increases in proportion to the alignment degree of the polymer main chain. Specifically, a polymer film having a large retardation value has a large alignment angle, and therefore, it is considered that, when used as a liquid crystal alignment film, a liquid crystal alignment film having a larger anisotropy can have a larger alignment controlling force to a liquid crystal composition.

The liquid crystal alignment film of the present invention is favorably used as a horizontal field-type liquid crystal display device. In the case where the film is used in a horizontal field-type liquid crystal display device, the black display level is higher in a dark state when the Pt angle is smaller or when the liquid crystal alignment performance is higher, and the contrast is higher in that state. The Pt angle is preferably 0.1° or less.

The liquid crystal alignment film of the present invention can be used for alignment control of liquid crystal compositions for liquid crystal displays for smartphones, tablets, in-car monitors and televisions. Except for use for alignment of liquid crystal compositions for liquid crystal displays, the film may also be used for alignment control of optical compensation materials and other all liquid crystal materials. In addition, as having a large anisotropy, the liquid crystal alignment film of the present invention can be used for optical compensation materials all by itself.

Liquid Crystal Display Device

Next, the liquid crystal display device of the present invention is described.

The liquid crystal display device of the present invention is characterized by having the liquid crystal alignment film of the present invention.

The liquid crystal display device of the present invention can keep a high voltage holding ratio and can realize a high-level display quality even when a high-brightness backlight is mounted therein.

The liquid crystal display device of the present invention is described in detail. The liquid crystal display device of the present invention has a pair of substrates arranged to face each other, an electrode formed on one or both of the pair of facing electrodes, a liquid crystal alignment film formed on the facing surfaces of the pair of substrates, a liquid crystal layer formed between the pair of substrates, a pair of polarization films arranged to sandwich the pair of substrates, a back light and a driving system, in which the liquid crystal alignment film is formed of the liquid crystal alignment film of the present invention.

With no specific limitation, the electrode may be any one capable of being formed on one surface of the substrate. Examples of the electrode include ITO or metal deposition films. The electrode may be formed on the entire surface of one side of the substrate, or may be formed in a desired form, for example, in a patterned form thereon. Examples of the desired form of the electrode include a comb-shaped or zigzag structure. The electrode may be formed on one substrate of the pair of substrates, or may be formed both of the substrates. The mode of forming the electrode differs depending on the type of the liquid crystal display device, and for example, in the case of an IPS-mode liquid crystal display device (horizontal field-type liquid crystal display device), an electrode is formed on one substrate of the pair of substrates, and in the other liquid crystal display devices, an electrode is arranged on both substrates of the pair of substrates. The liquid crystal alignment film is formed on the substrate or the electrode.

In the case of a homogeneous alignment liquid crystal display device (for example, IPS, FFS), the device has, because of the structure thereof, at least a backlight, a first polarization film, a first substrate, a first liquid crystal alignment film, a liquid crystal layer, a second substrate, and a second polarization film in that order from the side of the backlight, in which the polarization films are so arranged that the polarization axis (direction of polarization absorption) of the first polarization film and the polarization axis of the second polarization film may cross with each other (preferably vertically). At this time, the polarization films are so arranged that the polarization axis of the first polarization film can be parallel to the liquid crystal alignment direction, or can be vertical thereto. A liquid crystal display device in which the first polarization film is so arranged that the polarization axis thereof can be in parallel to the liquid crystal alignment direction is referred to as an O-mode device, while the device in which the polarization axis of the first polarization film can be vertical to the liquid crystal alignment direction may be referred to as an E-mode device. The liquid crystal alignment film of the present invention is applicable to both of such O-mode and E-mode, and may be selectively applied thereto depending on the intended purpose.

Dichromatic compounds are used in many optical anisotropic materials. Accordingly, when the polarization axis of a polarizing light to be applied to a liquid crystal aligning agent for imparting anisotropy to the agent is made to be in parallel to the polarization axis of the polarized light from the polarization film arranged on the side of a backlight (that is, when the liquid crystal aligning agent of the present invention is used, an O-mode arrangement is employed), the transmittance in the light absorption wavelength range of the liquid crystal alignment film increases. Accordingly, in the case, the transmittance of the liquid crystal display device can be further improved.

The liquid crystal layer is so arranged that the liquid crystal composition can be sandwiched between the pair of substrates whose sides having the liquid crystal alignment film formed thereon face to each other. In forming the liquid crystal layer, a spacer formed of fine particles or a resin sheet may be optionally arranged between the pair of substrates to thereby secure a suitable distance between the substrates.

As a method for forming the liquid crystal layer, a vacuum instillation method and an ODF (one drop fill) method are known.

In a vacuum instillation method, substrates are stuck to each other in such a manner that the liquid crystal alignment films thereon can face to each other via a cell gap provided therebetween and are sealed up by printing except a part to be the liquid crystal injection mouth. Liquid crystal molecules are injected and filled into the cell gap as partitioned by the substrate surfaces and the sealant agent, utilizing vacuum differential pressure, and then the injection mouth is sealed up to produce a liquid crystal display device.

In an ODF method, a sealant agent is printed on the outer periphery of the liquid crystal alignment film on one of the pair of substrates, then liquid crystal molecules are dropwise applied to the region inside the sealant, and thereafter the other substrate is stuck thereto in such a manner that the liquid crystal alignment film surfaces of the two substrates could face with each other. With that, the liquid crystal molecules are spread by pressure to the entire surfaces of the substrates, and then the entire surfaces of the substrates are exposed to UV light to cure the sealant agent to produce a liquid crystal display device.

The sealant agent to be used for sticking the substrates may be any known UV-curable one or heat-curable one. For printing with the sealant agent, for example, a screen printing method is employable.

With no specific limitation, various liquid crystal compositions having a positive or negative dielectric anisotropy may be used herein. Preferred are liquid crystal compositions having a positive dielectric anisotropy, disclosed in JP 3086228, JP 2635435, JP 5-501735 A, JP 8-157826 A, JP 8-231960 A, JP 9-241644 A (EP 885272A1), JP 9-302346 A (EP 806466A1), JP 8-199168 A (EP 722998A1), JP 9-235552 A, JP 9-255956 A, JP 9-241643 A (EP 885271A1), JP 10-204016 A (EP 844229A1), JP 10-204436 A, JP 10-231482 A, JP 2000-087040 A, and JP 2001-48822 A.

Preferred examples of liquid crystal compositions having a negative dielectric anisotropy are disclosed in JP 57-114532 A, JP 2-4725 A, JP 4-224885 A, JP 8-40953 A, JP 8-104869 A, JP 10-168076 A, JP 10-168453 A, JP 10-236989 A, JP 10-236990 A, JP 10-236992 A, JP 10-236993 A, JP 10-236994 A, JP 10-237000 A, JP 10-237004 A, JP 10-237024 A, JP 10-237035 A, JP 10-237075 A, JP 10-237076 A, JP 10-237448 A (EP 967261A1), JP 10-287874 A, JP 10-287875 A, JP 10-291945 A, JP 11-029581 A, JP 11-080049 A, JP 2000-256307 A, JP 2001-019965 A, JP 2001-072626 A, JP 2001-192657 A, JP 2010-037428 A, WO 2011/024666, WO 2010/072370, JP 2010-537010 A, JP 2012-077201 A, and JP 2009-084362 A.

With no trouble at all, one or more optically-active compounds may be added to the liquid crystal composition having a positive or negative dielectric anisotropy for use herein.

For example, from the viewpoint of increasing alignment performance, any further additive may be added to the liquid crystal composition for use in the liquid crystal display device of the present invention. Such additives include a photopolymerizable monomer, an optically-active compound, an antioxidant, a UV absorbent, a dye, a defoaming agent, a polymerization initiator, and a polymerization inhibitor. Preferred examples of a photopolymerizable monomer, an optically-active compound, an antioxidant, a UV absorbent, a dye, a defoaming agent, a polymerization initiator, and a polymerization inhibitor are disclosed in WO 2015/146330.

A polymerizable compound may be mixed in the liquid crystal composition for adapting the composition to a PSA (polymer sustained alignment) mode liquid crystal display device. Preferred examples of a polymerizable compound includes compounds having a polymerizable group such as acrylates, methacrylates, vinyl compounds, vinyloxy compounds, propenyl ethers, epoxy compounds (oxiranes, oxetanes), and vinyl ketones. Preferred compounds are disclosed in WO 2015/146330.

EXAMPLES

The characteristic features of the present invention are described more concretely with reference to Examples and Comparative Examples given below. In the following Examples, the material used, its amount and ratio, the details of the treatment and the treatment process may be suitably modified or changed not overstepping the spirit and the scope of the invention. Accordingly, the invention should not be limitatively interpreted by the Examples mentioned below.

Measurement Methods and Evaluation Methods
[Measurement of Weight-Average Molecular Weight (Mw)]

The weight-average molecular weight of a polyamic acid was measured in terms of polystyrene through GPC using 2695 Separation Module/2414 Differential Refractometer (by Waters Corporation). The sample used for the measurement was prepared by diluting the resultant polyamic acid with a mixed solution of phosphoric acid-DMF (phosphoric acid/N,N-dimethylformamide=0.6/100, by weight) so as to have a polyamic acid concentration of about 2% by weight. As the column, HSPgel RT MB-M (by Waters Corporation) was used, and the mixed solution of phosphoric acid-DMF was used as a developing solvent. The column temperature was 50° C., and the sample flow rate was 0.4 mL/min. As the standard polystyrene, TSK standard polyethylene by Tosoh Corporation was used.

[Evaluation of Voltage Holding Ratio]

The voltage holding ratio of a liquid crystal display device was measured according to the method described in "Mizushima et al., Proceedings of 14th Liquid Crystal Discussion, p. 78 (1988)", in which a rectangular wave having a wave height ±5 V was applied to the cell at 60° C. The voltage holding ratio is an index showing how much the applied voltage could be held after frame period, and 100% of the value means that all charges were held. When a cell having a negative liquid crystal has a voltage holding ratio of 97.5% or more, the liquid crystal display device having the cell can be considered to have good display quality.

[Evaluation of Transmittance]

A liquid crystal alignment film was formed on a transparent glass substrate, and using a UV-visible light spectrophotometer V-660 (by JASCO Corporation), the transmittance thereof at 330 nm to 480 nm was measured, and a mean value of the transmittance at 380 nm to 430 nm was calculated. The mean value of the transmittance was referred to as a relative value, 100% of the transparent glass substrate on which a liquid crystal alignment film was not formed, and relative to the reference value, the mean transmittance of the liquid crystal alignment film formed on a transparent glass substrate was evaluated under the following criteria.

<In the Case of Using a Monolayer-Type Liquid Crystal Aligning Agent>
Mean transmittance of 85% or more: best
Mean transmittance of 80% or more and less than 85%: good
Mean transmittance of less than 80%: not good <In the Case of Using a Blend-Type Liquid Crystal Aligning Agent>
Mean transmittance of 92% or more: best
Mean transmittance of 90% or more and less than 92%: good
Mean transmittance of less than 90%: not good

[Measurement of AC Image Sticking (Evaluation of Liquid Crystal Alignment Performance)]

AC image sticking may be measured according to the method described in WO 2000/43883.

Specifically, the brightness-voltage characteristic (B-V characteristic) of the produced liquid crystal cell was measured, and this is referred to as a brightness-voltage characteristic: B (before) before stress application to the cell. Next, the liquid crystal cell was given an alternating current of 4.5 V and 60 Hz for 20 minutes, then short-circuited for 1 second, and again the brightness-voltage characteristic (B-V characteristic) thereof was measured. This is referred to as a brightness-voltage characteristic: B (after) after stress application to the cell. Here, the brightness at a voltage of 1.3 V of each brightness-voltage characteristic thus measured was employed, and the brightness change ΔB (%) was calculated according to the following equation. A smaller value of ΔB (%) means that the AC image sticking generation can be reduced more, that is, the tested sample has good liquid crystal alignment performance.

$$\Delta B(\%)=[B(\text{after})-B(\text{before})]/B(\text{before})$$

The evaluation criteria for liquid crystal alignment performance are shown below.
ΔB (%) is less than 3.0%: best
DB (%) is 3.0% or more and less than 6.0%: good
ΔB (%) is 6.0% or more: not good

[Evaluation of in-Plane Unevenness in Inkjet Printing]

Using an inkjet apparatus (EB100XY100 by Konica Minolta Corporation), a liquid crystal aligning agent was applied to an ITO-having substrate. After coated, the substrate was left as such for 180 seconds, and then dried on a hot plate at 60° C. for 80 seconds. Subsequently, the coated substrate was visually checked for the presence or absence of in-plane unevenness. The driving conditions for the inkjet apparatus used for coating are shown below.

Head: KM512MN (number of nozzles: 512, droplets 14 pL)
Head temperature: 25° C.
Applied voltage: 19 V
Frequency: 709 Hz
Resolution: 360 dpi
Transport velocity: 50 mm/sec
Head/glass substrate distance: 28 mm Compounds Used
[Diamines Represented by Formula (2) or Formula (10)]

The diamines represented by the formula (2) or (10) used in preparing varnishes in the present Examples are shown below.

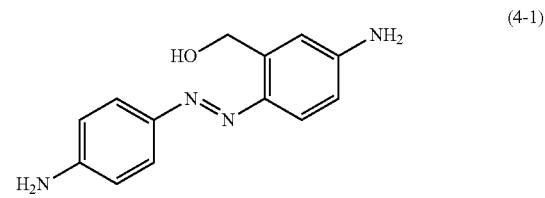
(4-1)

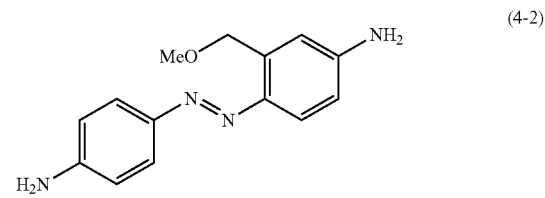
(4-2)

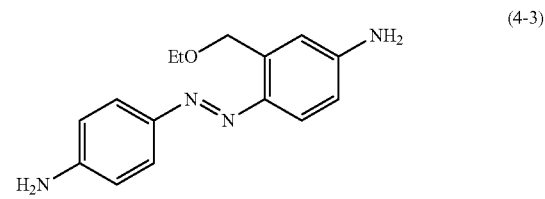
(4-3)

-continued
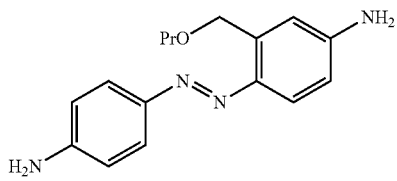 (4-4)
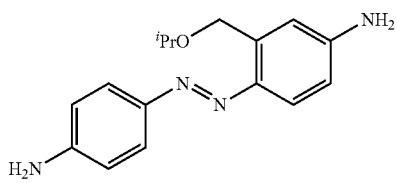 (4-5)
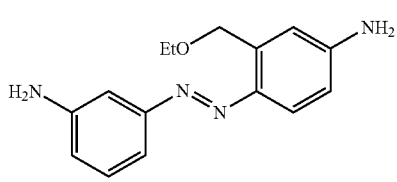 (8-3)
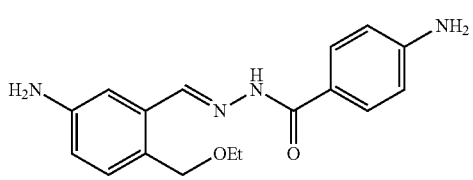 (16-3)
[Tetracarboxylic Acid Dianhydrides]
The tetracarboxylic acid dianhydrides used in preparing the varnishes in the present Examples are shown below.
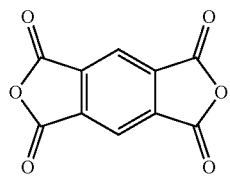 (AN-1-1)
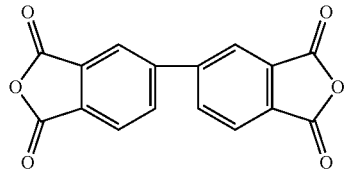 (AN-1-2)
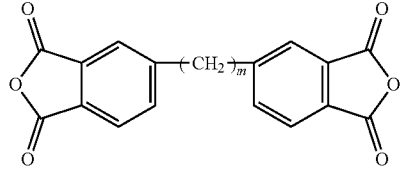 (AN-2-1)
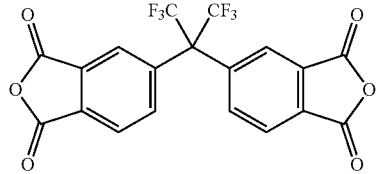 (AN-3-1)
-continued
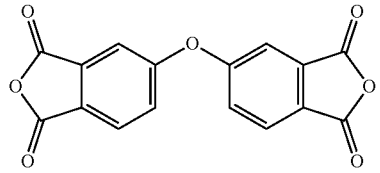 (AN-3-2)
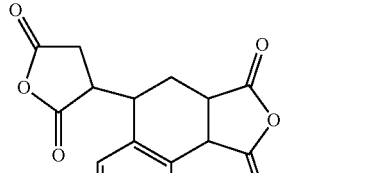 (AN-4-5)
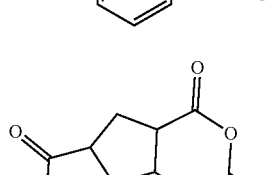 (AN-4-17)
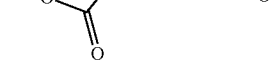 (AN-4-18)
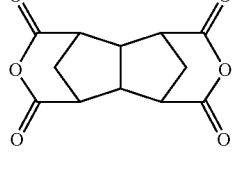 (AN-4-21)
 (AN-5-1)
 (AN-7-2)
 (AN-10-1)

[Diamines Except Both Diamines of the Diamines Represented by the Formula (2) and the Diamines Represented by the Formula (10)]
The other diamines than both diamines of the diamines represented by the formula (2) and the diamines represented by the formula (10) used in preparing the varnishes in the present Examples are shown below.
(DI-4-1)
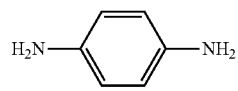
(DI-4-10)
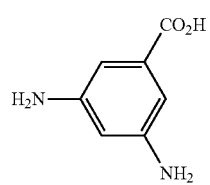
(DI-4-13)
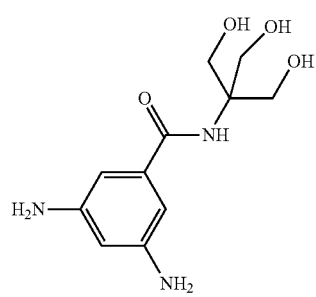
(DI-4-15)
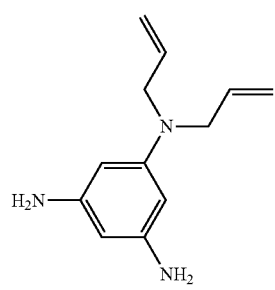
(DI-4-18)
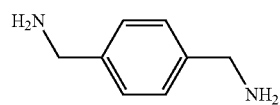
(DI-4-19)
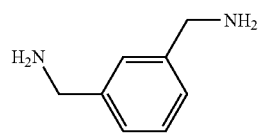
(DI-4-20)
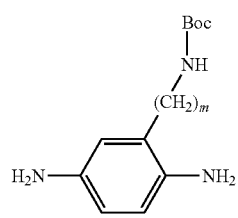
(DI-4-26)
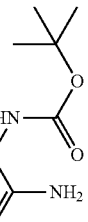
(DI-5-1)
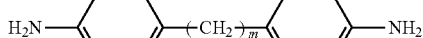
(DI-5-9)
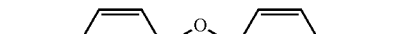
(DI-5-12)
(DI-5-28)
(DI-5-30)
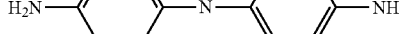
(DI-5-49)
(DI-5-50)
(DI-7-7)
(DI-13-1)

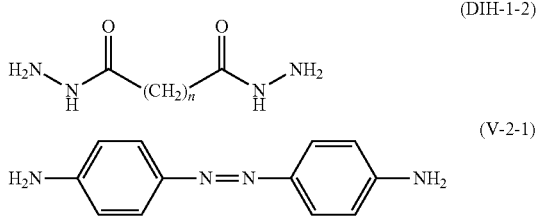

(DIH-1-2)

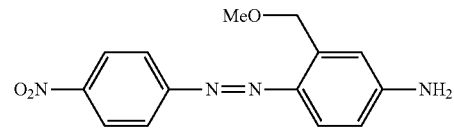

(V-2-1)

[Solvents]

The solvents used in preparing the liquid crystal aligning agents in the present Examples are shown below.
NMP: N-methyl-2-pyrrolidone
BC: butyl cellosolve (ethylene glycol monobutyl ether)
GBL: γ-butyrolactone
DPM: dipropylene glycol monomethyl ether
GVL: γ-valerolactone
EDM: diethylene glycol ethyl methyl ether
BP: 1-butoxy-2-propanol
BDM: diethylene glycol butyl methyl ether
EDE: diethylene glycol diethyl ether
BCA: butyl cellosolve acetate
DIBK: diisobutyl ketone
MIBC: 4-methyl-2-pentanol
DIBC: diisobutyl carbinol
Synthesis of Diamines Represented by Formula (2)

Among the diamines represented by the formula (2) used in the present Examples, the diamines (4-2) and (4-3) were produced according to the following process. The diamines (4-1), (4-4), (4-5), and (8-3) were produced in the same manner as the production process for the diamines (4-2) and (4-3).

[Synthesis Example 1] Synthesis of Diamine (4-2)

<First Stage: Ether Synthesis>

Sodium methoxide (29.0 g, 509.2 mmol), methanol (1000 mL) and dimethylformamide (200 mL) were put into a 3000-mL three-neck flask equipped with a reflux tube, a dropping funnel, a thermometer, and a nitrogen introducing pipe, and cooled in an ice bath. 1-Bromomethyl-3-nitrobenzene (100.0 g, 462.9 mmol) and methanol (1000 mL) were dropwise added to the solution of the mixture, and then in a nitrogen atmosphere, these were stirred under reflux for 5 hours. The solvent was evaporated away under reduced pressure from the reaction liquid, and then water (1000 mL) and ethyl acetate (1000 mL) were added thereto for extraction. The resultant organic layer was dried with magnesium sulfate, and the solvent was evaporated away under reduced pressure to give a crude product. The crude product was purified through silica gel chromatography to give 1-methoxymethyl-3-nitrobenzene, of which the production quantity was 63.5 g and the yield was 82%.

<Second Stage: Reduction>

1-Methoxymethyl-3-nitrobenzene (63.5 g, 379.9 mmol) obtained in the first stage, sodium sulfide 9-hydrate (273.5 g, 1138.8 mmol), ethanol (600 mL) and water (300 mL) were put into a 2000-mL three-neck flask equipped with a reflux tube, a thermometer and a nitrogen introducing pipe, and stirred under reflux for 2 hours in a nitrogen atmosphere. The solvent was evaporated away under reduced pressure from the reaction liquid, and water (5000 mL) and ethyl acetate (1000 mL) was added for extraction. The resultant organic layer was dried with magnesium sulfate, and the solvent was evaporated away under reduced pressure to give a crude product. The crude product was purified through silica gel chromatography to give 3-methoxymethylaniline, of which the production quantity was 36.4 g and the yield was 70%.

<Third Stage: Diazocoupling>

4-Nitroaniline (36.7 g, 265.7 mmol) and 6 mol/L hydrochloric acid (150 mL) were put into a 500-mL three neck-flask equipped with a dropping funnel, a thermometer and a nitrogen introducing pipe, and cooled in an ice bath. Sodium nitrite (22.0 g, 318.9 mmol) and water (150 mL) were dropwise added to the solution of the mixture, and while still kept in the ice bath, this was further stirred for 1 hour in a nitrogen atmosphere to give a diazonium salt solution. 3-Methoxymethylaniline (36.4 g, 265.7 mmol) obtained in the second stage, water (350 mL) and methanol (700 mL) were put into a separately-prepared, 2000-mL three-neck flask equipped with a thermometer and a nitrogen introducing pipe, and cooled in an ice bath. The diazonium salt solution obtained in the previous step was dropwise added to the solution of the mixture, and while still kept in the ice bath, this was stirred for 1 hour in a nitrogen atmosphere. The reaction liquid was filtered to give a crude product, which was then purified through silica gel column chromatography to give an intermediate A represented by the following formula. The production quantity of the intermediate was 19.0 g and the yield thereof was 25%.

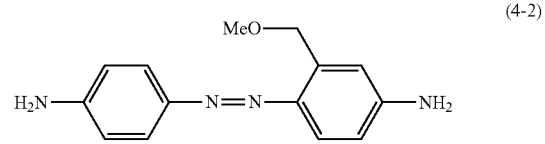

Intermediate A

<Fourth Stage: Reduction>

The intermediate A (19.0 g, 66.4 mmol) obtained in the third stage, sodium sulfide 9-hydrate (47.8 g, 199.2 mmol), ethanol (1000 mL) and water (250 mL) were put into a 2000-mL three-neck flask equipped with a reflux tube, a thermometer and a nitrogen introducing pipe, and stirred under reflux for 1 hour in a nitrogen atmosphere. The solvent was evaporated away under reduced pressure from the reaction liquid, and then water (250 mL) and ethyl acetate (500 mL) were added thereto for extraction. The resultant organic layer was dried with magnesium sulfate, and then the solvent was evaporated away under reduced pressure to give a crude product. The crude product was purified through silica gel chromatography to give a diamine (4-2) represented by the following formula. The production quantity of the diamine was 5.3 g and the yield thereof was 31%.

(4-2)

[Synthesis Example 2] Synthesis of Diamine (4-3)

<First Stage: Ether Synthesis>

Sodium ethoxide (36.5 g, 509.2 mmol), ethanol (1000 mL) and dimethylformamide (200 mL) were put into a 3000-mL three-neck flask equipped with a reflux tube, a dropping funnel, a thermometer, and a nitrogen introducing pipe, and cooled in an ice bath. 1-Bromomethyl-3-nitrobenzene (100.0 g, 462.9 mmol) and methanol (1000 mL) were dropwise added to the solution of the mixture, and then in a nitrogen atmosphere, these were stirred under reflux for 5 hours. The solvent was evaporated away under reduced pressure from the reaction liquid, and then water (1000 mL) and ethyl acetate (1000 mL) were added thereto for extraction. The resultant organic layer was dried with magnesium sulfate, and the solvent was evaporated away under reduced pressure to give a crude product. The crude product was purified through silica gel chromatography to give 1-ethoxymethyl-3-nitrobenzene, of which the production quantity was 73.0 g and the yield was 87%.

<Second Stage: Reduction>

1-Ethoxymethyl-3-nitrobenzene (73.0 g, 402.7 mmol) obtained in the first stage, sodium sulfide 9-hydrate (290.2 g, 1208.1 mmol), ethanol (600 mL) and water (300 mL) were put into a 2000-mL three-neck flask equipped with a reflux tube, a thermometer and a nitrogen introducing pipe, and stirred under reflux for 2 hours in a nitrogen atmosphere. The solvent was evaporated away under reduced pressure from the reaction liquid, and water (5000 mL) and ethyl acetate (1000 mL) were added for extraction. The resultant organic layer was dried with magnesium sulfate, and the solvent was evaporated away under reduced pressure to give a crude product. The crude product was purified through silica gel chromatography to give 3-ethoxymethylaniline, of which the production quantity was 45.1 g and the yield was 74%.

<Third Stage: Diazocoupling>

4-Nitroaniline (41.2 g, 298.0 mmol) and 6 mol/L hydrochloric acid (170 mL) were put into a 500-mL three neck-flask equipped with a dropping funnel, a thermometer and a nitrogen introducing pipe, and cooled in an ice bath. Sodium nitrite (24.7 g, 357.6 mmol) and water (170 mL) were dropwise added to the solution of the mixture, and while still kept in the ice bath, this was further stirred for 1 hour in a nitrogen atmosphere to give a diazonium salt solution. 3-Ethoxymethylaniline (45.1 g, 298.0 mmol) obtained in the second stage, water (450 mL) and methanol (900 mL) were put into a separately-prepared, 2000-mL three-neck flask equipped with a thermometer and a nitrogen introducing pipe, and cooled in an ice bath. The diazonium salt solution obtained in the previous step was dropwise added to the solution of the mixture, and while still kept in the ice bath, this was stirred for 1 hour in a nitrogen atmosphere. The reaction liquid was filtered to give a crude product, which was then purified through silica gel column chromatography to give an intermediate B represented by the following formula. The production quantity of the intermediate was 18.8 g and the yield thereof was 21%.

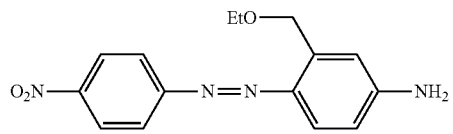

Intermediate B

<Fourth Stage: Reduction>

The intermediate B (18.8 g, 62.6 mmol) obtained in the third stage, sodium sulfide 9-hydrate (45.1 g, 187.8 mmol), ethanol (1000 mL) and water (250 mL) were put into a 2000-mL three-neck flask equipped with a reflux tube, a thermometer and a nitrogen introducing pipe, and stirred under reflux for 1 hour in a nitrogen atmosphere. The solvent was evaporated away under reduced pressure from the reaction liquid, and then water (250 mL) and ethyl acetate (500 mL) were added thereto for extraction. The resultant organic layer was dried with magnesium sulfate, and then the solvent was evaporated away under reduced pressure to give a crude product. The crude product was purified through silica gel chromatography to give a diamine (4-3) represented by the following formula. The production quantity of the diamine was 6.6 g and the yield thereof was 39%.

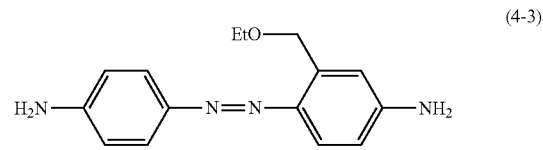 [SMILES: COCc1cc(N)ccc1N=Nc1ccc(N)cc1]

$^1$H-NMR (DMSO-$d_6$) δ 7.51 (d, J=8.7 Hz, 2H, $C_6H_4$), 7.44 (d, J=8.8 Hz, 1H, $C_6H_3$), 6.73 (d, J=2.4 Hz, 1H, $C_6H_3$), 6.62 (d, J=8.7 Hz, 2H, $C_6H_4$), 6.49 (dd, J=2.4, 8.8 Hz, 1H, $C_6H_3$), 5.75 (s, 4H, $NH_2$), 4.88 (s, 2H, $CH_2$), 3.56 (q, J=7.0 Hz, 2H, $C_2H_5$), 1.17 (t, J=7.0 Hz, 3H, $C_2H_5$)

<Confirmation of Cyclization>

5.0 mg of the diamine (4-3) was put on an aluminum sample pan, and using a differential thermal analysis/thermogravimetric analysis system (EXSTAR6200 by Hitachi High-Technologies Corporation), this as heated from 50° C. up to 230° C. at a heating rate of 10° C./min in a nitrogen atmosphere, and then kept at 230° C. for 5 minutes. Subsequently, the formed compound was taken out of the sample pan and analyzed for $^1$H-NMR spectrometry. From the measurement results, the formed compound was identified as the compound represented by the following formula in which the azo group and the ethoxymethyl group had cyclized to give an indazole ring.

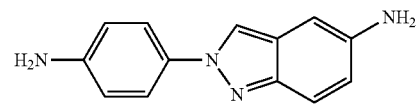

$^1$H-NMR (DMSO-$d_6$) δ 8.34 (s, 1H, $C_7H_4N$), 7.60 (d, J=7.6 Hz, 2H, $C_6H_4$), 7.33 (d, J=7.4 Hz, 1H, $C_7H_4N$), 6.76 (d, J=7.1 Hz, 1H, $C_7H_4N$), 6.64 (d, J=7.6 Hz, 2H, $C_6H_4$), 6.57 (s, 1H, $C_7H_4N$), 5.22-5.55 (br, 4H, $NH_2$)

Synthesis of Diamines Represented by Formula (10)

The diamines represented by the formula (10) used in the present Examples were produced according to the following process.

[Synthesis Example 3] Synthesis of Diamine (16-3)

<First Stage: Ring-Opening Reaction>

6-Nitrophthalide (10.0 g, 55.8 mmol), boric acid (0.10 g, 1.7 mmol) and triphenyl phosphine oxide (0.47 g, 1.7 mmol) were put into a 100-mL three-neck flask equipped with a reflux tube, a dropping funnel, a thermometer, and a nitrogen introducing pipe, and heated at 150° C. Thionyl chloride (8.6 g, 72.6 mmol) was dropwise added to the solution of the mixture, and stirred at 150° C. for 5 hours. The reaction liquid was cooled, and then filtered to give an intermediate C of which the production quantity was 10.2 g and the yield was 78%. (JP 2003-516375 A was referred to.)

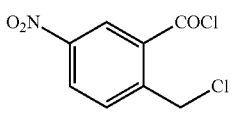 [SMILES: O=C(Cl)c1cc([N+](=O)[O-])ccc1CCl]

Intermediate C
<Second Stage: Ester Synthesis>

The intermediate C (10.0 g, 42.7 mmol) obtained in the first stage, and ethanol (50 mL) were put into a 200-mL three-neck flask equipped with a thermometer and a nitrogen introducing pipe, and stirred for 1 hour in a nitrogen atmosphere. The solvent was evaporated away from the reaction liquid, and then water (100 mL) and ethyl acetate (100 mL) were added thereto for extraction. The resultant organic layer was dried with magnesium sulfate and the solvent was evaporated away under reduced pressure to give a crude product. The crude product was purified through silica gel chromatography to give an intermediate D, of which the production quantity was 10.1 g and the yield was 97%.

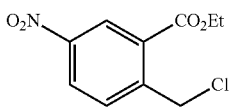 [SMILES: CCOC(=O)c1cc([N+](=O)[O-])ccc1CCl]

Intermediate D
<Third Stage: Ether Synthesis>

Sodium ethoxide (3.3 g, 45.6 mmol) and ethanol (100 mL) were put into a 300-mL three neck-flask equipped with a reflux tube, a dropping funnel, a thermometer and a nitrogen introducing pipe, and cooled in an ice bath. The intermediate D (10.1 g, 41.5 mmol) obtained in the second stage and ethanol (50 mL) were dropwise added to the solution of the mixture, and then stirred under reflux for 20 hours in a nitrogen atmosphere. The solvent was evaporated away under reduced pressure from the reaction liquid and then water (200 mL) and ethyl acetate (200 mL) were added thereto for extraction. The resultant organic layer was dried with magnesium sulfate, and the solvent was evaporated away under reduced pressure to give a crude product. The crude product was purified through silica gel chromatography to give an intermediate E, of which the production quantity was 4.6 g and the yield was 44%.

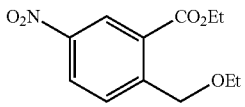 [SMILES: CCOCc1ccc([N+](=O)[O-])cc1C(=O)OCC]

Intermediate E
<Fourth Stage: Reduction>

The intermediate E (4.6 g, 18.2 mmol) obtained in the third stage, and tetrahydrofuran (100 mL) were put into a 300-mL three-neck flask equipped with a dropping funnel, a thermometer and a nitrogen introducing pipe, and cooled to −78° C. in an acetone-dry ice bath. One mol/L diisobutyl-aluminum hydride (27.4 mL, 27.4 mmol) was dropwise added to the solution of the mixture, and stirred for 1 hour in a nitrogen atmosphere. The reaction liquid was restored to room temperature, water (100 mL) was added thereto, this was filtered through Celite, and toluene (100 mL) was added thereto for extraction. The resultant organic layer was dried with magnesium sulfate, and the solvent was evaporated away under reduced pressure to give a crude product. The crude product was purified through silica gel chromatography to give an intermediate F, of which the production quantity was 3.1 g and the yield was 82%.

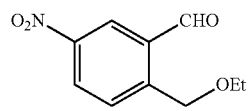 [SMILES: CCOCc1ccc([N+](=O)[O-])cc1C=O]

Intermediate F
<Fifth Stage: Dehydration>

The intermediate F (3.1 g, 15.0 mmol) obtained in the fourth stage, 4-nitrobenzohydrazide (2.7 g, 15.0 mmol), trifluoroacetic acid (0.17 g, 1.5 mmol) and ethanol (100 mL) were put into a 300-mL three-neck flask equipped with a reflux tube, a thermometer and a nitrogen introducing pipe. The solution was stirred under reflux for 1 hour in a nitrogen atmosphere, then cooled, and filtered to give the following intermediate G, of which the production quantity was 5.1 g and the yield was 92%.

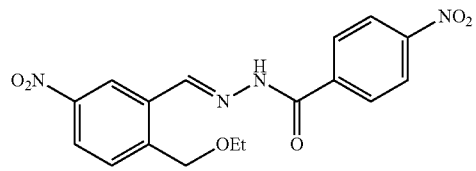 [SMILES: CCOCc1ccc([N+](=O)[O-])cc1/C=N/NC(=O)c1ccc([N+](=O)[O-])cc1]

Intermediate G
<Sixth Stage: Reduction>

The intermediate G (5.1 g, 13.7 mmol) obtained in the fifth stage, sodium sulfide 9-hydrate (13.2 g, 54.8 mmol), ethanol (70 mL) and water (30 mL) were put into a 300-mL three-neck flask equipped with a reflux tube, a thermometer and a nitrogen introducing pipe. Then this was stirred under reflux for 1 hour in a nitrogen atmosphere. The solvent was evaporated away under reduced pressure from the reaction liquid, and water (200 mL) and ethyl acetate (200 mL) were added thereto for extraction. The resultant organic layer was dried with magnesium sulfate, and the solvent was evaporated away under reduced pressure to give a crude product. The crude product was purified through silica gel chromatography to give a compound (16-3), of which the production quantity was 1.5 g and the yield was 35%.

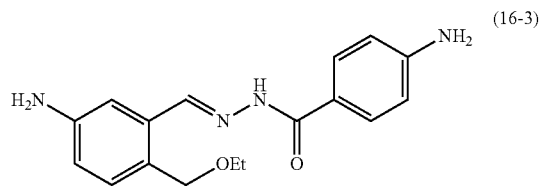 [SMILES: CCOCc1ccc(N)cc1/C=N/NC(=O)c1ccc(N)cc1]

Preparation of Varnishes

The varnishes used in the present Examples were prepared according to the following process. Here, in the varnishes 1 to 43, a photoreactive structure was introduced into the polymer using the diamine represented by the formula (2) or the formula (10). The varnishes for blending 1 to 19 were prepared using other diamines than the two diamines of the diamine represented by the formula (2) and the diamine represented by the formula (10), and are to be blended with any of the varnishes 1 to 43. The comparative diamines 1 and 2 were prepared using a diamine (V-2-1) not having a substituent at the ortho-position relative to the azo group of the azobenzene structure therein, and are comparative ones.

[Varnish Preparation Example 1] Preparation of Varnish 1

2.3204 g of the diamine (4-2) was put into a 100-mL three-neck flask equipped with a stirrer and a nitrogen introducing pipe, and N-methyl-2-pyrrolidone (74.0 g) was added thereto. 3.6796 g of a compound (AN-4-17), as a tetracarboxylic acid dianhydride where m is 8, was added to the above, and stirred at room temperature for 24 hours. γ-butyrolactone (10.0 g) and butyl cellosolve (10.0 g) were added to the reaction liquid, and heated with stirring at 80° C. until the formed polymer could have the intended weight-average molecular weight. As a result, a varnish 1 was obtained, in which the weight-average molecular weight of the polymer was 13,000 and the resin concentration (polymer concentration as a solid content) was 6% by weight.

[Varnish Preparation Examples 2 to 36] Preparation of Varnishes 2 to 36

Varnishes 2 to 36 each having a resin concentration of 6% by weight were prepared in the same manner as in Preparation Example 1, except that the compounds to be used as the diamine and the tetracarboxylic acid dianhydride were changed as in Tables 1 and 2. At this, the polymer synthesis conditions were so controlled that the weight-average molecular weight of the resultant polymer could be within a range of 5,000 to 20,000. The weight-average molecular weight of each polymer produced is shown in Tables 1 and 2. In Tables 1 and 2, Preparation Examples where 2 or more compounds are shown as diamines mean that all the compounds were used in combination as diamines, and Preparation Examples where 2 or more compounds are shown as tetracarboxylic acid dianhydrides mean that all the compounds were used in combination as tetracarboxylic acid dianhydrides. The parenthesized numerical data indicate blending ratio (mol %). The same shall apply to Tables 3 to 6.

[Varnish Preparation Examples 37 to 43] Preparation of Varnishes 37 to 43

Varnishes 37 to 43 each having a resin concentration of 6% by weight were prepared in the same manner as in Preparation Example 1, except that the compounds to be used as the diamine and the tetracarboxylic acid dianhydride, and the type and the blending ratio of the solvent to be used as a reaction medium were changed as in Table 3. The weight-average molecular weight of each polymer produced is shown in Table 3.

[Varnish Preparation Examples 44 to 59] Preparation of Varnishes for Blending 1 to 16

Varnishes for blending 1 to 16 each having a resin concentration of 6% by weight were prepared in the same manner as in Preparation Example 1, except that the compounds to be used as the diamine and the tetracarboxylic acid dianhydride were changed as in Table 4. The polymer synthesis conditions were so controlled that the weight-average molecular weight of the resultant polymer could be within a range of 45,000 to 51,000. The weight-average molecular weight of each polymer produced is shown in Table 4.

[Varnish Preparation Examples 60 to 62] Preparation of Varnishes for Blending 17 to 19

Varnishes for blending 17 to 19 each having a resin concentration of 6% by weight were prepared in the same manner as in Preparation Example 1, except that the compounds to be used as the diamine and the tetracarboxylic acid dianhydride, and the type and the blending ratio of the solvent to be used as a reaction medium were changed as in Table 5. The polymer synthesis conditions were so controlled that the weight-average molecular weight of the resultant polymer could be within a range of 45,000 to 51,000. The weight-average molecular weight of each polymer produced is shown in Table 5.

[Comparative Varnish Preparation Examples 1 and 2] Preparation of Comparative Varnishes 1 and 2

Comparative varnishes 1 and 2 each having a resin concentration of 6% by weight were prepared in the same manner as in Preparation Example 1, except that the compounds to be used as the diamine and the tetracarboxylic acid dianhydride were changed as in Table 6. The weight-average molecular weight of each polymer produced is shown in Table 6.

TABLE 1

| Preparation Example | Varnish No. | Acid Dianhydride | | Diamine | | | Weight-Average Molecular Weight |
|---|---|---|---|---|---|---|---|
| 1 | 1 | AN-4-17 m = 8 [100] | | 4-2 [100] | | | 13,000 |
| 2 | 2 | AN-4-17 m = 8 [100] | | 4-3 [100] | | | 16,000 |
| 3 | 3 | AN-4-17 m = 8 [80] | AN-3-1 [20] | 4-2 [90] | DI-13-1 [10] | | 15,000 |
| 4 | 4 | AN-4-17 m = 8 [80] | AN-3-1 [20] | 4-3 [90] | DI-13-1 [10] | | 17,000 |
| 5 | 5 | AN-4-17 m = 8 [50] | AN-2-1 [50] | 4-2 [90] | DI-13-1 [5] | DI-4-15 [5] | 16,000 |

TABLE 1-continued

| Preparation Example | Varnish No. | Acid Dianhydride | | | Diamine | | | Weight-Average Molecular Weight |
|---|---|---|---|---|---|---|---|---|
| 6 | 6 | AN-4-17 m = 8 [50] | AN-2-1 [50] | | 4-3 [90] | DI-13-1 [5] | DI-4-15 [5] | 17,000 |
| 7 | 7 | AN-4-17 m = 8 [90] | AN-4-5 [10] | | 4-2 [70] | DI-13-1 [5] | DI-5-1 m = 4 [25] | 12,000 |
| 8 | 8 | AN-4-17 m = 8 [90] | AN-4-5 [10] | | 4-3 [70] | DI-13-1 [5] | DI-5-1 m = 4 [25] | 9,000 |
| 9 | 9 | AN-4-17 m = 8 [50] | AN-2-1 [25] | AN-1-1 [25] | 4-2 [70] | DI-5-1 m = 4 [20] | DI-4-13 [10] | 10,000 |
| 10 | 10 | AN-4-17 m = 8 [50] | AN-2-1 [25] | AN-1-1 [25] | 4-3 [70] | DI-5-1 m = 4 [20] | DI-4-13 [10] | 11,000 |
| 11 | 11 | AN-4-17 m = 8 [100] | | | 4-1 [100] | | | 9,000 |
| 12 | 12 | AN-4-17 m = 8 [100] | | | 4-4 [100] | | | 14,000 |
| 13 | 13 | AN-4-17 m = 8 [100] | | | 4-5 [100] | | | 16,000 |
| 14 | 14 | AN-4-17 m = 8 [50] | AN-2-1 [25] | AN-1-1 [25] | 4-1 [90] | DI-13-1 [5] | DI-4-13 [5] | 10,000 |
| 15 | 15 | AN-4-17 m = 8 [50] | AN-2-1 [25] | AN-1-1 [25] | 4-2 [90] | DI-13-1 [5] | DI-4-13 [5] | 8,000 |
| 16 | 16 | AN-4-17 m = 8 [50] | AN-2-1 [25] | AN-1-1 [25] | 4-3 [90] | DI-13-1 [5] | DI-4-13 [5] | 14,000 |
| 17 | 17 | AN-4-17 m = 8 [50] | AN-2-1 [25] | AN-1-1 [25] | 4-4 [90] | DI-13-1 [5] | DI-4-13 [5] | 10,000 |
| 18 | 18 | AN-4-17 m = 8 [50] | AN-2-1 [25] | AN-1-1 [25] | 4-5 [90] | DI-13-1 [5] | DI-4-13 [5] | 16,000 |

TABLE 2

| Preparation Example | Varnish No. | Acid Dianhydride | | | Diamine | | | Weight-Average Molecular Weight |
|---|---|---|---|---|---|---|---|---|
| 19 | 19 | AN-1-2 m = 6 [100] | | | 4-2 [100] | | | 7,000 |
| 20 | 20 | AN-1-2 m = 6 [50] | AN-4-17 m = 8 [50] | | 4-4 [100] | | | 12,000 |
| 21 | 21 | AN-1-2 m = 6 [50] | AN-2-1 [25] | AN-1-1 [25] | 4-3 [90] | DI-13-1 [5] | DI-4-13 [5] | 10,000 |
| 22 | 22 | AN-4-17 m = 8 [50] | AN-2-1 [25] | AN-7-2 [25] | 4-5 [85] | DI-4-26 [10] | DI-13-1 [5] | 10,000 |
| 23 | 23 | AN-4-21 [70] | AN-4-18 [30] | | 4-3 [100] | | | 18,000 |
| 24 | 24 | AN-4-21 [100] | | | 4-2 [100] | | | 15,000 |
| 25 | 25 | AN-4-17 m = 8 [50] | AN-2-1 [25] | AN-1-1 [25] | 4-3 [80] | DI-5-12 m = 3 [10] | DI-5-49 [10] | 9,000 |
| 26 | 26 | AN-4-21 [50] | AN-2-1 [50] | | 4-5 [80] | DI-5-12 m = 1 [15] | DI-5-50 [5] | 13,000 |
| 27 | 27 | AN-2-1 [50] | AN-7-2 [50] | | 4-3 [80] | DI-4-1 [10] | DI-5-1 m = 1 [10] | 12,000 |
| 28 | 28 | AN-2-1 [70] | AN-5-1 [30] | | 4-2 [70] | DI-5-28 [20] | DI-5-1 m = 1 [10] | 9,000 |

TABLE 2-continued

| Preparation Example | Varnish No. | Acid Dianhydride | | | Diamine | | | Weight-Average Molecular Weight |
|---|---|---|---|---|---|---|---|---|
| 29 | 29 | AN-4-17 m = 8 [50] | AN-2-1 [50] | | 4-2 [70] | DI-4-1 [20] | DI-4-20 m = 1 [10] | 10,000 |
| 30 | 30 | AN-4-17 m = 4 [100] | | | 4-3 [100] | | | 14,000 |
| 31 | 31 | AN-4-17 m = 4 [75] | AN-1-1 [25] | | 4-3 [100] | | | 18,000 |
| 32 | 32 | AN-4-17 m = 2 [35] | AN-4-17 m = 8 [35] | AN-2-1 [30] | 4-3 [80] | DI-13-1 [10] | DI-5-1 m = 4 [10] | 12,000 |
| 33 | 33 | AN-4-17 m = 8 [100] | | | 8-3 [100] | | | 8,000 |
| 34 | 34 | AN-1-2 m = 6 [40] | AN-4-21 [35] | AN-2-1 [25] | 8-3 [85] | DI-5-28 [10] | DI-5-1 m = 1 [5] | 6,000 |
| 35 | 35 | AN-4-17 m = 8 [50] | AN-2-1 [25] | AN-1-1 [25] | 8-3 [90] | DI-13-1 [5] | DI-4-13 [5] | 7,000 |
| 36 | 36 | AN-4-17 m = 8 [100] | | | 16-3 [100] | | | 7,000 |

TABLE 3

| Preparation Example | Varnish No. | Acid Dianhydride | | | Diamine | | | Weight-Average Molecular Weight | Proportion of Solvent in Solution (% by weight) | | | | |
|---|---|---|---|---|---|---|---|---|---|---|---|---|---|
| | | | | | | | | | NMP | BC | GBL | EDM | BP |
| 37 | 37 | AN-4-17 m = 8 [50] | AN-2-1 [25] | AN-1-1 [25] | 4-3 [90] | DI-13-1 [5] | DI-4-13 [5] | 12,000 | 64 | 30 | — | — | — |
| 38 | 38 | AN-1-2 m = 6 [50] | AN-2-1 [25] | AN-1-1 [25] | 4-3 [90] | DI-13-1 [5] | DI-4-13 [5] | 14,000 | 64 | 30 | — | — | — |
| 39 | 39 | AN-4-17 m = 8 [50] | AN-2-1 [50] | | 4-2 [70] | DI-4-1 [20] | DI-4-20 m = 1 [10] | 10,000 | 64 | 30 | — | — | — |
| 40 | 40 | AN-4-17 m = 8 [90] | AN-4-5 [10] | | 4-2 [70] | DI-13-1 [5] | DI-5-1 m = 4 [25] | 11,000 | 74 | — | — | 15 | 5 |
| 41 | 41 | AN-4-17 m = 8 [50] | AN-2-1 [25] | AN-1-1 [25] | 4-3 [90] | DI-13-1 [5] | DI-4-13 [5] | 14,000 | 74 | — | — | 15 | 5 |
| 42 | 42 | AN-1-2 m = 6 [50] | AN-2-1 [25] | AN-1-1 [25] | 4-3 [90] | DI-13-1 [5] | DI-4-13 [5] | 16,000 | 74 | — | — | 15 | 5 |
| 43 | 43 | AN-4-17 m = 8 [50] | AN-2-1 [50] | | 4-2 [70] | DI-4-1 [20] | DI-4-20 m = 1 [10] | 11,000 | 74 | — | — | 15 | 5 |

TABLE 4

| Preparation Example | Varnish No. for blending | Acid Dianhydride | | | Diamine | | | Weight-Average Molecular Weight |
|---|---|---|---|---|---|---|---|---|
| 44 | 1 | AN-3-2 [35] | AN-1-1 [65] | | DI-13-1 [50] | DI-5-9 [30] | DI-4-1 [20] | 50,200 |
| 45 | 2 | AN-3-2 [35] | AN-1-1 [65] | | DI-13-1 [50] | DI-5-9 [30] | DI-4-19 [20] | 50,100 |
| 46 | 3 | AN-3-2 [35] | AN-1-1 [65] | | DI-13-1 [50] | DI-5-9 [30] | DI-4-18 [20] | 50,000 |
| 47 | 4 | AN-3-2 [50] | AN-2-1 [50] | | DI-13-1 [50] | DI-5-9 [50] | | 46,000 |
| 48 | 5 | AN-3-2 [40] | AN-1-1 [40] | AN-2-1 [20] | DI-13-1 [50] | DI-5-9 [30] | DI-4-1 [20] | 47,000 |

TABLE 4-continued

| Preparation Example | Varnish No. for blending | Acid Dianhydride | | | Diamine | | | Weight-Average Molecular Weight |
|---|---|---|---|---|---|---|---|---|
| 49 | 6 | AN-2-1 [80] | AN-1-1 [20] | | DI-5-1 m = 1 [70] | DI-4-1 [30] | | 51,000 |
| 50 | 7 | AN-1-1 [60] | AN-4-17 m = 8 [40] | | DI-13-1 [90] | DI-4-1 [10] | | 50,000 |
| 51 | 8 | AN-2-1 [45] | AN-3-2 [35] | AN-1-1 [20] | DI-4-19 [65] | DI-13-1 [35] | | 47,000 |
| 52 | 9 | AN-3-1 [100] | | | DI-4-1 [80] | DI-5-28 [20] | | 49,000 |
| 53 | 10 | AN-3-2 [55] | AN-2-1 [45] | | DI-5-28 [80] | DI-5-12 m = 2 [20] | | 46,000 |
| 54 | 11 | AN-4-5 [70] | AN-10-1 [30] | | DI-5-12 m = 1 [100] | | | 50,000 |
| 55 | 12 | AN-2-1 [50] | AN-10-1 [50] | | DI-4-10 [85] | DI-7-7 [15] | | 49,000 |
| 56 | 13 | AN-2-1 [80] | AN-1-1 [20] | | DI-4-1 [100] | | | 50,000 |
| 57 | 14 | AN-2-1 [50] | AN-3-2 [35] | AN-1-1 [15] | DIH-1-2 n = 4 [50] | DI-13-1 [40] | DI-5-9 [10] | 51,000 |
| 58 | 15 | AN-2-1 [65] | AN-3-2 [35] | | DIH-1-2 n = 4 [50] | DI-13-1 [40] | DI-5-9 [10] | 49,000 |
| 59 | 16 | AN-2-1 [65] | AN-3-2 [35] | | DIH-1-2 n = 4 [50] | DI-13-1 [40] | DI-5-30 k = 2 [10] | 46,000 |

TABLE 5

| Preparation Example | Varnish No. for blending | Acid Dianhydride | | | Diamine | | | Weight-Average Molecular Weight | Proportion of Solvent in Solution (% by weight) | | | | |
|---|---|---|---|---|---|---|---|---|---|---|---|---|---|
| | | | | | | | | | NMP | BC | GBL | EDM | BP |
| 60 | 17 | AN-3-2 [35] | AN-1-1 [65] | | DI-13-1 [50] | DI-5-9 [30] | DI-4-18 [20] | 46,000 | 64 | — | — | 30 | — |
| 61 | 18 | AN-1-1 [60] | AN-4-17 m = 8 [40] | | DI-13-1 [90] | DI-4-1 [10] | | 50,000 | 64 | — | — | 30 | — |
| 62 | 19 | AN-2-1 [45] | AN-3-2 [35] | AN-1-1 [20] | DI-4-19 [65] | DI-13-1 [35] | | 48,000 | 64 | — | — | 30 | — |

TABLE 6

| Comparative Preparation Example | Comparative Varnish No. | Acid Dianhydride | Diamine | | Weight-Average Molecular Weight |
|---|---|---|---|---|---|
| 1 | 1 | AN-4-17 m = 8 [100] | V-2-1 [100] | | 10,000 |
| 2 | 2 | AN-4-17 m = 8 [100] | V-2-1 [90] | DI-13-1 [10] | 12,000 |

Preparation of Liquid Crystal Aligning Agent

Using the varnishes 1 to 43, the varnishes for blending 1 to 19 and the comparative varnishes 1 and 2 prepared in Preparation Examples, liquid crystal aligning agents were prepared according to the following process.

[Example 1] Preparation of Aligning Agent 1

The varnish 1 (10.0 g) was weighed and put into a 50-mL eggplant flask equipped with a stirrer and a nitrogen introducing pipe, and N-methyl-2-pyrrolidone (1.0 g), butyl cellosolve (0.5 g) and diisobutyl ketone (0.5 g) were added thereto and stirred at room temperature for 1 hour to prepare an aligning agent 1 having a resin concentration of 5% by weight.

[Examples 2 to 36] Preparation of Aligning Agents 2 to 36

Aligning agents 2 to 36 were prepared in the same manner as in Example 1 except that the varnishes 2 to 36 were used in place of the varnish 1.

[Example 37] Preparation of Aligning Agent 37

The varnish 1 (3.0 g) and the varnish for blending 1 (7.0 g) were weighed and put into a 50-mL eggplant flask equipped with a stirrer and a nitrogen introducing pipe, and N-methyl-2-pyrrolidone (3.0 g), butyl cellosolve (1.0 g) and diisobutyl ketone (1.0 g) were added thereto and stirred at room temperature for 1 hour to prepare an aligning agent 37 having a resin concentration of 4% by weight.

[Examples 38 to 116] Preparation of Aligning Agents 38 to 116

Aligning agents 38 to 116 were prepared in the same manner as in Example 37, except that the varnishes and the varnishes for blending shown in Tables 8 and 9 were used in place of the varnish 1 and the varnish for blending 1, and that the blending ratio of the varnish and the varnish for blending was changed as in Tables 8 and 9.

[Examples 117 to 160] Preparation of Aligning Agents 117 to 160

Aligning agents 117 to 160 were prepared in the same manner as in Example 37, except that the varnishes and the varnishes for blending shown in Table 10 were used in place of the varnish 1 and the varnish for blending 1, and that the type and the blending ratio of solvent were changed as in Table 10.

[Comparative Examples 1 and 2] Preparation of Comparative Aligning Agents 1 and 2

Comparative aligning agents 1 and 2 were prepared in the same manner as in Example 1 except that the comparative varnishes shown in Table 11 were used in place of the varnish 1.

[Comparative Examples 3 and 4] Preparation of Comparative Aligning Agents 3 and 4

Comparative aligning agents 3 and 4 were prepared in the same manner as in Example 37 except that the comparative varnishes and the varnishes for blending shown in Table 12 were used in place of the varnish 1 and the varnish for blending 1.

The varnishes used for preparing the liquid crystal aligning agents in Examples and Comparative Examples are shown in Tables 7 to 12.

TABLE 7

| Example No. | Aligning Agent No. | Varnish No. |
|---|---|---|
| 1 | 1 | 1 |
| 2 | 2 | 2 |
| 3 | 3 | 3 |
| 4 | 4 | 4 |
| 5 | 5 | 5 |
| 6 | 6 | 6 |
| 7 | 7 | 7 |
| 8 | 8 | 8 |
| 9 | 9 | 9 |
| 10 | 10 | 10 |
| 11 | 11 | 11 |
| 12 | 12 | 12 |
| 13 | 13 | 13 |
| 14 | 14 | 14 |
| 15 | 15 | 15 |
| 16 | 16 | 16 |
| 17 | 17 | 17 |
| 18 | 18 | 18 |
| 19 | 19 | 19 |
| 20 | 20 | 20 |
| 21 | 21 | 21 |
| 22 | 22 | 22 |
| 23 | 23 | 23 |
| 24 | 24 | 24 |
| 25 | 25 | 25 |
| 26 | 26 | 26 |
| 27 | 27 | 27 |
| 28 | 28 | 28 |

TABLE 7-continued

| Example No. | Aligning Agent No. | Varnish No. |
|---|---|---|
| 29 | 29 | 29 |
| 30 | 30 | 30 |
| 31 | 31 | 31 |
| 32 | 32 | 32 |
| 33 | 33 | 33 |
| 34 | 34 | 34 |
| 35 | 35 | 35 |
| 36 | 36 | 36 |

TABLE 8

| Example No. | Aligning Agent No. | Varnish No. | Varnish No. for blending | Blending Ratio of Varnishes |
|---|---|---|---|---|
| 37 | 37 | 1 | 1 | 3:7 |
| 38 | 38 | 2 | 1 | 3:7 |
| 39 | 39 | 3 | 2 | 3:7 |
| 40 | 40 | 4 | 2 | 3:7 |
| 41 | 41 | 5 | 3 | 3:7 |
| 42 | 42 | 6 | 3 | 3:7 |
| 43 | 43 | 7 | 4 | 3:7 |
| 44 | 44 | 7 | 5 | 3:7 |
| 45 | 45 | 8 | 4 | 3:7 |
| 46 | 46 | 8 | 5 | 3:7 |
| 47 | 47 | 9 | 3 | 3:7 |
| 48 | 48 | 9 | 5 | 3:7 |
| 49 | 49 | 10 | 3 | 3:7 |
| 50 | 50 | 10 | 5 | 3:7 |
| 51 | 51 | 1 | 12 | 3:7 |
| 52 | 52 | 2 | 8 | 3:7 |
| 53 | 53 | 7 | 8 | 3:7 |
| 54 | 54 | 7 | 10 | 3:7 |
| 55 | 55 | 8 | 7 | 3:7 |
| 56 | 56 | 8 | 11 | 3:7 |
| 57 | 57 | 11 | 1 | 3:7 |
| 58 | 58 | 11 | 6 | 3:7 |
| 59 | 59 | 12 | 1 | 3:7 |
| 60 | 60 | 12 | 7 | 3:7 |
| 61 | 61 | 13 | 1 | 3:7 |
| 62 | 62 | 13 | 11 | 3:7 |
| 63 | 63 | 14 | 5 | 3:7 |
| 64 | 64 | 14 | 8 | 3:7 |
| 65 | 65 | 14 | 10 | 3:7 |
| 66 | 66 | 15 | 4 | 3:7 |
| 67 | 67 | 15 | 6 | 3:7 |
| 68 | 68 | 15 | 9 | 3:7 |
| 69 | 69 | 16 | 1 | 3:7 |
| 70 | 70 | 16 | 3 | 3:7 |
| 71 | 71 | 16 | 6 | 3:7 |
| 72 | 72 | 16 | 7 | 3:7 |
| 73 | 73 | 16 | 8 | 3:7 |
| 74 | 74 | 17 | 8 | 3:7 |
| 75 | 75 | 18 | 8 | 3:7 |
| 76 | 76 | 19 | 2 | 3:7 |

TABLE 9

| Example No. | Aligning Agent No. | Varnish No. | Varnish No. for blending | Blending Ratio of Varnishes |
|---|---|---|---|---|
| 77 | 77 | 19 | 12 | 3:7 |
| 78 | 78 | 20 | 3 | 3:7 |
| 79 | 79 | 20 | 8 | 3:7 |
| 80 | 80 | 21 | 6 | 3:7 |
| 81 | 81 | 21 | 7 | 3:7 |
| 82 | 82 | 21 | 8 | 3:7 |
| 83 | 83 | 21 | 11 | 3:7 |
| 84 | 84 | 22 | 4 | 3:7 |
| 85 | 85 | 22 | 9 | 3:7 |
| 86 | 86 | 23 | 1 | 3:7 |
| 87 | 87 | 23 | 9 | 3:7 |
| 88 | 88 | 25 | 5 | 3:7 |
| 89 | 89 | 25 | 11 | 3:7 |

TABLE 9-continued

| Example No. | Aligning Agent No. | Varnish No. | Varnish No. for blending | Blending Ratio of Varnishes |
|---|---|---|---|---|
| 90 | 90 | 26 | 6 | 3:7 |
| 91 | 91 | 26 | 10 | 3:7 |
| 92 | 92 | 27 | 2 | 3:7 |
| 93 | 86 | 27 | 10 | 3:7 |
| 94 | 87 | 27 | 12 | 3:7 |
| 95 | 88 | 28 | 2 | 3:7 |
| 96 | 89 | 28 | 6 | 3:7 |
| 97 | 90 | 28 | 10 | 3:7 |
| 98 | 91 | 29 | 4 | 3:7 |
| 99 | 92 | 29 | 12 | 3:7 |
| 100 | 100 | 5 | 14 | 3:7 |
| 101 | 101 | 16 | 14 | 3:7 |
| 102 | 102 | 16 | 15 | 3:7 |
| 103 | 103 | 21 | 15 | 4:6 |
| 104 | 104 | 16 | 16 | 3:7 |
| 105 | 105 | 26 | 16 | 3:7 |
| 106 | 106 | 30 | 13 | 4:6 |
| 107 | 107 | 31 | 13 | 4:6 |
| 108 | 108 | 31 | 14 | 4:6 |
| 109 | 109 | 32 | 8 | 3:7 |
| 110 | 110 | 33 | 1 | 3:7 |
| 111 | 111 | 33 | 13 | 4:6 |
| 112 | 112 | 34 | 3 | 3:7 |
| 113 | 113 | 34 | 13 | 4:6 |
| 114 | 114 | 35 | 6 | 3:7 |
| 115 | 115 | 35 | 8 | 3:7 |
| 116 | 116 | 35 | 14 | 3:7 |

TABLE 10

| Example No. | Aligning Agent No. | Varnish No. | Varnish No. for blending | Proportion of Solvent in Solution (% by weight) | | | | | | | | | | | | |
|---|---|---|---|---|---|---|---|---|---|---|---|---|---|---|---|---|
| | | | | NMP | BC | GBL | DPM | GVL | EDM | BP | BDM | EDE | BCA | DIBK | MIBC | DIBC |
| 117 | 117 | 40 | 17 | 50 | 13 | | 10 | | 19 | 4 | | | | | | |
| 118 | 118 | 40 | 18 | 50 | | 13 | | | 21 | 4 | 1 | | 7 | | | |
| 119 | 119 | 40 | 19 | 50 | | 13 | | | 21 | 4 | 1 | | 7 | | | |
| 120 | 120 | 16 | 3 | 50 | 10 | 29 | | | | | | | 7 | | | |
| 121 | 121 | 37 | 17 | 50 | 6 | 13 | | | 19 | | | 1 | 7 | | | |
| 122 | 122 | 16 | 7 | 60 | 15 | 13 | 8 | | | | | | | | | |
| 123 | 123 | 37 | 7 | 50 | 15 | 21 | | 10 | | | | | | | | |
| 124 | 124 | 41 | 18 | 50 | | 13 | | | 21 | 4 | 1 | | 7 | | | |
| 125 | 125 | 16 | 8 | 50 | 10 | 29 | | | | | | | 7 | | | |
| 126 | 126 | 16 | 8 | 60 | 15 | 13 | 8 | | | | | | | | | |
| 127 | 127 | 37 | 8 | 50 | 15 | 21 | | 10 | | | | | | | | |
| 128 | 128 | 37 | 19 | 50 | 6 | 13 | | | 19 | | 1 | | | 7 | | |
| 129 | 129 | 37 | 19 | 50 | 6 | 13 | | | 19 | | 1 | | | | | 7 |
| 130 | 130 | 37 | 19 | 50 | 6 | 13 | | | 19 | | | 1 | 7 | | | |
| 131 | 131 | 41 | 19 | 50 | 13 | | 10 | | 19 | 4 | | | | | | |
| 132 | 132 | 41 | 19 | 50 | | 13 | | | 21 | 4 | 1 | | 7 | | | |
| 133 | 133 | 21 | 3 | 50 | 10 | 29 | | | | | | | 7 | | | |
| 134 | 134 | 21 | 3 | 60 | 15 | 13 | 8 | | | | | | | | | |
| 135 | 135 | 38 | 3 | 50 | 15 | 21 | | 10 | | | | | | | | |
| 136 | 136 | 38 | 17 | 50 | 6 | 13 | | | 19 | | 1 | | | 7 | | |
| 137 | 137 | 38 | 17 | 50 | 6 | 13 | | | 19 | | 1 | | | | | 7 |
| 138 | 138 | 38 | 17 | 50 | 6 | 13 | | | 19 | | | 1 | 7 | | | |
| 139 | 139 | 42 | 17 | 50 | 13 | | 10 | | 19 | 4 | | | | | | |
| 140 | 140 | 42 | 17 | 50 | | 13 | | | 21 | 4 | 1 | | 7 | | | |
| 141 | 141 | 38 | 7 | 50 | 15 | 21 | | 10 | | | | | | | | |
| 142 | 142 | 38 | 18 | 50 | 6 | 13 | | | 19 | | 1 | | 7 | | | |
| 143 | 143 | 42 | 18 | 50 | 13 | | 10 | | 19 | 4 | | | | | | |
| 144 | 144 | 21 | 8 | 50 | 10 | 29 | | | | | | | 7 | | | |
| 145 | 145 | 38 | 19 | 50 | 6 | 13 | | | 19 | | 1 | | | | | 7 |
| 146 | 146 | 42 | 19 | 50 | | 13 | | | 21 | 4 | 1 | | 7 | | | |
| 147 | 147 | 29 | 3 | 50 | 10 | 29 | | | | | | | 7 | | | |
| 148 | 148 | 39 | 17 | 50 | 6 | 13 | | | 19 | | 1 | | | 7 | | |
| 149 | 149 | 43 | 17 | 50 | | 13 | | | 21 | 4 | 1 | | 7 | | | |
| 150 | 150 | 29 | 7 | 50 | 10 | 29 | | | | | | | 7 | | | |
| 151 | 151 | 29 | 7 | 60 | 15 | 13 | 8 | | | | | | | | | |
| 152 | 152 | 39 | 7 | 50 | 15 | 21 | | 10 | | | | | | | | |
| 153 | 153 | 39 | 18 | 50 | 6 | 13 | | | 19 | | 1 | | | 7 | | |
| 154 | 154 | 39 | 18 | 50 | 6 | 13 | | | 19 | | 1 | | | | | 7 |
| 155 | 155 | 39 | 18 | 50 | 6 | 13 | | | 19 | | | 1 | 7 | | | |
| 156 | 156 | 43 | 18 | 50 | 13 | | 10 | | 19 | 4 | | | | | | |
| 157 | 157 | 43 | 18 | 50 | | 13 | | | 21 | 4 | 1 | | 7 | | | |
| 158 | 158 | 39 | 8 | 50 | 15 | 21 | | 10 | | | | | | | | |
| 159 | 159 | 39 | 19 | 50 | 6 | 13 | | | 19 | | | 1 | 7 | | | |
| 160 | 160 | 43 | 19 | 50 | 13 | | 10 | | 19 | 4 | | | | | | |

TABLE 11

| Comparative Example No. | Comparative Aligning Agent No. | Comparative Varnish No. |
|---|---|---|
| 1 | 1 | 1 |
| 2 | 2 | 2 |

TABLE 12

| Comparative No. | Comparative Aligning Agent No. | Comparative Varnish No. | Varnish No. for blending |
|---|---|---|---|
| 3 | 3 | 1 | 1 |
| 4 | 4 | 2 | 1 |

Evaluation

[Evaluation of Voltage Holding Ratio]

The liquid crystal aligning agent prepared in Examples 1 to 35, 37 to 116 and Comparative Example 1 to 4 was dropwise applied onto an IPS electrode-having glass substrate and a column spacer-having glass substrate, and the substrates were rotated at 2,000 rpm for 15 seconds according to a spinner method to be coated with the aligning agent. After coated, the substrates were heated at 60° C. for 1 minute to evaporate the solvent, thereby forming a film of the liquid crystal aligning agent thereon. Using Multilight ML-501C/B by Ushio Inc., the liquid crystal alignment film was exposed to a linearly-polarized UV ray having a wavelength of 365 nm via a polarizer in the direction vertical to the substrate at an intensity of 2.0±0.1 J/cm² for photoalignment treatment. Thus photoalignment-treated, the liquid crystal aligning agent film was heated and baked at 230° C. for 30 minutes to form a liquid crystal alignment film having a thickness of 100 nm. Apart from this, a film of the aligning agent 1 or 73 was formed on an IPS electrode-having glass substrate and a column spacer-having glass substrate under the same conditions as above, then treated for photoalignment, and thereafter heated and baked under the conditions shown in Table 16. In Table 16, the baking conditions in Examples 1-2 to 1-17 and Example 73-2 include heating and baking at the temperature for the time shown in the first stage column followed by heating and baking at the temperature and for the time shown in the second stage column. The baking conditions in Example 1-18 include continuously heating from 110° C. up to 220° C. in a period of 20 minutes followed by keeping at the temperature for 15 minutes for baking treatment. The same as in Examples 1-2 to 1-17, Example 1-18 and Example 73-2 in Table 16 shall apply to Examples 1-2 to 1-17, Example 1-18 and Example 73-2, respectively, in the following Tables 20, 24 and 25. In the manner as above, various liquid crystal alignment films were formed using different aligning agents and under different heating and baking conditions.

Next, the two substrates on which the liquid crystal alignment film was formed were combined and stuck together in such a manner that the surfaces thereof each having the liquid crystal alignment film formed thereon could face each other via a space kept therebetween so that a liquid crystal composition could be injected into the space between the facing liquid crystal alignment films. At this, the substrates were so oriented that the polarization directions of the linearly-polarized lights applied to the liquid crystal alignment films could be in parallel to each other. Into the space between the thus-stuck substrates, a negative liquid crystal composition A composed of the ingredients mentioned below was injected to construct a liquid crystal cell having a cell thickness of 7 μm (liquid crystal display device).

<Negative Liquid Crystal Composition A>

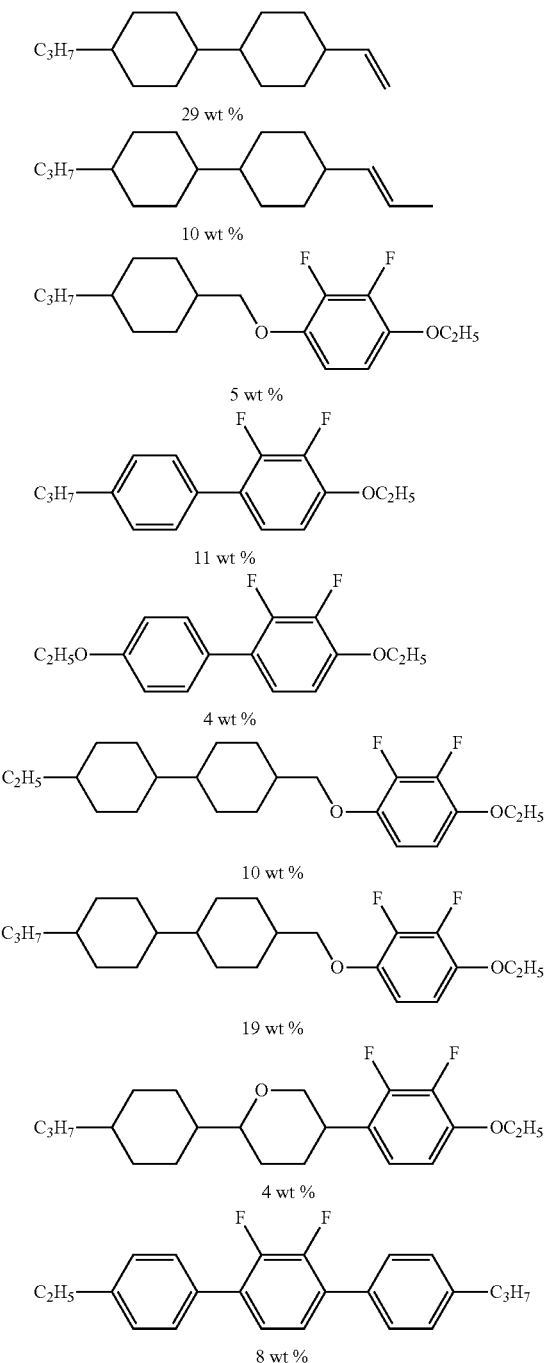

Physical Properties: NI 75.7° C.; Δε −4.1; Δn 0.101; η 14.5 mPa·s.

The voltage holding ratio (initial voltage holding ratio) of the thus-produced liquid crystal cells was measured at 5 V and 30 Hz. Subsequently, the liquid crystal cell was put on a turned-on backlight tester (FujiCOLOR LED Viewer Pro HR-2, by FUJIFILM Corporation; brightness 2,700 cd/m²), and kept as such for 300 hours, and thereafter the voltage holding ratio of each cell after photoirradiation was measured. The results are shown in Tables 13 to 18.

TABLE 13

| Example No. | Aligning Agent No. | Varnish No. | Voltage Holding Ratio (%) Initial | Voltage Holding Ratio (%) After 300 hours |
|---|---|---|---|---|
| 1 | 1 | 1 | 98.3 | 97.6 |
| 2 | 2 | 2 | 98.5 | 97.7 |
| 3 | 3 | 3 | 98.5 | 97.8 |
| 4 | 4 | 4 | 98.6 | 97.8 |
| 5 | 5 | 5 | 98.4 | 97.6 |
| 6 | 6 | 6 | 98.7 | 97.7 |
| 7 | 7 | 7 | 98.8 | 98.0 |
| 8 | 8 | 8 | 98.6 | 97.9 |
| 9 | 9 | 9 | 98.4 | 97.9 |
| 10 | 10 | 10 | 98.5 | 97.7 |
| 11 | 11 | 11 | 98.2 | 97.6 |
| 12 | 12 | 12 | 98.4 | 97.7 |
| 13 | 13 | 13 | 98.5 | 97.7 |
| 14 | 14 | 14 | 98.4 | 97.8 |
| 15 | 15 | 15 | 98.3 | 97.7 |
| 16 | 16 | 16 | 98.5 | 97.9 |
| 17 | 17 | 17 | 98.5 | 97.9 |
| 18 | 18 | 18 | 98.4 | 97.8 |
| 19 | 19 | 19 | 98.4 | 97.6 |
| 20 | 20 | 20 | 98.5 | 97.7 |
| 21 | 21 | 21 | 98.5 | 97.8 |
| 22 | 22 | 22 | 98.3 | 97.6 |
| 23 | 23 | 23 | 98.5 | 97.7 |
| 24 | 24 | 24 | 98.2 | 97.7 |
| 25 | 25 | 25 | 98.6 | 97.8 |
| 26 | 26 | 26 | 98.4 | 97.7 |
| 27 | 27 | 27 | 98.5 | 97.8 |
| 28 | 28 | 28 | 98.4 | 97.6 |
| 29 | 29 | 29 | 98.5 | 97.7 |
| 30 | 30 | 30 | 98.5 | 97.7 |
| 31 | 31 | 31 | 98.5 | 97.6 |
| 32 | 32 | 32 | 98.3 | 97.8 |
| 33 | 33 | 33 | 98.4 | 97.6 |
| 34 | 34 | 34 | 98.3 | 97.8 |
| 35 | 35 | 35 | 98.3 | 97.8 |

TABLE 14

| Example No. | Aligning Agent No. | Varnish No. | Varnish No. for blending | Voltage Holding Ratio (%) Initial | Voltage Holding Ratio (%) After 300 hours |
|---|---|---|---|---|---|
| 37 | 37 | 1 | 1 | 98.8 | 98.3 |
| 38 | 38 | 2 | 1 | 98.9 | 98.6 |
| 39 | 39 | 3 | 2 | 98.7 | 98.3 |
| 40 | 40 | 4 | 2 | 99.0 | 98.5 |
| 41 | 41 | 5 | 3 | 98.9 | 98.6 |
| 42 | 42 | 6 | 3 | 98.5 | 98.3 |
| 43 | 43 | 7 | 4 | 99.1 | 98.7 |
| 44 | 44 | 7 | 5 | 98.9 | 98.7 |
| 45 | 45 | 8 | 4 | 99.0 | 98.6 |
| 46 | 46 | 8 | 5 | 99.0 | 98.7 |
| 47 | 47 | 9 | 3 | 99.1 | 98.7 |
| 48 | 48 | 9 | 5 | 98.8 | 98.7 |
| 49 | 49 | 10 | 3 | 99.0 | 98.8 |
| 50 | 50 | 10 | 5 | 99.1 | 98.8 |
| 51 | 51 | 1 | 12 | 98.8 | 98.5 |
| 52 | 52 | 2 | 8 | 98.8 | 98.7 |
| 53 | 53 | 7 | 8 | 99.0 | 98.7 |
| 54 | 54 | 7 | 10 | 99.1 | 98.8 |
| 55 | 55 | 8 | 7 | 98.9 | 98.8 |
| 56 | 56 | 8 | 11 | 98.9 | 98.7 |
| 57 | 57 | 11 | 1 | 98.6 | 98.4 |
| 58 | 58 | 11 | 6 | 98.7 | 98.3 |
| 59 | 59 | 12 | 1 | 98.9 | 98.4 |
| 60 | 60 | 12 | 7 | 99.0 | 98.6 |
| 61 | 61 | 13 | 1 | 99.0 | 98.7 |
| 62 | 62 | 13 | 11 | 99.1 | 98.9 |
| 63 | 63 | 14 | 5 | 98.9 | 98.4 |
| 64 | 64 | 14 | 8 | 99.0 | 98.6 |
| 65 | 65 | 14 | 10 | 98.9 | 98.3 |
| 66 | 66 | 15 | 4 | 99.2 | 98.8 |
| 67 | 67 | 15 | 6 | 99.1 | 98.8 |
| 68 | 68 | 15 | 9 | 99.1 | 98.6 |
| 69 | 69 | 16 | 1 | 99.2 | 98.6 |
| 70 | 70 | 16 | 3 | 99.1 | 98.6 |
| 71 | 71 | 16 | 6 | 98.8 | 98.8 |
| 72 | 72 | 16 | 7 | 99.1 | 98.7 |
| 73 | 73 | 16 | 8 | 99.2 | 98.7 |
| 74 | 74 | 17 | 8 | 99.2 | 98.6 |
| 75 | 75 | 18 | 8 | 99.1 | 98.7 |
| 76 | 76 | 19 | 2 | 99.3 | 98.9 |

TABLE 15

| Example No. | Aligning Agent No. | Varnish No. | Varnish No. for blending | Voltage Holding Ratio (%) Initial | Voltage Holding Ratio (%) After 300 hours |
|---|---|---|---|---|---|
| 77 | 77 | 19 | 12 | 99.1 | 98.9 |
| 78 | 78 | 20 | 3 | 99.1 | 98.8 |
| 79 | 79 | 20 | 8 | 99.0 | 98.7 |
| 80 | 80 | 21 | 6 | 99.2 | 99.0 |
| 81 | 81 | 21 | 7 | 99.1 | 98.6 |
| 82 | 82 | 21 | 8 | 99.1 | 98.9 |
| 83 | 83 | 21 | 11 | 99.2 | 98.7 |
| 84 | 84 | 22 | 4 | 98.9 | 98.7 |
| 85 | 85 | 22 | 9 | 99.0 | 98.8 |
| 86 | 86 | 23 | 1 | 98.8 | 98.6 |
| 87 | 87 | 23 | 9 | 99.0 | 98.5 |
| 88 | 88 | 25 | 5 | 99.1 | 98.7 |
| 89 | 89 | 25 | 11 | 99.0 | 98.7 |
| 90 | 90 | 26 | 6 | 99.1 | 98.9 |
| 91 | 91 | 26 | 10 | 99.2 | 98.8 |
| 92 | 92 | 27 | 2 | 99.0 | 98.6 |
| 93 | 86 | 27 | 10 | 99.9 | 98.7 |
| 94 | 87 | 27 | 12 | 99.0 | 98.5 |
| 95 | 88 | 28 | 2 | 99.2 | 98.8 |
| 96 | 89 | 28 | 6 | 99.2 | 98.6 |
| 97 | 90 | 28 | 10 | 99.0 | 98.6 |
| 98 | 91 | 29 | 4 | 99.1 | 98.5 |
| 99 | 92 | 29 | 12 | 99.0 | 98.7 |
| 100 | 100 | 5 | 14 | 98.9 | 98.5 |
| 101 | 101 | 16 | 14 | 99.2 | 98.6 |
| 102 | 102 | 16 | 15 | 99.1 | 98.8 |
| 103 | 103 | 21 | 15 | 99.1 | 98.4 |
| 104 | 104 | 16 | 16 | 99.2 | 98.8 |
| 105 | 105 | 26 | 16 | 99.1 | 98.8 |
| 106 | 106 | 30 | 13 | 98.7 | 98.4 |
| 107 | 107 | 31 | 13 | 98.9 | 98.4 |
| 108 | 108 | 31 | 14 | 98.6 | 98.3 |
| 109 | 109 | 32 | 8 | 99.2 | 98.7 |
| 110 | 110 | 33 | 1 | 99.1 | 98.5 |
| 111 | 111 | 33 | 13 | 99.2 | 98.3 |
| 112 | 112 | 34 | 3 | 98.9 | 98.7 |
| 113 | 113 | 34 | 13 | 99.1 | 98.3 |
| 114 | 114 | 35 | 6 | 99.1 | 98.5 |
| 115 | 115 | 35 | 8 | 99.2 | 98.6 |
| 116 | 116 | 35 | 14 | 99.2 | 98.7 |

TABLE 16

| Example No. | Aligning Agent No. | Varnish No. | Varnish No. for blending | Baking Conditions First Stage | Baking Conditions Second Stage | Voltage Holding Ratio (%) Initial | Voltage Holding Ratio (%) After 300 hours |
|---|---|---|---|---|---|---|---|
| 1-2 | 1 | 1 | | 110° C., 20 minutes | 200° C., 15 minutes | 98.1 | 97.5 |
| 1-3 | 1 | 1 | | 110° C., 20 minutes | 210° C., 15 minutes | 98.2 | 98.6 |
| 1-4 | 1 | 1 | | 110° C., 20 minutes | 220° C., 15 minutes | 98.3 | 97.7 |
| 1-5 | 1 | 1 | | 110° C., 20 minutes | 230° C., 15 minutes | 98.3 | 97.7 |
| 1-6 | 1 | 1 | | 130° C., 20 minutes | 200° C., 15 minutes | 98.3 | 97.5 |
| 1-7 | 1 | 1 | | 130° C., 20 minutes | 210° C., 15 minutes | 98.3 | 97.5 |
| 1-8 | 1 | 1 | | 130° C., 20 minutes | 220° C., 15 minutes | 98.3 | 97.7 |
| 1-9 | 1 | 1 | | 130° C., 20 minutes | 230° C., 15 minutes | 98.4 | 97.8 |
| 1-10 | 1 | 1 | | 150° C., 20 minutes | 200° C., 15 minutes | 98.3 | 97.6 |
| 1-11 | 1 | 1 | | 150° C., 20 minutes | 210° C., 15 minutes | 98.3 | 97.6 |
| 1-12 | 1 | 1 | | 150° C., 20 minutes | 220° C., 15 minutes | 98.4 | 97.7 |
| 1-13 | 1 | 1 | | 150° C., 20 minutes | 230° C., 15 minutes | 98.4 | 97.8 |
| 1-14 | 1 | 1 | | 170° C., 20 minutes | 200° C., 15 minutes | 98.2 | 97.6 |
| 1-15 | 1 | 1 | | 170° C., 20 minutes | 210° C., 15 minutes | 98.2 | 97.7 |
| 1-16 | 1 | 1 | | 170° C., 20 minutes | 220° C., 15 minutes | 98.3 | 97.7 |
| 1-17 | 1 | 1 | | 170° C., 20 minutes | 230° C., 15 minutes | 98.4 | 97.9 |
| 1-18 | 1 | 1 | | Heated from 110° C. up to 220° C. in a period of 20 minutes, then kept at 220° C. for 15 minutes. | | 98.4 | 97.7 |
| 73-2 | 73 | 16 | 8 | 150° C., 20 minutes | 230° C., 15 minutes | 99.1 | 98.7 |

TABLE 17

| Comparative Example No. | Comparative Aligning Agent No. | Comparative Varnish No. | Voltage Holding Ratio (%) Initial | Voltage Holding Ratio (%) After 300 hours |
|---|---|---|---|---|
| 1 | 1 | 1 | 97.9 | 79.7 |
| 2 | 2 | 2 | 98.1 | 80.9 |

TABLE 18

| Comparative Example No. | Comparative Aligning Agent No. | Comparative Varnish No. | Varnish No. for blending | Voltage Holding Ratio (%) Initial | Voltage Holding Ratio (%) After 300 hours |
|---|---|---|---|---|---|
| 3 | 3 | 1 | 1 | 97.9 | 79.7 |
| 4 | 4 | 2 | 1 | 98.1 | 80.9 |

As shown in Tables 13 to 18, the liquid crystal cells using any of the aligning agents 1 to 35, and 37 to 116 containing any of the varnishes 1 to 35 prepared using the diamine represented by the formula (2) all had a voltage holding ratio of 97.5% or more in the initial and after backlight irradiation for 300 hours. In particular, the liquid crystal cells using any of the aligning agents 37 to 116 each containing the diamine represented by the formula (2) and the diamine for blending had a high voltage holding ratio of 98.3% or more after backlight irradiation. As opposed to these, the voltage holding ratio of the liquid crystal cells using any of the comparative aligning agents 1 to 4 each containing the varnish 1 or 2 prepared using the diamine (V-2-1) not having a substituent at the ortho-position relative to the azo group of the azobenzene structure was lower than 97.5% after backlight irradiation. This is considered because, owing to backlight irradiation, the azobenzene structure would have undergone photochemical reaction to worsen the electric characteristics of the liquid crystal alignment films. This confirms that, when a polymer in which the structural unit having a photoreactive structure undergoes chemical reaction (in the present Examples, cyclization between the azo group and the ortho-positioned substituent) by heating is used, the stability to light of the resultant liquid crystal alignment films increases, and accordingly, the electric characteristics of the liquid crystal cells using the polymer can be thereby improved.

[Evaluation of Transmittance]

Figure 2:
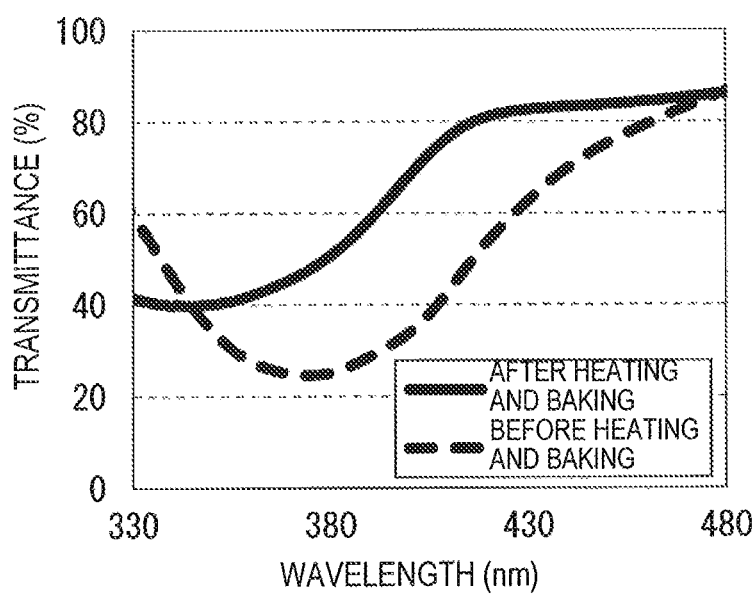
FIG. 2 shows UV-visible light transmittance spectra of a substrate with a liquid crystal alignment film formed thereon using the comparative aligning agent 1.

Using the liquid crystal aligning agents prepared in Examples 1 to 36 and Comparative Examples 1 and 2, a coating film of the liquid crystal alignment film was formed on a transparent glass substrate under the same conditions as in the above-mentioned section of evaluation of voltage holding ratio, and the substrate having the film formed thereon was subjected to UV-visible light transmittance spectrometry to determine the transmittance at 365 nm which is an absorption wavelength of azobenzene (transmittance before heating and baking). Subsequently, the film was subjected to photoalignment treatment, then heated and baked at 230° C. for 30 minute to give a liquid crystal alignment film having a thickness of 100 nm. Apart from these, a film of the aligning agent 1 was formed on a transparent glass substrate under the same conditions as mentioned above, then subjected to photoalignment treatment, and heated and balked under the conditions shown in Table 20 to form various liquid crystal alignment films each having a thickness of 100 nm. These substrates were subjected to UV-visible light transmittance spectrometry to measure the transmittance (transmittance after heating and baking) thereof at 365 nm and a mean value of the transmittance within a range of 380 nm to 430 nm was obtained. Based on the equation mentioned below, a variation of the transmittance at 365 nm before heating and baking and after heating and baking was calculated. The results are shown in Tables 19 to 21. As typical examples, the UV-visible light transmittance spectra before heating and baking and after heating and baking of the substrate having, formed thereon, a liquid crystal alignment film of the aligning agent 1 are shown in FIG. 1; and the UV-visible light transmittance spectra before heating and baking and after heating and baking of the substrate having, formed thereon, a liquid crystal alignment film of the comparative aligning agent 1 are shown in FIG. 2.

Variation (%)=(transmittance (%) before heating and baking)−(transmittance (%) after heating and baking)

In addition, using the liquid crystal aligning agents prepared in Examples 37 to 116 and Comparative Examples 3 and 4, a coating film of the liquid crystal alignment film was formed on a transparent glass substrate under the same conditions as in the section of evaluation of voltage holding ratio, then the film was subjected to photoalignment treatment, and heated and balked at 230° C. for 30 minutes to give a liquid crystal alignment film having a thickness of 100 nm. However, in the case where the aligning agent 73 was used, the film was, after photoalignment treatment, heated and baked under the conditions shown in Table 24 to give a liquid crystal alignment film having a thickness of 100 nm. These substrates each having the liquid crystal alignment film formed thereon were subjected to UV-visible light transmittance spectrometry to determine a mean value of the transmittance within a range of 380 nm to 430 nm (mean transmittance after heating and baking). The results are shown in Tables 22 to 24.

TABLE 19

| Example No. | Aligning Agent No. | Varnish No. | Mean Transmittance (%) at 380 to 430 nm after heating and baking | Transmittance (%) at 365 nm before heating and baking | Transmittance (%) at 365 nm after heating and baking | Variation |
|---|---|---|---|---|---|---|
| 1 | 1 | 1 | 83 | 32 | 66 | 34 |
| 2 | 2 | 2 | 87 | 33 | 69 | 36 |
| 3 | 3 | 3 | 84 | 35 | 67 | 32 |
| 4 | 4 | 4 | 87 | 36 | 69 | 33 |
| 5 | 5 | 5 | 84 | 34 | 67 | 33 |
| 6 | 6 | 6 | 88 | 34 | 70 | 36 |
| 7 | 7 | 7 | 84 | 37 | 67 | 30 |
| 8 | 8 | 8 | 87 | 38 | 69 | 31 |
| 9 | 9 | 9 | 83 | 36 | 66 | 30 |
| 10 | 10 | 10 | 87 | 36 | 69 | 33 |
| 11 | 11 | 11 | 86 | 33 | 68 | 35 |
| 12 | 12 | 12 | 88 | 33 | 69 | 36 |
| 13 | 13 | 13 | 89 | 33 | 69 | 36 |
| 14 | 14 | 14 | 86 | 35 | 68 | 33 |
| 15 | 15 | 15 | 85 | 35 | 67 | 32 |
| 16 | 16 | 16 | 87 | 36 | 68 | 32 |
| 17 | 17 | 17 | 88 | 36 | 69 | 33 |
| 18 | 18 | 18 | 89 | 36 | 70 | 34 |
| 19 | 19 | 19 | 85 | 33 | 68 | 35 |
| 20 | 20 | 20 | 89 | 34 | 72 | 38 |
| 21 | 21 | 21 | 88 | 36 | 71 | 35 |
| 22 | 22 | 22 | 89 | 35 | 72 | 37 |
| 23 | 23 | 23 | 86 | 32 | 69 | 37 |
| 24 | 24 | 24 | 82 | 32 | 66 | 34 |
| 25 | 25 | 25 | 87 | 35 | 70 | 35 |
| 26 | 26 | 26 | 88 | 34 | 71 | 37 |
| 27 | 27 | 27 | 87 | 34 | 71 | 37 |
| 28 | 28 | 28 | 84 | 35 | 68 | 33 |
| 29 | 29 | 29 | 85 | 35 | 69 | 34 |
| 30 | 30 | 30 | 87 | 33 | 68 | 35 |
| 31 | 31 | 31 | 87 | 34 | 68 | 34 |
| 32 | 32 | 32 | 88 | 36 | 69 | 33 |
| 33 | 33 | 33 | 86 | 32 | 69 | 37 |
| 34 | 34 | 34 | 87 | 35 | 70 | 35 |
| 35 | 35 | 35 | 87 | 36 | 69 | 33 |
| 36 | 36 | 36 | 85 | 45 | 74 | 29 |

TABLE 20

| Example No. | Aligning Agent No. | Varnish No. | Baking Conditions First Stage | Baking Conditions Second Stage | Mean Transmittance (%) at 380 to 430 nm after heating and baking | Transmittance (%) at 365 nm before heating and baking | Transmittance (%) at 365 nm after heating and baking | Variation |
|---|---|---|---|---|---|---|---|---|
| 1-2 | 1 | 1 | 110° C., 20 minutes | 200° C., 15 minutes | 81 | 32 | 64 | 32 |
| 1-3 | 1 | 1 | 110° C., 20 minutes | 210° C., 15 minutes | 82 | 32 | 65 | 33 |
| 1-4 | 1 | 1 | 110° C., 20 minutes | 220° C., 15 minutes | 83 | 32 | 66 | 34 |
| 1-5 | 1 | 1 | 110° C., 20 minutes | 230° C., 15 minutes | 83 | 32 | 66 | 34 |
| 1-6 | 1 | 1 | 130° C., 20 minutes | 200° C., 15 minutes | 81 | 32 | 64 | 32 |
| 1-7 | 1 | 1 | 130° C., 20 minutes | 210° C., 15 minutes | 82 | 32 | 65 | 33 |
| 1-8 | 1 | 1 | 130° C., 20 minutes | 220° C., 15 minutes | 83 | 32 | 66 | 34 |

TABLE 20-continued

| Example No. | Aligning Agent No. | Varnish No. | Baking Conditions First Stage | Baking Conditions Second Stage | Mean Transmittance (%) at 380 to 430 nm after heating and baking | Transmittance (%) at 365 nm before heating and baking | Transmittance (%) at 365 nm after heating and baking | Transmittance (%) at 365 nm Variation |
|---|---|---|---|---|---|---|---|---|
| 1-9 | 1 | 1 | 130° C., 20 minutes | 230° C., 15 minutes | 83 | 32 | 66 | 34 |
| 1-10 | 1 | 1 | 150° C., 20 minutes | 200° C., 15 minutes | 82 | 32 | 65 | 33 |
| 1-11 | 1 | 1 | 150° C., 20 minutes | 210° C., 15 minutes | 82 | 32 | 65 | 33 |
| 1-12 | 1 | 1 | 150° C., 20 minutes | 220° C., 15 minutes | 83 | 32 | 66 | 34 |
| 1-13 | 1 | 1 | 150° C., 20 minutes | 230° C., 15 minutes | 83 | 32 | 66 | 34 |
| 1-14 | 1 | 1 | 170° C., 20 minutes | 200° C., 15 minutes | 82 | 32 | 65 | 33 |
| 1-15 | 1 | 1 | 170° C., 20 minutes | 210° C., 15 minutes | 83 | 32 | 66 | 34 |
| 1-16 | 1 | 1 | 170° C., 20 minutes | 220° C., 15 minutes | 83 | 32 | 66 | 34 |
| 1-17 | 1 | 1 | 170° C., 20 minutes | 230° C., 15 minutes | 84 | 32 | 67 | 35 |
| 1-18 | 1 | 1 | Heated from 110° C. up to 220° C. in a period of 20 minutes, then kept at 220° C. for 15 minutes. | | 83 | 32 | 66 | 34 |

TABLE 21

| Comparative Example No. | Comparative Aligning Agent No. | Comparative Varnish No. | Mean Transmittance (%) at 380 to 430 nm after heating and baking | Transmittance (%) at 365 nm before heating and baking | Transmittance (%) at 365 nm after heating and baking | Transmittance (%) at 365 nm Variation |
|---|---|---|---|---|---|---|
| 1 | 1 | 1 | 70 | 26 | 44 | 18 |
| 2 | 2 | 2 | 71 | 29 | 45 | 16 |

TABLE 22

| Example No. | Aligning Agent No. | Varnish No. | Varnish No. for blending | Mean Transmittance (%) at 380 to 430 nm |
|---|---|---|---|---|
| 37 | 37 | 1 | 1 | 91 |
| 38 | 38 | 2 | 1 | 93 |
| 39 | 39 | 3 | 2 | 92 |
| 40 | 40 | 4 | 2 | 93 |
| 41 | 41 | 5 | 3 | 92 |
| 42 | 42 | 6 | 3 | 94 |
| 43 | 43 | 7 | 4 | 92 |
| 44 | 44 | 7 | 5 | 92 |
| 45 | 45 | 8 | 4 | 93 |
| 46 | 46 | 8 | 5 | 93 |
| 47 | 47 | 9 | 3 | 92 |
| 48 | 48 | 9 | 5 | 91 |
| 49 | 49 | 10 | 3 | 93 |
| 50 | 50 | 10 | 5 | 93 |
| 51 | 51 | 1 | 12 | 91 |
| 52 | 52 | 2 | 8 | 93 |
| 53 | 53 | 7 | 8 | 92 |
| 54 | 54 | 7 | 10 | 92 |
| 55 | 55 | 8 | 7 | 93 |
| 56 | 56 | 8 | 11 | 93 |
| 57 | 57 | 11 | 1 | 92 |
| 58 | 58 | 11 | 6 | 93 |
| 59 | 59 | 12 | 1 | 93 |
| 60 | 60 | 12 | 7 | 92 |
| 61 | 61 | 13 | 1 | 93 |
| 62 | 62 | 13 | 11 | 93 |
| 63 | 63 | 14 | 5 | 92 |
| 64 | 64 | 14 | 8 | 92 |
| 65 | 65 | 14 | 10 | 92 |
| 66 | 66 | 15 | 4 | 92 |
| 67 | 67 | 15 | 6 | 93 |
| 68 | 68 | 15 | 9 | 93 |
| 69 | 69 | 16 | 1 | 93 |
| 70 | 70 | 16 | 3 | 93 |
| 71 | 71 | 16 | 6 | 93 |
| 72 | 72 | 16 | 7 | 92 |
| 73 | 73 | 16 | 8 | 93 |
| 74 | 74 | 17 | 8 | 93 |
| 75 | 75 | 18 | 8 | 93 |
| 76 | 76 | 19 | 2 | 93 |

TABLE 23

| Example No. | Aligning Agent No. | Varnish No. | Varnish No. for blending | Mean Transmittance (%) at 380 to 430 nm |
|---|---|---|---|---|
| 77 | 77 | 19 | 12 | 92 |
| 78 | 78 | 20 | 3 | 94 |
| 79 | 79 | 20 | 8 | 93 |
| 80 | 80 | 21 | 6 | 94 |
| 81 | 81 | 21 | 7 | 92 |
| 82 | 82 | 21 | 8 | 93 |
| 83 | 83 | 21 | 11 | 93 |
| 84 | 84 | 22 | 4 | 93 |
| 85 | 85 | 22 | 9 | 94 |
| 86 | 86 | 23 | 1 | 92 |
| 87 | 87 | 23 | 9 | 93 |
| 88 | 88 | 25 | 5 | 93 |
| 89 | 89 | 25 | 11 | 93 |
| 90 | 90 | 26 | 6 | 94 |
| 91 | 91 | 26 | 10 | 93 |
| 92 | 92 | 27 | 2 | 93 |
| 93 | 86 | 27 | 10 | 93 |
| 94 | 87 | 27 | 12 | 93 |
| 95 | 88 | 28 | 2 | 92 |
| 96 | 89 | 28 | 6 | 92 |
| 97 | 90 | 28 | 10 | 92 |
| 98 | 91 | 29 | 4 | 92 |

TABLE 23-continued

| | | | | Mean Transmittance (%) at 380 to 430 nm |
|---|---|---|---|---|
| 99 | 92 | 29 | 12 | 92 |
| 100 | 100 | 5 | 14 | 92 |
| 101 | 101 | 16 | 14 | 93 |
| 102 | 102 | 16 | 15 | 93 |
| 103 | 103 | 21 | 15 | 93 |
| 104 | 104 | 16 | 16 | 93 |
| 105 | 105 | 26 | 16 | 93 |
| 106 | 106 | 30 | 13 | 91 |
| 107 | 107 | 31 | 13 | 91 |
| 108 | 108 | 31 | 14 | 91 |
| 109 | 109 | 32 | 8 | 92 |
| 110 | 110 | 33 | 1 | 93 |
| 111 | 111 | 33 | 13 | 91 |
| 112 | 112 | 34 | 3 | 93 |
| 113 | 113 | 34 | 13 | 91 |
| 114 | 114 | 35 | 6 | 93 |
| 115 | 115 | 35 | 8 | 92 |
| 116 | 116 | 35 | 14 | 93 |

| Comparative Example No. | Comparative Aligning Agent No. | Comparative Varnish No. | Varnish No. for blending | Mean Transmittance (%) at 380 to 430 nm |
|---|---|---|---|---|
| 3 | 3 | 1 | 1 | 88 |
| 4 | 4 | 2 | 1 | 88 |

TABLE 24

| Example No. | Aligning Agent No. | Varnish No. | Varnish No. for blending | Baking Conditions First Stage | Baking Conditions Second Stage | Mean Transmittance (%) at 380 to 430 nm |
|---|---|---|---|---|---|---|
| 73-2 | 73 | 16 | 8 | 150° C., 20 minutes | 230° C., 15 minutes | 93 |

As shown in Tables 19 to 21, it is confirmed that the liquid crystal alignment films formed using any of the aligning agents 1 to 36 containing any of the varnishes 1 to 36 prepared using the diamine represented by the formula (2) of (10) had a large transmittance variation at 365 nm and had a high mean transmittance. This is considered because the azobenzene structure or the acylhydrazone structure would have reduced owing to partial cyclization of the azobenzene structure or the acylhydrazone structure. On the other hand, the liquid crystal alignment films formed using any of the comparative aligning agents 1 and 2 containing any of the comparative varnishes 1 and 2 had a small transmittance variation at 365 nm and had a low mean transmittance. The reason why the transmittance variation at 365 nm is low and the mean transmittance is low in that manner is considered to be because the azobenzene structure did not form an indazole ring in the heating and baking treatment but remained as an azobenzene structure of itself.

As shown in Tables 22 to 24, the liquid crystal alignment films formed using any of the aligning agents 37 to 116 containing the varnish prepared using the diamine of the formula (2) and the varnish for blending also had a high mean transmittance of 91% or more after heating and baking. As opposed to these, the liquid crystal alignment films formed using any of the comparative aligning agents 3 and 4 containing any of the comparative varnish 1 and 2 and the varnish for blending had a mean transmittance of 88%, that is, the mean transmittance thereof was lower than that of the liquid crystal alignment films of the liquid crystal aligning agents of Examples of the present invention. This suggests that, also in the blend-type liquid crystal aligning agents, the same mechanism (azo group reduction owing to indazole ring formation) would contribute toward transmittance increase.

[Measurement of AC Image Sticking (Evaluation of Liquid Crystal Aligning Performance)]

Using the aligning agents 1, 2 and 73 prepared in Examples 1, 2 and 73, a liquid crystal alignment film having a thickness of 100 nm was formed on an FFS electrode-having glass substrate and a column spacer-having glass substrate under the same conditions as in the above-mentioned section of evaluation of voltage holding ratio. The two substrates on which the liquid crystal alignment film was formed were combined and stuck together in such a manner that the surfaces thereof each having the liquid crystal alignment film formed thereon could face each other via a space kept therebetween so that a liquid crystal composition could be injected into the space between the facing liquid crystal alignment films. At this, the substrates were so oriented that the polarization directions of the linearly-polarized lights applied to the liquid crystal alignment films could be in parallel to each other. Into the space between the thus-stuck substrates, the negative liquid crystal composition A composed of the ingredients mentioned above was injected, and the injection mouth was sealed up with a photocuring agent to construct a liquid crystal cell having a cell thickness of 4 μm (liquid crystal display device). The resultant liquid crystal display devices were tested to measure the brightness at 1.3 V before stress application and after stress application, and the difference between the two, ΔB was calculated. The results are shown in Table 25.

TABLE 25

| Example No. | Aligning Agent No. | Varnish No. | Varnish No. for blending | Baking Conditions First Stage | Baking Conditions Second Stage | ΔB |
|---|---|---|---|---|---|---|
| 1 | 1 | 1 | | 230° C., 30 minutes | | 0.9 |
| 1-2 | 1 | 1 | | 110° C., 20 minutes | 200° C., 15 minutes | 0.9 |
| 1-3 | 1 | 1 | | 110° C., 20 minutes | 210° C., 15 minutes | 0.7 |
| 1-4 | 1 | 1 | | 110° C., 20 minutes | 220° C., 15 minutes | 0.6 |
| 1-5 | 1 | 1 | | 110° C., 20 minutes | 230° C., 15 minutes | 0.6 |
| 1-6 | 1 | 1 | | 130° C., 20 minutes | 200° C., 15 minutes | 0.7 |
| 1-7 | 1 | 1 | | 130° C., 20 minutes | 210° C., 15 minutes | 0.7 |
| 1-8 | 1 | 1 | | 130° C., 20 minutes | 220° C., 15 minutes | 0.7 |
| 1-9 | 1 | 1 | | 130° C., 20 minutes | 230° C., 15 minutes | 0.7 |

TABLE 25-continued

| Example No. | Aligning Agent No. | Varnish No. | Varnish No. for blending | Baking Conditions First Stage | Baking Conditions Second Stage | ΔB |
|---|---|---|---|---|---|---|
| 1-10 | 1 | 1 | | 150° C., 20 minutes | 200° C., 15 minutes | 0.5 |
| 1-11 | 1 | 1 | | 150° C., 20 minutes | 210° C., 15 minutes | 0.5 |
| 1-12 | 1 | 1 | | 150° C., 20 minutes | 220° C., 15 minutes | 0.4 |
| 1-13 | 1 | 1 | | 150° C., 20 minutes | 230° C., 15 minutes | 0.6 |
| 1-14 | 1 | 1 | | 170° C., 20 minutes | 200° C., 15 minutes | 0.7 |
| 1-15 | 1 | 1 | | 170° C., 20 minutes | 210° C., 15 minutes | 0.8 |
| 1-16 | 1 | 1 | | 170° C., 20 minutes | 220° C., 15 minutes | 0.8 |
| 1-17 | 1 | 1 | | 170° C., 20 minutes | 230° C., 15 minutes | 0.9 |
| 1-18 | 1 | 1 | | Heated from 110° C. up to 220° C. in a period of 20 minutes, then kept at 220° C. for 15 minutes. | | 0.6 |
| 2 | 2 | 2 | | 230° C., 30 minutes | | 0.4 |
| 73 | 73 | 16 | 8 | 230° C., 30 minutes | | 0.7 |
| 73-2 | 73 | 16 | 8 | 150° C., 20 minutes | 230° C., 15 minutes | 0.4 |

As shown in Table 25, it is confirmed that the liquid crystal alignment films formed of the liquid crystal aligning agents containing the varnish prepared using the diamine represented by the formula (2) have good liquid crystal alignment performance. In particular, regarding the liquid crystal alignment films of the aligning agent 1, the liquid crystal alignment films of Examples 1-3 to 1-16 in which the heating and baking operation was carried out in two stages and the liquid crystal alignment film of Example 1-18 in which the film was heated up to the intended temperature in a period of 20 minutes had a smaller value of ΔB than the liquid crystal alignment film of Example 1 in which the film was heated at once up to the intended temperature. From this, it is known that, by stepwise heating or gradually heating up to the intended temperature in a period of time, a liquid crystal alignment film having more excellent liquid crystal alignment performance can be obtained.

[Evaluation of in-Plane Unevenness in Inkjet Printing]

Using an inkjet apparatus, each liquid crystal aligning agent prepared in Examples 117 to 160 was applied to an ITO-having substrate and dried, and the thus coated substrates were checked for the presence or absence of in-plane unevenness. The results are shown in Table 26. As shown in Table 26, the liquid crystal aligning agents prepared in Examples 117 to 160 were all free from in-plane unevenness when applied to substrates.

TABLE 26

| Example No. | Aligning Agent No. | Varnish No. | Varnish No. for blending | Inkjet In-plane Unevenness |
|---|---|---|---|---|
| 117 | 117 | 40 | 17 | no |
| 118 | 118 | 40 | 18 | no |
| 119 | 119 | 40 | 19 | no |
| 120 | 120 | 16 | 3 | no |
| 121 | 121 | 37 | 17 | no |
| 122 | 122 | 16 | 7 | no |
| 123 | 123 | 37 | 7 | no |
| 124 | 124 | 41 | 18 | no |
| 125 | 125 | 16 | 8 | no |
| 126 | 126 | 16 | 8 | no |
| 127 | 127 | 37 | 8 | no |
| 128 | 128 | 37 | 19 | no |
| 129 | 129 | 37 | 19 | no |
| 130 | 130 | 37 | 19 | no |
| 131 | 131 | 41 | 19 | no |
| 132 | 132 | 41 | 19 | no |
| 133 | 133 | 21 | 3 | no |
| 134 | 134 | 21 | 3 | no |
| 135 | 135 | 38 | 3 | no |
| 136 | 136 | 38 | 17 | no |
| 137 | 137 | 38 | 17 | no |
| 138 | 138 | 38 | 17 | no |
| 139 | 139 | 42 | 17 | no |
| 140 | 140 | 42 | 17 | no |
| 141 | 141 | 38 | 7 | no |
| 142 | 142 | 38 | 18 | no |
| 143 | 143 | 42 | 18 | no |
| 144 | 144 | 21 | 8 | no |
| 145 | 145 | 38 | 19 | no |
| 146 | 146 | 42 | 19 | no |
| 147 | 147 | 29 | 3 | no |
| 148 | 148 | 39 | 17 | no |
| 149 | 149 | 43 | 17 | no |
| 150 | 150 | 29 | 7 | no |
| 151 | 151 | 29 | 7 | no |
| 152 | 152 | 39 | 7 | no |
| 153 | 153 | 39 | 18 | no |
| 154 | 154 | 39 | 18 | no |
| 155 | 155 | 39 | 18 | no |
| 156 | 156 | 43 | 18 | no |
| 157 | 157 | 43 | 18 | no |
| 158 | 158 | 39 | 8 | no |
| 159 | 159 | 39 | 19 | no |
| 160 | 160 | 43 | 19 | no |

[Confirmation of Cyclization Temperature and Alignment Amplification Temperature]

Using the liquid crystal aligning agent 10 prepared in Example 16, a film of the liquid crystal aligning agent was formed on a transparent glass substrate under the same conditions as those in the section of evaluation of voltage holding ratio mentioned above, and subjected to photoalignment treatment. The substrate was put on a hot plate set at a predetermined temperature falling between 140° C. and 200° C., and thus heated thereon for 20 minutes to form a liquid crystal alignment film. Apart from this, other various liquid crystal alignment films were formed under the same conditions except that the heating temperature on the hot plate was varied. These substrate were subjected to UV-visible light transmittance spectrometry to determine the transmittance at 365 nm of an absorption wavelength of azobenzene. The transmittance data at 365 nm at different heating temperatures were plotted on a graph where the heating temperature is on the horizontal axis and the transmittance is on the vertical axis to give a correlation diagram of FIG. 3. The retardation value at 589 nm of the substrate having the liquid crystal alignment film formed thereon was measured using a spectroscopic ellipsometer. The retardation values at different heating temperatures were plotted on a graph where the heating temperature is on the horizontal axis and the retardation value is on the vertical axis to give a correlation diagram of FIG. 4.

Figure 3:
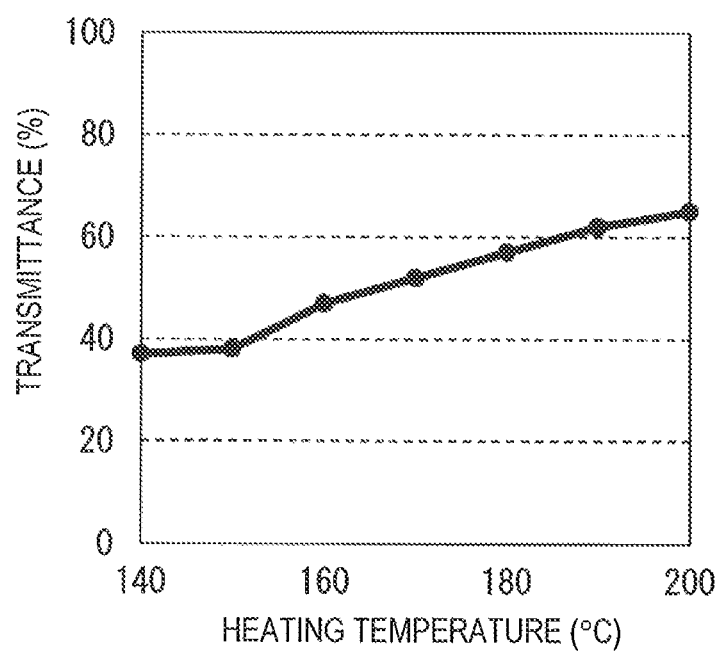
FIG. 3 is a graph drawn by plotting the visible light (365 nm) transmittance at a different heating temperature in forming a liquid crystal alignment film on a substrate using the aligning agent 16.
Figure 4:
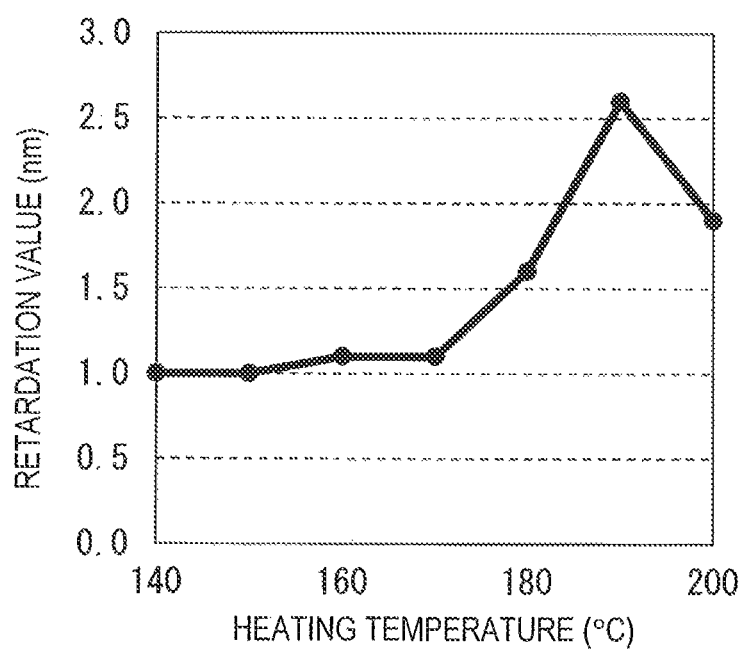
FIG. 4 is a graph drawn by plotting the retardation value (589 nm) at a different heating temperature in forming a liquid crystal alignment film on a substrate using the aligning agent 16.

Here, the transmittance at 365 nm reflects the degree of cyclization of the azobenzene structure, and the rising temperature of the transmittance curve corresponds to the cyclization onset temperature. The retardation value reflects the degree of alignment of the polymer chain, and the rising temperature of the retardation value curve corresponds to the alignment amplification onset temperature. FIG. 3 and FIG. 4 are discussed from these viewpoints. The liquid crystal alignment film of the aligning agent 16 has a cyclization onset temperature of about 150° C. and an alignment amplification onset temperature of about 170° C., and a difference is known between the cyclization onset temperature and the alignment amplification onset temperature. This suggests that, when the liquid crystal alignment film is kept at a temperature falling within a range of 150° C. or higher and lower than 170° C., the cyclization may be first carried out in some degree and then the alignment amplification may be carried out.

In Example 73, using the liquid crystal aligning agent 73 prepared by blending the varnish 16 constituting the liquid crystal aligning agent 16 and the varnish for blending 8, the coating film was baked at 230° C. for 30 minutes to form a liquid crystal alignment film. In Example 73-2, using the same agent, the coating film was baked at 150° C. for 20 minutes and then further baked at 230° C. for 15 minutes to form a liquid crystal alignment film. These two liquid crystal alignment films formed here were evaluated. The film of Example 73-2 where it was baked at 150° C. for 20 minutes and then further baked at 230° C. for 15 minutes had a smaller value ΔB (see Table 25). In addition, the film of Example 73-2 had a high transmittance and a high voltage holding ratio (see Tables 16 and 24). These suggest that, when cyclization is attained previously in some degree and then alignment amplification is carried out, the liquid crystal alignment performance can be markedly bettered.

The cyclization onset temperature, the alignment amplification onset temperature and the imidation onset temperature (in the case of a polyamic acid) vary depending on the structure of the polymer to be used in the liquid crystal alignment film, but a polymer in which the structural unit having a photoreactive structure undergoes cyclization by heating can make a difference between these onset temperatures relatively easily by appropriate molecular planning thereof, and the polymer of the type can obtain a result of the same tendency as that obtained in the present Examples.

INDUSTRIAL APPLICABILITY

When the liquid crystal aligning agent for photoalignment of the present invention is used, a liquid crystal display device having a high display quality can be provided, which can have a high voltage holding ratio and can maintain light resistance even in use for a long period of time. The liquid crystal aligning agent for photoalignment of the present invention is favorably used for horizontal field type liquid crystal display devices.

The invention claimed is:

1. A liquid crystal aligning composition for photoalignment, which comprises a polymer having a structural unit comprising a photoreactive structure represented by the following formula (1):

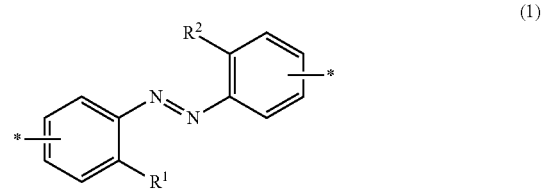

wherein $R^1$ and $R^2$ each independently represent a hydrogen atom, or a group represented by the following formula (1-1) or (1-2), wherein at least one of $R^1$ and $R^2$ is a group represented by the formula (1-1) or (1-2);
* represents a bonding position at a benzene ring, and is a position substitutable with a hydrogen atom in one of the benzene rings, and a position substitutable with a hydrogen atom in the other benzene ring;
a hydrogen atom in the benzene rings may be substituted with a substituent,

wherein $R^4$ and $R^5$ each independently represent a hydrogen atom, a substituted or unsubstituted alkyl group, a substituted or unsubstituted alkanoyl group, or a substituted or unsubstituted arylcarbonyl group; and
* represents a bonding position to a benzene ring in the formula (1),
wherein the structural unit comprising the photoreactive structure undergoes a chemical reaction by heating, and
wherein the polymer is at least one polymer selected from the group consisting of a polyamic acid, a polyimide, a partial polyimide, a polyamic acid ester, a polyamic acid-polyamide copolymer, and a polyamideimide.

2. The liquid crystal aligning composition for photoalignment according to claim 1, wherein the chemical reaction is a cyclization reaction.

3. The liquid crystal aligning composition for photoalignment according to claim 1, wherein the polymer a reaction product from of a raw material containing comprising a tetracarboxylic acid dianhydride and a diamine, and wherein the raw material comprises at least one diamine represented by the following formula (2):

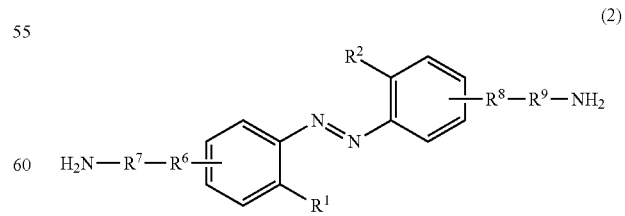

wherein $R^1$ and $R^2$ each independently represent a hydrogen atom, or a group represented by the following formula (1-1) or (1-2), wherein at least one of $R^1$ and $R^2$ is a group represented by the formula (1-1) or (1-2);

R⁶ and R⁸ each independently represent a linear alkylene group having 1 to 20 carbon atoms, —COO—, —OCO—, —NHCO—, —CONH—, —N(CH₃)CO—, —CON(CH₃)—, or a single bond, and in R⁶ and R⁸, one or two (—CH₂—)'s not adjacent to each other in the linear alkylene group may be substituted with —O—;

R⁷ and R⁹ each independently represent a monocyclic hydrocarbon, a condensed polycyclic hydrocarbon, a hetero ring or a single bond;

the bonding position of H₂N—R⁷—R⁶— is a position substitutable with a hydrogen atom in one benzene ring, and the bonding position of H₂N—R⁹—R⁸— is a position substitutable with a hydrogen atom in the other benzene ring;

a hydrogen atom in the benzene rings may be substituted with a substituent,

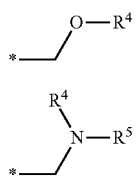

(1-1)

(1-2)

wherein R⁴ and R⁵ each independently represent a hydrogen atom, a substituted or unsubstituted alkyl group, a substituted or unsubstituted alkanoyl group, or a substituted or unsubstituted arylcarbonyl group; and
* represents a bonding position to a benzene ring in the formula (2).

4. The liquid crystal aligning composition for photoalignment according to claim 3, wherein the diamine represented by the formula (2) is a diamine represented by any of the following formulae (3) to (8):

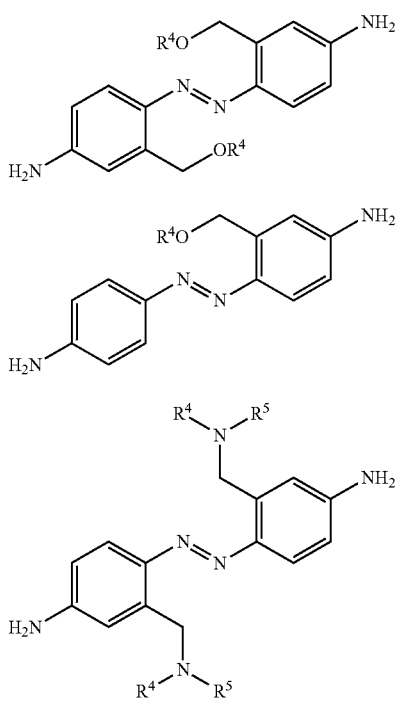

(3)

(4)

(5)

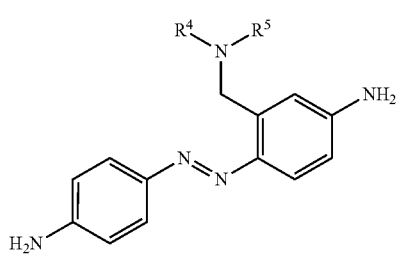

(6)

(7)

(8)

wherein R⁴ independently represents a hydrogen atom, a substituted or unsubstituted alkyl group, a substituted or unsubstituted alkanoyl group, or a substituted or unsubstituted arylcarbonyl group;
a hydrogen atom in the benzene rings may be substituted with a substituent; and
R⁵ independently represents a hydrogen atom, a substituted or unsubstituted alkyl group, a substituted or unsubstituted alkanoyl group, or a substituted or unsubstituted arylcarbonyl group.

5. The liquid crystal aligning composition for photoalignment according to claim 3, wherein the diamine is a diamine represented by any of the following formulae (3-1) to (3-8), formulae (4-1) to (4-8), formula (5-1), formula (5-2), formula (6-1), formula (6-2), formulae (7-1) to (7-3), and formulae (8-1) to (8-3):

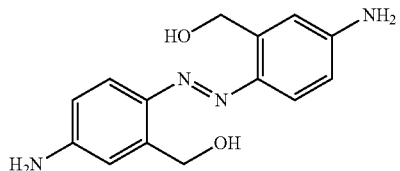

(3-1)

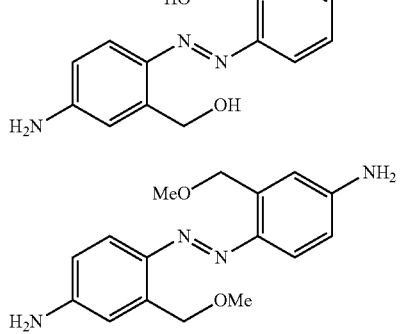

(3-2)

(3-3)

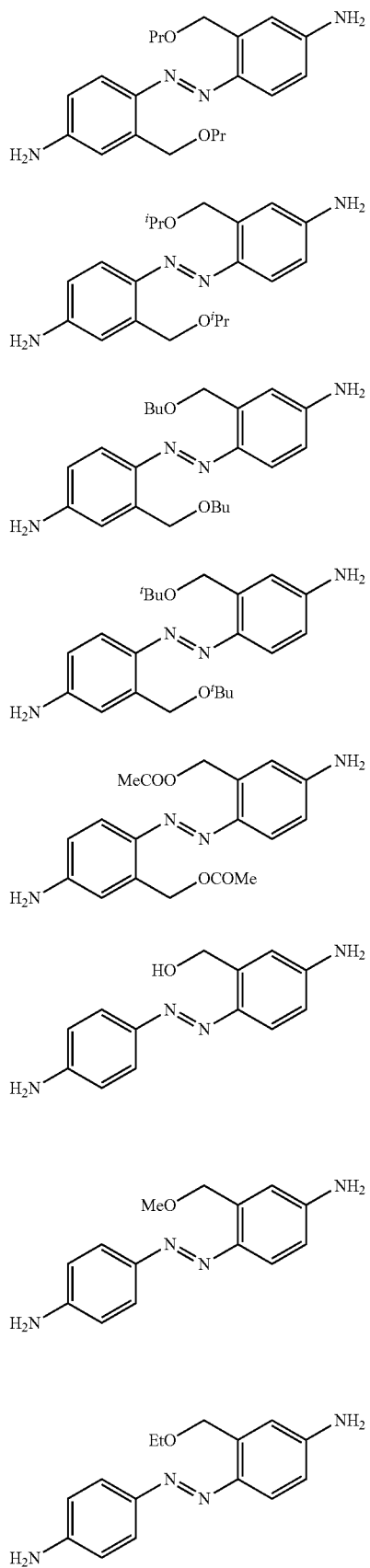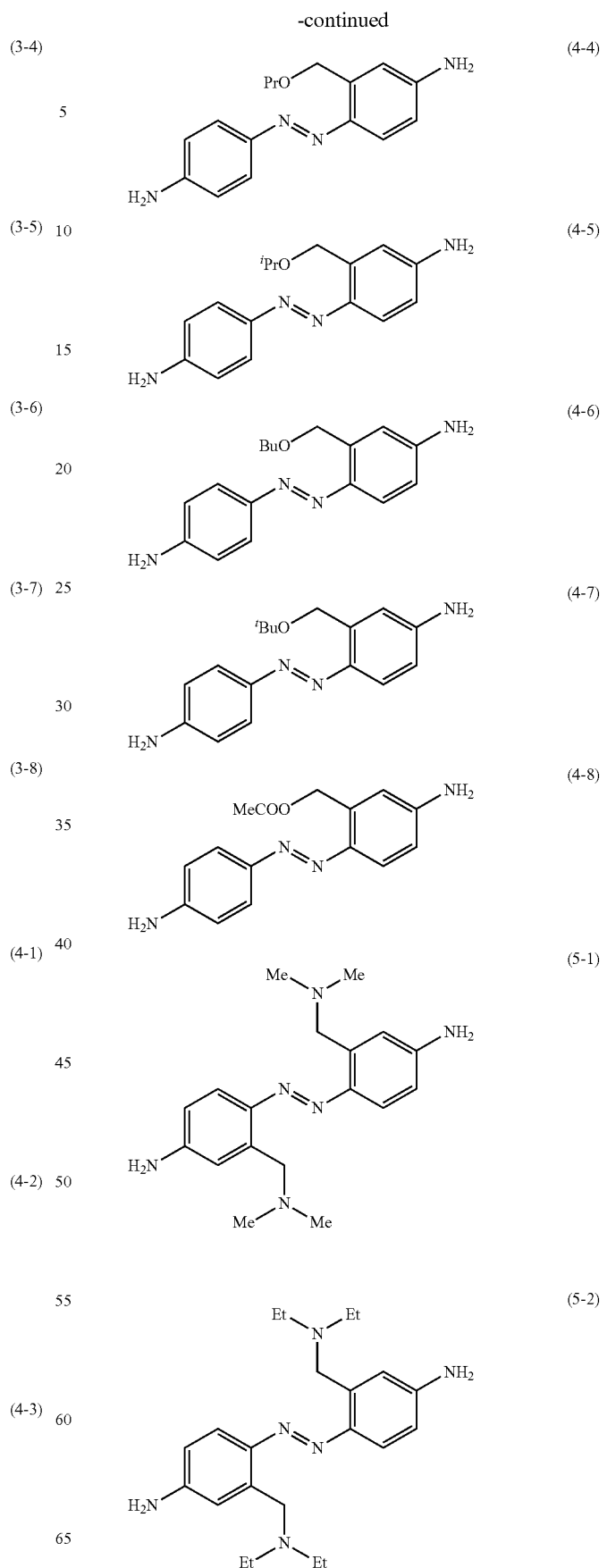

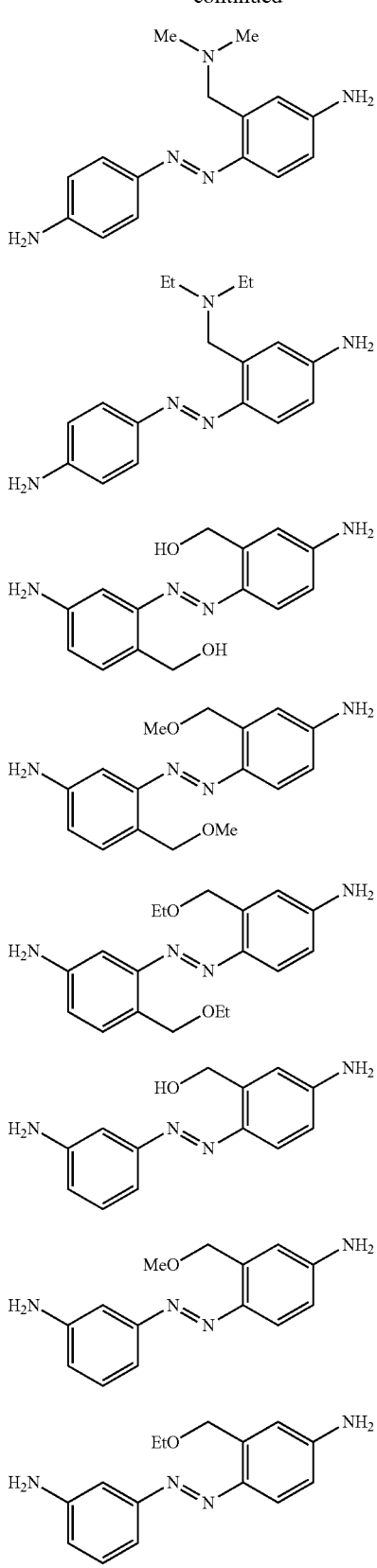

an isopropyl group, Bu represents a butyl group, and $^t$Bu represents a t-butyl group.

6. The liquid crystal aligning composition for photoalignment according to claim 1, wherein, when a film formed of the liquid crystal aligning composition for photoalignment is heated and baked at 230° C. for 30 minutes, a transmittance at 365 nm of the film increases by 25% or more from the transmittance at 365 nm of the film before heating and baking.

7. The liquid crystal aligning composition for photoalignment according to claim 1, which is used for production of a horizontal field type liquid crystal display device.

8. A liquid crystal alignment film formed from the liquid crystal aligning composition for photoalignment according to claim 1.

9. A liquid crystal display device comprising the liquid crystal alignment film according to claim 8.

10. A horizontal field type liquid crystal display device comprising the liquid crystal alignment film according to claim 8.

11. A diamine represented by the following formula (2):

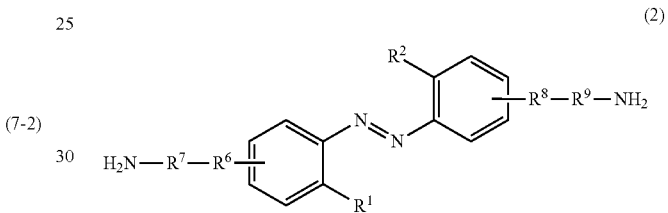

wherein $R^1$ and $R^2$ each independently represent a hydrogen atom, or a group represented by the following formula (1-1) or (1-2), wherein at least one of $R^1$ and $R^2$ is a group represented by the formula (1-1) or (1-2);

$R^6$ and $R^8$ each independently represent a linear alkylene group having 1 to 20 carbon atoms, —COO—, —OCO—, —NHCO—, —CONH—, —N(CH$_3$)CO—, —CON(CH$_3$)—, or a single bond, and in $R^6$ and $R^8$, one or two (—CH$_2$—)'s not adjacent to each other in the linear alkylene group may be substituted with —O—;

$R^7$ and $R^9$ each independently represent a monocyclic hydrocarbon, a condensed polycyclic hydrocarbon, a hetero ring or a single bond;

the bonding position of H$_2$N—R$^7$—R$^6$— is a position substitutable with a hydrogen atom in one benzene ring, and the bonding position of H$_2$N—R$^9$—R$^8$— is a position substitutable with a hydrogen atom in the other benzene ring;

a hydrogen atom in the benzene rings may be substituted with a substituent,

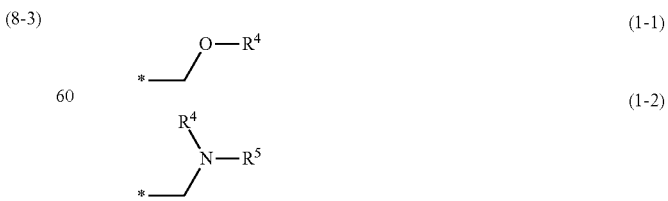

wherein $R^4$ and $R^5$ each independently represent a hydrogen atom, a substituted or unsubstituted alkyl group, a wherein Me represents a methyl group, Et represents an ethyl group, Pr represents a propyl group, $^i$Pr represents substituted or unsubstituted alkanoyl group, or a substituted or unsubstituted arylcarbonyl group; and
* represents a bonding position to one of the benzene rings in the formula (2).
12. The diamine according to claim 11, which is represented by any of the following formulae (3-1) to (3-8), formulae (4-1) to (4-8), formula (5-1), formula (5-2), formula (6-1), formula (6-2), formulae (7-1) to (7-3), and formulae (8-1) to (8-3):
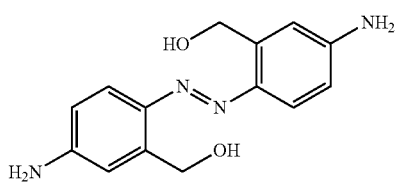
(3-1)
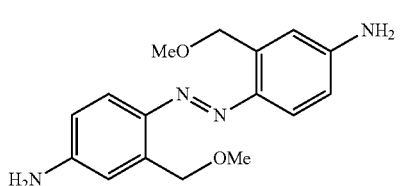
(3-2)
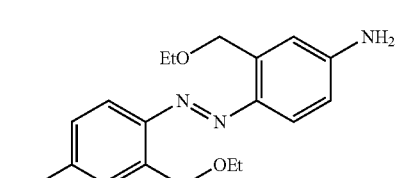
(3-3)
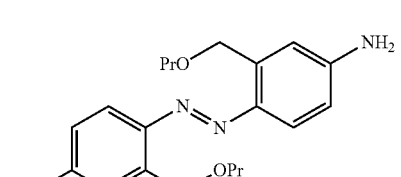
(3-4)
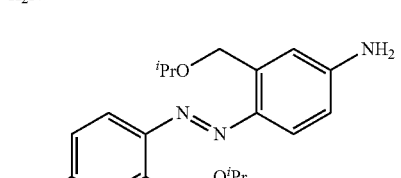
(3-5)
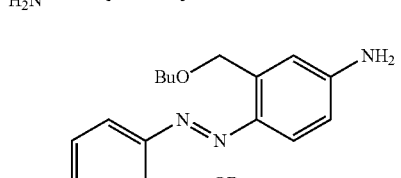
(3-6)
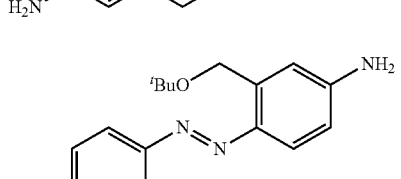
(3-7)
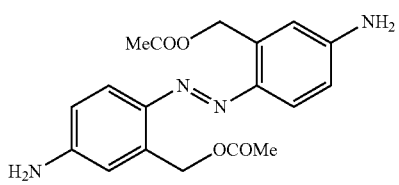
(3-8)
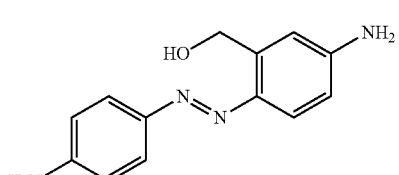
(4-1)
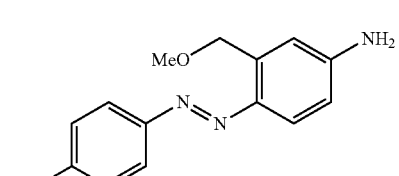
(4-2)
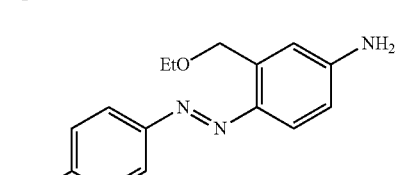
(4-3)
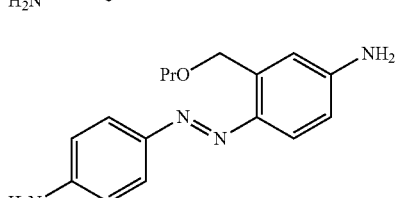
(4-4)
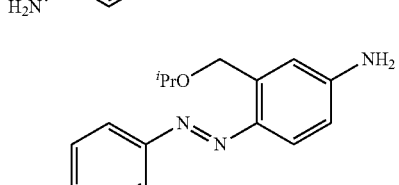
(4-5)
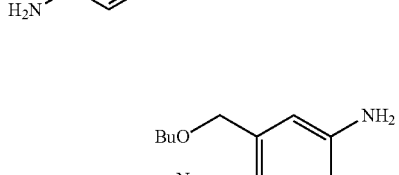
(4-6)
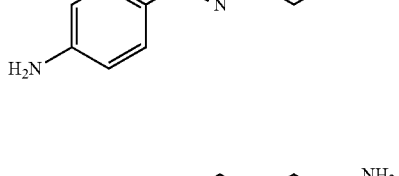
(4-7)

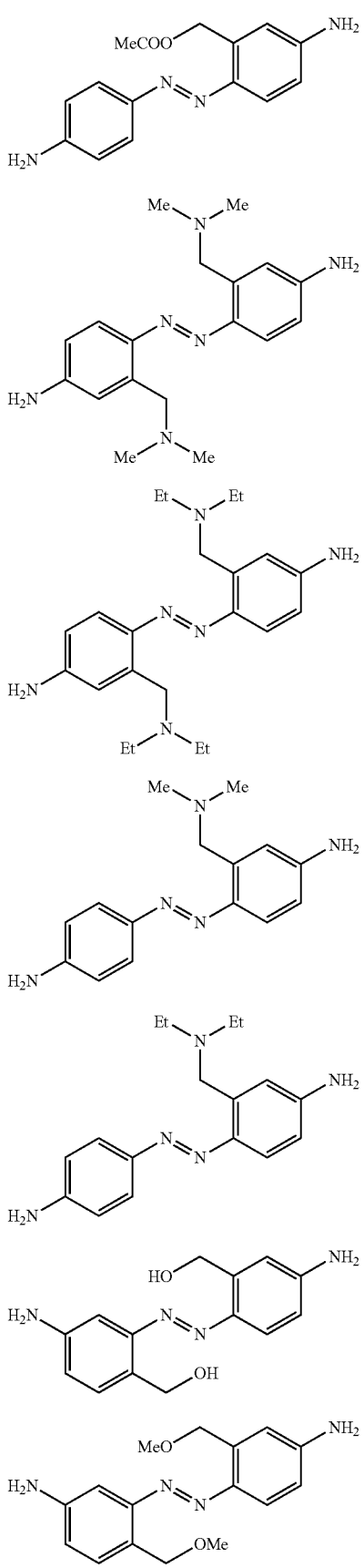

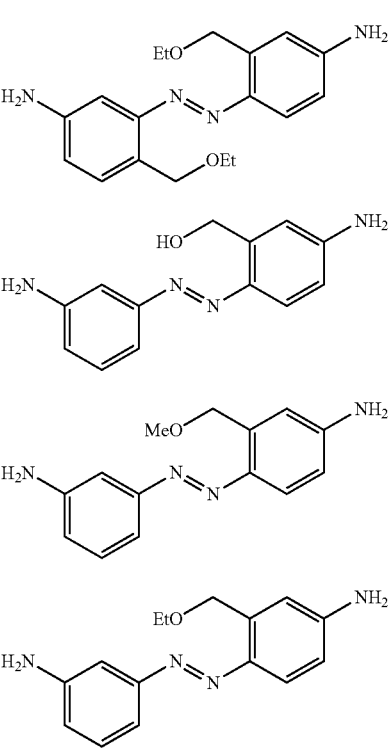

wherein Me represents a methyl group, Et represents an ethyl group, Pr represents a propyl group, $^i$Pr represents an isopropyl group, Bu represents a butyl group, and $^t$Bu represents a t-butyl group.

13. A polymer having a structural unit comprising a photoreactive structure in the main chain thereof represented by the following formula (1):

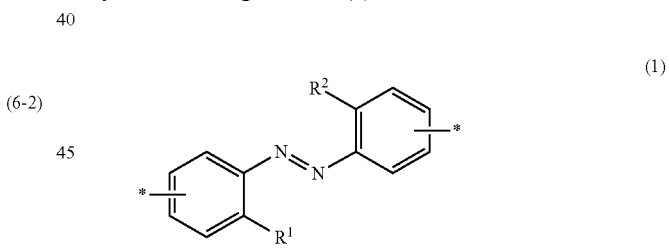

wherein $R^1$ and $R^2$ each independently represent a hydrogen atom, or a group represented by the following formula (1-1) or (1-2), wherein at least one of $R^1$ and $R^2$ is a group represented by the formula (1-1) or (1-2);

\* represents a bonding position at a benzene ring, and is a position substitutable with a hydrogen atom in one of the benzene rings, and a position substitutable with a hydrogen atom in the other benzene ring;

a hydrogen atom in the benzene rings may be substituted with a substituent,

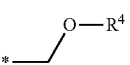

-continued (1-2)

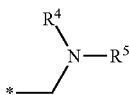

wherein R⁴ and R⁵ each independently represent a hydrogen atom, a substituted or unsubstituted alkyl group, a substituted or unsubstituted alkanoyl group, or a substituted or unsubstituted arylcarbonyl group; and
* represents a bonding position to a benzene ring in the formula (1),
wherein the structural unit comprising the photoreactive structure undergoes a chemical reaction by heating, and
wherein the polymer is at least one polymer selected from the group consisting of a polyamic acid, a polyimide, a partial polyimide, a polyamic acid ester, a polyamic acid-polyamide copolymer, and a polyamideimide.

14. The polymer according to claim 13, which is a reaction product from a raw material comprising a tetracarboxylic acid dianhydride and a diamine, and wherein:
the raw material comprises at least one diamine represented by the following formula (2):

(2)

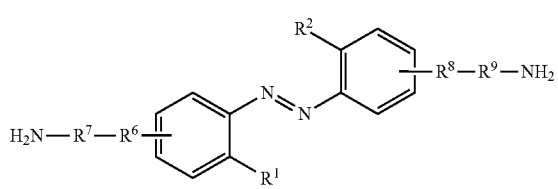

wherein R¹ and R² each independently represent a hydrogen atom, or a group represented by the following formula (1-1) or (1-2), wherein at least one of R¹ and R² is a group represented by the formula (1-1) or (1-2);
R⁶ and R⁸ each independently represent a linear alkylene group having 1 to 20 carbon atoms, —COO—, —OCO—, —NHCO—, —CONH—, —N(CH₃)CO—, —CON(CH₃)—, or a single bond, and in R⁶ and R⁸, one or two (—CH₂—)'s not adjacent to each other in the linear alkylene group may be substituted with —O—;
R⁷ and R⁹ each independently represent a monocyclic hydrocarbon, a condensed polycyclic hydrocarbon, a hetero ring or a single bond;
the bonding position of H₂N—R⁷—R⁶— is a position substitutable with a hydrogen atom in one benzene ring, and the bonding position of H₂N—R⁹—R⁸— is a position substitutable with a hydrogen atom in the other benzene ring;
a hydrogen atom in the benzene rings may be substituted with a substituent, (1-1)

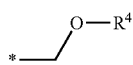

(1-2)

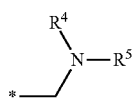

wherein R⁴ and R⁵ each independently represent a hydrogen atom, a substituted or unsubstituted alkyl group, a substituted or unsubstituted alkanoyl group, or a substituted or unsubstituted arylcarbonyl group;
* represents a bonding position to one of the benzene rings in the formula (2).

15. A method for forming a liquid crystal alignment film using a liquid crystal aligning composition for photoalignment comprising a polymer having a photoreactive structure,
the method comprising a step of irradiating a film of a liquid crystal aligning composition formed by applying the liquid crystal aligning composition for photoalignment according to claim 1 to a support, with a polarized light to give anisotropy to the film followed by heating and baking the film, wherein the photoreactive structure is cyclized in heating and baking to be a non-photoreactive structure.

16. The method for forming a liquid crystal alignment film according to claim 15, wherein the heating and baking is carried out in two or more stages at different heating temperatures.

17. A method for producing a liquid crystal display device, comprising forming a liquid crystal alignment film according to the liquid crystal alignment film formation method according to claim 15.

18. A method for producing a horizontal field type liquid crystal display device, comprising forming a liquid crystal alignment film according to the liquid crystal alignment film formation method according to claim 15.

* * * * *